United States Patent
Fryer et al.

(10) Patent No.: US 10,377,989 B2
(45) Date of Patent: Aug. 13, 2019

(54) METHODS FOR SUSPENSION CULTURES OF HUMAN PLURIPOTENT STEM CELLS

(71) Applicant: Janssen Biotech, Inc., Horsham, PA (US)

(72) Inventors: Benjamin Fryer, Horsham, PA (US); Daina Laniauskas, Horsham, PA (US); Marcia Blackmoore, Horsham, PA (US); Haiyun Wang, Horsham, PA (US); Kostadinka LiLova, Spring House, PA (US); Shelley Nelson, Titusville, NJ (US); Elizabeth Rosocha, Raritan, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 373 days.

(21) Appl. No.: 13/998,974

(22) Filed: Dec. 30, 2013

(65) Prior Publication Data

US 2014/0242693 A1 Aug. 28, 2014

Related U.S. Application Data

(60) Provisional application No. 61/747,799, filed on Dec. 31, 2012, provisional application No. 61/962,158, filed on Nov. 1, 2013.

(51) Int. Cl.
*C12N 5/071* (2010.01)
*C12N 5/0735* (2010.01)

(52) U.S. Cl.
CPC ......... *C12N 5/0677* (2013.01); *C12N 5/0606* (2013.01); *C12N 2500/02* (2013.01); *C12N 2500/25* (2013.01); *C12N 2500/34* (2013.01); *C12N 2501/117* (2013.01); *C12N 2501/15* (2013.01); *C12N 2501/16* (2013.01); *C12N 2501/19* (2013.01); *C12N 2501/385* (2013.01); *C12N 2501/415* (2013.01); *C12N 2501/42* (2013.01); *C12N 2501/727* (2013.01); *C12N 2501/999* (2013.01); *C12N 2506/02* (2013.01); *C12N 2506/45* (2013.01); *C12N 2509/00* (2013.01); *C12N 2513/00* (2013.01); *C12N 2531/00* (2013.01)

(58) Field of Classification Search
CPC .............. C12N 5/0606; C12N 2500/02; C12N 2500/25; C12N 2500/34; C12N 2501/117; C12N 2501/15; C12N 2501/16; C12N 2501/19; C12N 2501/385; C12N 2501/415; C12N 2501/42; C12N 2501/727; C12N 2501/999; C12N 2506/02; C12N 2506/45; C12N 2509/00; C12N 2513/00
See application file for complete search history.

(56) References Cited

U.S. PATENT DOCUMENTS

| | | | |
|---|---|---|---|
| 3,209,652 | A | 10/1965 | Burgsmueller |
| 3,845,641 | A | 11/1974 | Waller |
| 3,935,067 | A | 1/1976 | Thayer |
| 4,499,802 | A | 2/1985 | Simpson |
| 4,537,773 | A | 8/1985 | Shenvi |
| 4,557,264 | A | 12/1985 | Hinsch |
| 4,737,578 | A | 4/1988 | Evans et al. |
| 5,215,893 | A | 6/1993 | Mason et al. |
| 5,449,383 | A | 9/1995 | Chatelier et al. |
| 5,525,488 | A | 6/1996 | Mason et al. |
| 5,567,612 | A | 10/1996 | Vacanti et al. |
| 5,665,568 | A | 9/1997 | Mason et al. |
| 5,686,090 | A | 11/1997 | Schilder et al. |
| 5,713,957 | A | 2/1998 | Steele et al. |
| 5,716,810 | A | 2/1998 | Mason et al. |
| 5,718,922 | A | 2/1998 | Herrero-Vanrell |
| 5,759,830 | A | 6/1998 | Vacanti et al. |
| 5,770,417 | A | 6/1998 | Vacanti et al. |
| 5,780,454 | A | 7/1998 | Adams et al. |
| 5,834,308 | A | 11/1998 | Peck et al. |
| 5,843,780 | A | 12/1998 | Thomson |
| 5,888,816 | A | 3/1999 | Coon et al. |
| 5,908,782 | A | 6/1999 | Marshank et al. |
| 5,914,262 | A | 6/1999 | MacMichael et al. |
| 5,942,435 | A | 8/1999 | Wheeler |
| 6,001,647 | A | 12/1999 | Peck et al. |
| 6,022,743 | A | 2/2000 | Naughton et al. |
| 6,087,113 | A | 6/2000 | Caplan et al. |
| 6,083,903 | A | 7/2000 | Adams et al. |
| 6,200,806 | B1 | 3/2001 | Thomson |
| 6,261,549 | B1 | 6/2001 | Fernandez et al. |
| 6,281,012 | B1 | 8/2001 | McIntosh et al. |
| 6,297,217 | B1 | 10/2001 | Adams et al. |
| 6,306,424 | B1 | 10/2001 | Vyakarnan et al. |
| 6,328,960 | B1 | 12/2001 | McIntosh et al. |
| 6,331,298 | B1 | 12/2001 | Ferguson et al. |

(Continued)

FOREIGN PATENT DOCUMENTS

| | | |
|---|---|---|
| CN | 1389565 A | 7/2002 |
| CN | 1602351 A | 3/2005 |

(Continued)

OTHER PUBLICATIONS

Thomson H. "Bioprocessing of embryonic stem cells for drug discovery."Trends Biotechnol. May 2007;25(5):224-30.*

(Continued)

*Primary Examiner* — Titilayo Moloye
(74) *Attorney, Agent, or Firm* — Klarquist Sparkman, LLP

(57) ABSTRACT

The present invention provides methods of preparing aggregated pluripotent stem cell clusters for differentiation.

31 Claims, 159 Drawing Sheets

(56) References Cited

U.S. PATENT DOCUMENTS

| | | |
|---|---|---|
| 6,333,029 B1 | 12/2001 | Vyakarnam et al. |
| 6,365,149 B2 | 2/2002 | Vyakarnam et al. |
| 6,413,773 B1 | 7/2002 | Ptasznik et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 | 9/2003 | Bryhan et al. |
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |
| 6,703,017 B1 | 3/2004 | Peck et al. |
| 6,713,446 B2 | 3/2004 | Gupta |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Misty et al. |
| 7,442,548 B2 | 10/2008 | Thomson et al. |
| 7,449,334 B2 | 11/2008 | Thomsom et al. |
| 7,510,873 B2 | 3/2009 | Mistry et al. |
| 7,510,876 B2 | 3/2009 | D'Amour et al. |
| 7,534,608 B2 | 5/2009 | Martinson et al. |
| 7,541,185 B2 | 6/2009 | D'Amour et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 8,859,286 B2 | 10/2014 | Agulnick |
| 8,987,471 B2 | 3/2015 | Takeuchi et al. |
| 9,528,090 B2 | 12/2016 | Rezania |
| 10,066,210 B2 | 9/2018 | Rezania |
| 2002/0072117 A1 | 7/2002 | Xu |
| 2003/0082155 A1 | 5/2003 | Habener |
| 2003/0138948 A1 | 7/2003 | Fisk et al. |
| 2003/0180268 A1 | 9/2003 | Atala |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0118148 A1 | 6/2005 | Stein et al. |
| 2005/0148070 A1 | 7/2005 | Thomson et al. |
| 2005/0158852 A1 | 7/2005 | D'Amour et al. |
| 2005/0187298 A1 | 8/2005 | Vasudevan et al. |
| 2005/0037488 A1 | 9/2005 | Mitalipova |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003313 A1 | 1/2006 | D'Amour et al. |
| 2006/0003446 A1 | 1/2006 | Keller |
| 2006/0030042 A1 | 2/2006 | Brivaniou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0122903 A1 | 5/2007 | Rezania et al. |
| 2007/0122905 A1 | 5/2007 | D'Amour et al. |
| 2007/0141702 A1 | 6/2007 | Revazova et al. |
| 2007/0154981 A1 | 7/2007 | Hori et al. |
| 2007/0155013 A1 | 7/2007 | Akaike et al. |
| 2007/0155661 A1 | 7/2007 | Kim |
| 2007/0254359 A1 | 11/2007 | Rezania et al. |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis et al. |
| 2008/0139662 A1 | 6/2008 | Brinkmann et al. |
| 2008/0159994 A1 | 7/2008 | Mantalaris et al. |
| 2008/0241107 A1 | 10/2008 | Copland, III et al. |
| 2008/0260700 A1 | 10/2008 | Accilli et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1 | 1/2009 | Martinson et al. |
| 2009/0029462 A1 | 1/2009 | Beardsley et al. |
| 2009/0029947 A1 | 1/2009 | Wallace et al. |
| 2009/0053182 A1 | 2/2009 | Ichim et al. |
| 2009/0093055 A1 | 4/2009 | Fisk et al. |
| 2009/0170198 A1 | 7/2009 | Rezania |
| 2009/0203141 A1 | 8/2009 | Lin et al. |
| 2009/0263896 A1 | 10/2009 | Kelly et al. |
| 2009/0269845 A1 | 10/2009 | Rezania et al. |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0009442 A1* | 1/2010 | Sasai .................... C12N 5/0603 435/366 |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1* | 4/2010 | Oh ....................... C12N 5/0062 435/176 |
| 2010/0112691 A1 | 5/2010 | Green et al. |
| 2010/0112693 A1 | 5/2010 | Rezania et al. |
| 2010/0255580 A1 | 10/2010 | Rezania |
| 2011/0014702 A1 | 1/2011 | Xu |
| 2011/0014703 A1 | 1/2011 | Xu et al. |
| 2011/0104805 A1 | 5/2011 | Fung et al. |
| 2011/0151560 A1 | 6/2011 | Xu |
| 2011/0151561 A1 | 6/2011 | Davis et al. |
| 2011/0229441 A1 | 9/2011 | Benchoua et al. |
| 2011/0280842 A1 | 11/2011 | Melton et al. |
| 2011/0281355 A1 | 11/2011 | Xu |
| 2012/0045830 A1 | 2/2012 | Green et al. |
| 2012/0052576 A1* | 3/2012 | Rezania ............... C12N 5/0678 435/377 |
| 2012/0101005 A1* | 4/2012 | Tatnell ............... G01N 33/5073 506/9 |
| 2012/0190111 A1 | 7/2012 | Davis et al. |
| 2012/0264209 A1 | 10/2012 | Odorico et al. |
| 2013/0115695 A1* | 5/2013 | Schulz ................ C12N 5/0606 435/366 |
| 2013/0189777 A1 | 7/2013 | Rezania |
| 2013/0224156 A1 | 8/2013 | Takahashi et al. |

(56) References Cited

U.S. PATENT DOCUMENTS

| | | |
|---|---|---|
| 2014/0186953 A1 | 7/2014 | Rezania |
| 2014/0228324 A1 | 8/2014 | Takeuchi et al. |

FOREIGN PATENT DOCUMENTS

| | | |
|---|---|---|
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 1391505 B1 | 2/2004 |
| EP | 0092302 B1 | 11/2006 |
| EP | 1873237 A1 | 1/2008 |
| EP | 2088190 A1 | 8/2009 |
| EP | 2479260 B1 | 6/2016 |
| GB | 2484873 B | 4/2014 |
| JP | 2005506074 A | 3/2005 |
| JP | 2005537803 A | 12/2005 |
| JP | 2006500003 A | 1/2006 |
| JP | 2008500809 A | 1/2008 |
| JP | 2009513143 A2 | 4/2009 |
| JP | 2013528356 A | 7/2013 |
| KR | 20080020098 A | 3/2008 |
| KR | 10-2012-0039025 A | 4/2012 |
| RU | 1767433 A1 | 10/1992 |
| RU | 2359030 C1 | 6/2009 |
| RU | 2359671 C2 | 6/2009 |
| WO | 199219759 A2 | 2/1992 |
| WO | 1996040172 A1 | 12/1996 |
| WO | 199830679 A1 | 7/1998 |
| WO | 199847892 A1 | 10/1998 |
| WO | 199920741 A1 | 4/1999 |
| WO | 200029549 A1 | 5/2000 |
| WO | 200123528 A1 | 4/2001 |
| WO | 200151616 A2 | 7/2001 |
| WO | 200181549 A3 | 11/2001 |
| WO | 200246183 A2 | 6/2002 |
| WO | 200246197 A1 | 6/2002 |
| WO | 2002086107 A2 | 10/2002 |
| WO | 02092756 A2 | 11/2002 |
| WO | 03033697 A1 | 4/2003 |
| WO | 2003026584 A2 | 4/2003 |
| WO | 2003029445 A1 | 4/2003 |
| WO | 2003042405 A2 | 5/2003 |
| WO | 200305049 A1 | 6/2003 |
| WO | 2003054169 A1 | 7/2003 |
| WO | 2003062405 A2 | 7/2003 |
| WO | 2003095452 A1 | 11/2003 |
| WO | 03103972 A1 | 12/2003 |
| WO | 2003102134 A2 | 12/2003 |
| WO | 2004011621 A2 | 2/2004 |
| WO | 2004016747 A2 | 2/2004 |
| WO | 2004044158 A2 | 5/2004 |
| WO | 2004050827 A2 | 6/2004 |
| WO | 2004055155 A2 | 7/2004 |
| WO | 2004073633 A1 | 9/2004 |
| WO | 2004087885 A2 | 10/2004 |
| WO | 2004090110 A2 | 10/2004 |
| WO | 2004067001 A1 | 12/2004 |
| WO | 2005001077 A2 | 1/2005 |
| WO | 2005014799 A1 | 2/2005 |
| WO | 2005017117 A2 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005080598 A1 | 9/2005 |
| WO | 2005086845 A2 | 9/2005 |
| WO | 2005097977 A2 | 10/2005 |
| WO | 2005097980 A2 | 10/2005 |
| WO | 2005116073 A3 | 12/2005 |
| WO | 2006016999 A1 | 2/2006 |
| WO | 2006020919 A2 | 2/2006 |
| WO | 2006088867 A2 | 2/2006 |
| WO | 2006026473 A1 | 3/2006 |
| WO | 2006029197 A1 | 3/2006 |
| WO | 2006036925 A1 | 4/2006 |
| WO | 2006080952 A2 | 8/2006 |
| WO | 2006083782 A2 | 8/2006 |
| WO | 2006094286 A2 | 9/2006 |
| WO | 2006100490 A1 | 9/2006 |
| WO | 2006108361 A1 | 10/2006 |
| WO | 2006113470 A2 | 10/2006 |
| WO | 2006114098 A2 | 11/2006 |
| WO | 2006126574 A1 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007026353 A2 | 3/2007 |
| WO | 2007027157 A1 | 3/2007 |
| WO | 2007030870 A1 | 3/2007 |
| WO | 2007047509 A1 | 4/2007 |
| WO | 2007051038 A2 | 5/2007 |
| WO | 2007069666 A1 | 6/2007 |
| WO | 2007082963 A1 | 7/2007 |
| WO | 2007101130 A2 | 9/2007 |
| WO | 2007103282 A1 | 9/2007 |
| WO | 2007127927 A2 | 11/2007 |
| WO | 2007136673 A1 | 11/2007 |
| WO | 2007139929 A2 | 12/2007 |
| WO | 2007143193 A1 | 12/2007 |
| WO | 2007149182 A2 | 12/2007 |
| WO | 2008004990 A2 | 1/2008 |
| WO | 2008013664 A1 | 1/2008 |
| WO | 2008015682 A2 | 2/2008 |
| WO | 2008035110 A1 | 3/2008 |
| WO | 2008036447 A2 | 3/2008 |
| WO | 2008048647 A1 | 4/2008 |
| WO | 2008048671 A1 | 4/2008 |
| WO | 2009096049 A1 | 5/2008 |
| WO | 2008086005 A1 | 7/2008 |
| WO | 2008094597 A2 | 8/2008 |
| WO | 2008102118 A1 | 8/2008 |
| WO | 2009012428 A1 | 1/2009 |
| WO | WO 2009/006399 A1 | 1/2009 |
| WO | 2009018453 A1 | 2/2009 |
| WO | 2009027644 A2 | 3/2009 |
| WO | WO2009048675 A1 | 4/2009 |
| WO | 2009061442 A1 | 5/2009 |
| WO | 2009070592 A1 | 6/2009 |
| WO | 2009096902 A1 | 8/2009 |
| WO | 2009101407 A2 | 8/2009 |
| WO | 2009105570 A2 | 8/2009 |
| WO | 2009110215 A1 | 9/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051213 A1 | 5/2010 |
| WO | 2010051223 A1 | 5/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | WO 2011/019092 A1 | 2/2011 |
| WO | WO 2011/058558 A2 | 5/2011 |
| WO | 2011067465 A1 | 6/2011 |
| WO | WO 2011/079017 A9 | 6/2011 |
| WO | WO 2011/081222 A1 | 7/2011 |
| WO | 2011096223 A1 | 8/2011 |
| WO | 2011108993 A1 | 9/2011 |
| WO | 2011123572 A1 | 10/2011 |
| WO | 2011139628 A1 | 11/2011 |

(56) References Cited

FOREIGN PATENT DOCUMENTS

| WO | WO 2011/158960 A1 | 12/2011 |
|---|---|---|
| WO | WO 2011/160066 A1 | 12/2011 |
| WO | 2012019122 A2 | 2/2012 |
| WO | WO 2012/030540 A2 | 3/2012 |
| WO | 2012117333 A1 | 9/2012 |
| WO | 2013055397 A1 | 4/2013 |
| WO | 2013055834 A2 | 4/2013 |
| WO | WO 2013/056072 A1 | 4/2013 |
| WO | 2013095953 A1 | 6/2013 |
| WO | 2013184888 A1 | 12/2013 |
| WO | 2014033322 A1 | 3/2014 |
| WO | 2014105546 A1 | 7/2014 |
| WO | 2014152321 A1 | 9/2014 |

OTHER PUBLICATIONS

Beers et al. "Passaging and colony expansion of human pluripotent stem cells by enzyme-free dissociation in chemically defined culture conditions." Nat Protoc. Nov. 2012;7(11):2029-40.*
Watanabe et al. "A ROCK inhibitor permits survival of dissociated human embryonic stem cells." Nat Biotechnol. Jun. 2007;25(6):681-6.*
Merten OW. "Advances in cell culture: anchorage dependence." Philos Trans R Soc Lond B Biol Sci. Feb. 5, 2015;370(1661):20140040.*
Amit, et al., Dynamic Suspension Culture for Scalable Expansion of Undifferentiated Human Pluripotent Stem Cells, Nature Protocols, Apr. 7, 2011, pp. 572-579, vol. 6, No. 5.
Eguizabal, et al., Embryonic Stem Cells/Induced Pluriptent Stem Complete Meiosis from Human Induced Pluripotent Stem Cells, Stem Cells, 2011, pp. 1186-1195, vol. 29.
Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.
Nie, et al., Scalable Passaging of Adherent Human Pluripotent Stem Cells, PLOS One, 2014, pp. 1-9, vol. 9, Issue 1.
Rowley, et al., Meeting Lot-Size Challenges of Manufacturing Adherent Cells for Therapy, Cell Therapies Manufacturing, 2012, pp. 16-22, vol. 10, No. 3.
Schulz, et al., A Scalable System for Production of Functional Pancreatic Progenitors from Human Embryonic Stem Cells, PLOS One, 2012, pp. 1-17, vol. 7, Issue 5.
Stacpoole, et al., Efficient Derivation of Neural Precursor Cells, Spinal Motor Neurons and Midbrain Dopaminergic Neurons from Human ES Cells at 3% Oxygen, Nat Protoc, 2012, pp. 1-26, vol. 6, Issue 8.
Vieira, et al., Modulation of Neuronal Stem Cell Differentiation by Hypoxia and Reactive Oxygen Species, Progress in Neurobiology, 2011, pp. 444-455, vol. 93.
Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.
Yang, et al., Evaluation of Humam MSCs Cell Cycle, Viability and Differentiation in Micromass Culture, Biorheology, 2006, p. 489-496, vol. 43 (Abstract Only).
Zuscik, et al., Regulation of Chondrogenesis and Chondrocyte Differentiation by Stress, J Clin Invest, 2008, pp. 429-438, vol. 118, Issue 2.
International Search Report and Written Opinion issued in International Application No. PCT/US2013/078191.
International Search Report issued in International Application No. PCT/US2014/042796.
International Search Report issued in International Application No. PCT/US2014/38993.
Abe, et al., Evidence That P13K, Rac, Rho, and Rho Kinase are Involved in Basic Fibroblast Growth Factor-Stimulated Fibroblast-Collagen Matrix Contraction, Journal of Cellular Biochemistry, 2007, pp. 1290-1299, vol. 102.

Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.
Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.
Ackermann, et al., Molecular Regulation of Pancreatic B-Cell Mass Development, Maintenance, and Expansion, Journal of Molecular Endocrinology, 2007, pp. 193-206, vol. 38.
Adams, J., Proteasome Inhibition in Cancer: Development of PS-341, Seminars in Oncology, 2001, pp. 613-619, vol. 28, No. 6.
Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.
Allegrucci, et al., Differences between Human Embryonic Stem Cell Lines, Human Reproduction Update, Aug. 26, 2006, pp. 1-18, Advance Access.
Almond, et al., The Proteasome: A Novel Target for Cancer Chemotherapy, Leukemia, 2002, pp. 433-443, vol. 16.
Amit et al., Human Feeder Layers for Human Embryonic Stem Cells, Biology of Reproduction, Jan. 22, 2003, 2150-2156, 68, No. 6, Society for the Study of Reproduction, Inc.
Amit, et al., Clonally Derived Human Embryonic Stem Cell Lines Maintain Pluripotency and Proliferative Potential for Prolonged Periods of Culture, Developmental Biology, 2000, pp. 271-278, vol. 227.
Amit, et al., Feeder Layer- and Serum-Free Culture of Human Embryonic Stem Cells, Biology of Reproduction, 2004, pp. 837-845, vol. 70.
Arai, et al., Purification of Recombinant Activin A Using the Second Follistatin Domain of Follistatin-Related Gene (FLRG), Protein Expression & Purification, 2006, pp. 78-82, vol. 49.
Armstrong, et al., The Role of P13K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.
Assady, et al., Insulin Production by Human Embryonic Stem Cells, Diabetes, 2001, pp. 1691-1697, vol. 50.
Baetge, Production of B-Cells from Human Embryonic Stem Cells, Diabetes, Obesity, Metabolism, 2008, pp. 186-194, vol. 10, Supplement 4.
Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.
Balsam, et al., Haematopoeitic Stem Cells Adopt Mature Haeatopoietic Fates in Ischaemic Myocardium, Nature, Apr. 8, 2004, pp. 668-673, Nature Publishing Group.
Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.
Barclay, et al., The Leucocyte Antigen Facts Book, The Leucocyte Antigen Facts Book, 1997, Textbook, 2[sup] edition, Academic Press.
Beltrami, et al., Adult Cardiac Stem Cells are Multipotent and Support Myocardial Regeneration, Cell, Sep. 19, 2003, pp. 763-776, vol. 114, Cell Press.
Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.
Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.
Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.

(56) References Cited

OTHER PUBLICATIONS

Bocian-Sobkowska, et al., Polyhormonal Aspect of the Endocrine Cells of the Human Fetal Pancreas, Histochem Cell Biol, 1999, pp. 147-153, vol. 112, Issue 2.

Bonner-Weir et al., In vitro cultivation of human islets from expanded ductal tissue, Proceedings of the National Academy of Sciences, Jul. 5, 2000, 7999-8004, 97-14, National Academy of Sciences.

Borowiak, et al., How to Make AB Cells, Current Opinion Cell Biology, 2009, pp. 727-732, vol. 21, Issue 6.

Borowitz, et al., Prognostic Significance of Fluorescence Intensity of Surface Marker . . . , Blood, Jun. 1, 1997, 3960-3966, 89-11, American Society of Hematology, Washington, D.C., US.

Braam, et al., Improved Genetic Manipulation of Human Embryonic Stem Cells, Nature Methods, May 2008, pp. 389-392, vol. 5, No. 5.

Brakenhoff et al., Development of a Human Interleukin-6 Receptor Antagonist, Journal of Biological Chemistry, Jan. 7, 1994, 86-93, 269-1, US.

Brambrink, et al., Sequential Expression of Pluripotency Markers During Direct Reprogramming of Mouse Somatic Cells, Cell Stem Cell, 2008, pp. 151-159, vol. 2.

Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.

Brevini, et al., No Shortcuts to Pig Embryonic Stem Cells, Theriogenology, 2010, pp. 544-550, vol. 74.

Bross, et al., Approval Summary for Bortezomib for Injection in the Treatment of Multiple Myeloma, Clinical Cancer Research, Jun. 15, 2004, pp. 3954-3964, vol. 10.

Brown, et al., Optimal Control of Blood Glucose: The Diabetic Patient or the Machine?, Science Translation Medicine, Apr. 14, 2010, pp. 1-5, vol. 2 Issue 27.

Burkard et al, Conditional Neuronal Nitric Oxide Synthase Overexpression Impairs Myocardial Contractility, Circulation Reseach, Jan. 18, 2007, pp. e32-e44, vol. 100.

Buzzard et al., Karyotype of human ES cells during extended culture, Nature Biotechnology, Apr. 1, 2004, 381-382, 22-4, Nature Publishing Group.

Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.

Castaing, et al., Blood Glucose Normalization Upon Transplantation of Human Embryonic Pancreas into Beta-Cell-Deficient SCID Mice, Diabetologica, 2001, pp. 2066-2076, vol. 44.

Chambers, et al., Functional Expression Cloning of Nanog, a Pluripotency Sustaining Factor in Embryonic Stem Cells, Cell, May 30, 2003, pp. 643-655, vol. 113.

Chapple, et al., Unfolding Retinal Dystrophies: A Role for Molecular Chaperones?, Trends in Molecluar Medicine, 2001, pp. 414-421, vol. 7, No. 9.

Chen, et al., A Small Molecule that Directs Differentiation of Human ESCs into the Pancreatic Lineage, Nature Chemical Biology, Apr. 11, 2009, pp. 258-265, vol. 5, No. 4.

Chen, et al., Chemically Defined Conditions for Human iPSC Derivation and Culture, Nature Methods, 2011, pp. 424-429, vol. 8, Issue 5.

Chen, et al., Differentiation of Embryonic Stem Cells Towards Pancreatic Progenitor Cells and their Transplantation into Strepozotocin-Induced Diabetic Mice, Cell Biology International, 2008, pp. 456-461, vol. 32.

Chen, et al., Differentiation of Rat Marrow Mesencymal Stem Cells in Pancreatic Islet Beta-Cells, World Journal of Gastroenterology, Oct. 15, 2004, pp. 3016-3020.

Cheon et al., Secretory Leukocyte Protease Inhibitor (SLPI) Regulate the Embryonic Differentiation During Periimplantation Stage, Biology of Reproduction, 2007, 64, 77, Society for the Study of Reproduction, Inc.

Cheon, et al., Defined Feeder-Free Culture System of Human Embryonic Stem Cells, Biol Reprod, 2005, 105.046870, DOI10/ 1095.

Chung, et al., Human Embryonic Stem Cell Lines Generated without Embryo Destruction, Cell Stem Cell, 2008, pp. 113-117, vol. 2.

Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.

Crane, et al., An Embryogenic Model to Explain Cytogenetic Inconsistencies Observed in Chorionic Villus Versus Fetal Tissue, Prenatal Diagnosis, 1988, pp. 119-129, vol. 8.

Cresta, et al., Phase I Study of Bortezomib with Weekly Paclitaxel in Patients with Advanced Solid Tumours, European Journal of Cancer, 2008, pp. 1829-1834, vol. 44.

Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.

D'Amour et al., Efficient differentiation of human embryonic stem cells to definitive endoderm, Nature Biotechnology, Oct. 28, 2005, 1-8, :W.1038/nbt1163, Nature Publishing Group.

D'Amour et al., Production of pancreatic hormone-expressing endocrine cells from human embryonic stem cells, Nature Biotechnology, Oct. 19, 2006, 1392-1401, 24-11, Nature Publishing Group, US.

Damy, et al., Increased Neuronal Nitric Oxide Synthase-Derived NO Production in the Failing Human Heart, Research Letters, Apr. 24, 2004, pp. 1365-1367, vol. 363.

David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.

De Coppi, et al., Isolation of Amniotic Stem Cell Lines with Potential for Therapy, Nature Biotechnology, 2007, pp. 100-106, vol. 25, No. 1.

De Rosa, 11-color, 13-parameter flow cytometry: Identification of . . . , Nature, Feb. 1, 2001, 245-248, 7-2, Nature Publishing Group, US.

Dekker, et al., Adhesion of Endothelial Cells and Adsorption of Serum Proteins on Gas Plasma-Treated Polytetrafluoroethylene, Biomaterials, 1991, pp. 130-138, vol. 12.

Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.

Donovan, et al., The End of the Beginning for Pluripotent Stem Cells, Nature, Nov. 2001, pp. 92-97, vol. 414.

Dorrell, et al., Editorial, Stem Cell Research, 2008, pp. 155-156, vol. 1.

Doyle, et al., Cell and Tissue Culture: Laboratory Procedures in Biotechnology, Cell and Tiossue Culture: Laboratory Procedures in Biotechnology, 1995, Textbook, Textbook, Wiley.

Draper, et al., Recurrent Gain of Chromosomes 17q and 12 in Cultured Human Embryonic Stem Cells, Nature Biotechnology, 2004, pp. 53-54, vol. 22, No. 1.

Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.

Dufour, et al., Development of an Ectopic Site for Islet Transplantation Using Biodegradable Scaffolds, Tissue Engineering, 2005, pp. 1323-1331 XP002699177, vol. 11, No. 9/10.

Dupont-Gillain, et al., Plasma-Oxidized Polystyrene: Wetting Properties and Surface Reconstruction, Langmuir, 2000, pp. 8194-8200, vol. 16.

Edlund, Pancreatic Organogenisis—Pancreatic Mechanisims and Implications for Therapy, Nature, Jul. 1, 2002, 524-532, 3, Nature Publishing Group, US.

Ellerstrom, et al., Derivation of a Xeno-Free Human Embryonic Stem Cell Line, Stem Cells, 2006, pp. 2170-2176, vol. 24.

(56) References Cited

OTHER PUBLICATIONS

Ellerstrom, et al., Facilitated Expansion of Human Embryonic Stem Cells by Single-Cell Enzymatic Dissociation, Stem Cells, 2007, pp. 1690-1696, vol. 25, No. 7.

Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.

Enzmann, et al., Enhanced Induction of RPE Lineage Markers in Pluripootent Neural Stem Cells Engrafted into the Adult Rat Subretinal Space, Ophthamology & Visual Science, Dec. 2003, pp. 5417-5422, vol. 44, No. 12, Association for Research in Vision and Ophthamology.

Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.

Ezashi, et al., Low 02 Tensions and the Prevention of Differentiation of hES Cells, Proceedings of the National Academy of Sciences of USA, Mar. 29, 2005, pp. 4783-4788, vol. 102, No. 13.

Fauza, Amniotic Fluid and Placental Stem Cells, Ballieres Best Practice and Research Clinical Obsterics and Gynaecology, 2004, pp. 877-891, vol. 18, No. 6.

Fidler et al., Selective Immunomodulation by the Antineoplastic Agent Mitoxantrone, Journal of Immunology, Jul. 15, 1986, 727-732, 137-2, American Society of Immunologists, US.

Fischer, et al., Residues in the C-Terminal Region of Activin a Determine Specificity for Follistatin and Type II Receptor Binding, Journal of Endocrinology, 2003, pp. 61-68, vol. 176, Society for Endocrinology.

Fok, et al., Shear-Controlled Single-Step Mouse Embryonic Stem Cell Expansion and Embryoid Body-Based Differentiation, Stem Cells, 2005, pp. 1333-1342, vol. 23.

Frandsen et al., Activin B mediated induction of Pdx1 in human embryonic stemcell derived embryoid bodies, Biochemical and Biophysical Research Communications, Aug. 15, 2007, 568-574, 362, Elsevier Inc.

Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.

Fung, et al., The Effect of Medical Therapy and Islet Cell Transplantation on Diabetic Nephropathy: An Interim Report, Transplantation, Jul. 15, 2007, pp. 17-22, vol. 84, No. 1.

Gadue, et al., Wnt and TGB-B Signaling Are Required for the Induction of an in vitro Model of Primitive Streak Formation Using Embryonic Stem Cells, Proceedings of the National Academy of Sciences, Nov. 7, 2006, 16806-16811, 103-45, National Academy of Sciences, US.

Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.

Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.

Gershengorn et al., Epithelial-to-Mesenchymal Transition Generates Proliferative Human Islet Precursor Cells, Science, Dec. 24, 2004, 2261-2264, 306, US.

Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.

Ginis, et al., Differences Between Human and Mouse Embryonic Stem Cells, Developmental Biology, 2004, pp. 360-380, vol. 269.

Gittes, Developmental Biology of the Pancreas: A comprehensive Review, Developmental Biology, 2009, pp. 4-35, vol. 326, No. 1.

Gosden, et al., Amniotic Fluid Cell Types and Culture, British Medical Bulletin, 1983, pp. 348-354, vol. 39, No. 4.

Graham, et al., Characteristics of a Human Cell Line Transformed by DNA from Human Adenovirus Type 5, Journal General Virology, 1977, pp. 59-72, vol. 36.

Guo, et al., Stem Cells to Pancreatic B-Cells: New Sources for Diabetes Cell Therapy, Endocrine Reviews, May 2009, pp. 214-227, vol. 30, No. 3, The Endocrine Society.

Hadley, et al., Extracellular Matrix Regulates Sertoli Cell Differentiation, Testicular Cord Formation, and Germ Cell Development In Vitro, The Journal of Cell Biology, Oct. 1985, 1511-1522, 101, Rockefeller University Press.

Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.

Harb, et al., The Rho-Rock-Myosin Signaling Axis Determines Cell-Cell Integrity of Self-Renewing Pluripotent Stem Cells, Plos One, 2008, Article e3001, XP002530386, vol. 3, Issue 8.

Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.

Hasegawa, et al., A Method for the Selection of Human Embryonic Stem Cell Sublines with High Replating Efficiency After Single-Cell Dissociation, Stem Cells, 2006, pp. 2649-2660, vol. 24.

Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.

Heinis, et al., HIF1a and Pancreatic Beta-Cell Development, The FASEB Journal, 2012, pp. 2734-2742, vol. 26.

Heinis, et al., Oxygen Tension Regulates Pancreatic Beta-Cell Differentiation Through Hypoxia-Inducible Factor 1x, Diabetes, 2010, pp. 662-669, vol. 59.

Heit, et al., Embryonic Stem Cells and Islet Replacement in Diabetes Mellitus, Pediatric Diabetes, 2004, pp. 5-15, vol. 5.

Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.

Henderson, et al., Preimplantation Human Embryos and Embryonic Stem Cells Show Comparable Expression of Stage-Specific Embryonic Antigens, Stem Cells, 2002, pp. 329-337, vol. 20.

Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, 33-37, 47, Portland Press Ltd., GB.

Heremans, et al., Recapitulation of Embryonic Neuroendocrine Differentiation in Adult Human Pancreatic Duct Cells Expressing Neurogenin 3, The Journal of Cell Biology, 2002, pp. 303-311, vol. 159.

Herrera, Adult-Insulin- and Glucagon-Producing Cells Differentiate from Two Independent Cell Lineages, Development, 2000, pp. 2317-2322 XP001004766, vol. 127, No. 11.

Herzenberg, et al., Fluorescence-activated Cell Sorting, Scientific American, 1976, 108-117, 234, Scientific American, US.

Hess, et al., Bone Marrow-Derived Stem Cells Initiate Pancreatic Regeneration, Nature Biotechnology, Jul. 2003, pp. 763-770, vol. 21, No. 7.

Ho, et al., Animal Cell Bioreactors, Animal Cell Bioreactors, 1991, 1-512, Hardcover, Butterworth-Heinemann.

Hoehn, et al., Morphological and Biochemical Heterogeneity of Amniotic Fluid Cells in Culture, Methods in Cell Biology, 1982, pp. 11-34, vol. 26, Academic Press, Inc.

Hoffman, et al., Characterization and Culture of Human Embryonic Stem Cells, Nature Biotechnology, 2005, pp. 699-708, vol. 23, No. 6.

Hori, et al., Growth inhibitors promote differentiation of insulin-producing tissue from embryonic stem cells, Proceedings of the National Academy of Sciences, Dec. 10, 2002, 16105-16110, 99-25, National Academy of Sciences.

Hosoya, et al., Induction of Differentiation of Undifferentiated Cells into Pancreatic Beta-Cells in Vertebrates, Int. J. Dev. Biol., 2012, pp. 313-323, vol. 56.

Hussain, et al., Stem-Cell Therapy for Diabetes Mellitus, Lancet, 2004, pp. 203-205, vol. 364.

(56) References Cited

OTHER PUBLICATIONS

Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.
Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010.96.
Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.
Int' Anker, et al., Amniotic Fluid as a Novel Source of Mesenchymal Stem Cells for Therapeutic Transplantation, Blood, Aug. 15, 2003, pp. 1548-1549, vol. 102, No. 4.
Inzunza, et al., Derivation of Human Embryonic Stem Cell Lines in Serum Replacement Medium Using Postnatal Human Fibroblasts as Feeder Cells, Stem Cells, 2005, 544-549, 23, AlphaMed Press.
Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.
Jeon, et al., Endocrine Cell Clustering During Human Pancreas Development, J Histochem Cytochem, 2009, pp. 811-824, vol. 57, Issue 9.
Jiang, et al., Generation of Insulin-Producing Islet-Like Clusters from Human Embryonic Stem Cells, Stem Cells, 2007, pp. 1940-1953, vol. 25, Issue 8.
Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.
Kahan, Pancreatic Precursors and Differentiated Islet Cell Types from Murine Embryonic Stem Cells, Diabetes, Aug. 2003, pp. 2016-2042, vol. 52.
Kelly, et al., Cell-Surface Markers for the Isolation of Pancreatic Cell Types Derived from Human Embryonic Stem Cells, Nature Biotechnology, 2011, pp. 750-756, vol. 29, Issue 8.
Kicic, et al., Differentiation of Marrow Stromal Cells into Photoreceptors in the Rat Eye, The Journal of Neuroscience, Aug. 27, 2003, pp. 7742-7749, vol. 23, Issue 21.
Kingsley, The TGF-B Superfamily: New Members, New Receptors, and New Genetic Tests of Function in Different Organisms, Genes & Development, 1994, pp. 133-146, XP009011502, vol. 8, Cold Spring Harbor Laboratory Press.
Kinkel, et al., Cyp26 Enzymes Function in Endoderm to Regulate Pancreatic Field Size, PNAS, May 12, 2009, pp. 7864-7869, vol. 106, No. 19.
Kleinman et al., Basement Membrane Complexes with Biological Activity, Biochemistry, 1986, 312-318, 25, American Chemical Society.
Klimanskaya, et al., Human Embryonic Stem Cells Derived without Feeder Cells, Lancet, May 2005, pp. 1636-1641, vol. 365, No. 9471.
Koblas, et al., Differentiation of CD133-Positive Pancreatic Cells Into Insulin-Producing Islet-Like Cell Clusters, Transplantation Proceedings, 2008, pp. 415-418, vol. 40.
Kohen, et al., Characterization of Matrigel Interfaces During Defined Human Embryonic Stem Cell Culture, Biointerphases, Dec. 2009, pp. 6979.
Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.
Konstantinova et al., EphA-Ephrin-A-Mediated Beta Cell Communication Regulates Insulin Secretion from Pancreatic Islets, Cell, Apr. 20, 2007, pp. 359-370, vol. 129.
Koyangi et al., Inhibitio not the Rho/ROCK Pathway Reduces Apoptosis During Transplantatation of Embryonic Stem Cell-Derived Neural Precursors, Journal of Neurosciene Research, Sep. 7, 2007, 270-280, 86, Wiley-Liss, Inc.
Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.
Krapcho et al., Synthesis and Antineoplastic Evaluations of 5,8-Bis[(aminoalkyl)amino]-1-azaanthracene-9,10-diones, Journal of Medical Chemistry, 1985, 1124-1126, 28, American Chemical Society.
Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.
Kron, et al., Expression of Human Activin C Protein in Insect Larvae Infected with a Recombinant Baculovirus, Journal of Virological Methods, 1998, pp. 9-14, vol. 72.
Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.
Krutzik, et al., Coordinate Analysis of Murine Immune Cell Surface Markers and Intracellular Phosphoproteins by Flow Cytometry, Journal of Immunology, May 30, 2005, 2357-2365, 175, American Association of Immunologists, Inc., US.
Ku et al., Committing Embryonic Stem Cells to Early Endocrine Pancreas In Vitro, Stem Cells, 2004, 1205-1217, 22, AlphaMed Press.
Kubo et al., Development of definitive endoderm from embryonic stem cells in culture, Development, 2004, 1651-1662, 131, The Company of Biologists.
Lanza, et al., Characteristics and Characterization of Human Pluripotent Stem Cells, Stem Cell Anthology, 2010, pp. 141, 142, 144 and 146, 1st Edition.
Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.
Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.
Lavon et al., The Effect of Overexpression of Pdx1 and Foxa2 on the Differentiation of Human Embryonic Stem Cells into Pancreatic Cells, Stem Cells, 2006, 1923-1930, 24, Alpha Med Press, IL.
Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.
Lee et al., Establishment and Maintenance of Human Embryonic Stem Cell Lines on Human Feeder Cells Derived from Uterine Endometrium under Serum-Free Condition, Biology of Reproduction, Aug. 18, 2004, 42-49, 72.
Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.
Lee, et al., Protein Kinase A- and C-Induced Insulin Release from Ca2+-Insensitive Pools, Cellular Signalling, 2003, pp. 529-537, vol. 15.
Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.
Leon-Quinto, et al., In Vitro Directed Differentiation of Mouse Embryonic Stem Cells into Insulin-Producing Cells, Diabetologia, 2004, pp. 1442-1451 XP002699175, vol. 47, No. 8.
Levenstein et al., Basic Fibroblast Growth Factor Support of Human Embryonic Stem Cell Self-Renewal, Stem Cells, Nov. 10, 2005, 568-574, 24, AlphaMed Press.
Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.
Li, et al., Pluripotency Can be Rapidly and Efficiently Induced in Human Amniotic Fluid-Derived Cells, Human Molecular Genetics, 2009, pp. 4340-4349, vol. 18, No. 22.

(56) References Cited

OTHER PUBLICATIONS

Lilja et al., Cyclin-dependent Kinase 5 Promotes Insulin Exocytosis, Journal of Biological Chemistry, Jul. 6, 2001, 34199-34205, 36-7, JBC Papers in Press.

Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.

Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.

Loh, et al., Genomic Approaches to Deconstruct Puripotency, Annu Rev Genomics Hum Genet, 2011, pp. 165-185, vol. 12.

Ludwig, et al., Derivation of Human Embryonic Stem Cells in Defined Conditions, Nature Biotechnology, Feb. 2006, pp. 185-187, vol. 24 No. 2.

Lumelsky, et al., Differentiation of Embryonic Stem Cells to Insulin-Secreting Structures Similar to Pancreatic Islets, Science, 2001, 1389-1394, 292, HighWire Press.

Lund, et al., Cell Transplantation as a Treatment for Retinal Disease, Progress in Retinal and Eye Research, 2001, pp. 415-449, vol. 20, No. 4, Elsevier Science Ltd.

Lund, et al., Retinal Transplantation: Progress and Problems in Clinical Application, Journal of Leukocyte Biology, Aug. 2003, pp. 151-160, vol. 74.

Lyttle, et al., Transcription Factor Expression in the Developing Human Fetal Endocrine Pancreas, Diabetologica, 2008, pp. 1169-1180, vol. 51, Spring-Verlag.

MacFarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.

Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.

Mao, et al., The Reversal of Hyperglycaemia in Diabetic Mice Using PLGA Scaffolds Seeded with Islet-like Cells Derived from Human Embyonica Stem Cells, Biomaterials, 2009, pp. 1706-1714, vol. 30.

Marshall, et al., Early Micro- and Macro-Angiopathy in the Streptozotocin, Research in Experimental Medicine, 1980, pp. 145-158, vol. 177, Springer-Verlag.

Marshall, et al., Isolation and Maintenance of Primate Embryonic Stem Cells, Methods in Molecular Biology, 2001, pp. 11-18, vol. 158.

Martin, et al., Bioreactors for Tissue Mass Culture: Design, Characterization, and Recent Advances, Biomaterials, Jul. 14, 2005, pp. 7481-7503, vol. 26.

Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.

McKiernan, et al., Directed Differentiation of Mouse Embryonic Stem Cells into Pancreatic-Like or Neuronal- and Glial-Like Phenotypes, Tissue Engineering, 2007, pp. 2419-2430, vol. 13, No. 10.

McLean et al., Activin A Efficiently Specifies Definitive Endoderm from Human Embryonic Stem Cells Only When Phosphatidylinositol 3-Kinase Signaling Is Suppressed, Stem Cells, 2007, 29-38, 25, AlphaMed Press.

McLin, et al., Repression of WNT/(szligbeta)-6atenin Signaling in the Anterior Endoderm is Essential for Liver and Pancreas Development, Development, 2007, pp. 2207-2217, vol. 134, Issue 12.

Meijer, et al., Pharmacological Inhibitors of Glycogen Synthase Kinase 3, Trends in Pharmacological Sciences, Sep. 2004, pp. 471-480, vol. 25, No. 9.

Micallef et al., Retinoic Acid Induces Pdx1-Positive Endoderm in Differentiating Mouse Embryonic Stem Cells, Diabetes, Feb. 2005, 301-305, 54, American Diabetes Association.

Miller, et al., The Pig as a Model for Human Nutrition, Annual Review of Nutrition, 1987, pp. 361-382, vol. 7, Annual Reviews Inc.

Milunsky, et al., Genetic Disorders and the Fetus: Diagnosis Prevention and Treatment, Pediatric and Developmental Pathology, 2011, pp. 84, vol. 14, Society for Pediatric Pathology.

Mitalipova, et al., Preserving the Genetic Integrity of Human Embyonic Stem Cells, Nature Biotechnology, 2005, pp. 19-20, vol. 23, No. 1.

Mitsui, et al., The Homeoprotein Nanog is Required for Maintenance of Pluripotency in Mouse Epiblast and ES Cells, Cell, May 30, 2003, pp. 631-642, vol. 113, Cell Press.

Miyamoto et al., Human Placenta Feeder Layers Support Undifferentiated Growth of Primate Embryonic Stem Cells, Stem Cells, 2004, 433-440, 22, AlphaMed Press.

Miyazaki et al., Regulated Expression of pdx-1 Promotes In Vitro Differentiation of Insulin-Producing Cells From Embryonic Stem Cells, Diabetes, Apr. 2004, 1030-1037, 53, American Diabetes Association.

Moore, et al., The Corneal Epithelial Stem Cell, DNA and Cell Biology, 2002, pp. 443-451, vol. 21, No. 5/6.

Moran, et al., Bidirectional-Barbed Sutured Knotless Running Anastomosis v Classic van Velthoven in a Model System, Journal of Endourology, 2007, pp. 1175-1177, vol. 21, No. 10.

Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.

Movassat, et al., Keratinocyte Growth Factor and Beta-Cell Differentiation in Human Fetal Pancreatic Endocrine Precursor Cells, Diabetologia, 2003, pp. 822-829, vol. 46.

Muchamuel, et al., Preclinical Pharmacology and in Vitro Characterization of PR-047, An Oral Inhibitor of the 20s Proteasome, Blood, Nov. 16, 2008, p. 1257, vol. 112, No. 11.

Murtha, et al., Evaluation of a Novel Technique for Wound Closure Using a Barbed Suture, Cosmetic, Aug. 2, 2005, pp. 1769-1780, vol. 117, No. 6.

Nakagawa, et al., Generation of Induced Pluripotent Stem Cells without Myc from Mouse and Human Fibroblasts, Jan. 2008, pp. 101-106, vol. 26, No. 1.

Nakamura, et al., Ocular Surface Reconstruction Using Cultivated Mucosal Epithelial Stem Cells, Cornea, Oct. 2003, S75-S80, vol. 22, Supplement 1.

Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.

Nicholas et al., A Method for Single-Cell Sorting and Expansion of Genetically modified Human Embryonic Stem Cells, Stem Cells and Development, 2007, 109-117, 16, Mary Ann Liebert, Inc.

Nishimura, et al., Expression of MafA in Pancreatic Progenitors is Detrimental for Pancreatic Development, Developmental Biology, 2009, pp. 108-120, vol. 333.

Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.

Odom, et al., Control of Pancreas and Liver Gene Expression by HNF Transcription Factors, Science, 2004, pp. 1378-1381, vol. 303, No. 5662.

Oh, et al., Human Embryonic Stem Cells: Technological Challenges Towards Therapy, Clinical and Experimental Pharmacology and Physiology, 2006, pp. 489-495, vol. 33.

Okita, et al., Generation of Germline-Competent Induced Pluripotent Stem Cells, Nature, Jul. 19, 2007, pp. 313-317, vol. 448.

Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.

Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.

(56) References Cited

OTHER PUBLICATIONS

Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.
Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.
Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.
Pancreatic Endoderm, http://www.mdsystems.com/molecule_group.aspx?g=801&r, 1 page web printout (dated May 31, 2013).
Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.
Pangas, et al., Production and Purification of Recombinant Human Inhibin and Activin, Journal of Endocrinology, 2002, pp. 199-210, vol. 172.
Pardo, et al., Coming CellBIND Surface: An Improved Surface for Enhanced Cell Attachment, Corning Technical Report, 2005, 8 page report, XP002530385.
Paris, et al., Equine Embryos and Embryonic Stem Cells: Defining Reliable Markers of Pluripotency, Theriogeneology, 2010, pp. 516-524, vol. 74.
Peerani, et al., Niche-Mediated Control of Human Embryonic Stem Cell Self-Renewal and Differentiation, The EMBO Journal, 2007, pp. 4744-4755, vol. 26.
Phillips, et al., Attachment and Growth of Human Embryonic Stem Cells on Microcarriers, Journal of Biotechnology, 2008, pp. 24-32, vol. 138.
Phillips, et al., Directed Differentiation of Human Embryonic Stem Cells into the Pancreatic Endocrine Lineage, Stem Cells and Development, 2007, pp. 561-578 XP009090586, vol. 16, No. 4.
Pouton, et al., Embryonic Stem Cells as a Source of Models for Drug Discovery, Nature Reviews Drug Discovery, Aug. 2007, pp. 1474-1776, vol. 6, No. 8.
Prichard, et al., Adult Adipose Derived Stem Cell Attachment to Biomaterials, Biomaterials, 2006, pp. 936-946, vol. 28, No. 6.
Prowse, et al., A Proteome Analysis of Conditioned Media from Human Neonatal Fibroblasts Used in the Maintenance of Human Embryonic Stem Cells, Proteomics, 2005, pp. 978-989, vol. 5.
Prusa, et al., Oct-4-Expressing Cells in Human Amniotic Fluid: a New Source for Stem Cell Research?, Human Reproduction, 2003, pp. 1489-1493, vol. 18, No. 7.
Ptasznik, et al., Phosphatidylinositol 3-Kinase Is a Negative Regulator of Cellular Differentiation, The Journal of Cell Biology, 1997, pp. 1127-1136, vol. 137, No. 5.
R&D Systems, Embryonic & Induced Pluripotent Stem Cell Transcription Factors, http://www.mdsystems.com/molecule_group.aspx?r=1&g-3041, 2 page web printout dated May 31, 2013.
Rajagopal, et al., Insulin Staining of ES Cell Progeny from Insulin Uptake, Science, Jan. 17, 2003, pp. 363, vol. 299.
Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.
Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.
Rebollar, et al., Proliferation of Aligned Mammalian Cells on Laser-Nanostructured Polystyrene, Biomaterials, 2008, pp. 1796-1806, vol. 29.
Reisner, Growing Organs for Transplantation form Embryonic Precursor Tissues, Immunol. Res., 2007, pp. 261-273, vol. 38.
Reubinoff et al., Embryonic stem cell lines from human blastocysts: somatic differentiation in vitro, Nature Biotech, Apr. 18, 2000, 399-404, 18, Nature America Inc.

Rezania, et al., Maturation of Human Embryonic Stem Cell-Derived Pancreatic Progenitors into Functional Islets Capable of Treating Pre-Existing Diabetes in Mice, Diabetes, 2012, pp. 2016-2029, vol. 61.
Rezania, Production of Functional Glucagon-Secreting-Cells from Human Embryonic Stem Cells, Diabetes, 2011, pp. 239-247, vol. 60, Issue 1.
Richards et al., Comparative Evaluation of Various Human Feeders for Prolonged Undifferentiated Growth of Human Embryonic Stem Cells, Stem Cells, 2003, 546-556, 21, AlphaMed Publlishing.
Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.
Ricordi et al., Automated Method for Isolation of Human Pancreatic Islets, Diabetes, Apr. 1988, 413-420, 37, American Diabetes Association.
Ryan, et al., Clinical Outcomes and Insulin Secretion After Islet Transplantation with the Edmonton Protocol, Diabetes, Apr. 2001, pp. 710-719, vol. 50.
Sakaguchi, et al., Integration of Adult mesenchymal Stem Cells in the CNS, Society for Neuroscience Abstract Viewer and Itineray Planner, 2002, XP002519394, Program 237.18.
Sander, et al., Homeobox Gene Nkk6.1 Lies Downstream of Nkx2.2 in the Major Pathway of Betta-Cell Formation in the Pancreats, Development, 2000, pp. 5533-5540, vol. 127.
Sato, et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.
Sato, et al., Manipulation of Self-Renewal in Human Embryonic Stem Cells Through a Novel Pharmacological GSK-3 Inhibitor, Methods in Molecular Biology, 2006, pp. 115-128, vol. 331.
Sato, et al., Molecular Signature of Human Embryonic Stem Cells and its Comparison with the Mouse, Developmental Biology, Apr. 23, 2003, pp. 404-413, vol. 260.
Savino et al., Generation of Interleukin-6 Receptor Antagonists by Molecular-Modeling Guided Mutagenesis of Residues Important for gp130 Activation, EMBO Journal, 1994, 1357-1367, 13-6, IT.
Schisler, et al., The Nkx6.1 Homeodomain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, XP002699176, vol. 102, No. 20.
Schraermeyer, et al., Subretinally Transplanted Embryonic Stem Cells Rescue Photoreceptor Cells From Degeneration in the RCS Rats, Cell Transplantation, 2001, pp. 673-680, vol. 10.
Schroeder, et al., Differentiation of Mouse Embryonic Stem Cells to Insulin-Producing Cells, Nature Protocols, 2005, pp. 495-507, vol. 1, No. 2.
Schuldiner, et al., Induced Neuronal Differentiation of Human Embryonic Stem Cells, Brain Research, 2001, pp. 201-205, vol. 913.
Scullica, et al., Diagnosis and Classification of Macular Degenerations: an Approach Based on Retinal Function Testing, Documenta Ophthalmologica, 2001, pp. 237-250, vol. 102.
Seaberg et al., Clonal identification of multipotent precursors from adult~mouse pancreas that generate neural and pancreatic lineages, Nature Biotechnology, Sep. 2004, 1115-1124, 22, Nature Publishing Group.
Segev, et al., Differentiation of Human Embryonic Stem Cells into Insulin-Producing Clusters, Stem Cells, Jan. 1, 2004, pp. 265-274.
Serafimidis, et al., Novel Effectors of Directed and Ngn3-Mediated Differentiation of Mouse Embryonic Stem Cells into Endocrine Pancreas Progenitors, Stem Cells, 2008, pp. 3-16, vol. 26.
Shackleton, et al., Generation of a Functional Mammary Gland from a Single Stem Cell, Nature, Jan. 5, 2006, pp. 84-88, XP002567665, vol. 439.
Shamblott et al., Derivation of pluripotent stem cells from cultured human primordial germ cells, Developmental Biology, Nov. 1998, 13726-13731, 95, National Academy of Sciences.
Shapiro, et al., Islet Transplantation in Seven Patients with Type 1 Diabetes Mellitus Using a Glucocorticoid-Free Immunosuppressive

(56) References Cited

OTHER PUBLICATIONS

Regimen, The New England Journal of Medicine, Jul. 27, 2000, pp. 230-238, vol. 343, No. 4, The Massachusetts Medical Society.
Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.
Sherwood, et al., Transcriptional Dynamics of Endodermal Organ Formation, Developmental Dynamics, 2009, pp. 29-42, vol. 238, Issue 1.
Shi et al., Inducing Embryonic Stem Cells to Differentiate into Pancreatic β Cells by a Novel Three-Step Approach with Activin A and All-Trans Retinoic Acid, Stem Cells, 2005, 656-662, 23, AlphaMed Press.
Shim, et al., Directed Differentiation of Human Embryonic Stem Cells Towards a Pancreatic Cell Fate, Diabetologia, 2007, pp. 1228-1238, vol. 50.
Schindler et al., A synthetic nanofibrillar matrix promotes in vivo-like organization and morphogenesis for cells in culture, Biomaterials, Apr. 18, 2005, 5624-5631, 26, Elsevier.
Shiraki et al., TGF-B Signaling Potentiates Differentiation of Embryonic Stem Cells to Pdx-1 Expressing Endodermal Cells, Genes to Cells, 2005, 503-516, 10, Blackwell Publishing Limited.
Shiraki, et al., Guided Differentiation of Embryonic Stem Cells into Pdx1-Expressing Regional-Specific Definitive Endoderm, Stem Cells, 2008, pp. 874-885, vol. 26.
Sidhu et al., Derivation of Three Clones from Human Embryonic Stem Cell Lines by FACS Sorting and Their Characterization, Stem Cells and Development, 2006, 61-69, 15, Mary Ann Liebert, Inc.
Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.
Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.
Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, 749-756, 379, Biochemical Society, GB.
Smith et al., Anti-Interleukin-6 Monocolnal Antibody Induces Regression of Human Prostate Cancer Xenografts in Nude Mice, The Prostate, Mar. 2, 2001, 47-53, 48, Wiley-Liss, Inc.
Soria, et al., Insulin-Secreting Cells Derived From Embryonic Stem Cells Normalize Glycemia in Streptozotocin-Diabetic Mice, Diabetes, 2000, pp. 157-162, vol. 49, No. 2.
Spence, et al., Translation Embryology: Using Embryonic Principles to Generate Pancreatic Endocrine Cells from Embryonic Stem Cells, Developmental Dynamics, 2007, pp. 3218-3227, vol. 236.
Stadtfeld, et al., Defining Molecular Cornerstones During Fibroblast to iPS Cell Reprogramming in Mouse, Cell Stem Cell, Mar. 2008, pp. 230-240, vol. 2.
Stafford, et al., Retinoic Acid Signaling is Required for a Critical Early Step in Zebrafish Pancreatic Development, Current Biology, 2002, pp. 1215-1220, vol. 12, Issue 14.
Stojkovic et al., An Autogeneic Feeder Cell System That Efficiently Supports Growth of Undifferentiated Human Embryonic Stem Cells, Stem Cells, 2005, 306-314, 23, AlphaMed Press.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.
Suh, et al., Characterization of His-X3-His Sites in a-Helices of Synthetic Metal-Binding Bovine Somatotropin, Protein Engineering, 1991, pp. 301-305, vol. 4, No. 3.
Sulzbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.
Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.
Takahashi, et al., Homogenous Seeding of Mesenchymal Stem Cells into Nonwoven Fabric for Tissue Engineering, Tissue Engineering, 2003, pp. 931-938, vol. 9, No. 5.
Takahashi, et al., Induction of Pluripotent Stem Cells from Adult Human Fibroblasts by Defined Factors, Cell, 2007, pp. 861-872, vol. 131.
Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.
Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.
Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.
Teare, et al., Cellular Attachment to Ultraviolet Ozone Modified Polystyrene Surfaces, Langmuir, 2000, pp. 2818-2824, vol. 16.
Thomson et al., Embryonic Stem Cell Lines Derived from Human Blastocysts, Science, Nov. 6, 1998, 1145-1147, 282, HighWire Press.
Thomson et al., Isolation of a primate embryonic stem cell line, Developmental Biology, Aug. 1995, 7844-7848, 92, Proc. Natl. Acad. Sci, US.
Thomson et al., Primate Embryonic Stem Cells, Current Topics in Developmental Biology, 1998, 133-154, 38, Academic Press, US.
Tomita, et al., Bone Marrow-Derived Stem Cells Can Differentiate into Retinal Cells in Injured Rat Retina, Stem Cells, 2002, pp. 279-283, vol. 20.
Totonchi, et al., Feeder- and Serum-Free Establishment and Expansion of Human Induced Pluripotent Stem Cells, Int. J. Dev. Biol., 2010, pp. 8770886, vol. 54.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tulachan et al., TGF-β isoform signaling regulates secondary transition and mesenchymal-induced endocrine in the embryonic mouse pancreas, Developmental Biology, 2007, 508-521, 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, 28858-28864, 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.
Unknown, MeSH Descriptor Data, National Library of Medicine—Medical Subject Headings, Feb. 26, 1992, XP002553615.
Unknown, Preserve the Stability of Your Stem Cells, Stem Cells, 2006, Internet Citation, XP002496166.
Vacanti, et al., Selective Cell Transplantation Using Bioabsorbable Artificial Polymers as Matrices, Journal of Pediatric Surgery, Jan. 1988, 3-9, 23-1.
Valet, et al., Pretherapeutic Identification of High-Risk Acute Myeloid Leukemia (AML) Patients from . . . , Clinical Cytometry, Feb. 17, 2003, 4-10, 53B, Wiley-Liss, Inc., US.
Vallier, et al., Activin/Nodal and FGF Pathways Cooperate to Maintain Pluripotency of Human Embryonic Stem Cells, Journal of Cell Sciences, 2005, pp. 4495-4509, vol. 118.

(56) References Cited

OTHER PUBLICATIONS

Van Der Greef et al., Rescuing drug discovery: in vivo systems pathology and systems pharmacology, Nature, Dec. 1, 2005, 961-967, 4-1, Nature Reviews, US.
Van Der Windt, et al., The Choice of Anatomical Site for Islet Transplantation, Cell Transplantation, 2008, pp. 1005-1014, vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., Vacuum Cell Seeding: a New Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, 138-142, 480, Elsevier.
Verfaillie, et al., Stem Cells: Hype and Reality, Hematology, 2002, pp. 369-391.
Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wang et al., Derivation and Growing Human Embryonic Stem Cells on Feeders Derived from Themselves, Stem Cells, 2005, 1221-1227, 23, AlphaMed Press.
Wang et al., Relationship of Chemical Structures of Anthraquinones with their Effects on the Suppression of Immune Responses, International Journal of Immunopharmacology, 1987, 733-739, 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, 1104-1108, 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
Wiles et al., Embryonic Stem Cell Development in a Chemically Defined Medium, Experimental Cell Research, 1999, 241-248, 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
Wong, et al., Directed Differentiation of Human Pluripotent Stem Cells into Mature Airway Epithelia Expressing Functional CFTR Protein, Nature Biotechnology, 2012, pp. 876-884, vol. 30, No. 9. XP002553616_1989, RecName: Full=lnhibin beta B Chain; AltName: Full=Activin beta-B chain; Flags; Precurso, Database UniProt [Online], Jul. 1, 1989, Database Accession No. P09529, EBI Accession No. Uniprot: P09529.
Xu et al., Immortalized Fibroblast-Like Cells Derived from Human Embryonic Stem Cells Support Undifferentiated Cell Growth, Stem Cells, 2004, 972-980, 22, AlphaMed Press.
Xu, et al., Basic FGF and Suppression of BMP Signalling Sustain Undifferentiated Proliferation of Human ES Cells, Nature Methods, 2005, pp. 185-189, vol. 2, Issue 3.

Xu, et al., Feeder-free Growth of Undifferentiated Human Embryonic Stem Cells, Nature Biotechnology, 2001, pp. 971-974, vol. 19.
Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yoneda, et al., The Rho Kinases I and II Regulate Different Aspects of Myosin II Acitivity, The Journal of Cell Biology, 2005, pp. 443-445, vol. 170, No. 3.
Young, et al., Three-Dimensional Culture of Human Uterine Smooth Muscle Nyocytes on a Resorbably Scaffolding, Tissue Engineering, 2003, pp. 451-459, vol. 9, No. 3.
Yu, et al., Induced Pluripotent Stem Cell Lines Derived from Human Somatic Cells, Science, Dec. 21, 2007, pp. 1917-1920, vol. 318.
Yu, et al., Isolation of a Novel Population of Multipotent Adult Stem Cells from Human Hair Follicles, American Journal of Pathology, Jun. 6, 2006, pp. 1879-1888, vol. 168, No. 6.
Zembower, et al., Peptide Boronic Acids Versatile Synthetic Ligands for Affinity Chromatography of Serine Proteinases, International Journal Peptide Protein, 1996, pp. 405-413, vol. 47.
Zhang et al., MafA Is a Key Regulator of Glucose-Stimulated Insulin Secretion, Molecular and Cellular Biology, Jun. 2005, 4969-4976, 25-12, American Society for Microbiology.
Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.
Zhang, Jie, The Differentiation of Bone Marrow Mesenchymal Stem Cells into Retina in Rat Eye and the Therapeutical Effect on Severe Injured Retina, A Doctoral Thesis of Chinese Pla Acadamey of Military Medical Sciences, 2003, 1-127, 1-127 (with English Abstract).
Zhang et al, Highly Efficient Differentiation of Human ES Cells and iPS Cells into Mature Pancreatic Insulin-Producing Cells, Cell Research, 2009, pp. 429-438, vol. 19, Issue 14.
Zhao et al., The Islet B Cell-enriched MafA Activator is a Key Regulator of Insulin Gene Transcription, Journal of Biological Chemistry, Mar. 25, 2005, 11887-11894, 280-12, The Amerian Society for Biochemistry and molecular Biology, Inc.
Zhao, et al., Derivation and Characterization of Hepatic Progenitor Cells from Human Embryonic Stem Cells, PLoS ONE Hepatic Progenitors from hESCs, Jul. 2009, e6468 pp. 1-10, vol. 4, Issue 7.
Zorn, et al., Vertebrate Endoderm Development and Organ Formation, Annual Review Cell Development Biology, 2009, pp. 221-251, vol. 25.
Zubaty, et al., Transplantation of Mesenchymal Stem Cells into RCS Rats for Retinal Repair, Investigative Ophthalmology and Visual Science, 2005, pp. 4160-B518, vol. 46, Supplement S.
Ali, et al., Exploitation of Protein Kinase C: A Useful Target for Cancer Therapy, Cancer Treatment Reviews, 2009, pp. 1-8, vol. 35.
Baertschiger, et al., Mesenchymal Stem Cells Derived From Human Exocrine Pancreas Express Transcription Factors Implicated in Beta-Cell Development, Pancreas, 2008, pp. 75-84, vol. 37, No. 1.
Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.
Best, et al., Embryonic Stem Cells to Beta-Cells by Understanding Pancreas Development, Molecular and Cellular Endocrinology, 2008, pp. 86-94, vol. 288.
Brevini et al, Embryonic Stem Cells in Domestic Animals, Theriogenology, 2010, 544-550, 74.
Cao, et al., High Glucose is Necssary for Complete Maturation of Pdx1-VP16-Expressing Hepatic Cells into Functional Insulin-Producing Cells, Diabetes, 2004, pp. 3168-3178, vol. 53.

(56) References Cited

OTHER PUBLICATIONS

Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.
Chetty, et al., A Simple Tool to Improve Pluripotent Stem Cell Differentiation, Nature Methods, 2013, pp. 553-558, vol. 10, No. 6.
Choi, et al., In Vitro Trans-Differentiation of Rat Mesenchymal Cells into Insulin-Producing Cells by Rat Pancreatic Extract, Biochemical and Biophysical Research Communications, 2005, pp. 1299-1305, vol. 330.
D'Amour et al, Production of pancreatic hormone, Nature Biotechnology, 2006, 1392-1401, vol. 24, No. 11.
Deramaudt, et al., The PDX1 Homeodomain Transcription Factor Negatively Regulates the Pancreatic Ductal Cell-specific Keratin 19 Promoter, Journal of Biological Chemistry, 2006, pp. 38385-38395, vol. 281, No. 50.
Florio, et al., Activin A Stimulates Insulin Secretion in Cultured Human Pancreatic Islets, J. Endocrinol. Invest., 2000, pp. 231-234, vol. 23.
Foster, et al., Differentiation of Transplanted Microencapsulated Fetal Pancreatic Cells, Experimental Transplantation, 2007, pp. 1440-1448, vol. 83, No. 11.
Furue, et al., Heparin Promotes the Growth of Human Embryonic Stem Cells in a Defined Serum-Free Medium, Proceedings of the National Academy of Sciences, 2008, pp. 13409-13414, vol. 105, No. 36.
Gibco, Solutions for Life Science Research and Drug Discovery, Catalogue Cell Culture Products, 2004-2005, pp. 1-4E, 281406 26 5 27.
Gordon Weir, Do Stem Cells Hold the Key to a Future Cure for Diabetes?, Diabetes Voice, 2008, pp. 29-31, vol. 53, No. 2.
Duester, et al., Retinoic Acid Synthesis and Signaling During Early Organogenesis, Cell, 2008, pp. 921-931, vol. 134.
Hainsworth, et al., Retinal Capillary Basement Membrane Thickening in a Porcine Model of Diabetes Mellitus, Comparative Medicine, 2002, pp. 523-529, vol. 52, No. 6.
Harmon, et al., GDF11 Modulates NGN3+ Islet Progenitor Cell Number and Promotes B-Cell Differentiation in Pancreas Development, Development, 2004, pp. 6163-6174, vol. 131.
Hay, et al., Highly Efficient Differentiation of hESCs to Functional Hepatic Endoderm Requires ActivinA and Wnt3a Signaling, PNAS, 2008, pp. 12301-12306, vol. 105, No. 34.
Itkin-Ansari, et al., Cell-Based Therapies for Diabetes: Progress Towards a Transplantable Human B Cell Line, Annals of the New York Academy of Sciences, 2003, pp. 138-147, vol. 1005.
Jiang, et al., In Vitro Derivation of Functional Insulin-Producing Cells from Human Embryonic Stem Cells, Cell Research, 2007, pp. 333-344, vol. 17.
Karvonen, et al., Incidence of Childhood Type 1 Diabetes Worldwide, Diabetes Care, 2000, pp. 1516-1526, vol. 23, No. 10.
Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.
Larsen, et al., Use of the Gootingen Minipig as a Model of Diabetes with Special Focus on Type 1 Diabetes Research, ILAR Journal, 2004, pp. 303-313, vol. 45, No. 3.
Lee, et al., PKC Inhibitors Sustain Self-Renewal of Mouse Embryonic Stem Cells Under Hypoxia in Vitro, Experimental and Molecular Medicine, Apr. 2010, pp. 294-301, vol. 42, No. 4.
Leeper, et al., Stem Cell Therapy for Vascular Regeneration Adult, Embryonic, and Induced Pluripotent Stem Cells, Circulation, 2010, pp. 517-526, vol. 122.
Ludwig, et al., Defined Culture Media for Human Embryonic Stem Cells, Embryonic Stem Cells, 2007, pp. 1-16.
Mathis, et al., B-Cell Death During Progression to Diabetes, Nature, 2001, pp. 792-798, vol. 414.
Matveyenko, et al., Inconsistent Formation and Nonfunction of Insulin-Positive Cells from Pancreatic Endoderm Derived from Human Embryonic Stem Cells in Athymic Nude Rats, American Journal of Physiol Endocrinol Metab, 2010, pp. E713-E720, vol. 299.
Munoz et al, Conventional Pluripotency Markers are Unspecific for Bovine Embryonic-Derived Cell Lines, Theriogenology, 2008, pp. 1159-1164, vol. 69.
Ouziel-Yahalom, et al., Expansion and Redifferentiation of Adult Human Pancreatic Islet Cells, Biochemical and Biophysical Research Communications, 2006, pp. 291-298, vol. 341.
Paris, et al., Embryonic Stem Cells in Domestic Animals, Theriogenology, 2010, pp. 516-524, vol. 74.
Park, et al., Effects of Activin A on Pancreatic Ductal Cells in Streptozotocin-Inducted Diabetic Rats, Experimental Transplantation, 2007, pp. 925-930, vol. 83.
Perrier, et al., Derivation of Midbrain Dopamine Neurons from Human Embryonic Stem Cells, PNAS, 2004, pp. 12543-12548, vol. 101, No. 34.
Rajala, et al., Testing of Nine Different Xeno-free Culture Media for Human Embryonic Stem Cell Cultures, Human Reproduction, 2007, pp. 1231-1238, vol. 22, No. 5.
Ramiya, et al., Reversal of Insulin-Dependent Diabetes Using Islets Generated in vitro from Pancreatic Stem Cells, Nature Medicine, 2000, pp. 278-281, vol. 6.
Rezania, E Al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.
Rezania, et al., Enrichment of Human Embryonic Stem Cell-Derived NKX6.1-Expressing Pancreatic Progenitor Cells Accelerates the Maturation of Insulin-Secreting Cells In Vivo, Stem Cells, 2013, pp. 2432-2442, vol. 31.
Richards, et al., Development of Defined Media for the Serum-Free Expansion of Primary Keratinocytes and Human Embryonic Stem Cells, Tissue Engineering, 2008, pp. 221-232, vol. 14, No. 3.
Ross, et al., Cytochrome P450s in the Regulation of Cellular Retinoic Acid Metabolism, Annu. Rev. Nutr., 2011, pp. 65-87, vol. 31.
Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.
Simandi, et al., Retinoid Signaling is a Context-Dependent Regulator of Embryonic Stem Cells, Embryonic Stem Cells—Differentiation and Pluripotent Alternatives, 2011, pp. 55-79, Chapter 3.
Sneddon, et al., Self-Renewal of Embryonic-Stem-Cell-Derived Progenitors by Organ-Matched Mesenchyme, Nature, 2012, pp. 765-770, vol. 491.
Soria, et al., From Stem Cells to Beta Cells: New Strategies in Cell Therapy of Diabetes Mellitus, Diabetologia, 2001, pp. 407-415, vol. 44.
Stafford, et al., Retinoids Signal Directly to Zebrafish Endoderm to Specify Insulin-Expressing B-cells, Development, 2005, pp. 949-956, vol. 133.
Stoffel, et al., Navigating the Pathway from Embryonic Stem Cells to Beta Cells, Seminars in Cell & Developmental Biology, 2004, pp. 327-336, vol. 15.
Swindle, et al., Swine in Biomedical Research: Management and Models, ILAR News, 1994, pp. 1-5, vol. 36, No. 1.
Tsuchida, et al., Activin Isoforms Signal Through Type I Receptor Serine/Threonin Kinase ALK7, Molecular and Cellular Endocrinology, 2004, pp. 59-65, vol. 22.
Wang, et al., Three-Dimensional Differentiation of Embryonic Stem Cells into Islet-Like Insulin-Producing Clusters, Tissue Engineering: Part A, 2009, pp. 1941-1952, vol. 15, No. 8.
White, et al., Complex Regulation of cyp26a1 Creates a Robust Retinoic Acid Gradient in the Zebrafish Embryo, PLoS Biology, 2007, pp. 2522-2533, vol. 5, Issue 11.
Xudong, et al., Research Progress in Inducing Stem Cells to Differentiate Toward the B-like Cells of Pancreatic Islet, Chinese Bulletin of Life Sciences, 2007, pp. 526-530, vol. 19, No. 5.

(56) References Cited

OTHER PUBLICATIONS

Zalzman, et al., Differentiation of Human Liver-Derived, Insulin-Producing Cells Toward the B-Cell Phenotype, Diabetes, 2005, pp. 2568-2575, vol. 54.
Cohick, et al., The Insulin-Like Growth Factors, Annual Reviews Physiol, 1993, pp. 131-153, vol. 55, Annual Reviews Inc.
Hebrok, et al., Notochord repression of endodermal Sonic hedgehog permits pancreas development, Genes & Development, Jun. 1, 1998, pp. 1705-1713, vol. 12 , Issue 11, Cold Spring Harbor Laboratory Press.
Jaenisch, et al., Stem Cells, the Molecular Circuitry of Pluripotency and Nuclear Reprogramming, cell, Feb. 22, 2008, pp. 567-582, vol. 132, Elsevier Inc.
Klajnert, et al., Fluorescence studies on PAMAM dendrimers interactions with bovine serum albumin, Bioelectrochemistry, 2002, pp. 33-35, vol. 55.
Kubota,et al., Growth factors essential for self-renewal and expansion of mouse spermatogonial stem cells, cell Biology, Nov. 23, 2004, pp. 16489-16494, vol. 101 , Issue 47.
Nostro, et al., Generation of Beta Cells from Human Pluripotent Stem Cells: Potential for Regenerative Medicine, Seminars in Cell & Developmental Biology, 2012, pp. 701-710, vol. 23.
Ratanasavanh,et al., Immunocytochemical Evidence for the Maintenance of Cytochrome P450 Isozymes, NADPH Cytochrome C Reductase, and Epoxide Hydrolase in Pure and Mixed Primary Cultures of Adult Human Hepatocytes1, The Journal of Histochemistry and Cytocheinistry, 1986, pp. 527-533, vol. 34 , Issue 4.
Rezania, et al., Reversal of Diabetes with Insulin-Producing Cells Derived in vitro from Human Pluripotent Stem Cells, Nature Biotechnology, 2014, pp. 1121-1133, vol. 32, No. 11.
Schaefer-Graf, et al., Patterns of congenital anomalies and relationship to initial maternal fasting glucose levels in pregnancies complicated by type 2 and gestational diabetes, Am J Obstet Gynecol, 2000, pp. 313-320, vol. 182 , Issue 2.
Thermofisher Scientific, B-27 Serum-Free Supplement (50x) Liquid, Technical Resources, 2016, URL:https://www.thermofisher.com/nl/en/home/technical-resources/media-formulation.250.html, retrieved from the internet.
Wachs, et al., High Efficacy of Clonal Growth and Expansion of Adult Neural Stem Cells, Laboratory Investigation, 2003, pp. 949-962, vol. 83, No. 7.
Beers, et al., Passaging and Colony Expansion of Human Pluripotent Stem Cells by Enzyme-Free Dissociation in Chemically Defined Culture Conditions, Nature Protocols, 2012, pp. 2029-2040, vol. 7, No. 11.
Brimble, S., et al., The Cell Surface Glycosphingolipis SSEA-3 and SSEA-4 are not Essential for Human ESC Pluripotency, Stem Cells, Jan. 2007, pp. 54-62, vol. 25.
Buta, et al., Reconsidering pluripotency tests: Do we still need teratoma assays?, Stem Cell Research, Mar. 26, 2013, pp. 552-562, vol. 11.
Chen, et al., Retinoic acid signaling is essential for pancreas development and promotes endocrine at the expense of exocrine cell differentiation in Xenopus, Developmental Biology, May 4, 2004, pp. 144-160, vol. 271.
Chen, et al., Scalable GMP Compliant Suspension Culture System for Human ES Cells, Stem Cell Research, 2012, pp. 388-402, vol. 8.
Cirulli, et al., Netrins: beyond the brain, Molecular Cell Biology, Apr. 2007, pp. 296-306, vol. 8.
Furue, et al., Heparin propotes the growth of human embryonic stem cells in a defined serum-free medium, PNAS, Sep. 9, 2008, pp. 13409-13414, vol. 105, Issue 36.
Gibco, Insulin-Transferin-Selenium-X 100X, Invitrogen Cell Culture, Apr. 2005, pp. 1, Form No. 3032.
Gomez, et al., Derivation of cat embryonic stem-like cells from in vitro-produced blastocysts on homologous and heterologous feeder cells, Theriogenology, May 11, 2010, pp. 498-515, vol. 74.
Gordon Weir, Do stem cells hold the key to a future cure for diabetes?, DiabetesVoice, Jun. 2008, pp. 29-31, vol. 53, Issue 2.
Guo, et al., Efficient differentiation of insulin-producing cells from skin-derived stem cells, Cell Proliferation, 2009, pp. 49-62, vol. 42.
Hiemisch, H., et al., Transcriptional Regulation in Endoderm Develoment: Characterization of an Enhancer Controlling Hnf3g Expression by Transgenesis and Targeted Mutagenesis, The EMBO Journal, 1997, 3995-4006, vol. 16(13).
Jean, et al., Pluripotent genes in avian stem cells, Development Growth & Differentitaion, 2013, pp. 41-51, vol. 55.
Kang, et al., Plasma treatment of textiles—Synthetic Polymer-Based Textiles, AATCC Review, 2004, pp. 29-33, vol. 4.
King, et al., Bioreactor development for stem cell expansion and controlled differentiation, Current Opinion in Chemical Biology, Jul. 25, 2007, pp. 394-398, vol. 11, Elsevier Ltd.
Kunisada, et al., Small molecules induce efficient differentiation into insulin-producing cells from human induced pluripotent stem cells, Stem Cell Research, Oct. 11, 2011, pp. 274-284, vol. 8.
Lavial, etal., Chicken Embryonic Stem Cells as a Non-Mammalian Ebryonic Stem Cell Model, Development Growth Differentiation, Jan. 2010, pp. 101-114, vol. 52(1).
Lin, C., et al., Coagulation Dysregulatin as a Barrier to Xenotransplantation n the Primate, Transplant Immunology, 2009, pp. 75-80, vol. 21.
Maria-Jesus Obregon, Thyroid hormone and adipocyte differentiation, Thyroid, 2008, pp. 185-195, vol. 18 Issue 2.
McMahon, et al., Noggin-mediated antagonsim of BMP signaling is required for growth and patterning of the neural tube and somite, Genes & Development, Mar. 16, 1998, pp. 1438-1452, vol. 12.
Nakase, et al., Myeliod Antigen, CD13, CD14, and/ or CD33 Expression is Restricted to Certain Lymphiod Neoplasms, Hematopathology, Jun. 1996, pp. 761-768, vol. 105, Issue 6.
Narang, A., et al., Biological and Biomaterial Approaches for Improved Islet Transplantation, Pharmacological Review, Jun. 2006, pp. 194-243, vol. 58(2).
Olmer, et al., Long Term Expansion of Undifferentiated Human iPS and ES Cells in Suspension Culture Using Defined Medium, Stem Cell Research, 2010, pp. 51-64, vol. 5.
Ouziel-Yahalom, et al., Expansion and redifferentiation of adult human pancreatic islet cells, Biochemical and Biophysical Research Communications, Jan. 19, 2006, pp. 291-298, vol. 341.
Petitte, J., et al., Avian Plluripotent Stem Cells, Mechanisms of Development, 2004, pp. 1159-1168, vol. 121.
Ramiya, et al., Reversal of insulin-dependent diabetes using islets generated in vitro from pancreatic stem cells, Nature Medicine, Mar. 2000, pp. 278-282, vol. 6, Issue 3.
Rother, et al., Challenges facing islet transplantation for the treatment of type 1 diabetes mellitus, The Journal of Clinical Investigation, 2004, pp. 877-883, vol. 114, Issue 7.
Rowely, et al., Meeting Lot-size Challenges of Manufacturing Adherent Cells for Therapy, Bio Process International, Mar. 2012, pp. 16-22, vol. 10, Issue 3.
Sjögren-Jansson, et al., Large-Scale Propagation of Four Undifferentiated Human Embryonic Stem Cell Lines in a Feeder-Free Culture System, Developmental Dynamics, Jun. 17, 2005, pp. 1304-1314, vol. 233.
Strizzi, et al., Netrin-1 regulates invasion and migration of mouse mammary epithelial cells overexpressing Cripto-1 in vitro and in vivo, Journal of Cell Science, Jul. 7, 2005, pp. 4633-4643, vol. 118 Issue 20.
Suzuken., Differentiation of Multifunctional Stem Cells Using Human Feeder Cells, Research Papers of the Suzuken Memorial Foundation, 2007, pp. 193-197, vol. 2.
Thomson, Bioprocessing of Embryonic Stem Cells for Drug Disvoery, Trends in Biotechnology, 2007, pp. 224-230, vol. 25, No. 5.
Yadlin, et al., Small-molecule inducers of insulin expression in pancreatic $\alpha$-cells, PNAS, Aug. 24, 2010, pp. 15099-15104, vol. 107 Issue 34.
Yang JW, et al., Evaluation of human MSCs cell cycle, viability and differentiation in micromass culture, Biorheology, 2006, pp. 1-2, vol. 43, Issue (3-4).
Yim,et al., Proliferation and differentiation of human embryonic germ cell derivatives in bioactive polymeric fibrous scaffold, J.Biomater. Sci.Polymer Edn,, Jan. 19, 2005, pp. 1193-1217, vol. 16, Issue 10.

(56) References Cited

OTHER PUBLICATIONS

Zulewski, et al., Multipotentital Nestin-Positive Stem Cells Iasolated From Adult Pancreatic Islets Differentiate Ex Vivo Into Pancreatic Endocrine, Exocrine, and Hepatic Phenotypes, Diabetes, 2001, pp. 521-533, vol. 50.
Balajthy, et al., Chapter 8. 8. Embryonic and adult stem cells in regenerative medicine I, Molecular therapies, 2011, pp. 1-6.
Condic, et al., Alternative Sources of Pluripotent Stem Cells: Ethical and Scientific Issues Revisited, Stem Cells and Development, 2010, pp. 1121-1129, vol. 19 Issue 8, Mary Ann Liebert, Inc.
Daheron, et al., LIF/STAT3 Signaling Fails to Maintain Self-Renewal of Human Embryonic Stem Cells, Stem Cells, 2004, pp. 770-778, vol. 22.
Findikli, et al., Establishment and characterization of new human embryonic stem cell lines, Reproductive BioMedicine Online, Mar. 3, 2005, pp. 617-627, vol. 10 Issue 5.
Foster, et al., Differentiation of Transplanted Microencapsulated Fetal Pancreatic Cells, Transplantation, Jun. 15, 2007, pp. 1440-1448, vol. 83 Issue 11.
Guillemain, et al., Glucose Is Necessary for Embryonic Pancreatic Endocrine Cell Differentiation*, The Journal of Biological Chemistry, May 18, 2007, pp. 15228-15237, vol. 282 Issue 20.
Kehoe, et al., Scalable Stirred-Suspension Bioreactor Culture of Human Pluripotent Stem Cells, Tissue Eng Part A, 2010, pp. 405-421, vol. 16 Issue 2.
Kim, et al., Reprogrammed Pluripotent Stem Cells from Somatic Cells, International Journal of Stem Cells, 2011, pp. 1-8, vol. 4 Issue 1.
Lee, et al., Available human feeder cells for the maintenance of human embryonic stem cells, Reproduction, 2004, pp. 727-735, vol. 128.
Ludwig, et al., Defined, Feeder-Independent Medium for human Embryonic Stem Cell Culture, Current Protocols in Stem Cell Biology, 2007, pp. 1C.2.1-1C.2.16, vol. 1, John Wiley & Sons, Inc.
Maimets, et al., Activation of p53 by nutlin leads to rapid differentiation of human embryonic stem cells, Oncogene, Jun. 2, 2008, pp. 5277-5287, vol. 27.
Micallef, et al., Pancreas Differentiation of Mouse ES Cells, Current Protocols in Stem Cell Biology, 2007, pp. 1C.2.1-1C.2.16, John Wiley & Sons, Inc.
Misiti, et al., 3,5,30-Triiodo-L-Thyronine Enhances the Differentiation of a Human Pancreatic Duct Cell Line (hPANC-1) Towards a b-Cell-Like Phenotype, Journal of Cellular Physiology, 2005, pp. 286-296, vol. 204.
Nakanishi, et al., Pancreatic tissue formation from murine embryonic stem cells in vitro, Differentiation, 2007, pp. 1-11, vol. 75.
Nekrasov, et al., Induced pluripotent stem cells as a model for studying human diseases, Cellular Transplantology and Tissue Engineering, 2011, pp. 32-37, vol. 6 Issue 2.
Osafune, et al., Marked differences in differentiation propensity among human embryonic stem cell lines, Nature Biotechnology, Feb. 17, 2008, pp. 313-315, vol. 26 Issue 3.
Sigma-Aldrich, MCDB-131 media composition, Sigma-Aldrich, 2007, pp. 1-2.
Verkhovskaya, et al., Effect of alkoxy-substituted of glycerin on the morphofunctional properties of continuous cell culture, Cryobiology, 1990, pp. 30-33, vol. 1 (English Abstract).
Wang, et al., Cultivation and identification of pancreatic endocrine progenitor cells, National Medical Journal of China, 2006, pp. 1850-1853, vol. 86 Issue 26 (English Abstract).
Wang, et al., Scalable expansion of human induced pluripotent stem cells in the defined xeno-free E8 medium under adherent and suspension culture conditions, Stem Cell Research, Nov. 2013, pp. 1103-1116, vol. 11 Issue 3.
Zhu, et al., A Small Molecule Primes Embryonic Stem Cells for Differentiation, Cell Stem Cell, May 8, 2009, pp. 416-426, vol. 4.
Blazhevich Kul'tivirovanie kletok. Kurs lektsij.—Mn.: BGU, (78 pages); pp. 56, 57, 59, with English translation (9 pages) (2004).
Cameron et al., "Improved development of human embryonic stem cell-derived embryoid bodies by stirred vessel cultivation," *Biotechnol Bioeng.* 94:938-948 (2006).
Cimbaljuk et al., "Spinnoj mozg. Jelegija nadezhdy: monografija", *Novaja kniga.* 944 pages (p. 245) (2010). Relevance is based on English translation of Russian OA, No. 2018108851, dated Oct. 17, 2018 (attached).
Gerecht-Nir et al., "Bioreactor cultivation enhances the efficiency of human embryoid body (hEB) formation and differentiation," *Biotechnol Bioeng.* 86:493-502 (2004).
Gilbert, "Developmental Biology," 3 volumes, the first volume: translation from English—M.: Mir, (228 pages): p. 187, with English translation (5 pages) (1993).
Kozhukharova I.V., "Novye linii ehmbrional'nykh stvolovykh kletok cheloveka S612 I S90," *Tsitologiya* 51: 551-558 (2009). (Relevance is based on the English translations of two Office Actions from Russian Application No. 2018108850 and Russian Application No. 2018108847, both attached).
Lian et al., "Directed cardiomyocyte differentiation from human pluripotent stem cells by modulating Wnt/β-catenin signaling under fully defined conditions," *Nat Protoc.* 8:162-175 (2013).
Menzorov "Embryonic Stem Cells of the Mouse and Human," *Vavilov J Genet Breed.* 17: 234-245(p. 237) with English translation (5 pages) (2013).
Nelson et al., "Therapeutic Potential of the Inhibition of the Retinoic Acid Hydroxylases CYP26A1 and CYP26B1 by Xenobiotics," *Curr Top Med Chem.* 13:1402-1428 (2013).
Serafimidis et al., "G Protein-Coupled Receptor Signaling and Sphingosine-1-Phosphate Play a Phylogenetically Conserved Role in Endocrine Pancreas Morphogenesis," *Mol Cell Biol.* 31:4442-4453 (2011).
Stacpoole et al., "Efficient derivation of neural precursor cells, spinal motor neurons and midbrain dopaminergic neurons from human ES cells at 3% oxygen," *Nat Protoc.* 6:1229-1240 (2011).
Stanford et al., "Sphingosine 1-phosphate S1P regulates glucose-stimulated insulin secretion in pancreatic beta cells," *J Biol Chem.* 287:13457-13464 (2012).

* cited by examiner

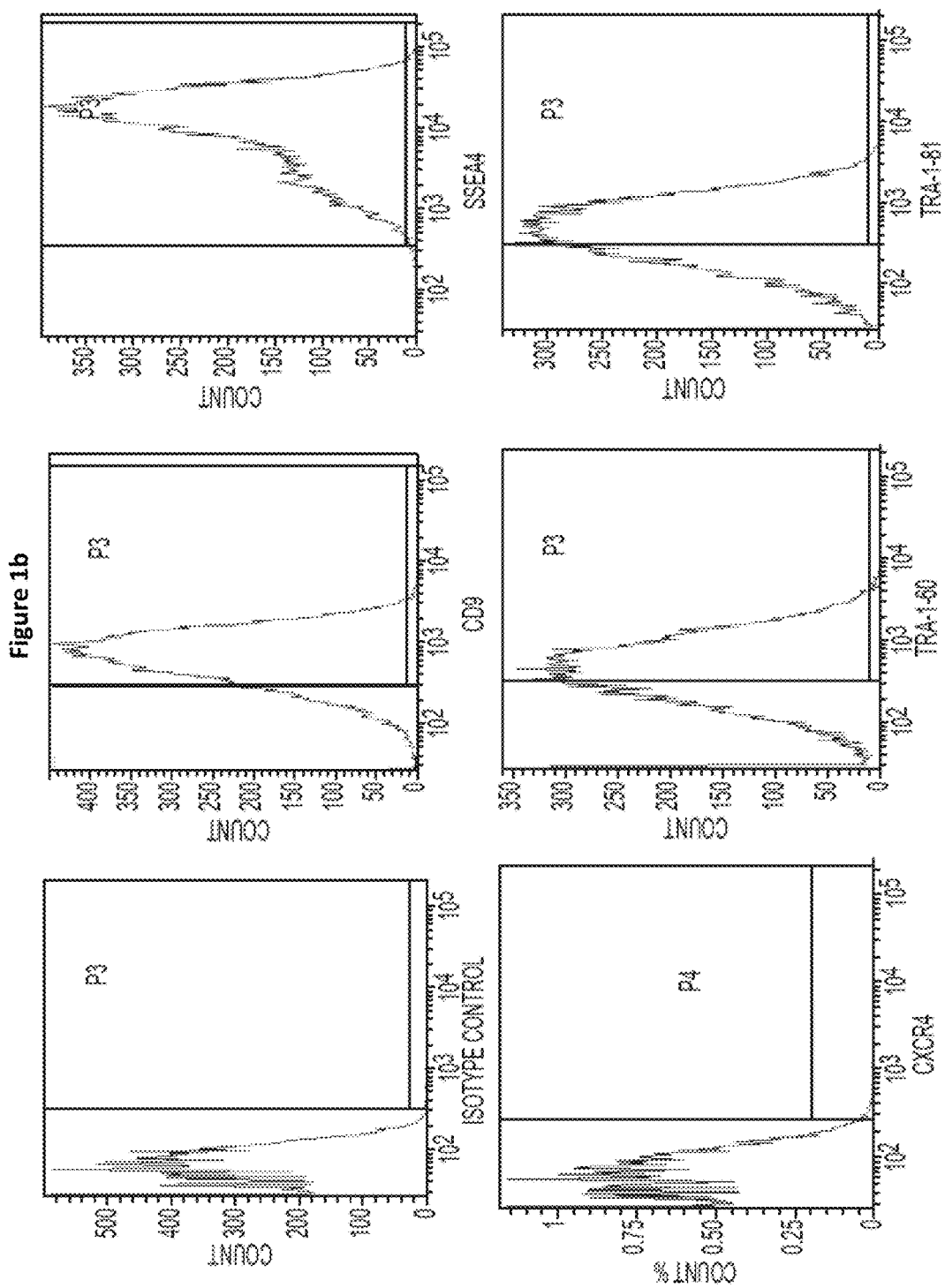

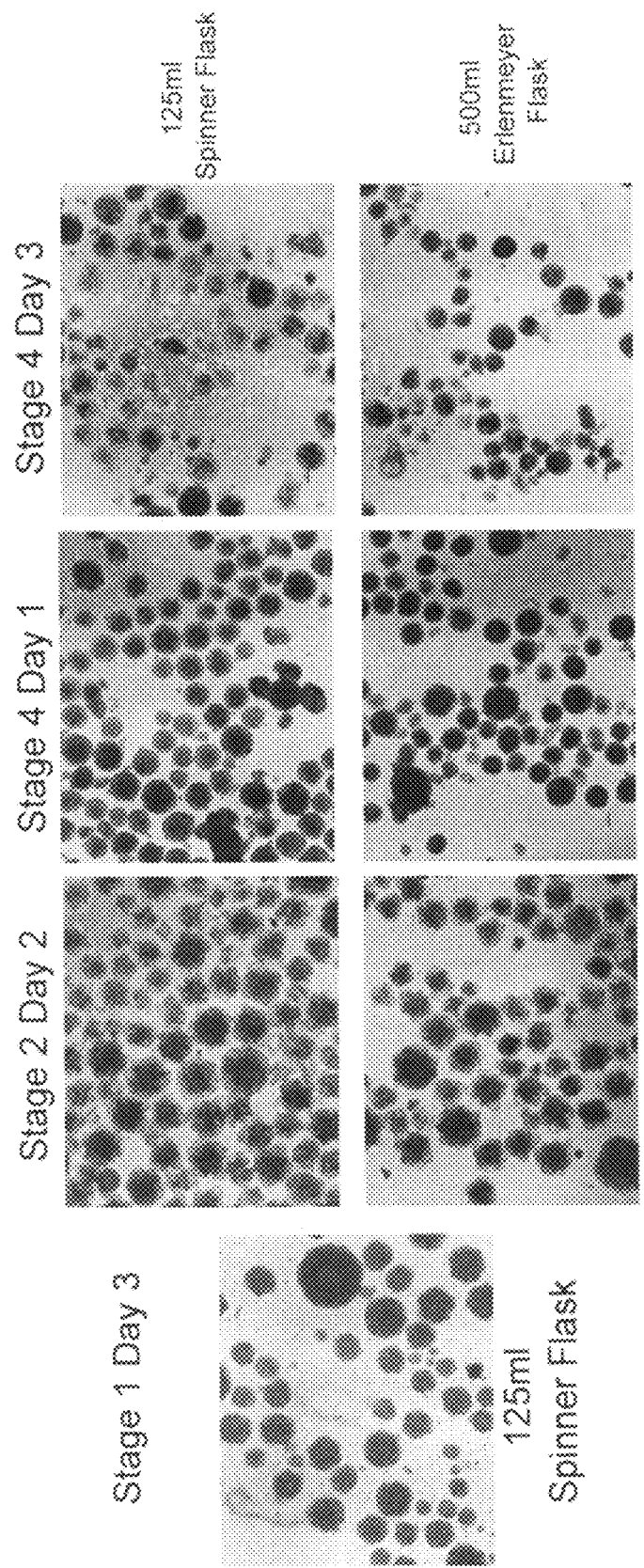

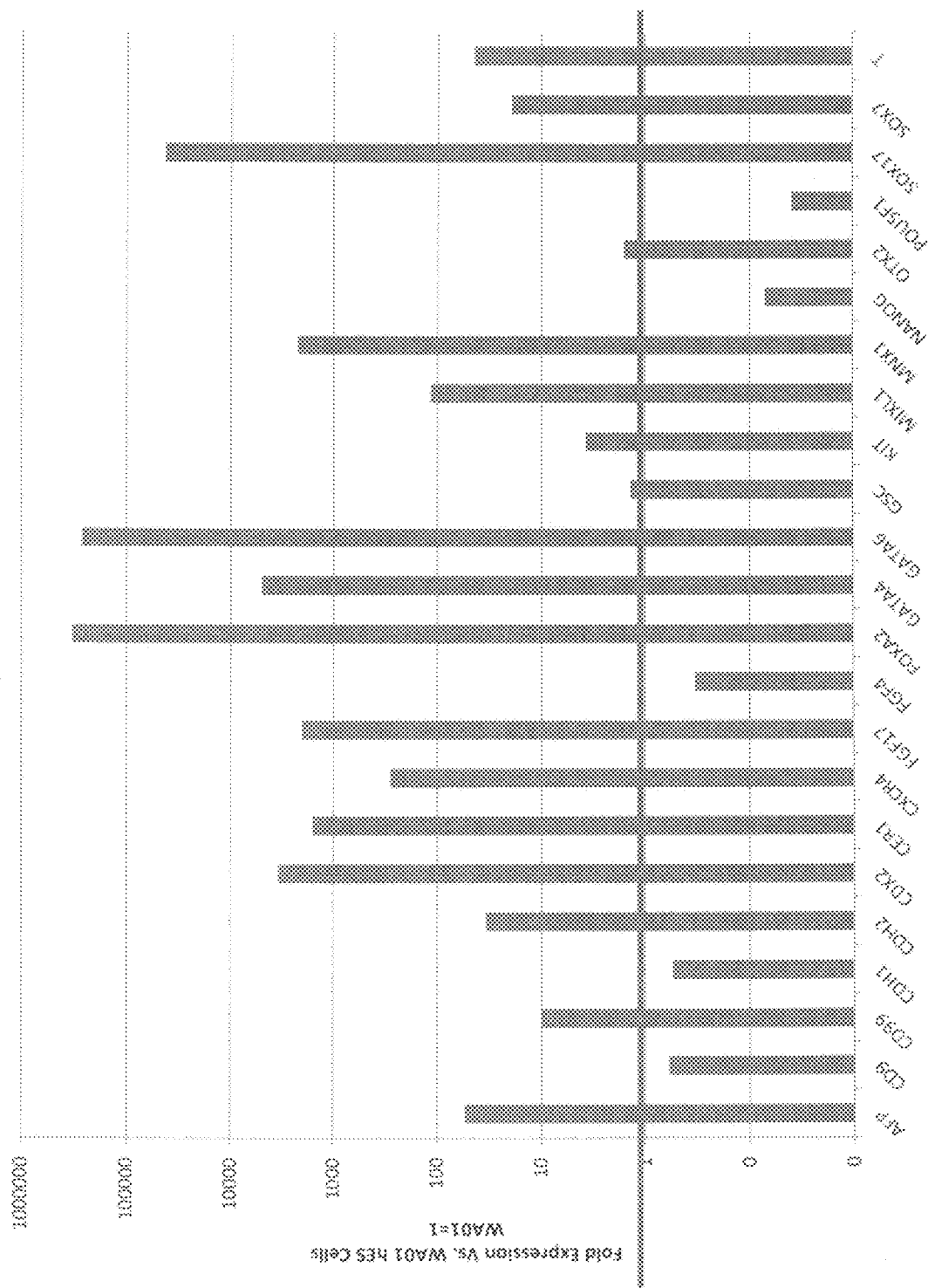

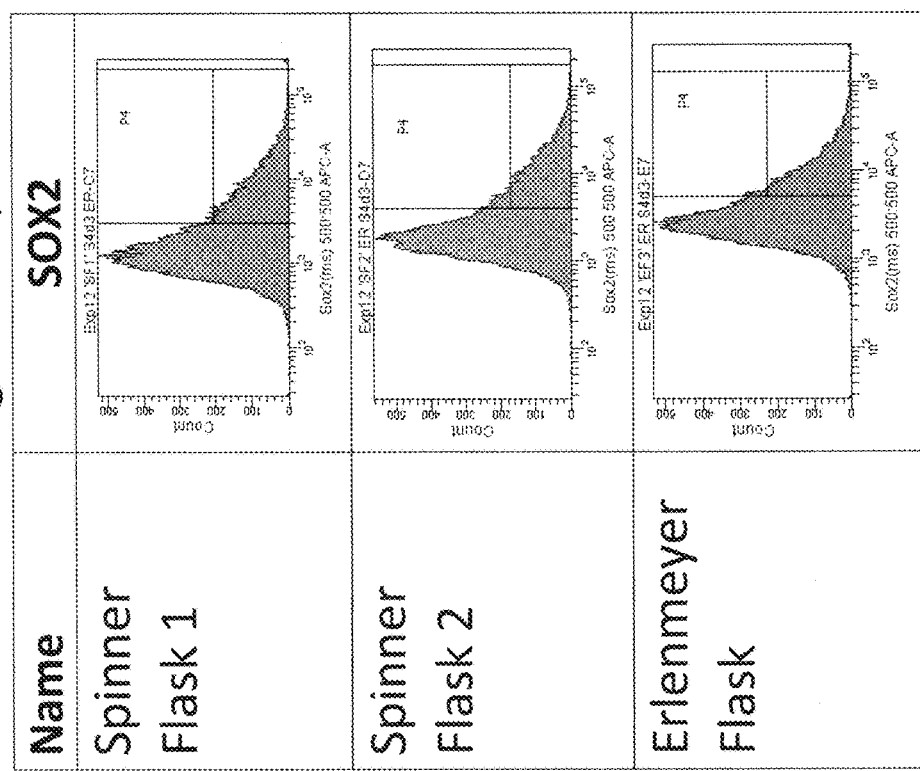

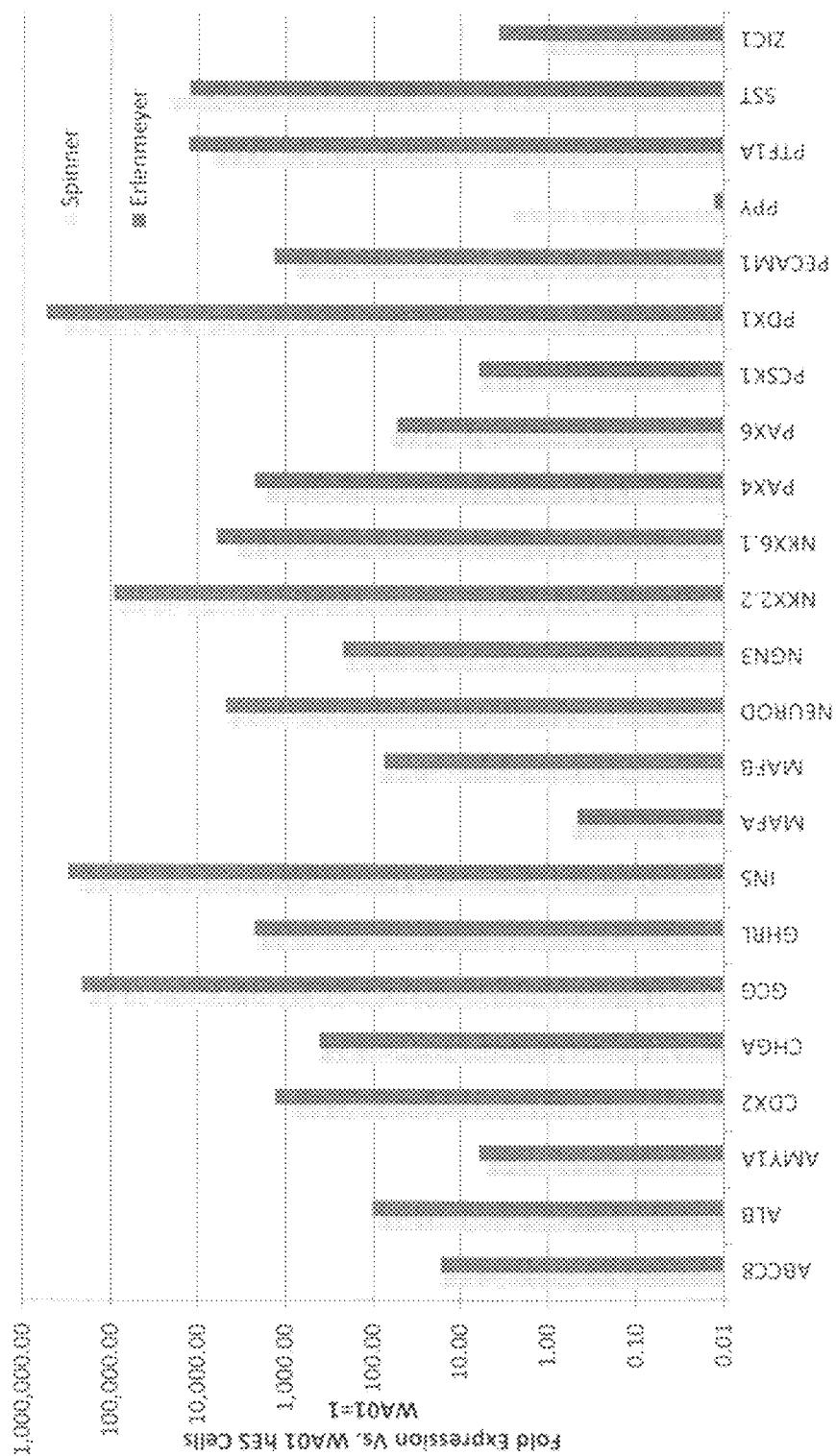

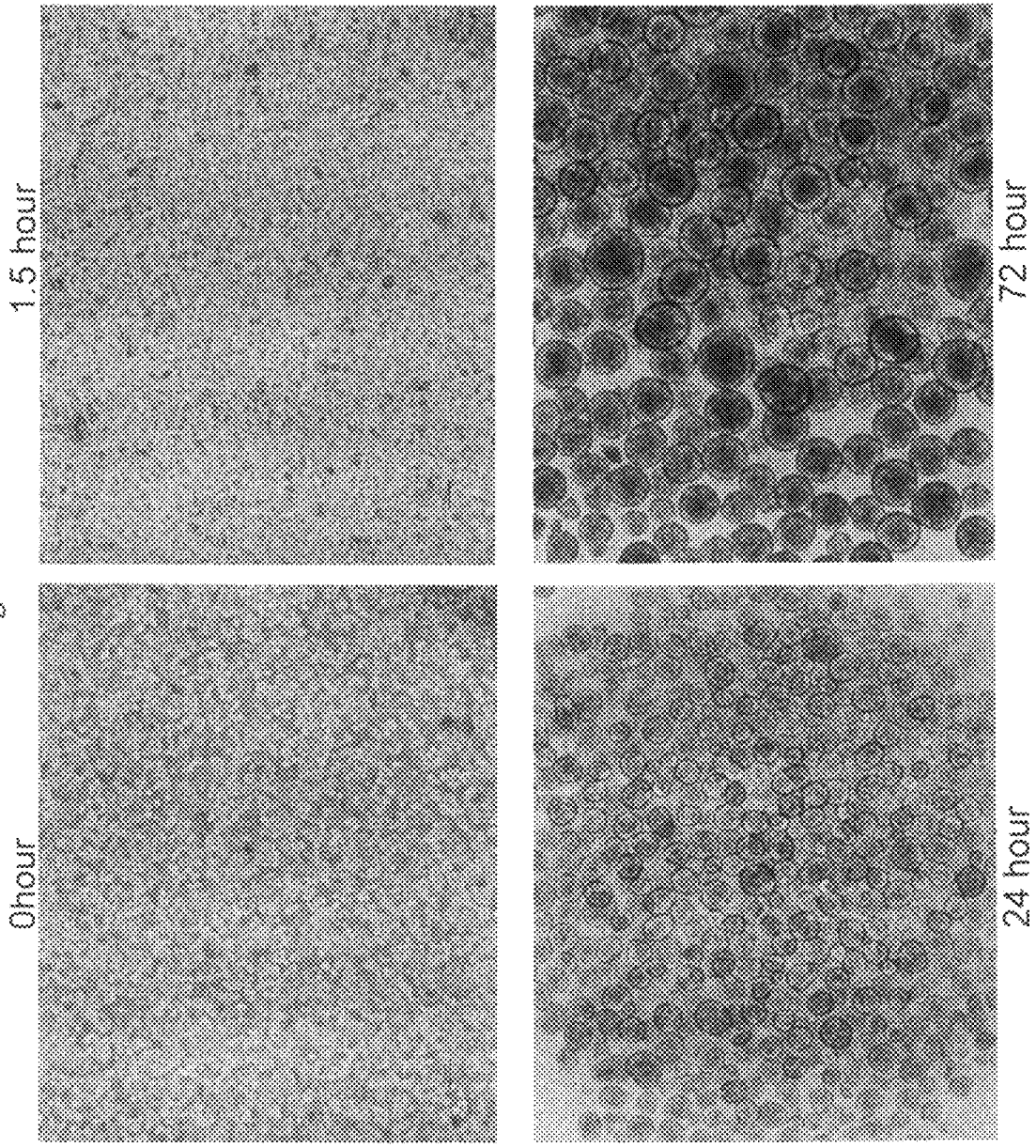

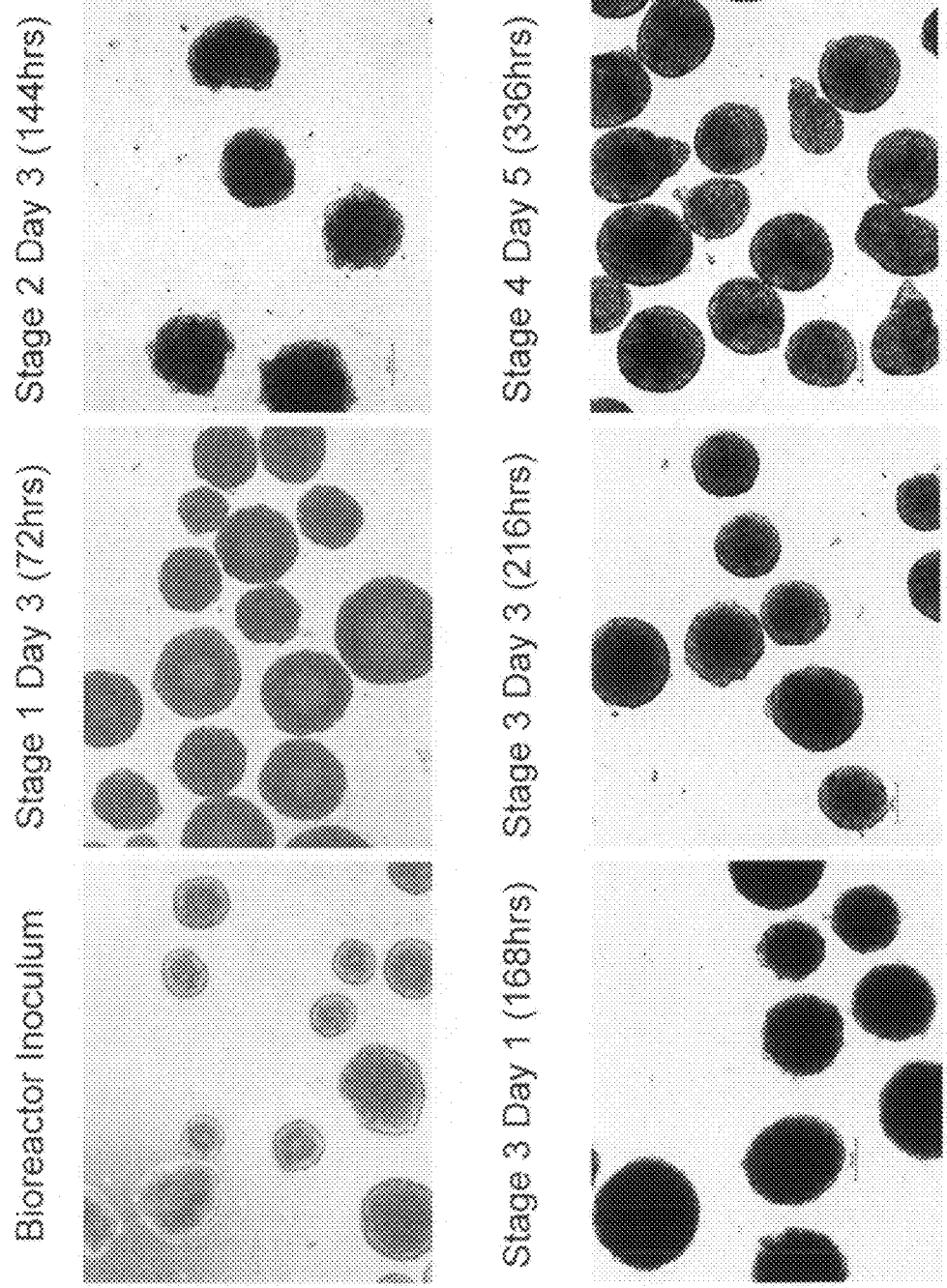

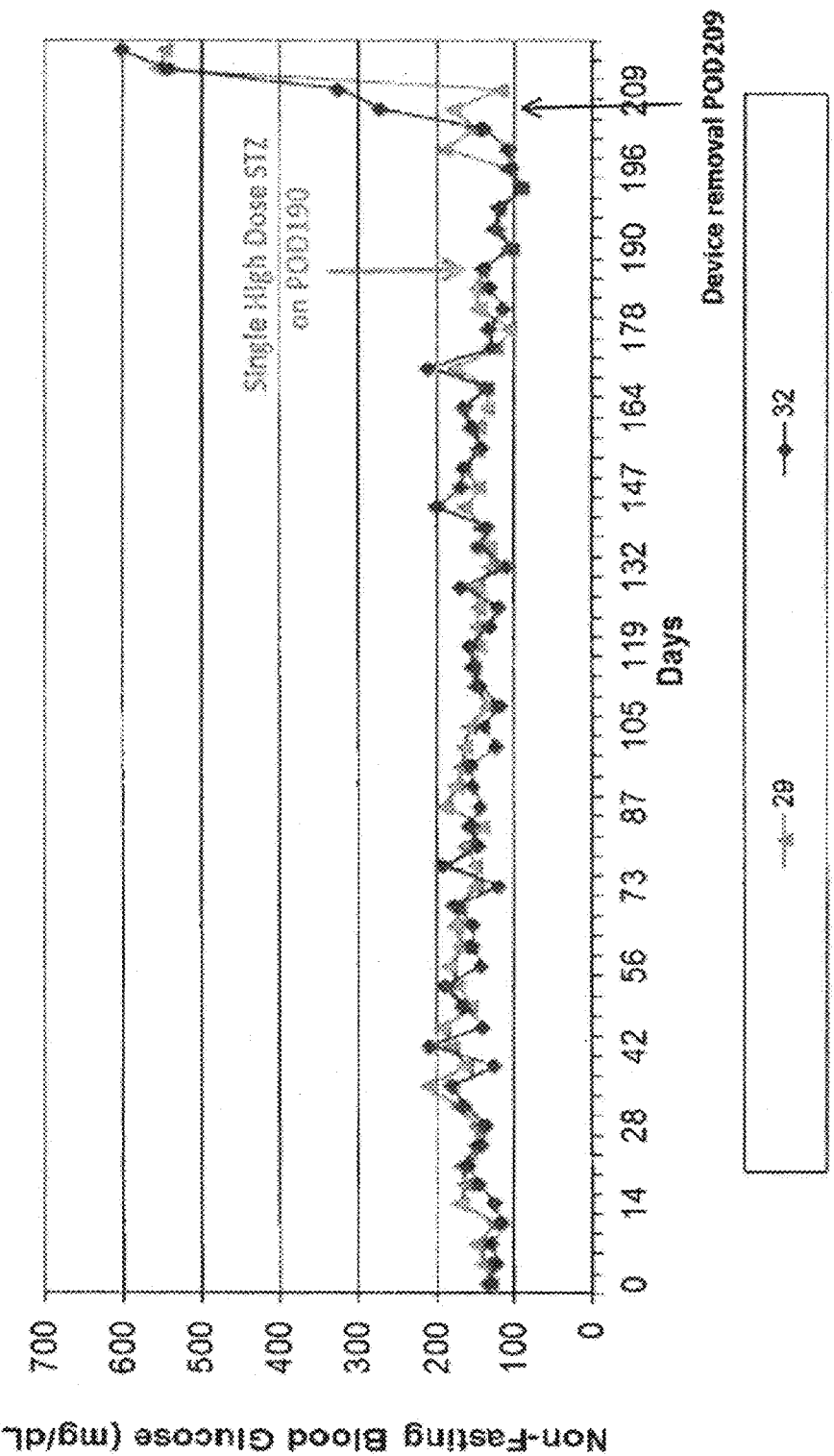

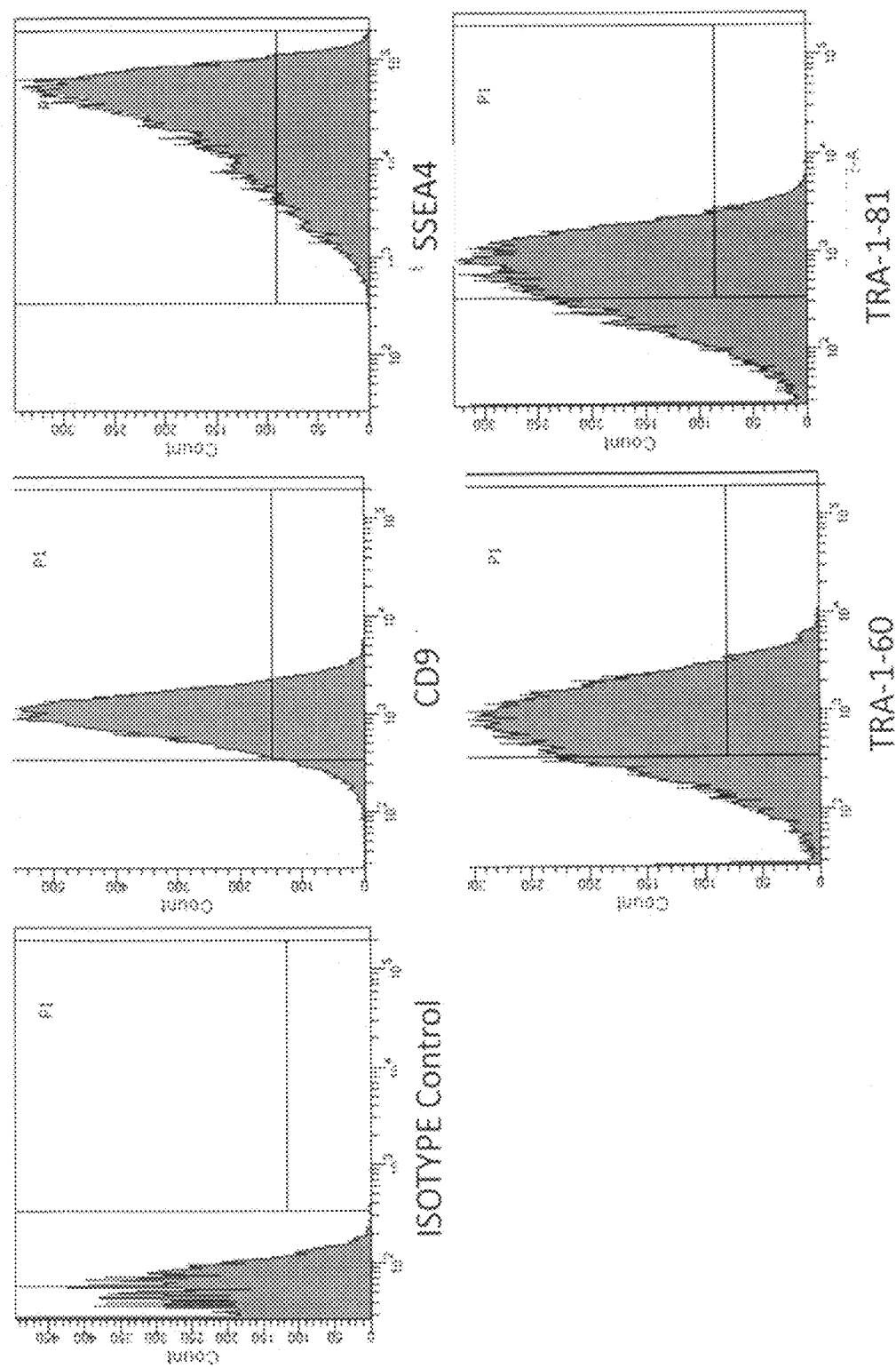

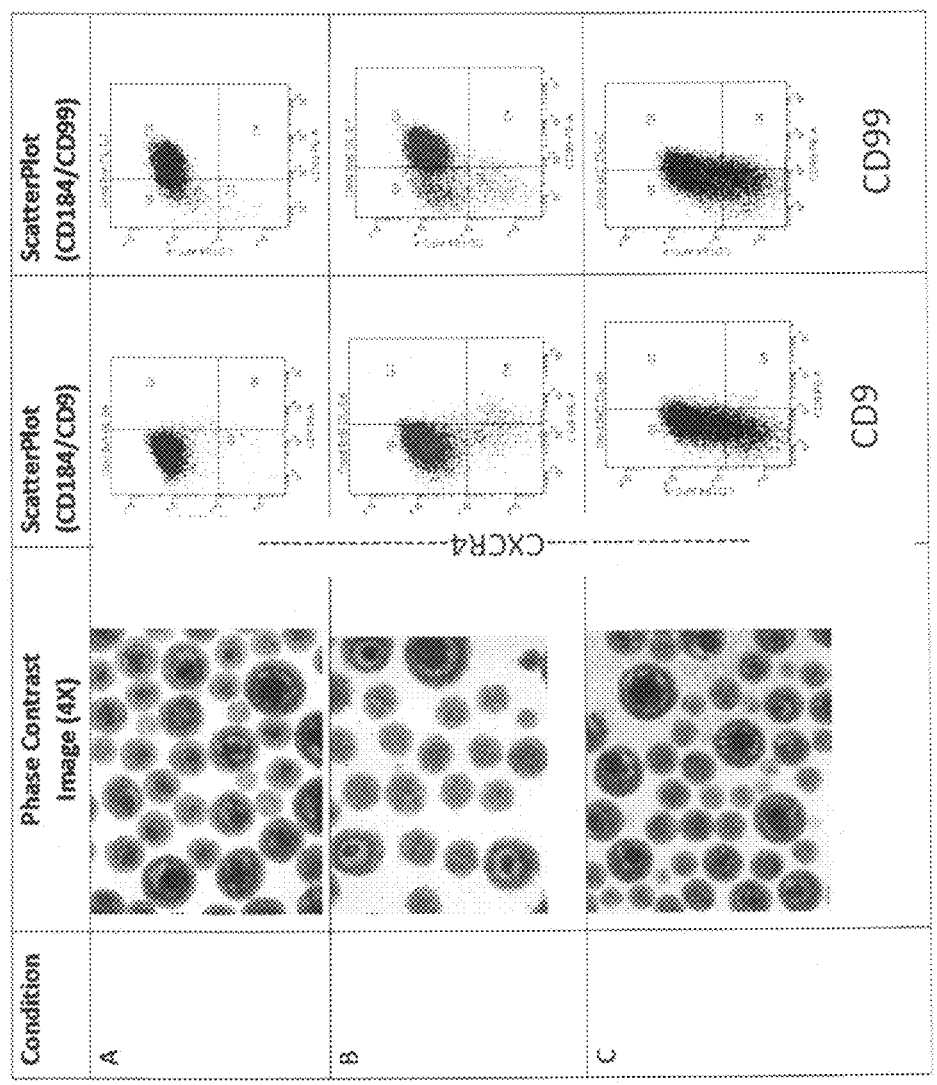

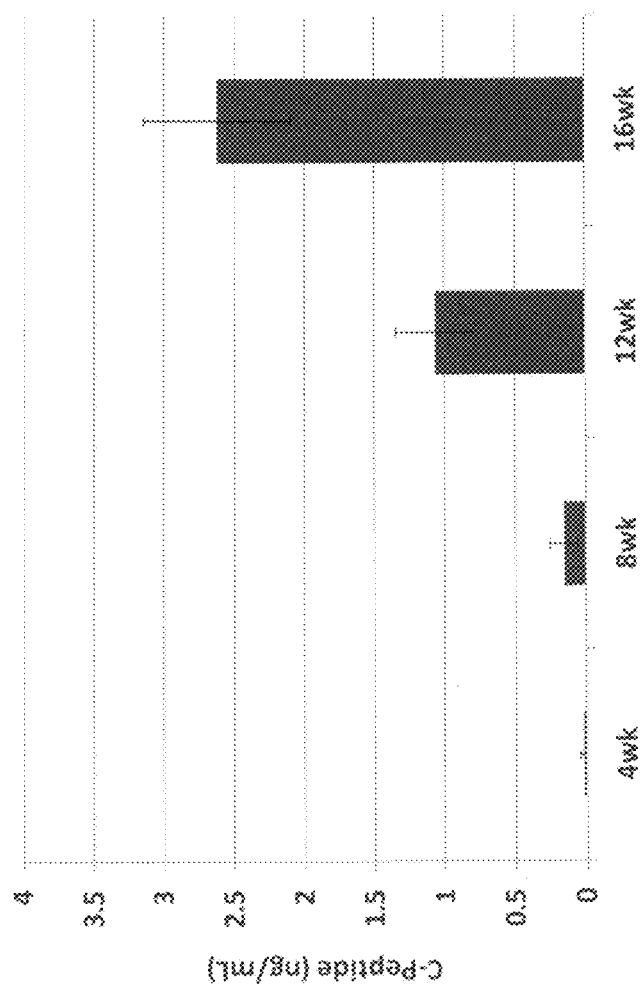

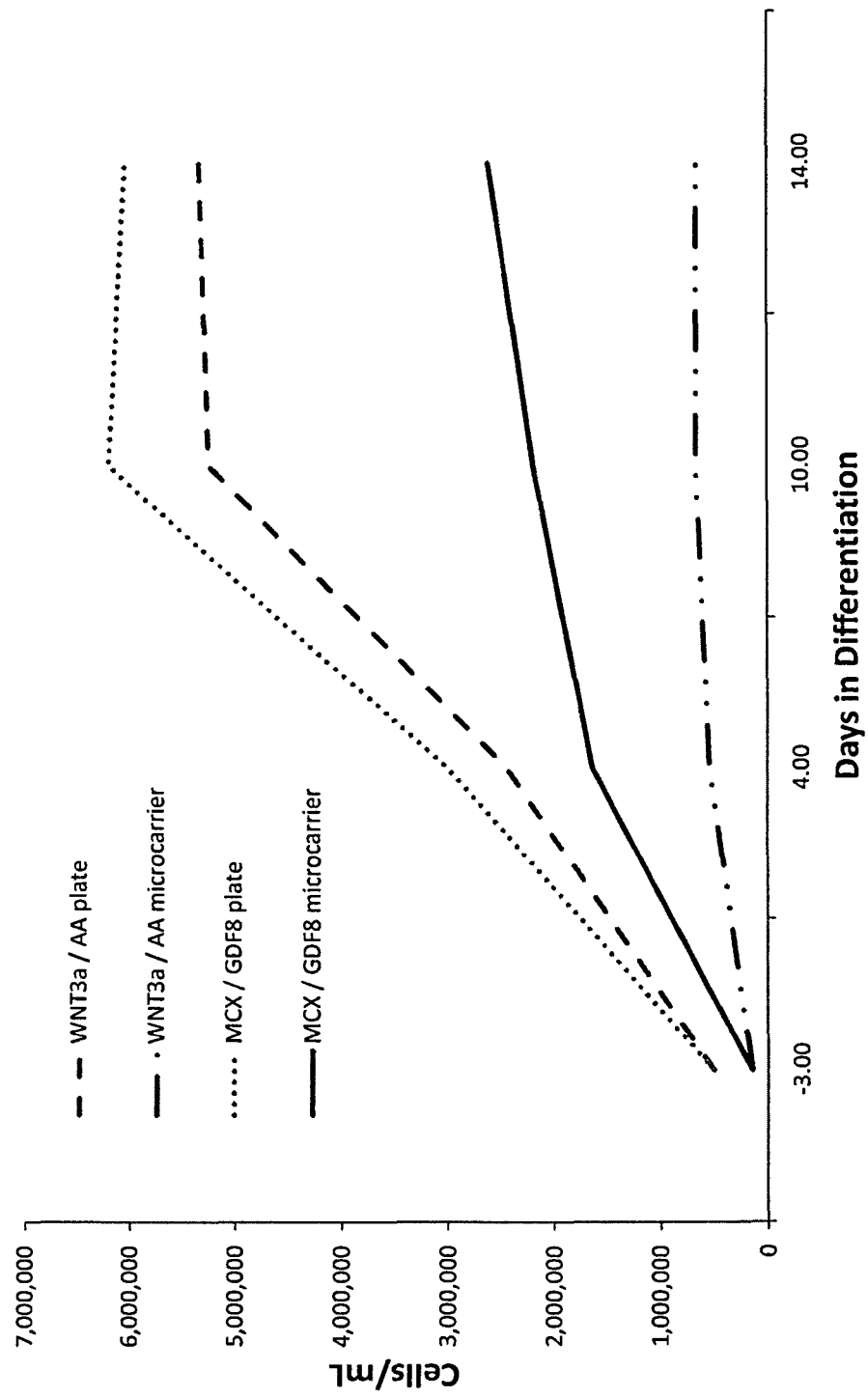

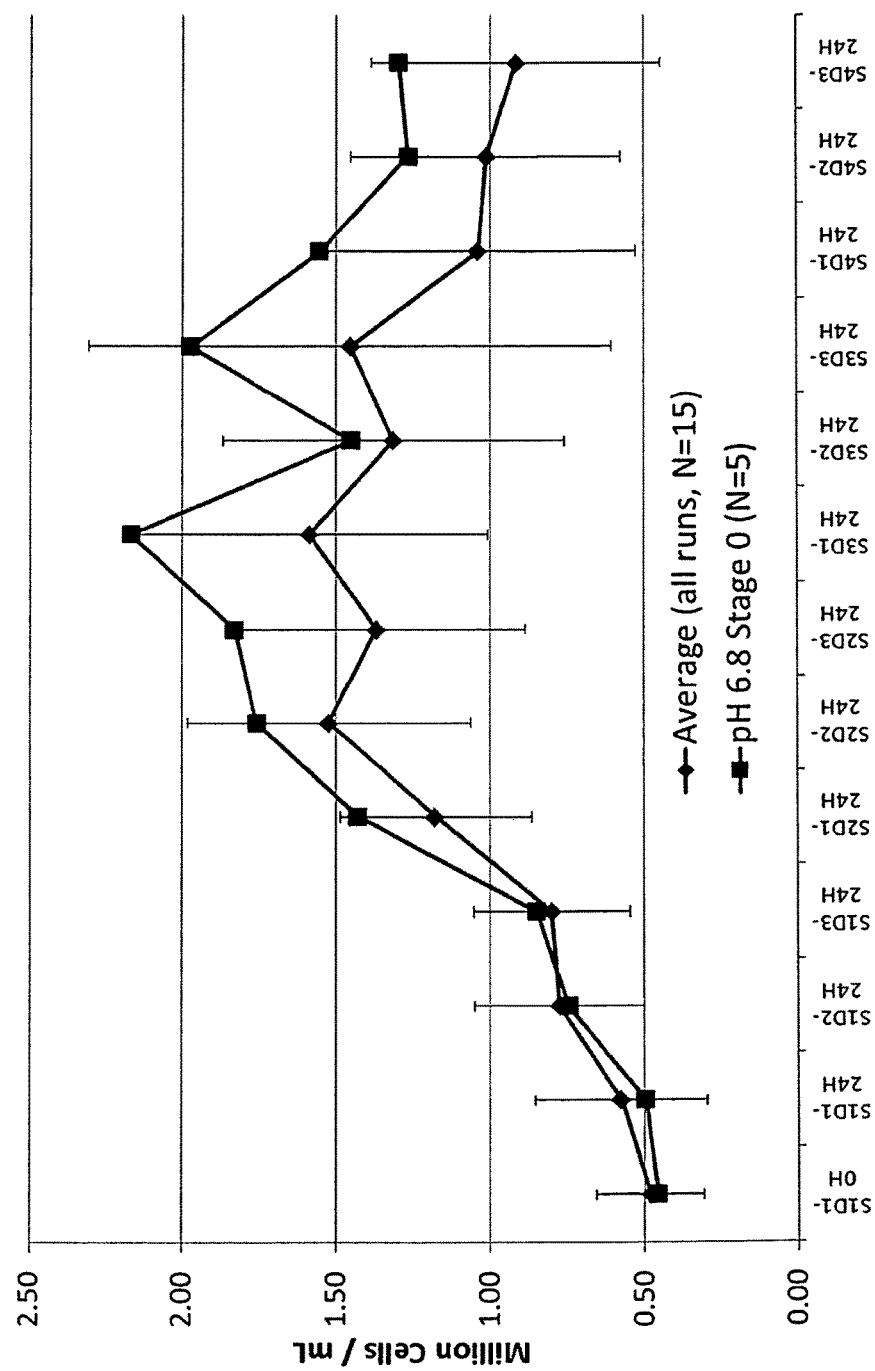

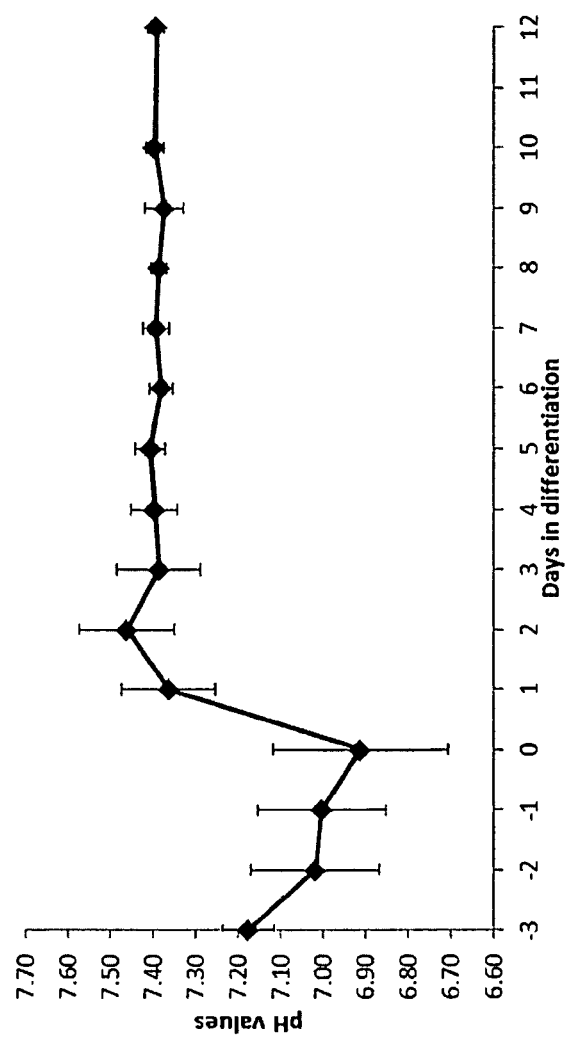
Figure 8: Average Daily Bioreactor pH Levels

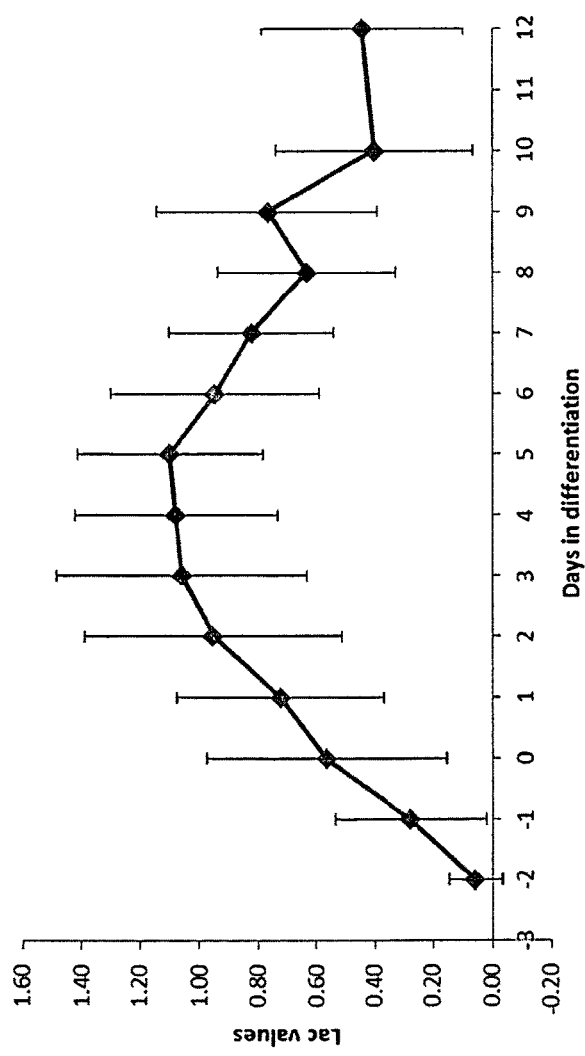
Figure 9: Average Daily Bioreactor Lactate Levels

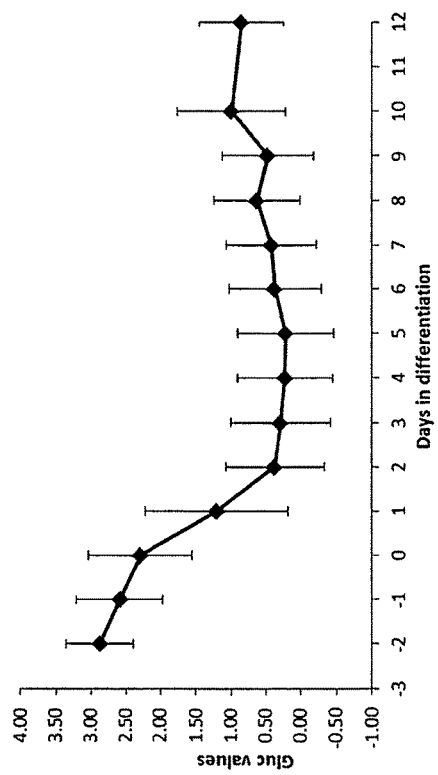
Figure 10: Average Daily Bioreactor Glucose Levels

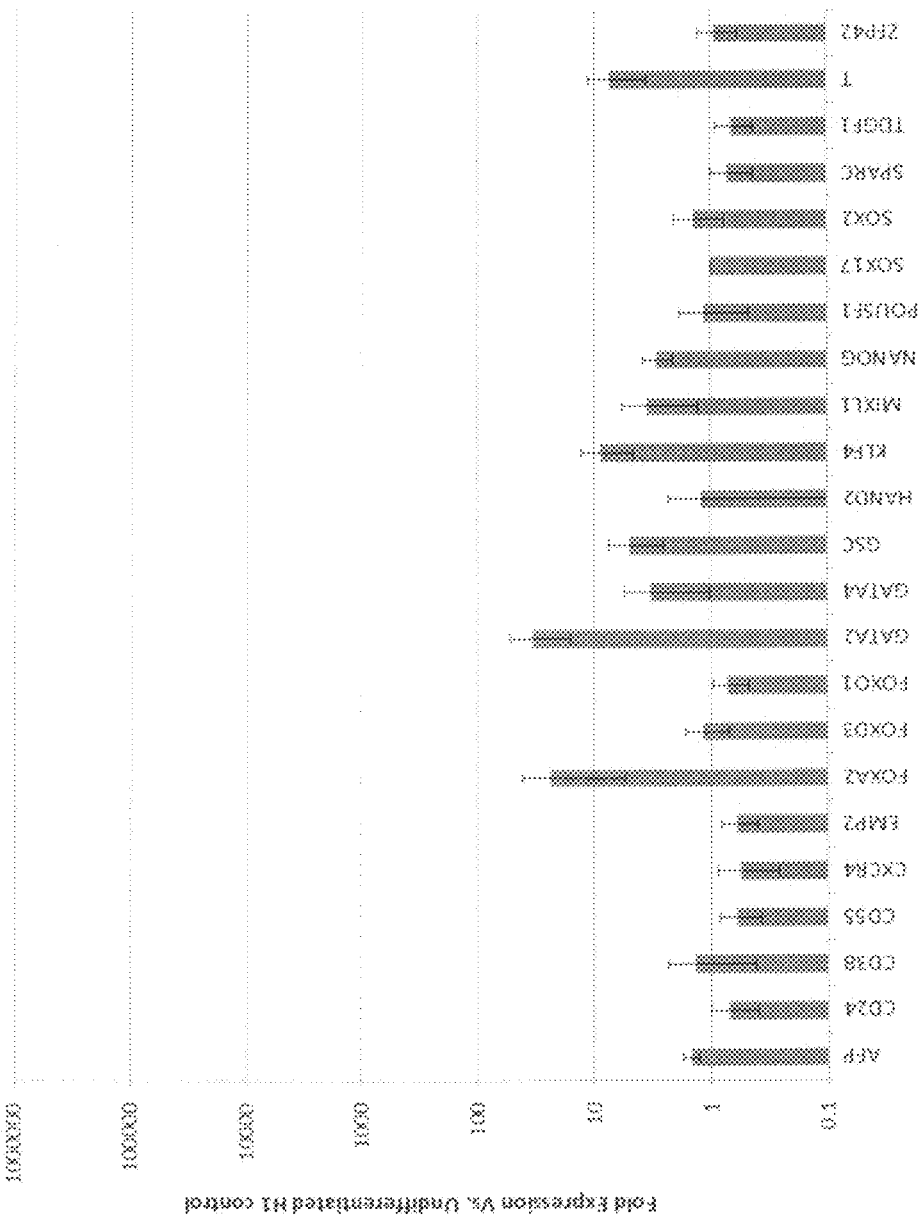
Figure 11: Average Stage 0 Day 1 Expression by qRT-PCR (n=12), Pluripotency Array (mean ± St. Dev.)

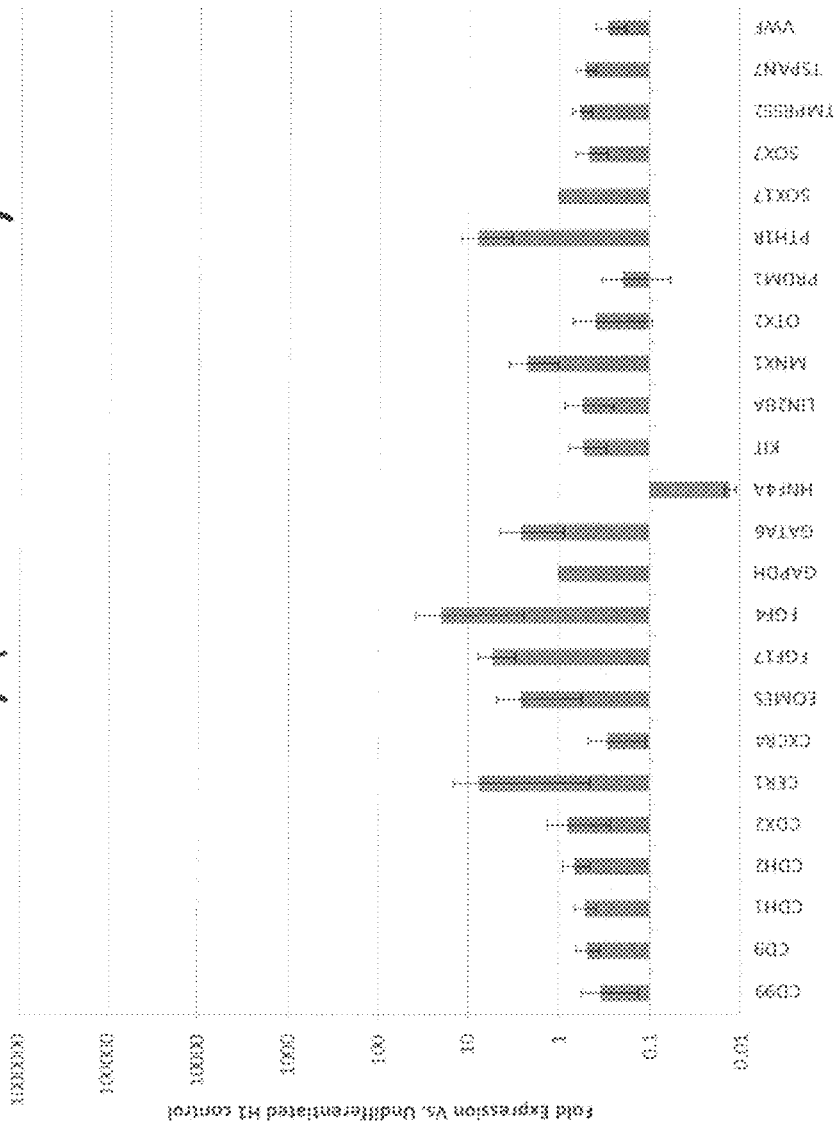
Figure 12: Average Stage 0 Day 1 Expression by qRT-PCR (n=10), DE Array (mean ± St. Dev.)

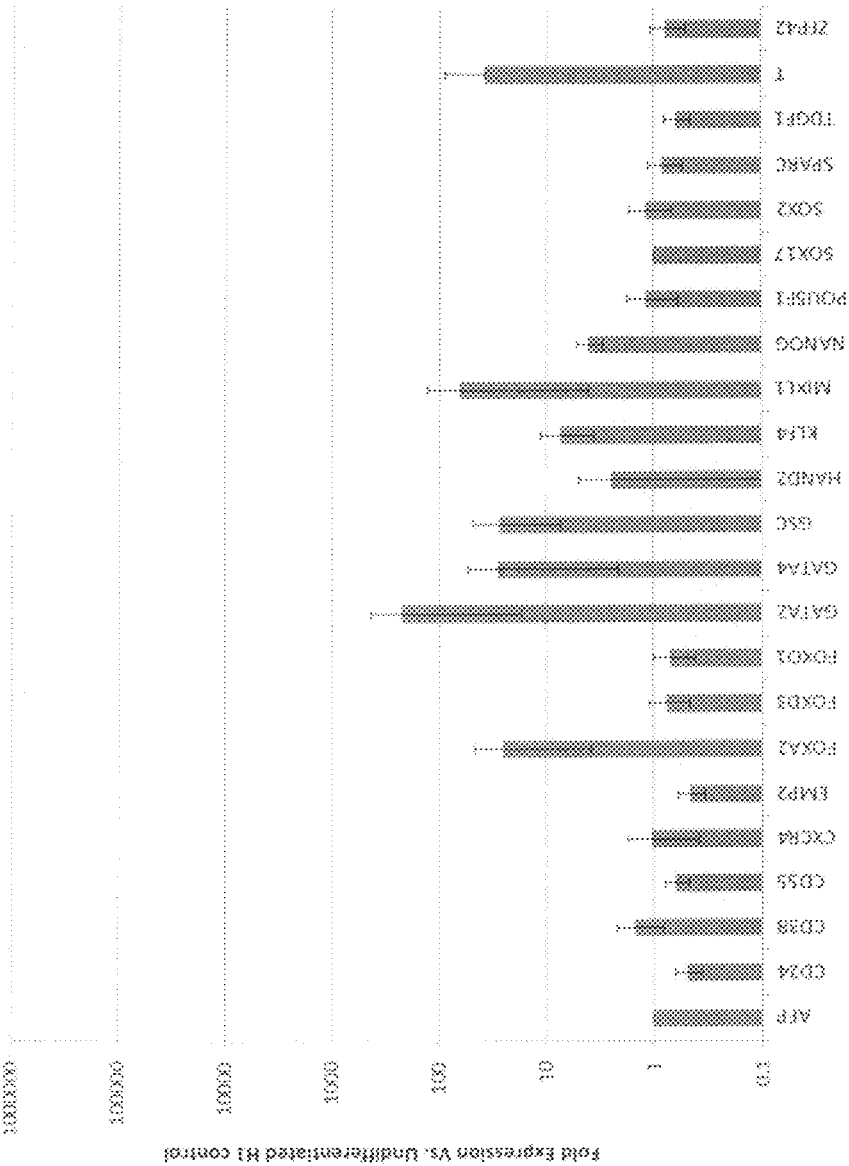

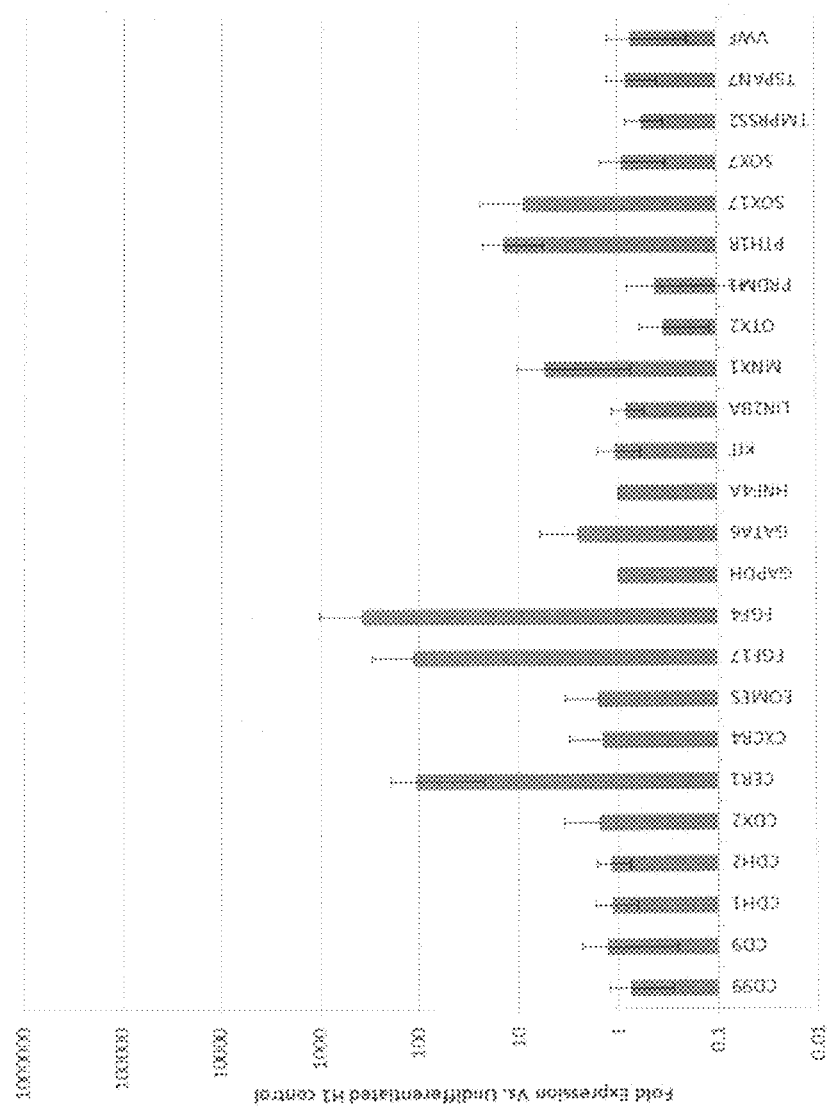

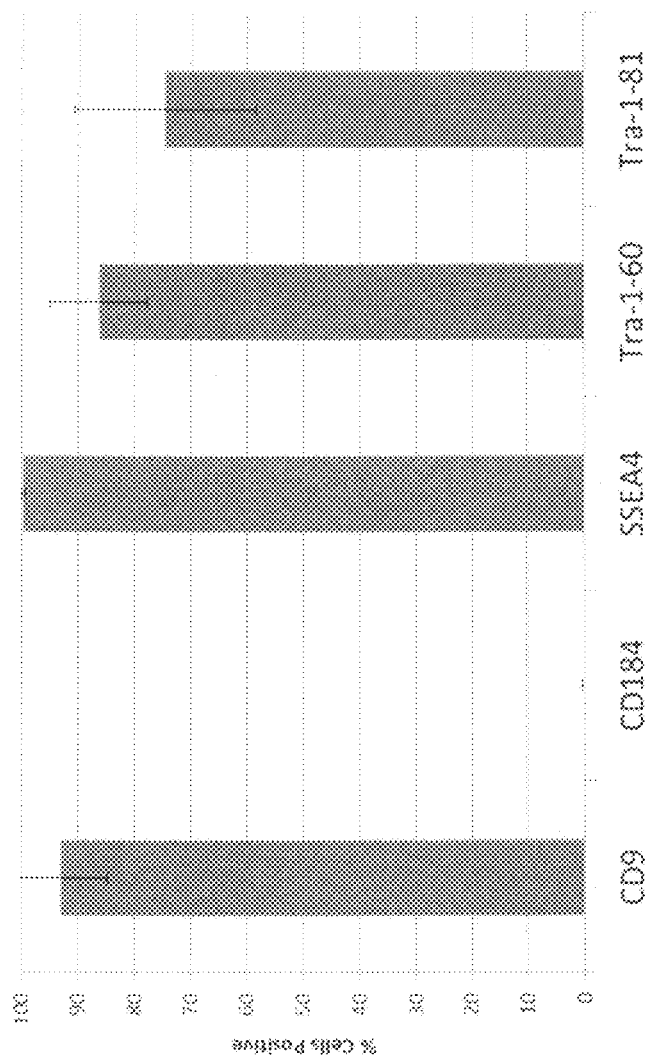

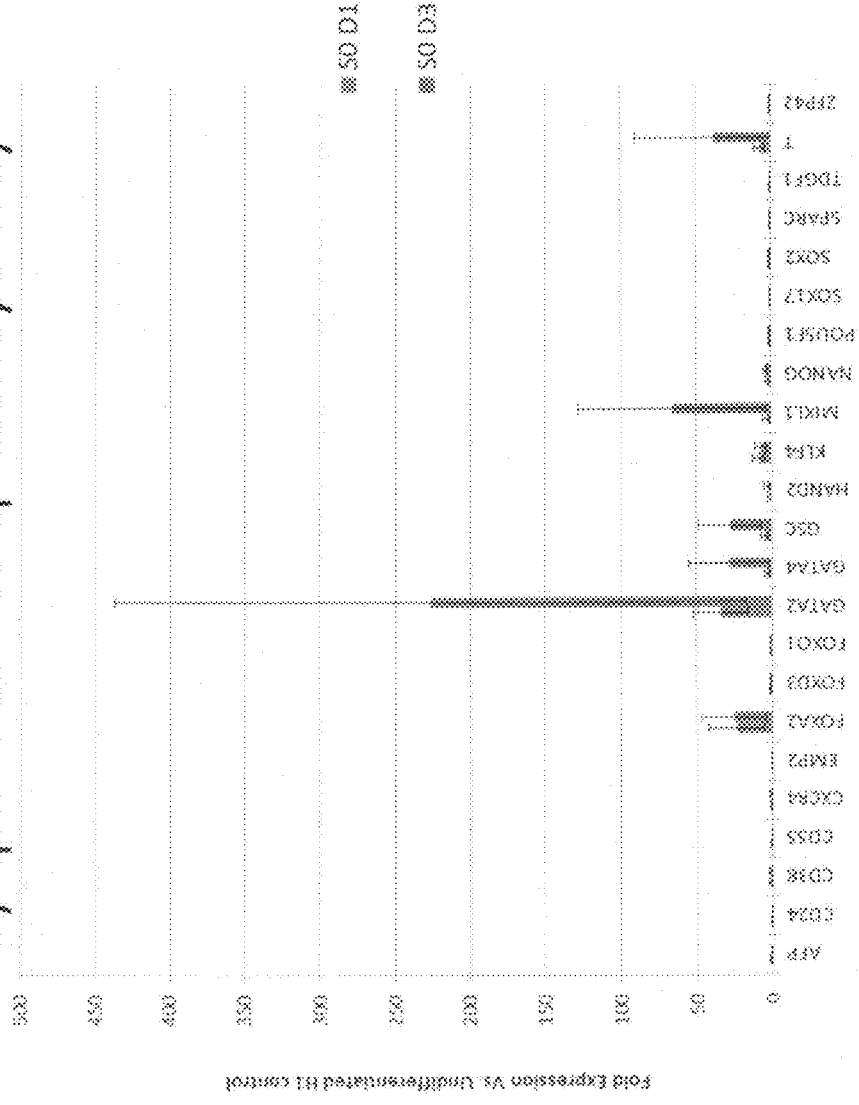

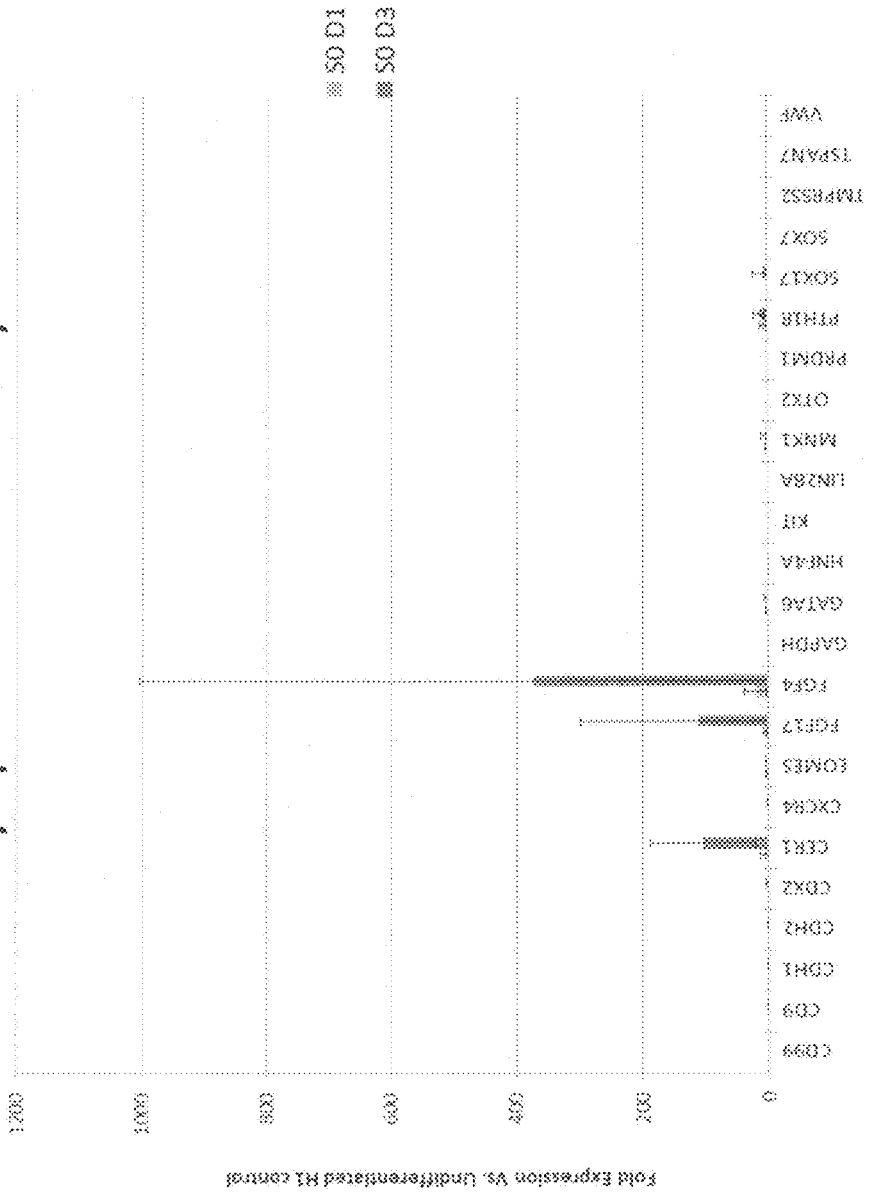

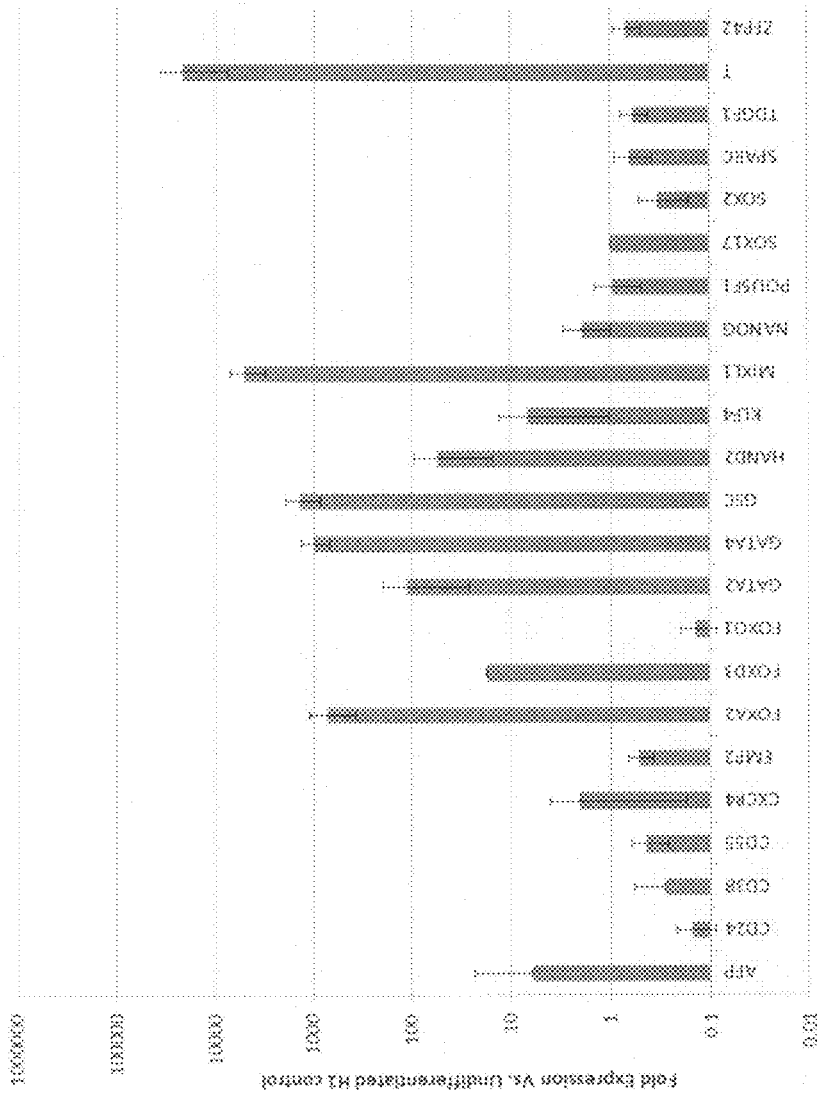

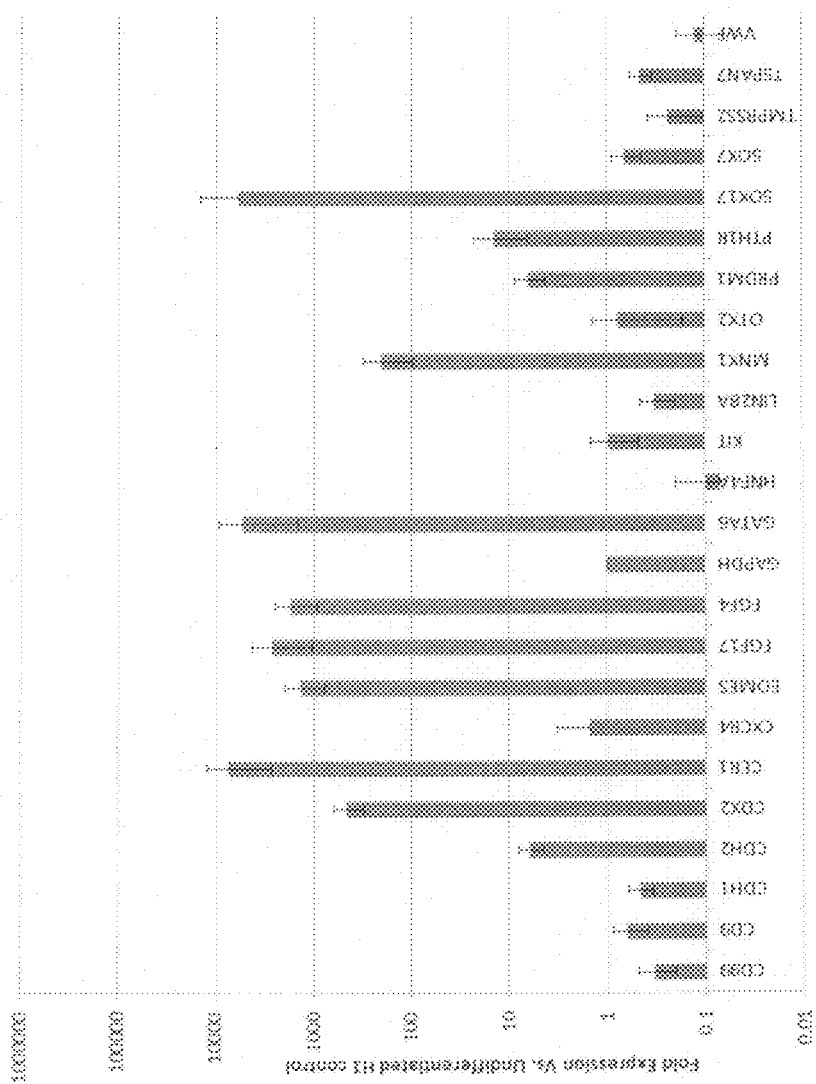

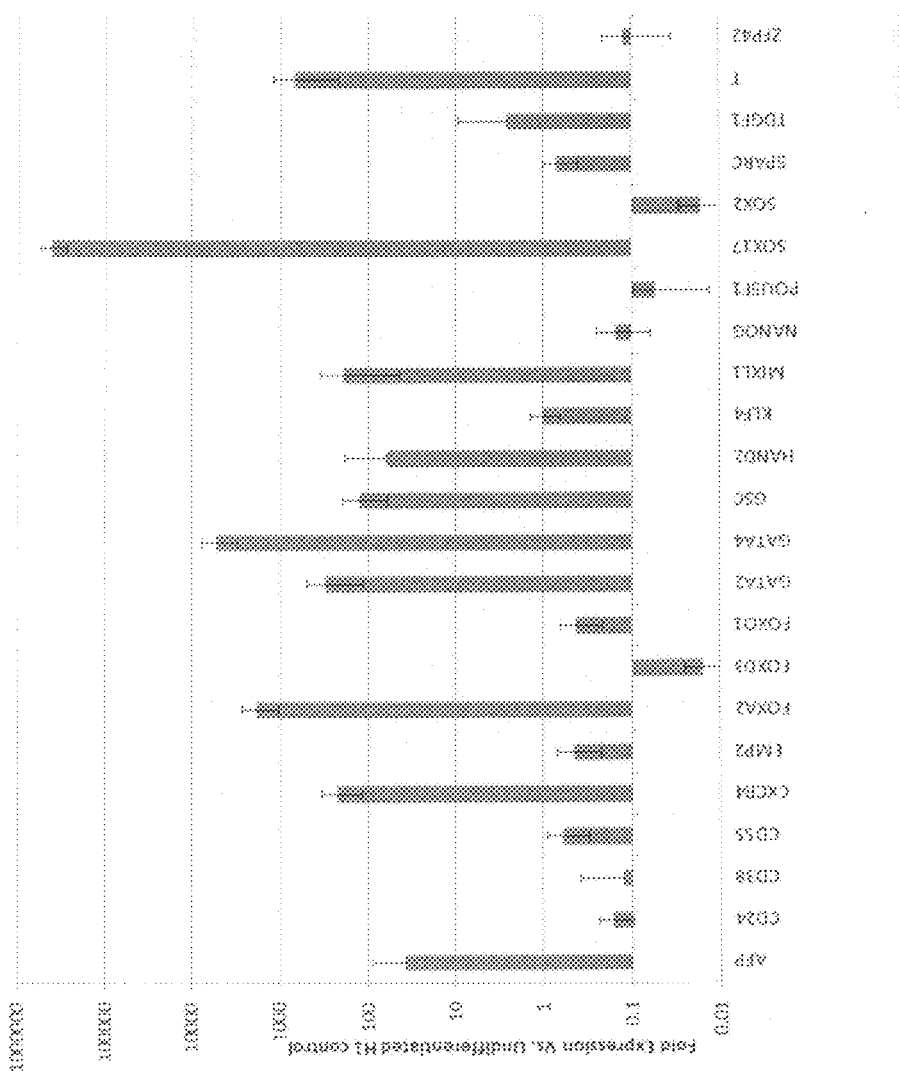

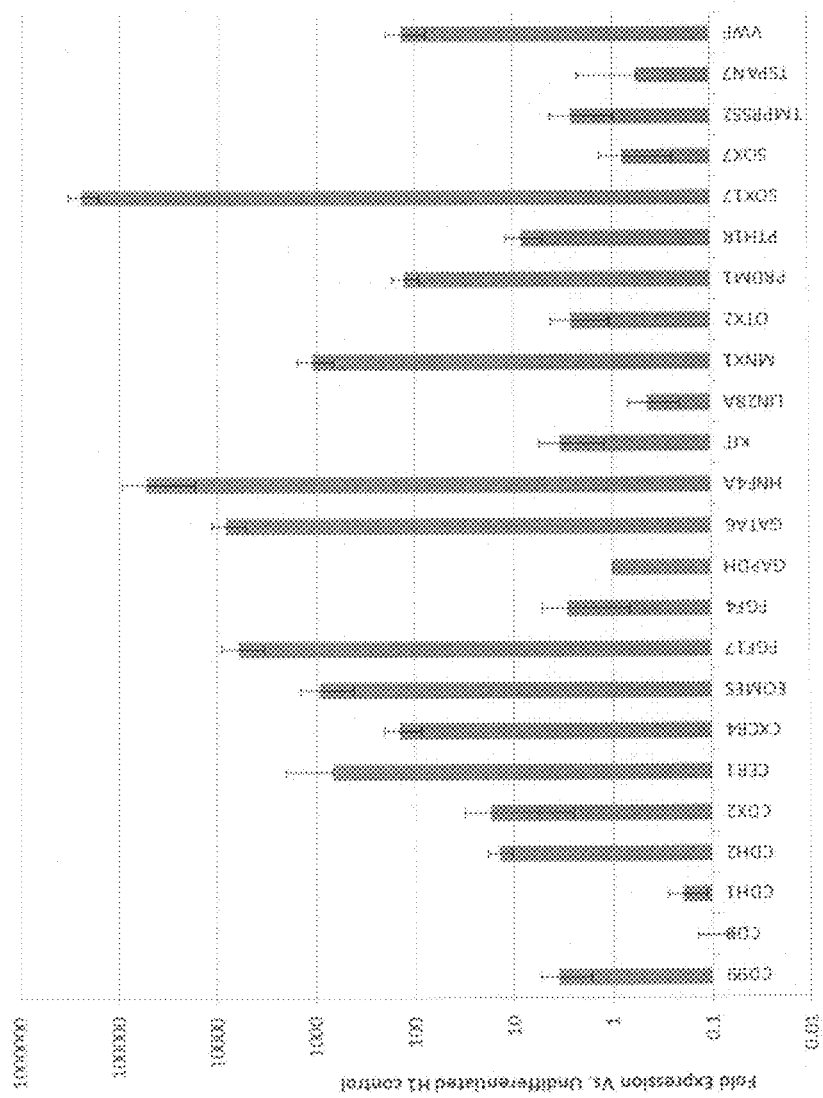
Figure 21: Stage 1 Day 3 expression (n=13, mean ± St. Dev.) by qRT-PCR DE Array

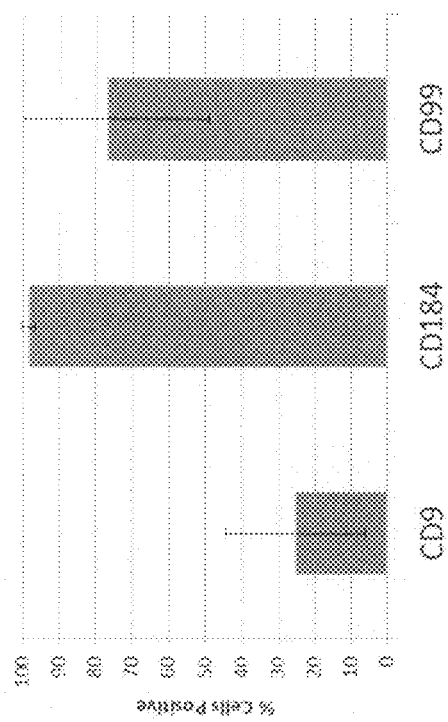
Figure 22: Average FACS results Stage 1 Day 3 (mean ± St. Dev.)

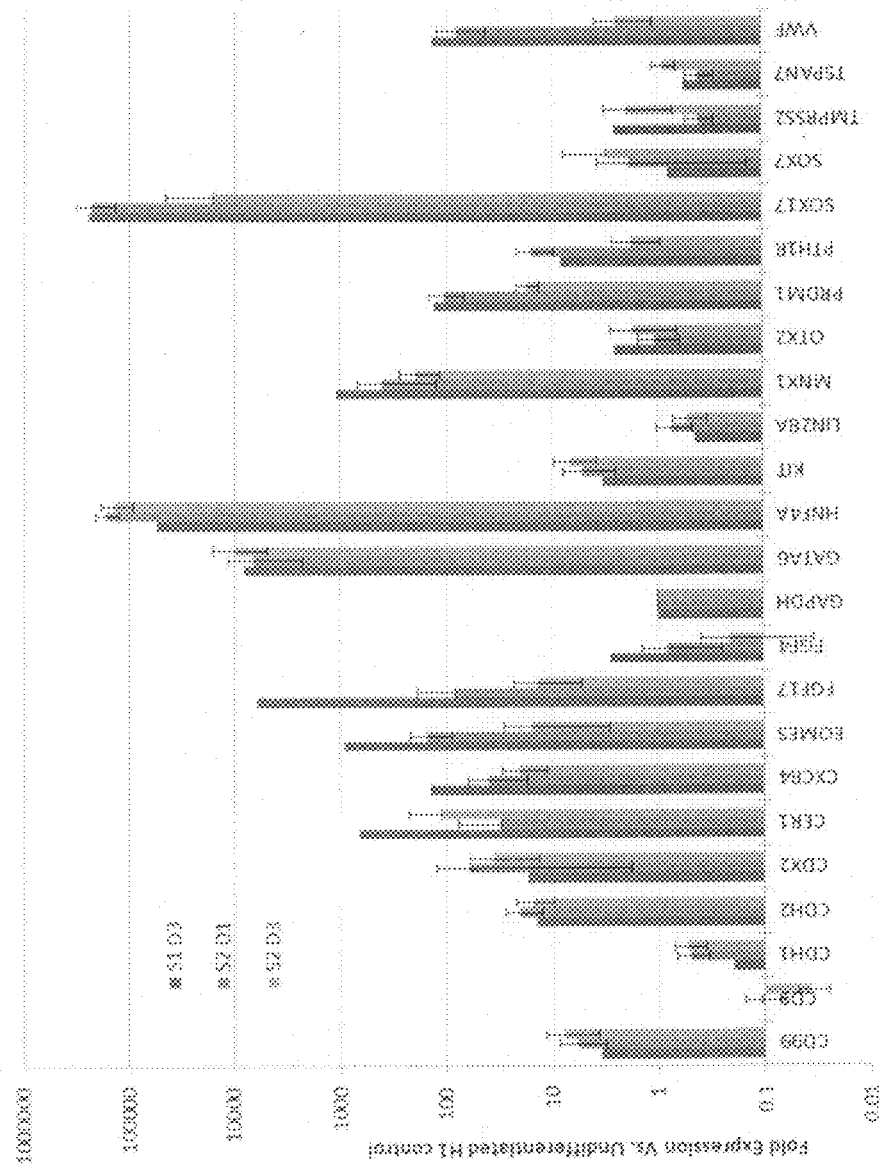
Figure 23: Stage 1 Day 3, Stage 2 Day 1, and Stage 2 Day 3 expression (n=14, mean ± St. Dev.) by qRT-PCR DE Array

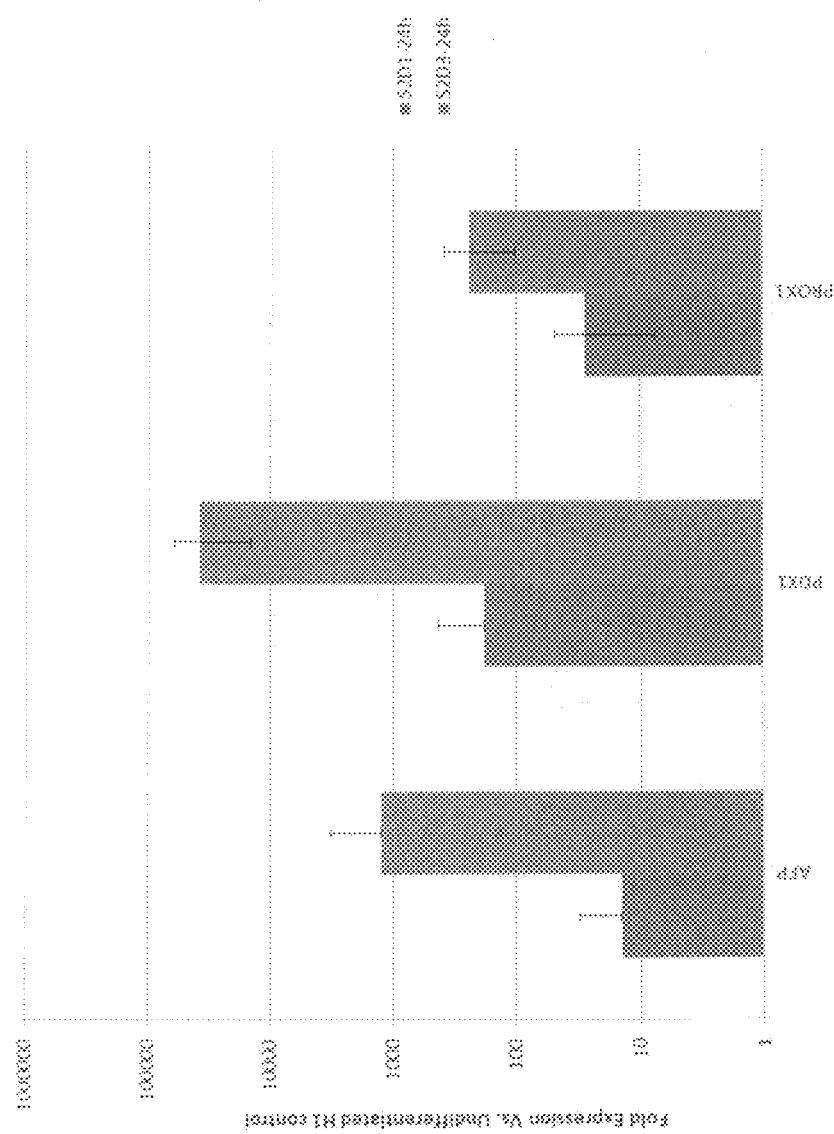
Figure 24: Stage 2 Day 1 and 3 expression (n=12, mean ± St. Dev.) by qRT-PCR GT Array

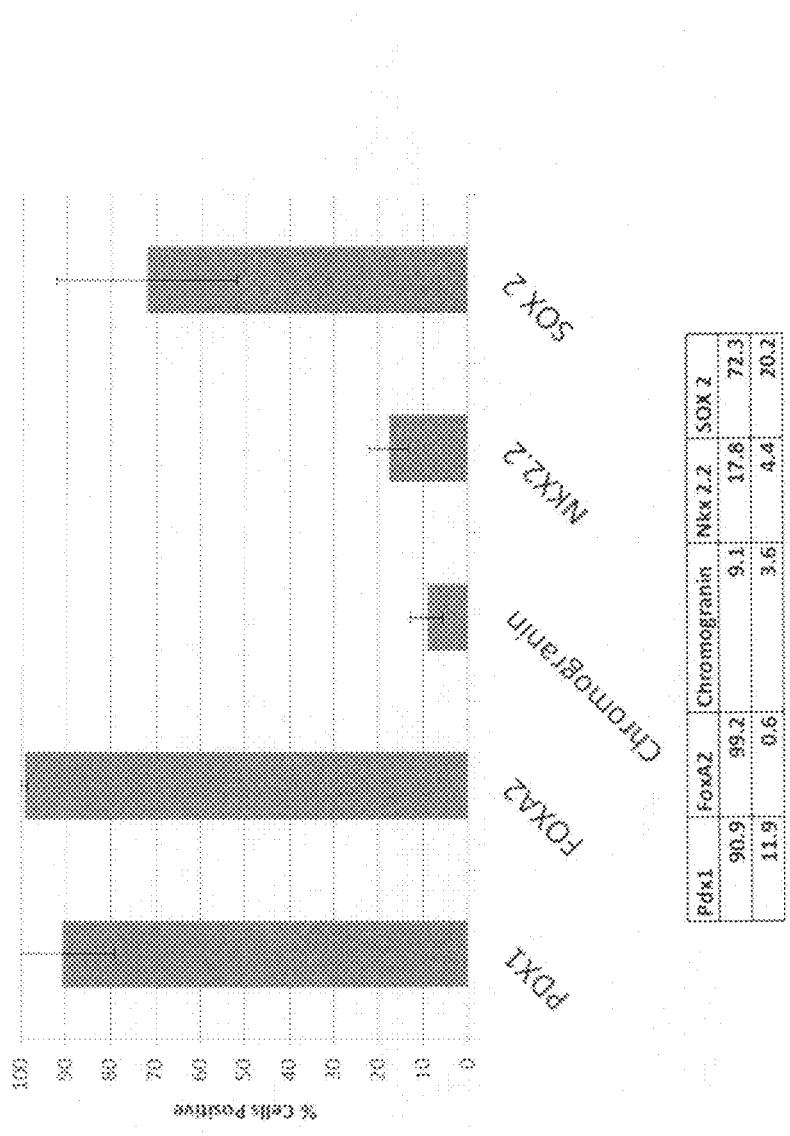
Figure 25: Average FACS results Stage 3 Day 3 (mean ± St. Dev.)

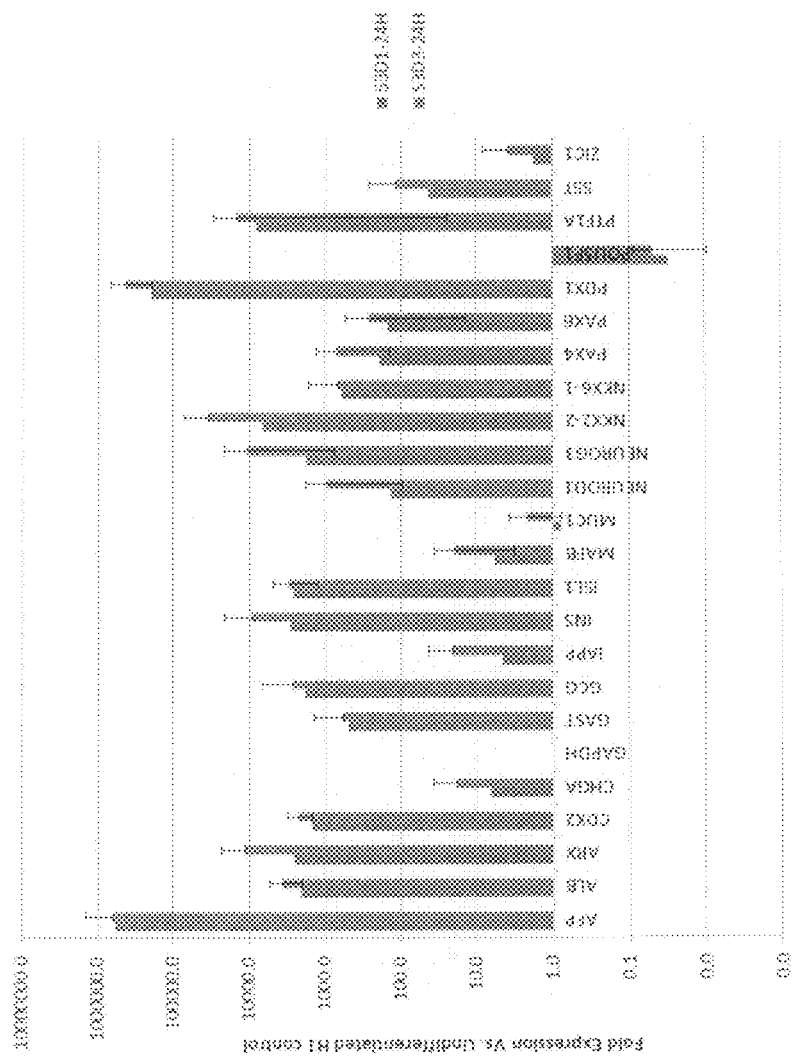

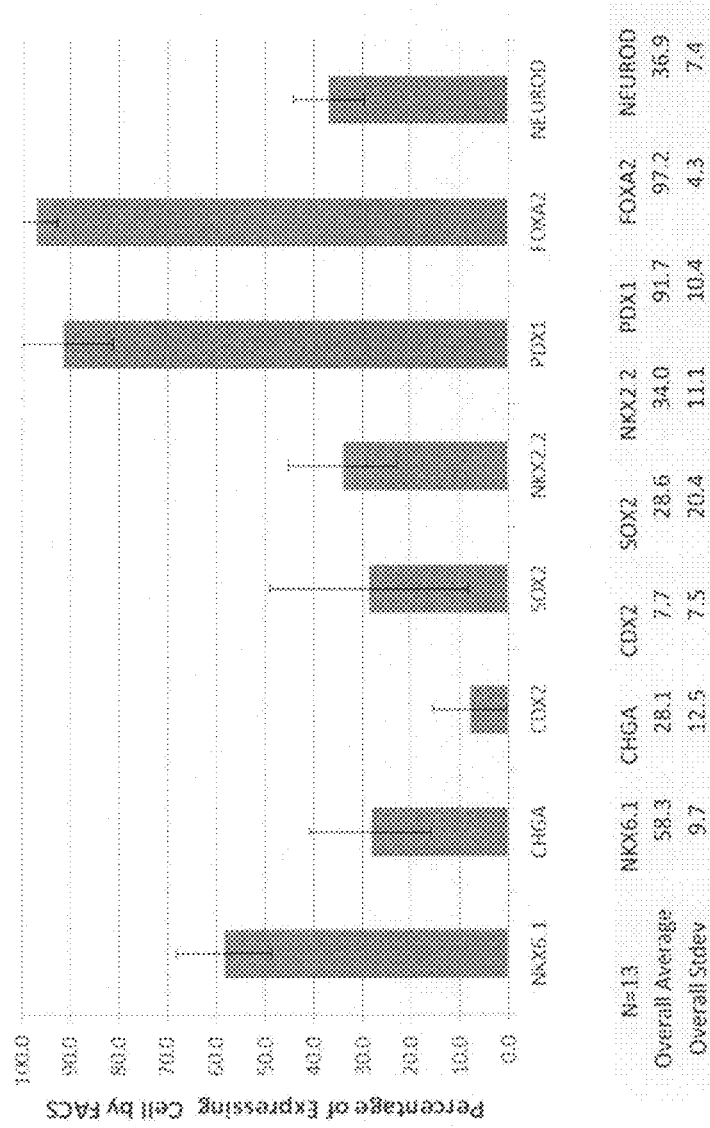
Figure 27: Average FACS results Stage 4 Day 3 (mean ± St. Dev.)

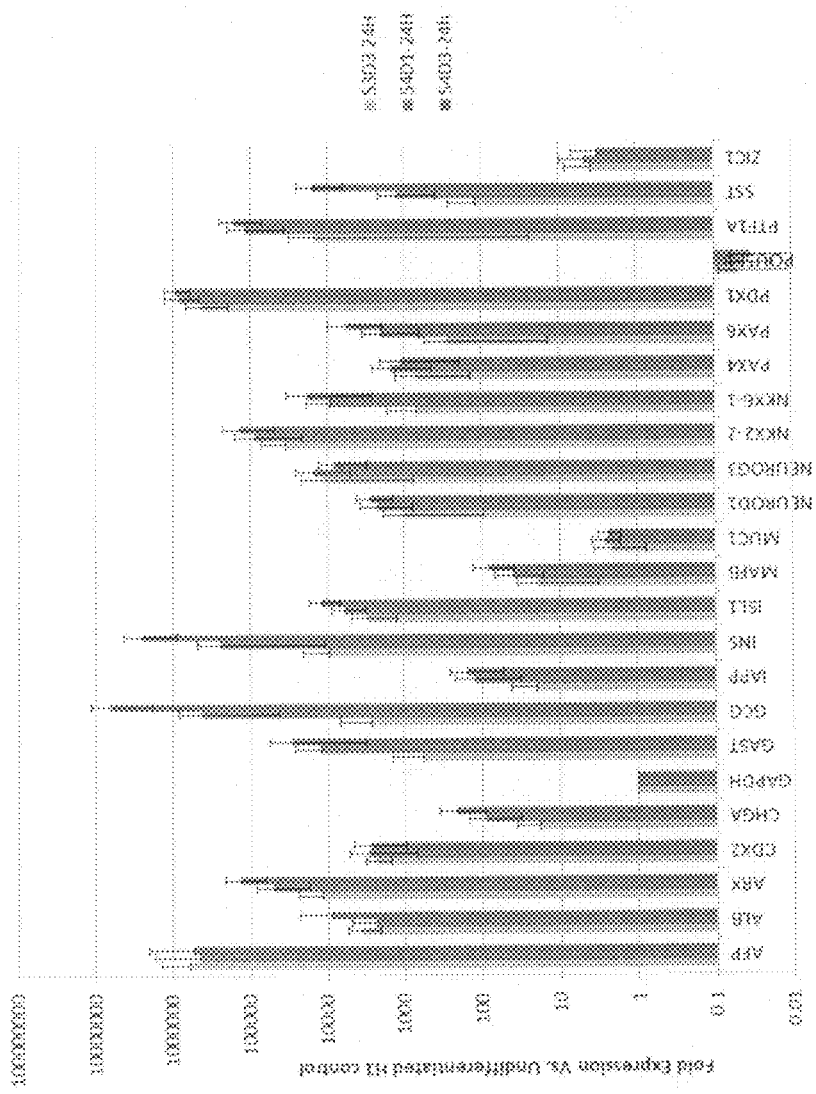
Figure 28: Stage 3 Day 3 and Stage 4 Days 1 and 3 expression (n=14, mean ± St. Dev.) by qRT-PCR S4 Array

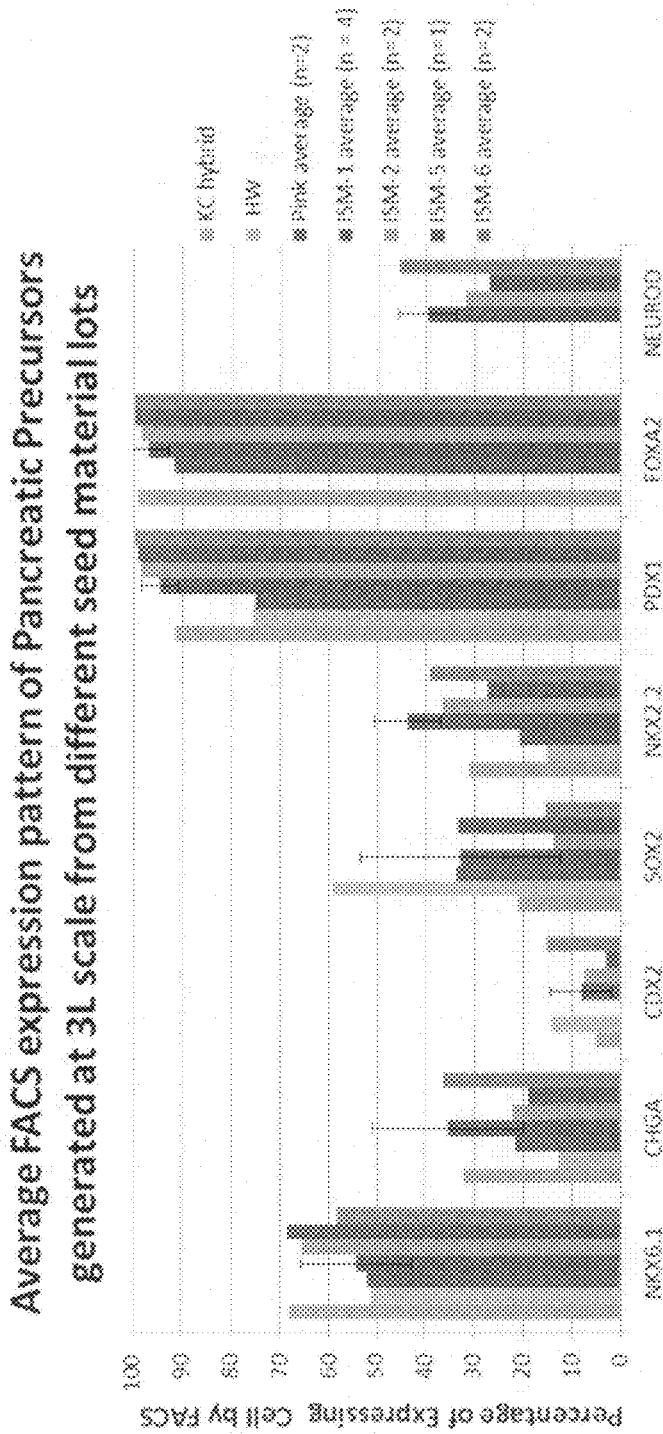
Figure 29: Average FACS results Stage 4 Day 3 (mean ± St. Dev.)

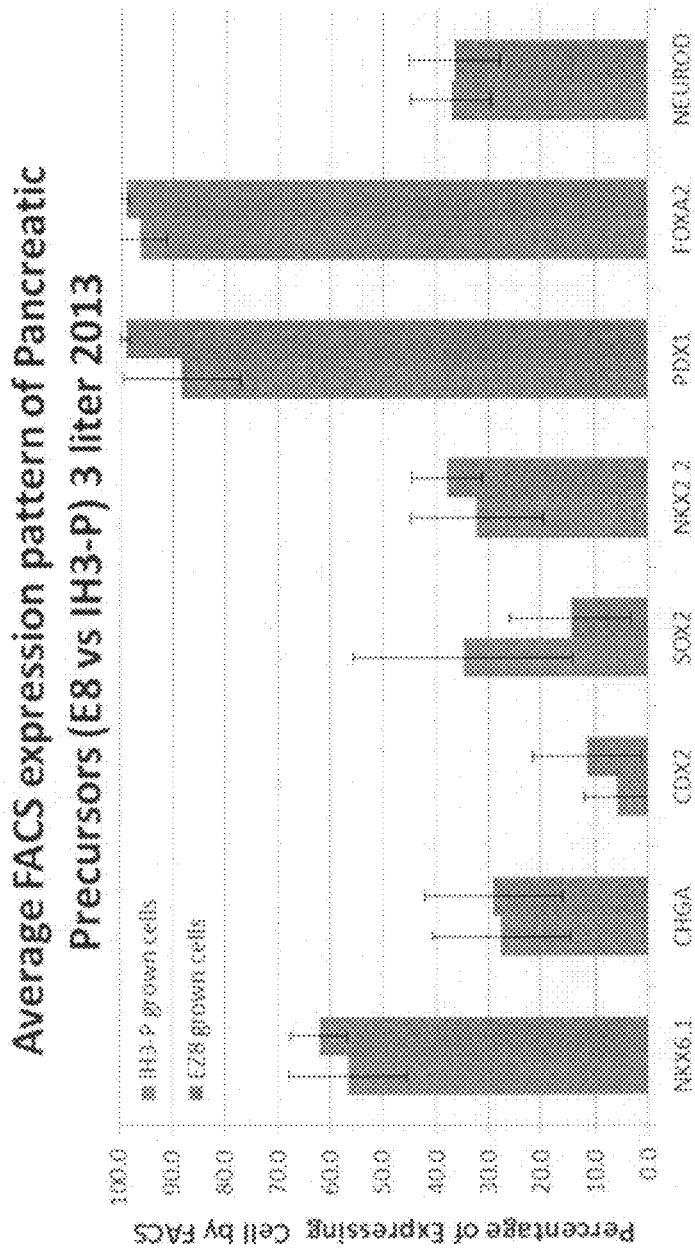

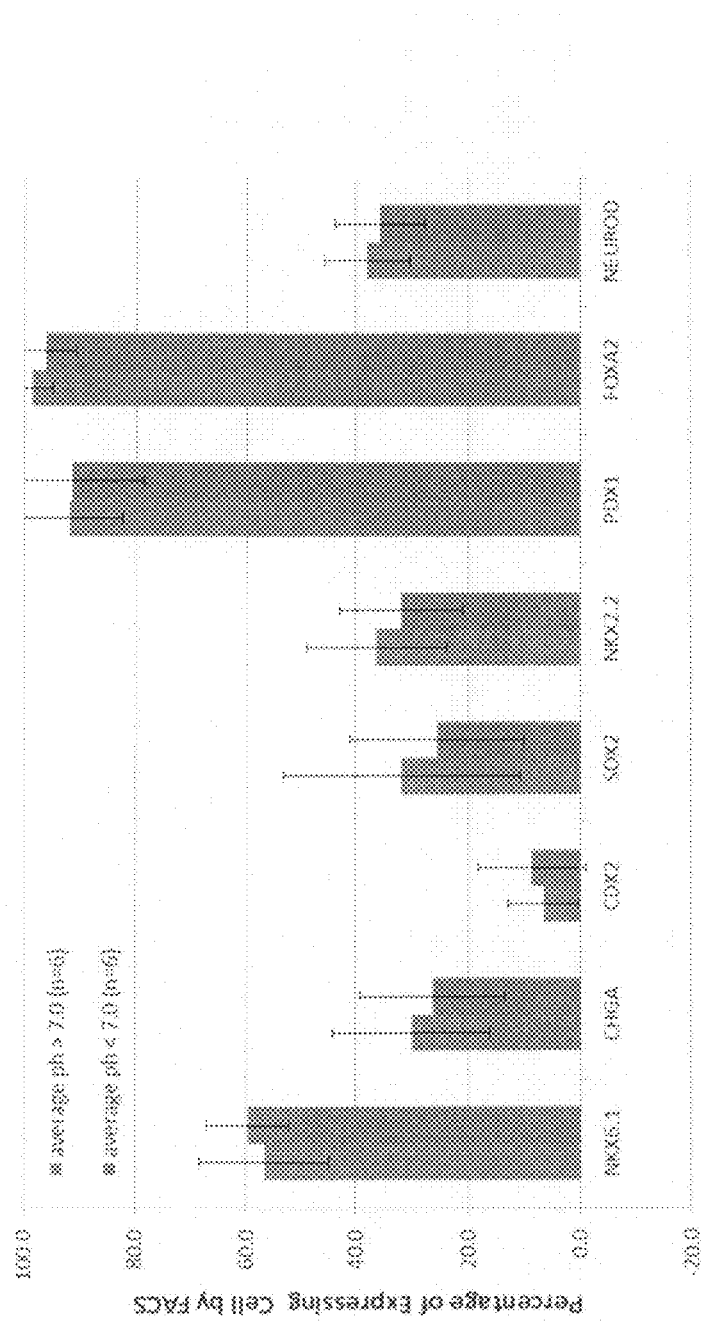

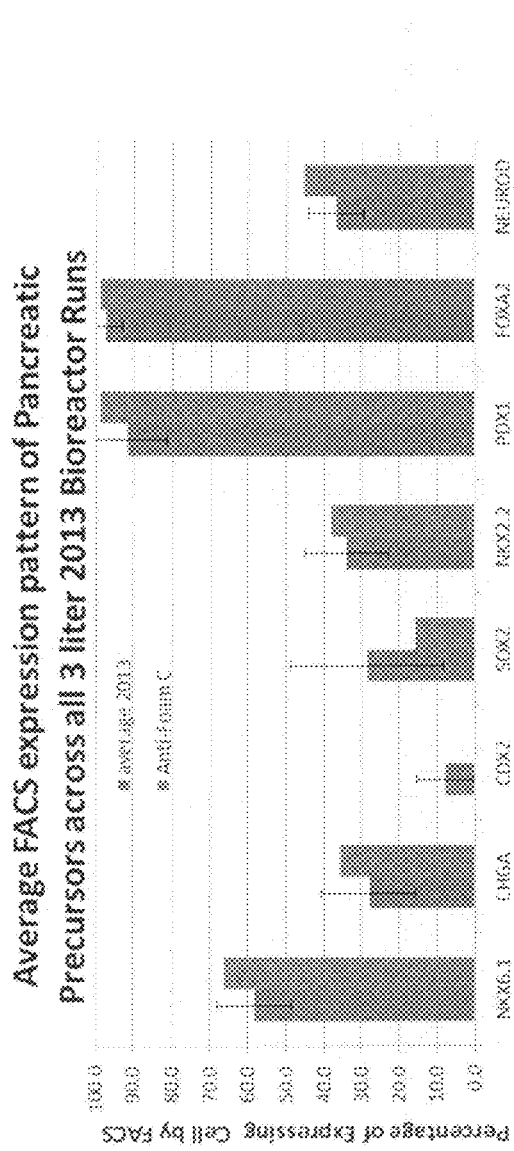
Figure 32: Average FACS results Stage 4 Day 3 (mean ± St. Dev.) vs. Run using Anti-Foam C

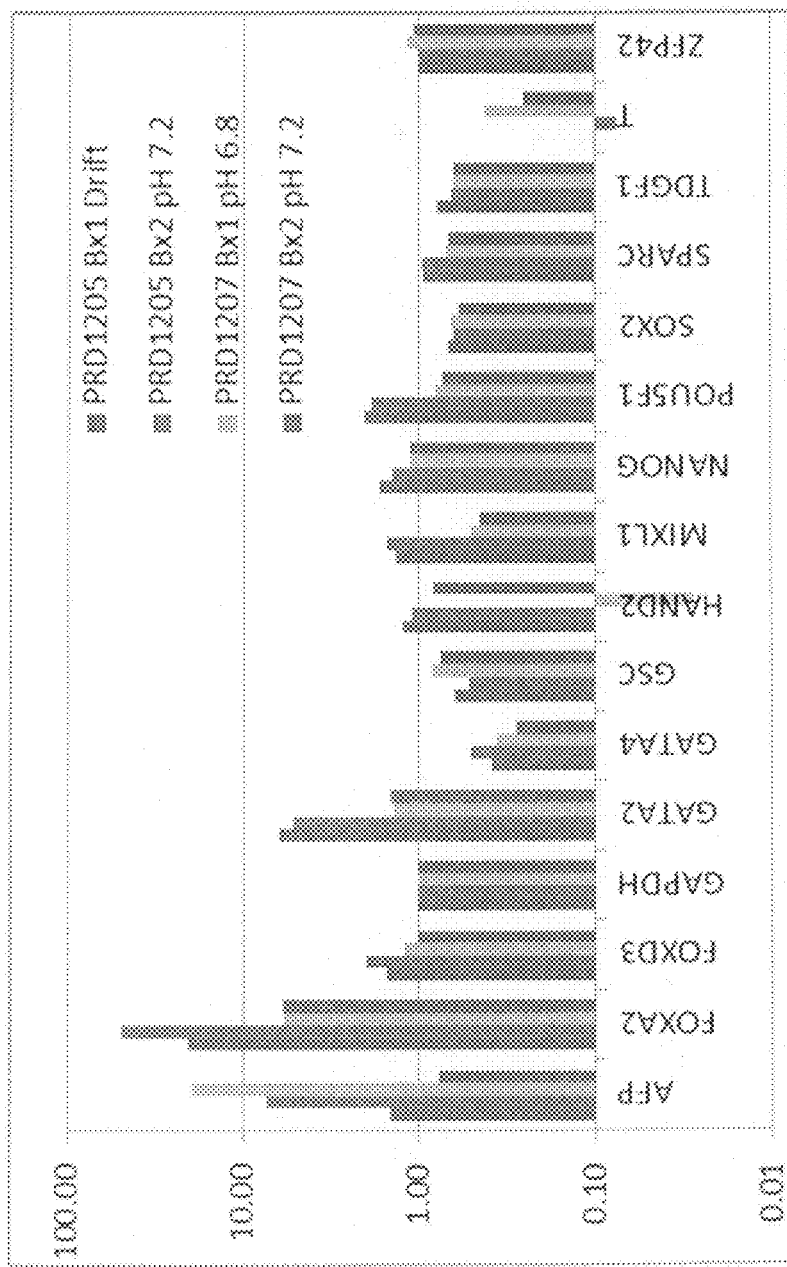
Figure 33: qRT-PCR Expression levels 24 hours prior to start of differentiation

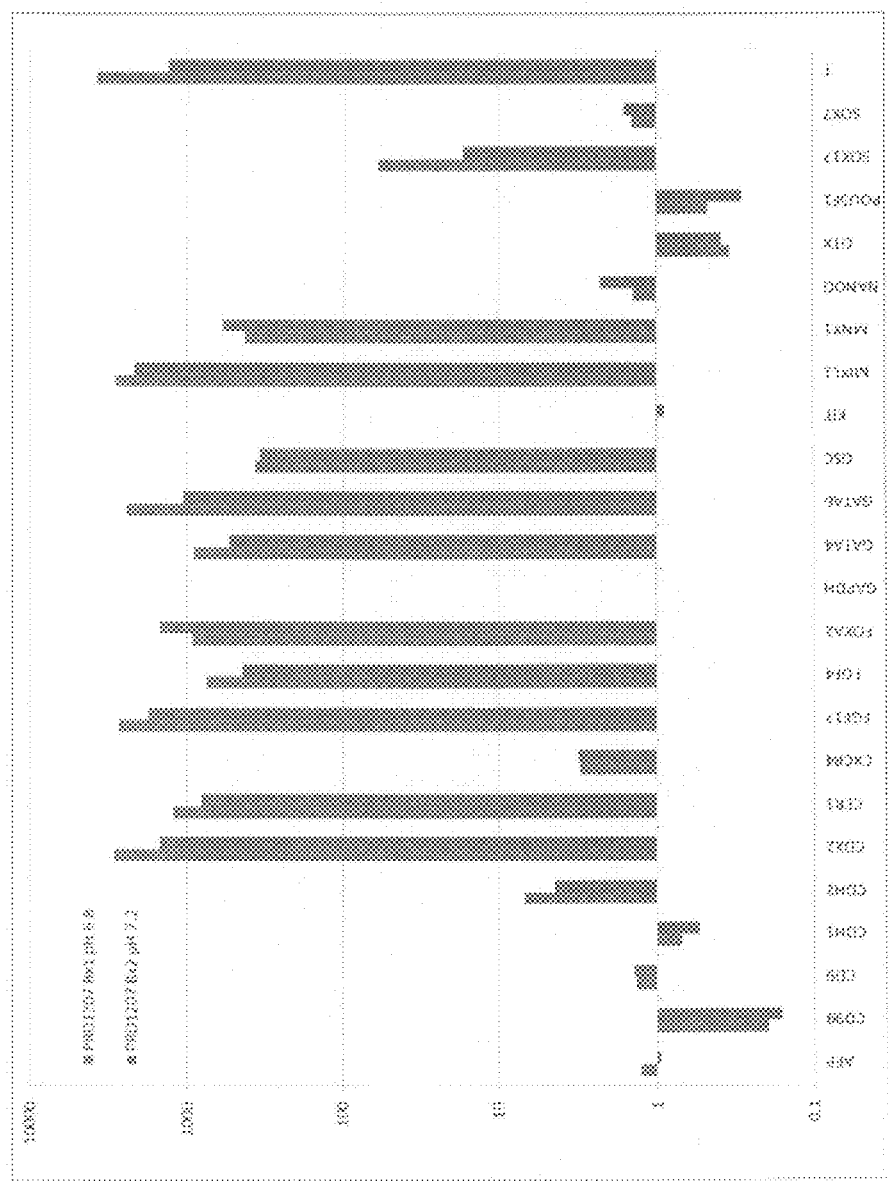
Figure 34: qRT-PCR Expression levels 24 hours after the start of differentiation

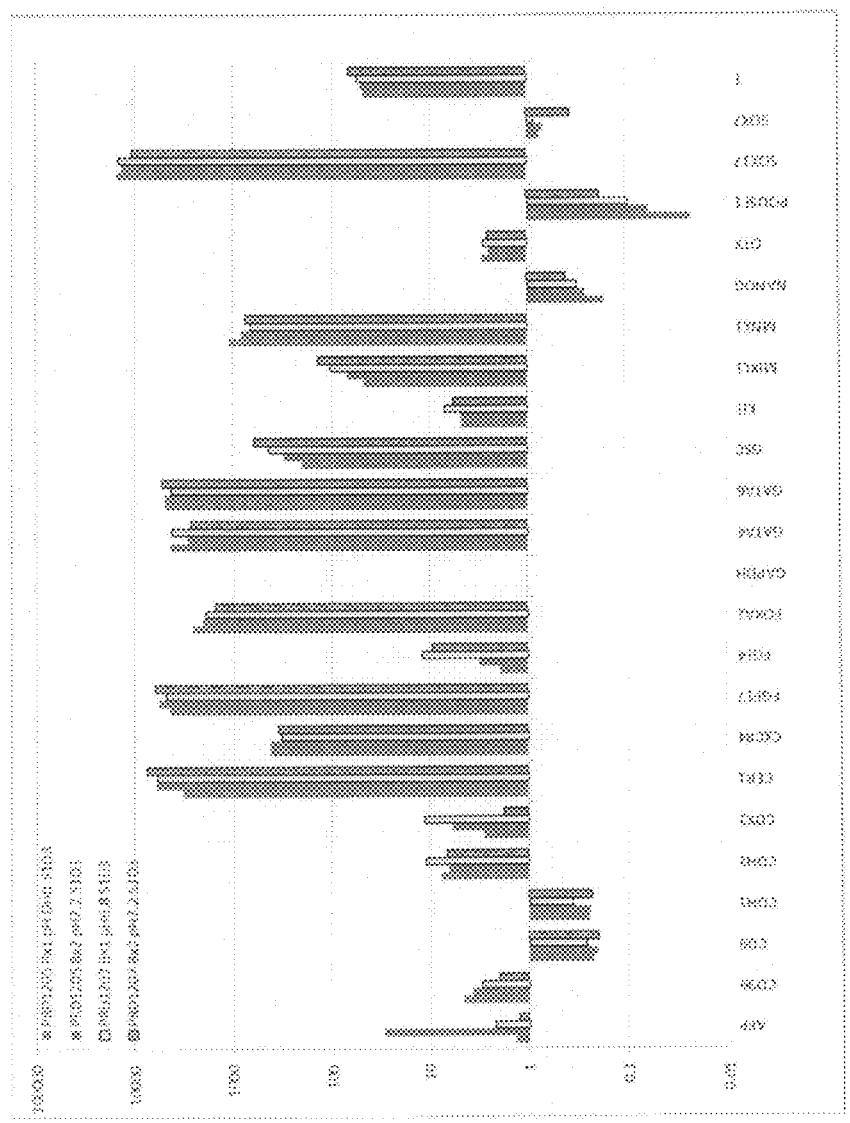
Figure 35: qRT-PCR Expression levels 72 hours after the start of differentiation

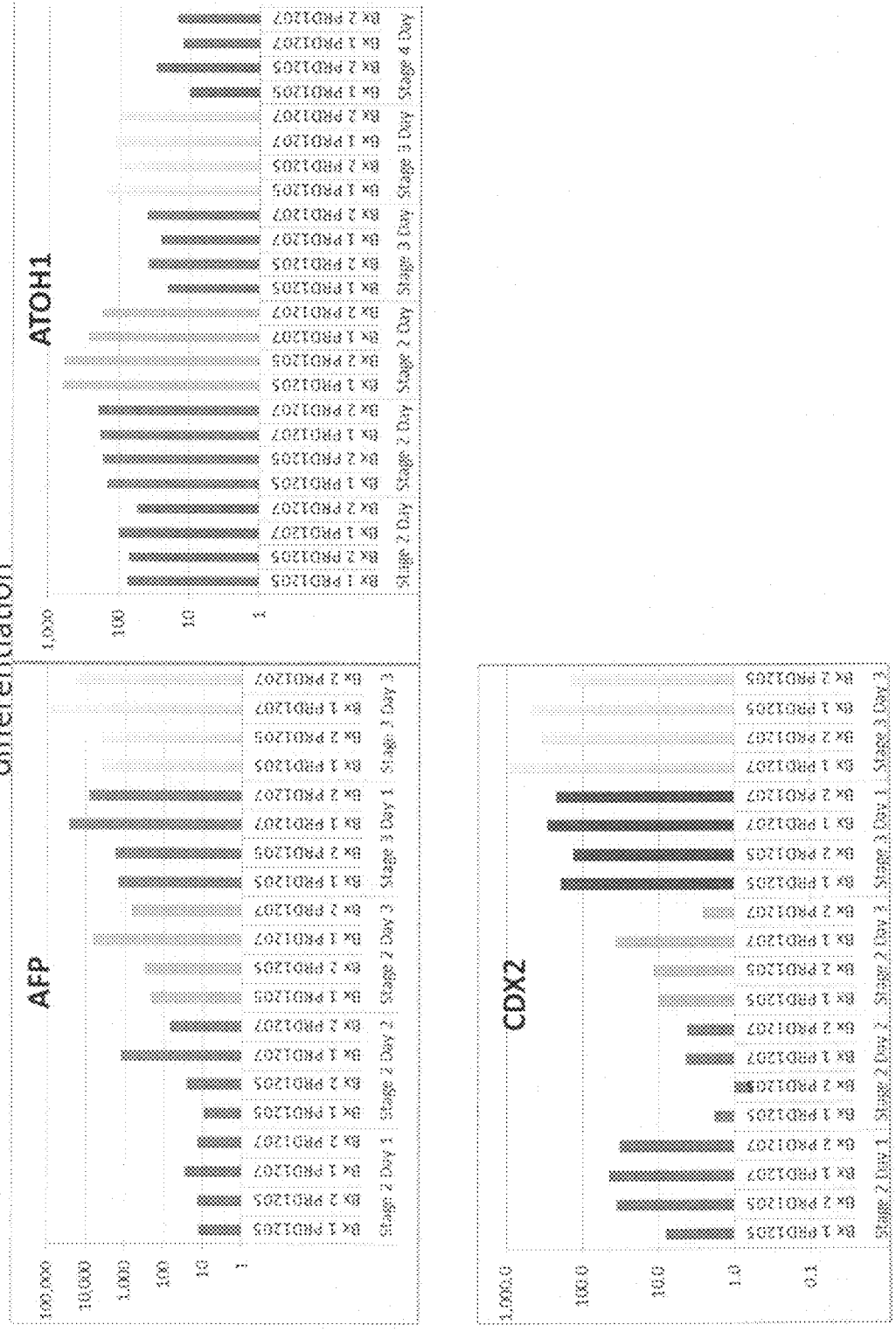

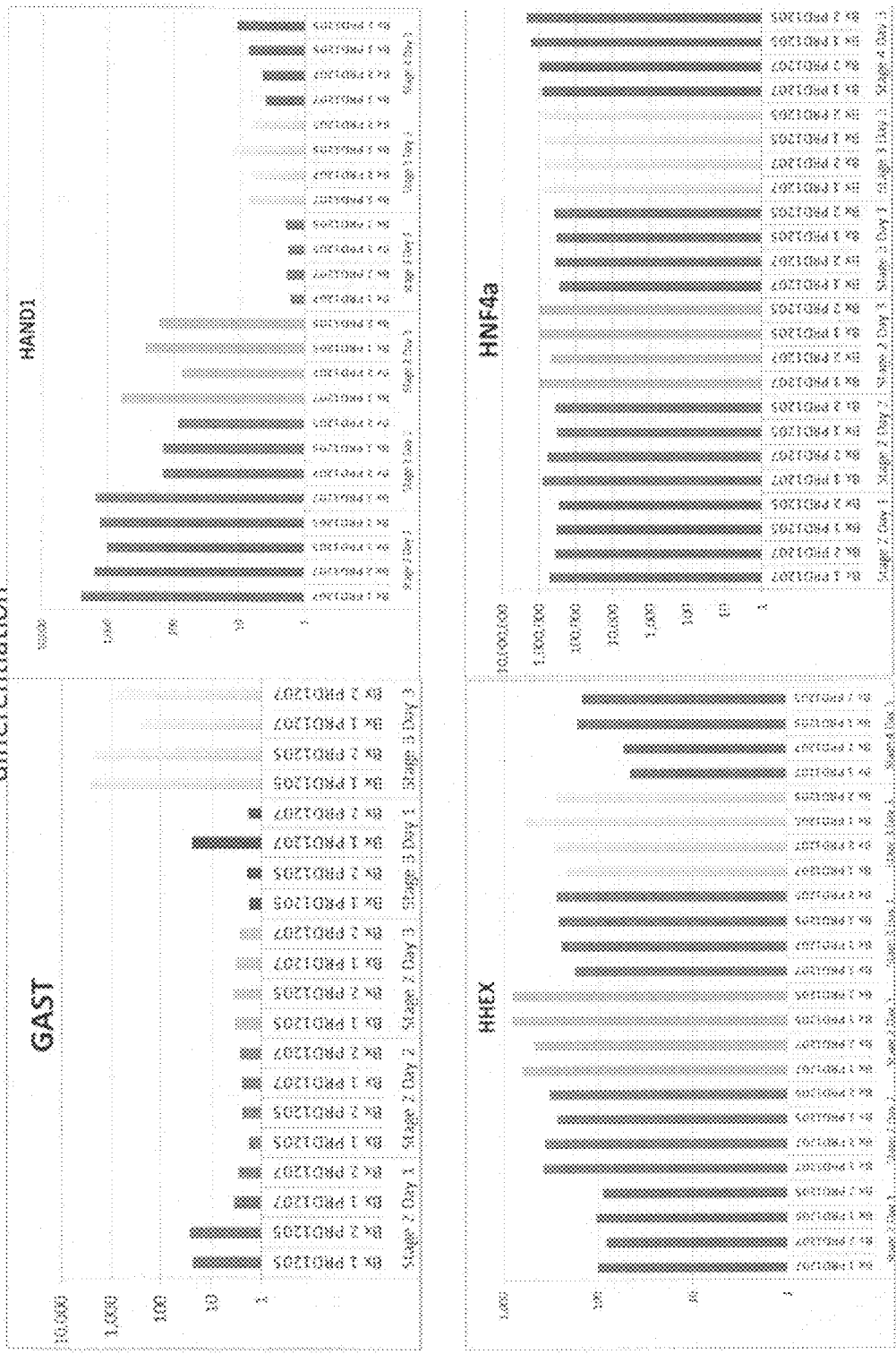

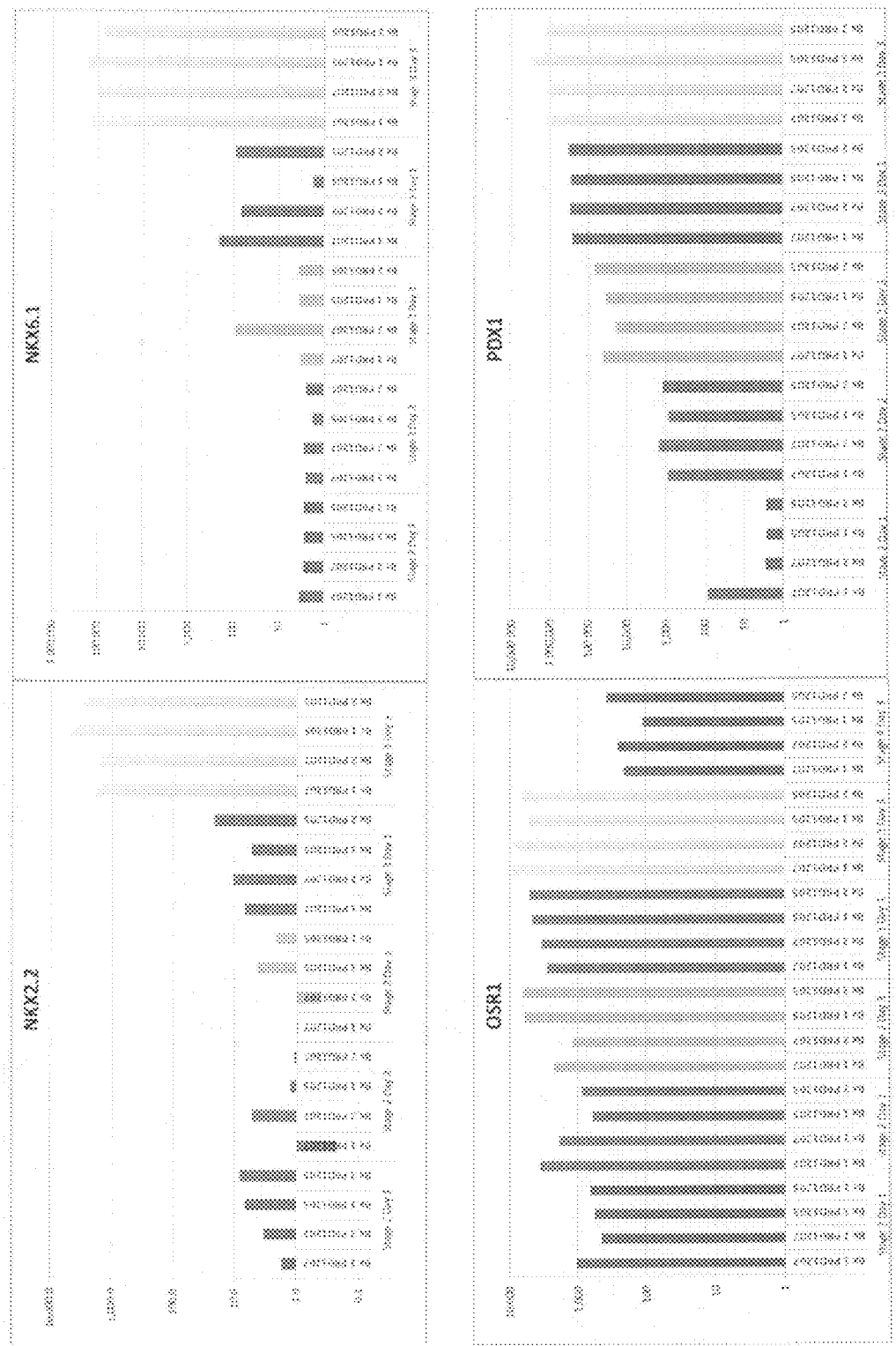
Figure 36(c) cont.: qRT-PCR Expression levels from Stage 2 to Stage 3 and 4 of differentiation

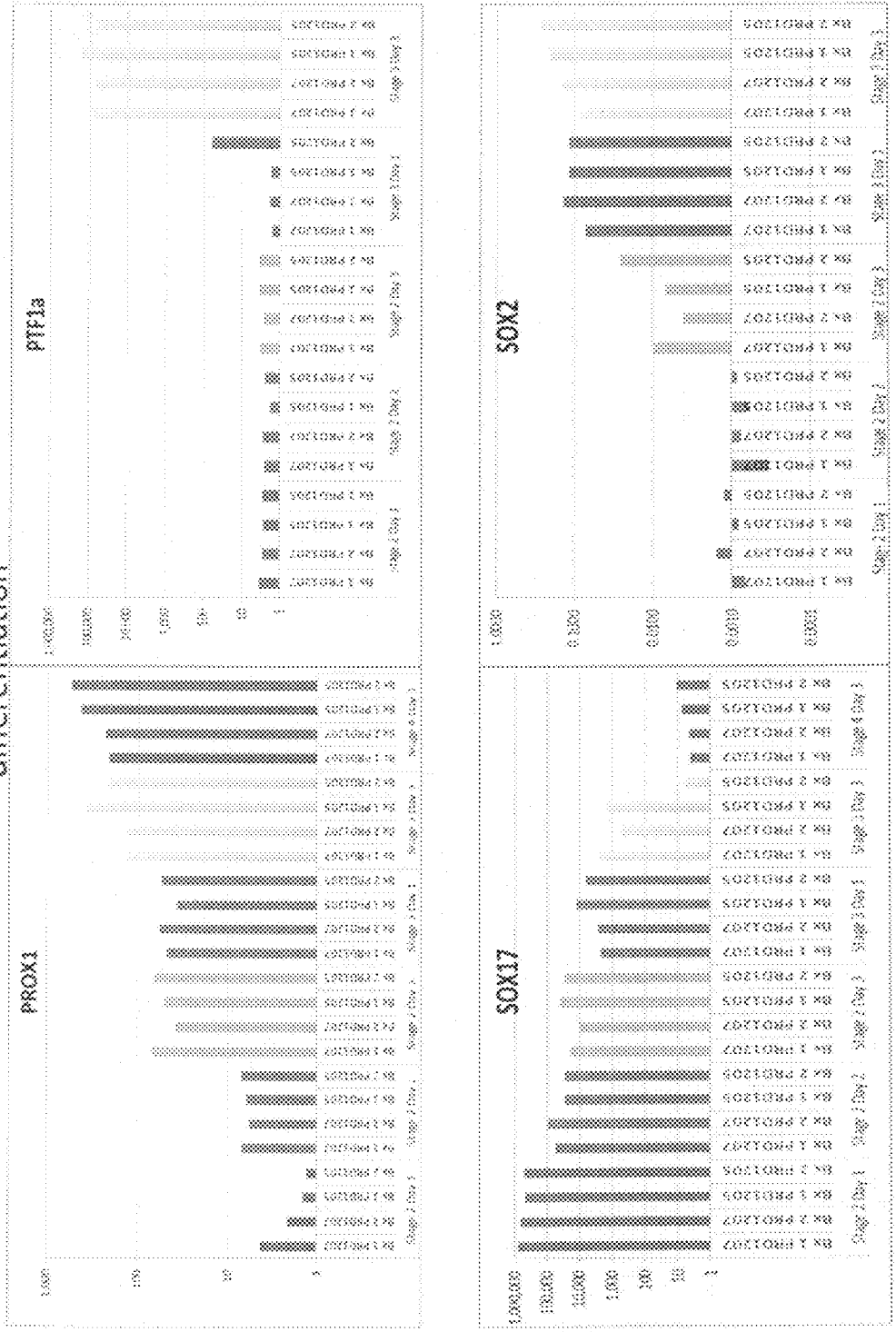
Figure 36(d) cont.: qRT-PCR Expression levels from Stage 2 to Stage 3 and 4 of differentiation

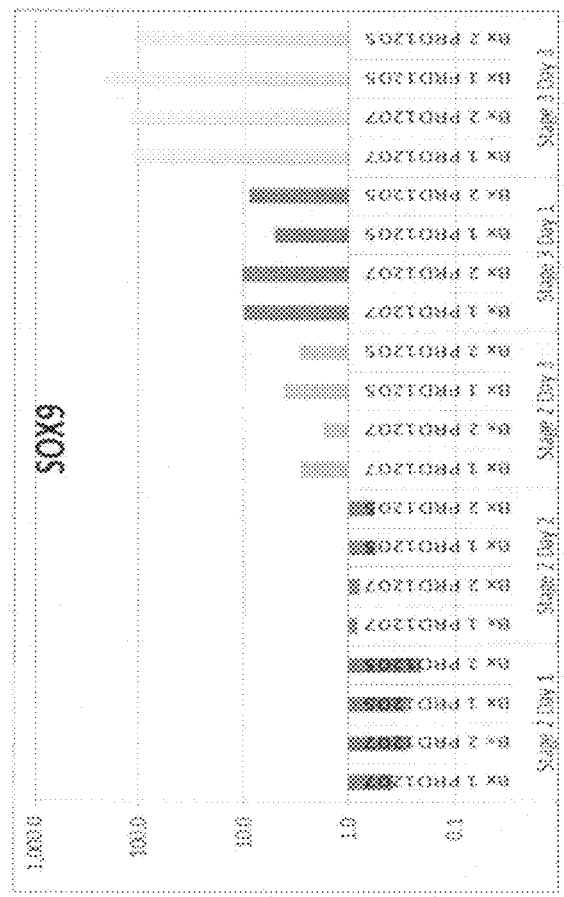
Figure 36(e) cont.: qRT-PCR Expression levels from Stage 2 to Stage 3 and 4 of differentiation

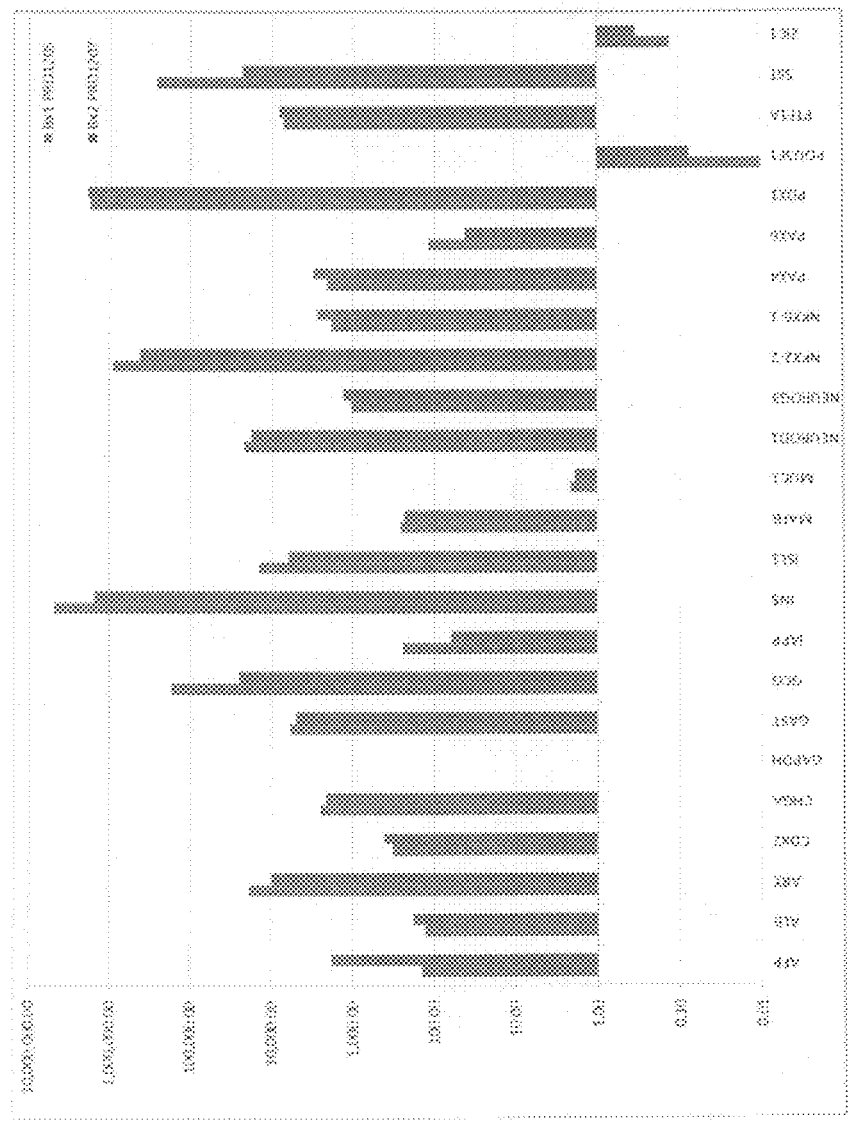
Figure 37: qRT-PCR Expression levels at Stage 4 Day 3 of differentiation

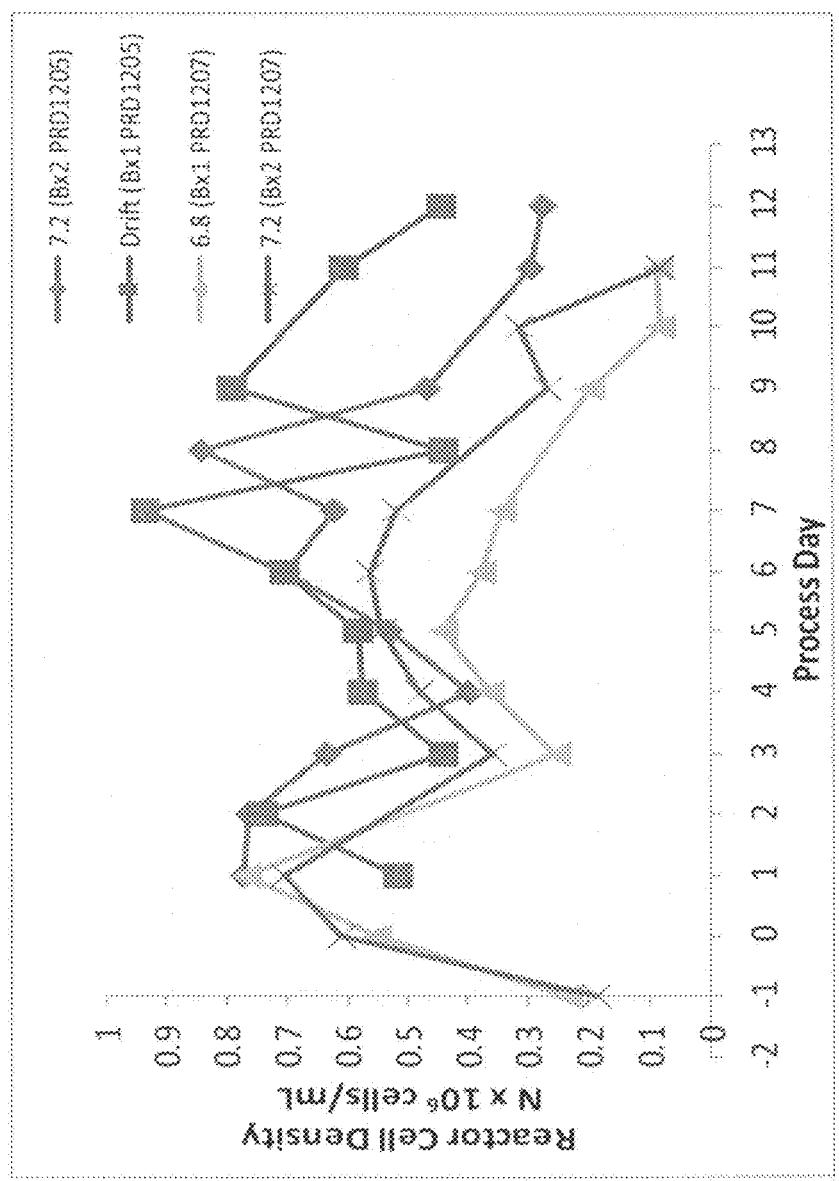
Figure 38: Cell Density in the bioreactor

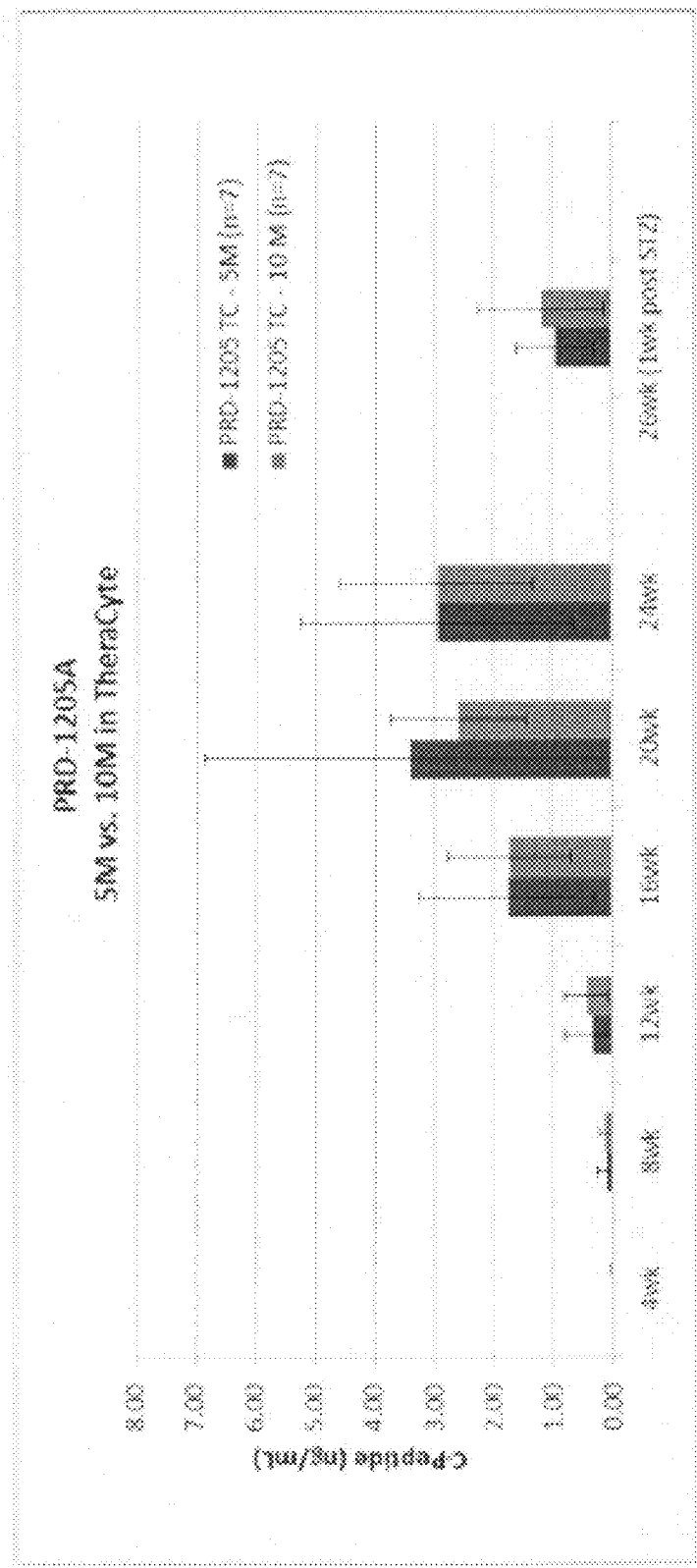
Figure 39(a): Stage 4 Day 3 bioreactor product function *in vivo*

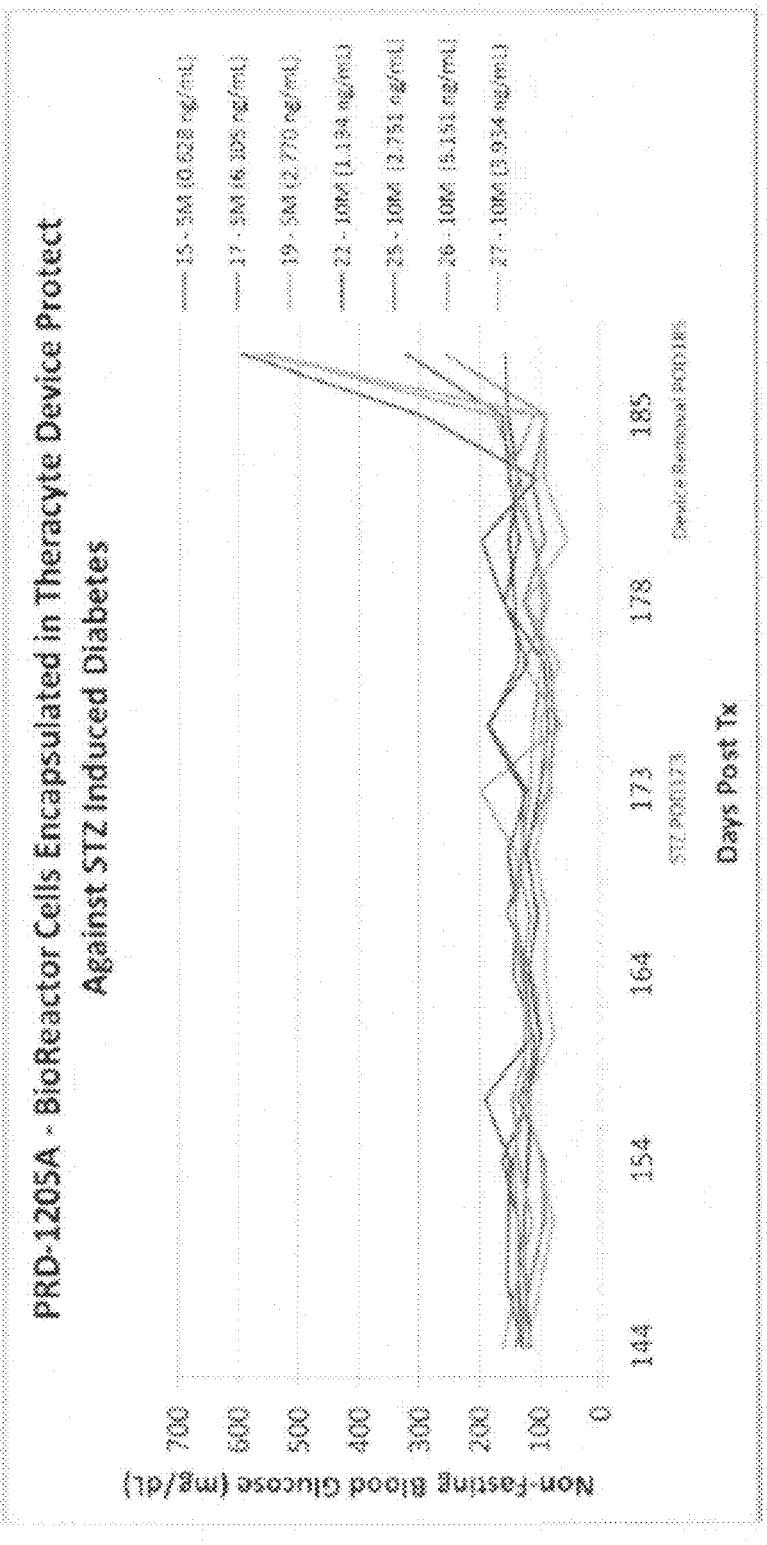
Figure 39(b): Stage 4 Day 3 bioreactor product function *in vivo*

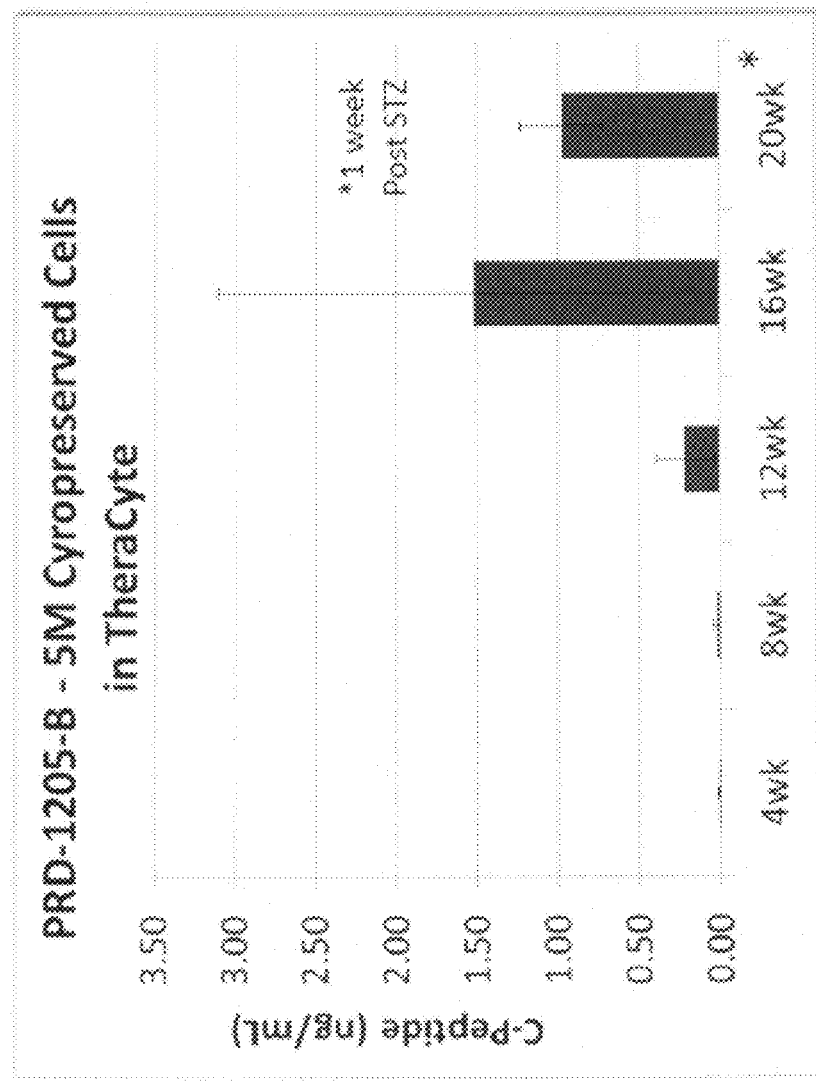
Figure 39(c): Stage 4 Day 3 bioreactor product function *in vivo*

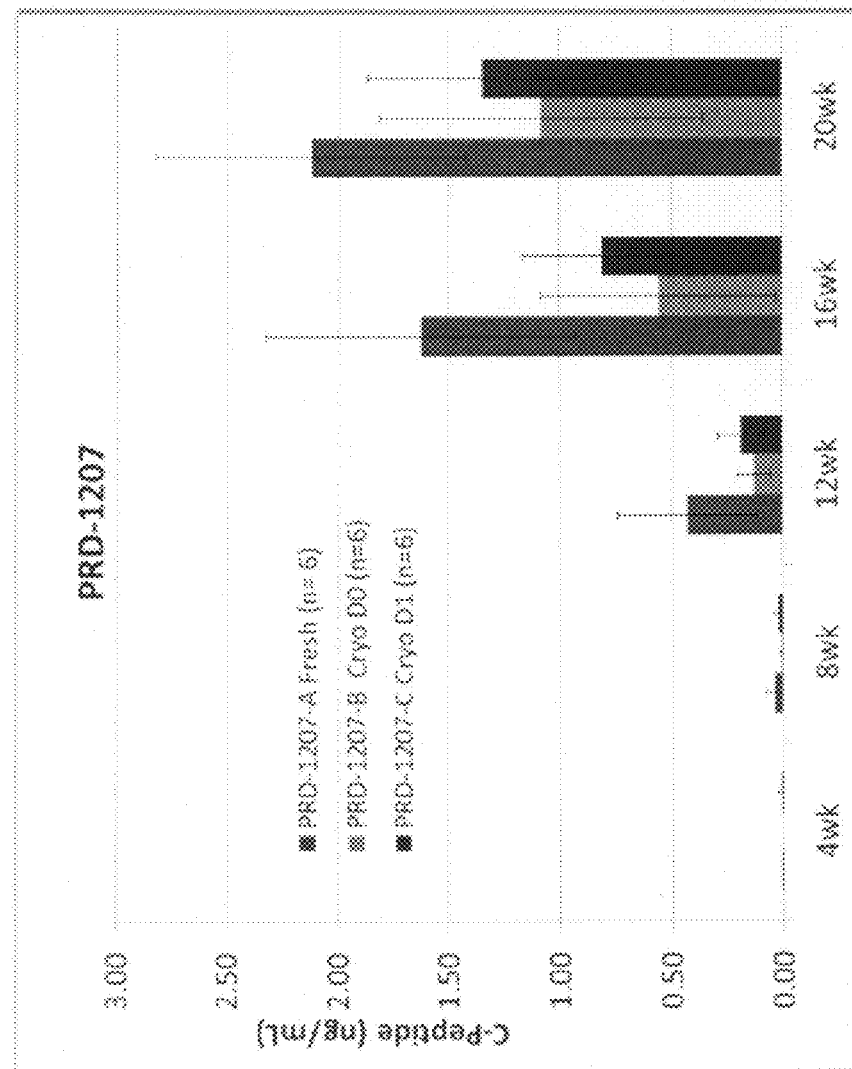
Figure 39(d): Stage 4 Day 3 bioreactor product function *in vivo*

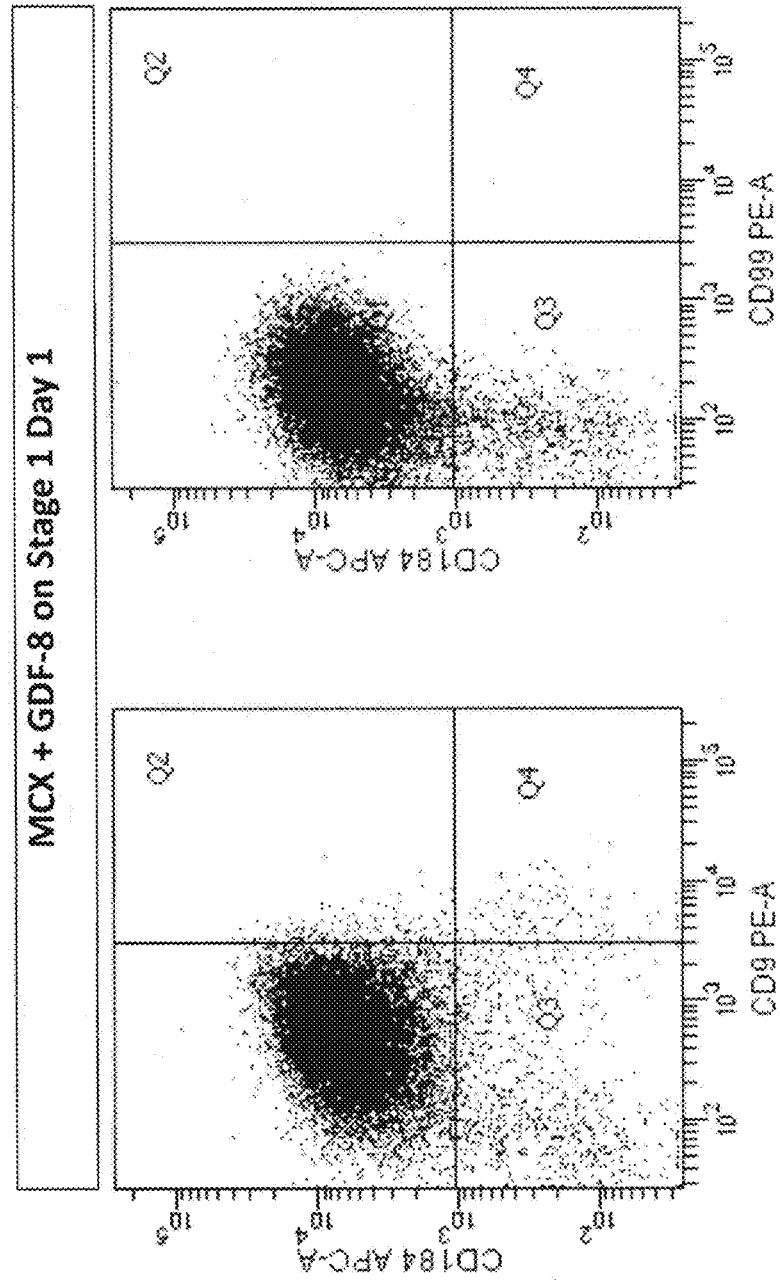

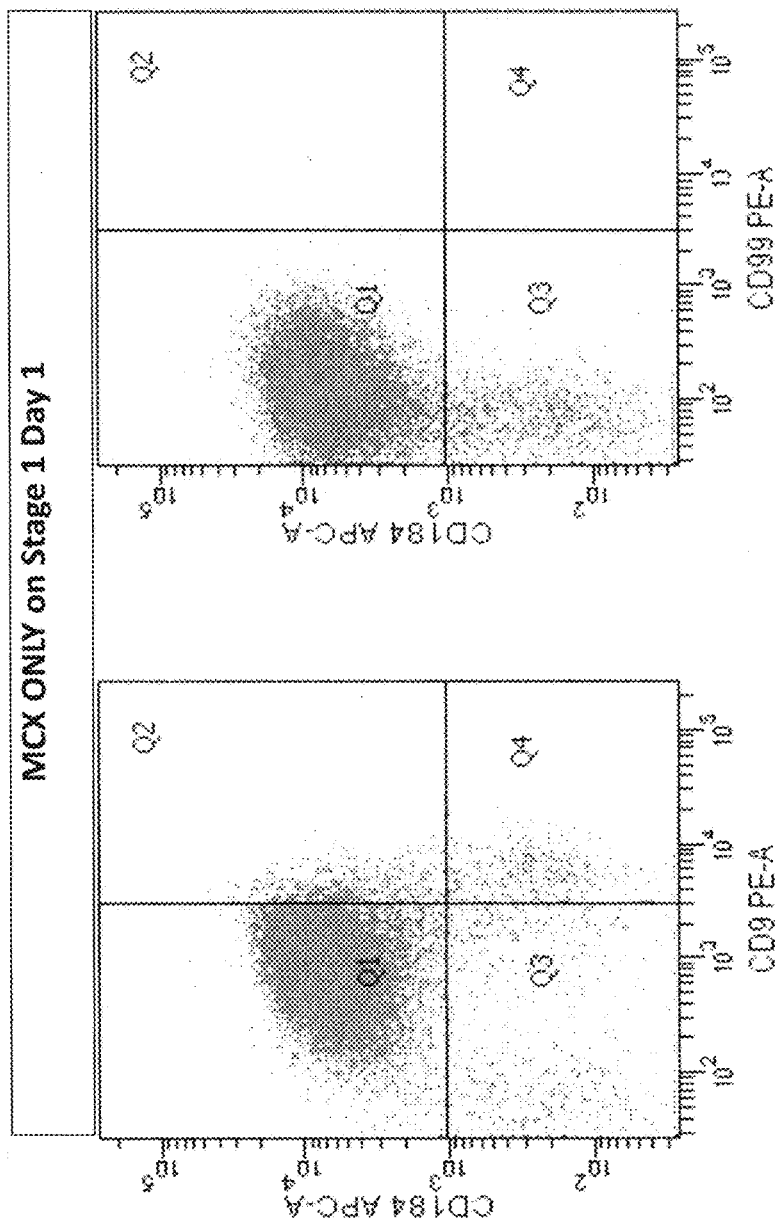

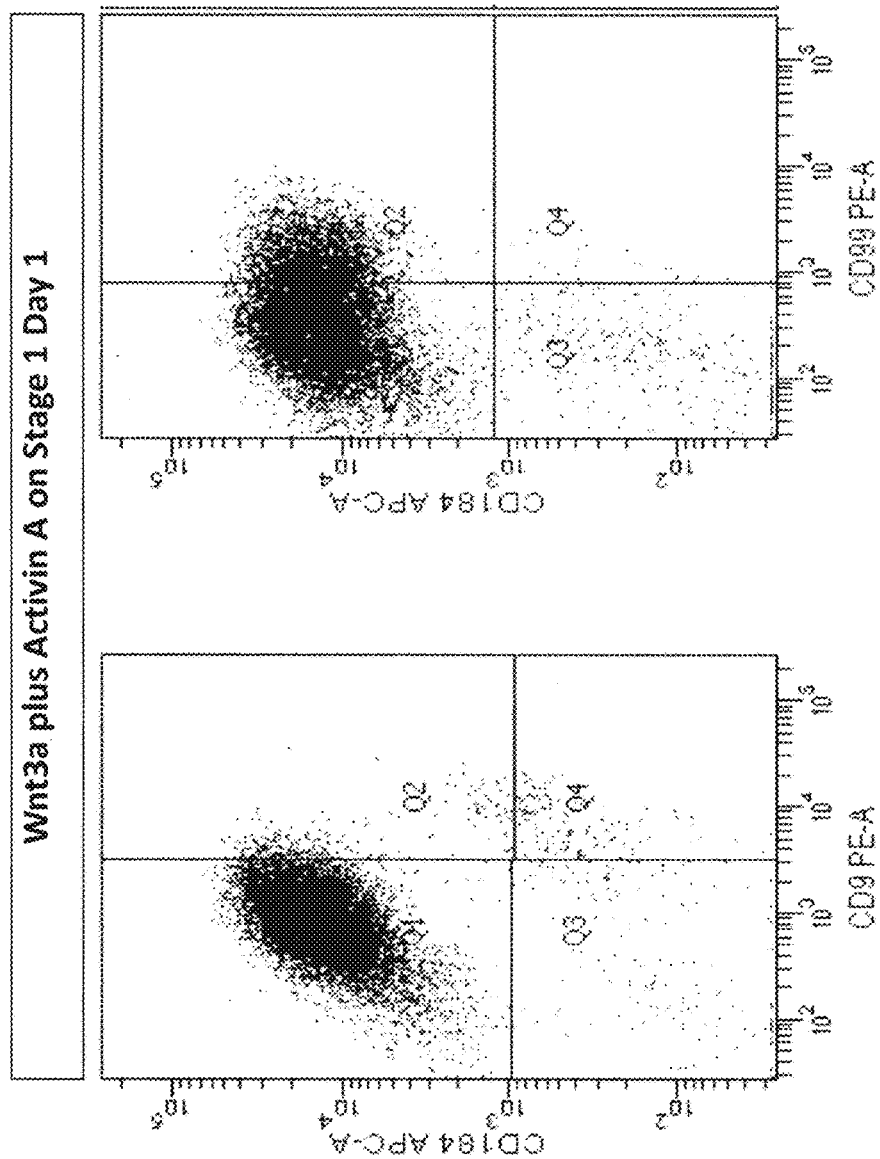

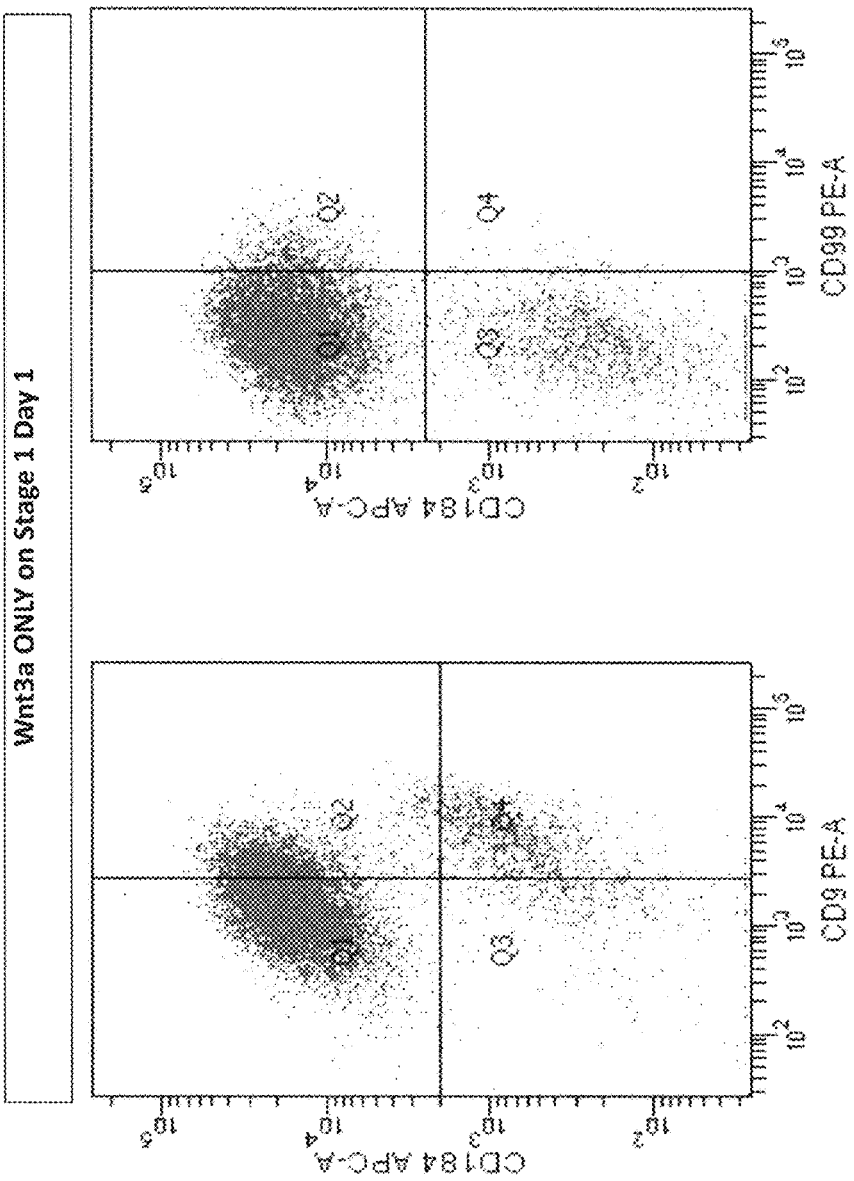

Figure 45: Daily Counts for Cell Density

Figure 46: Daily Media Sampling for pH

Figure 47: Daily Media Sampling for glucose (g/L)

Figure 48: Daily Media Sampling for lactate (g/L)

Figure 49: Daily Stage 0 and 1 Expression by qRT-PCR, Pluripotency Array

Figure 52: Definitive Endoderm Cell Expression by FACS

Figure 54: Daily Stage 2 and 3 Expression by qRT-PCR

Figure 68

| Stage | Description | GAPDH-Hs99999905_m1 | | | |
|---|---|---|---|---|---|
| | | Average of ddCT | Average of CT | StdDev of CT | StdDev of ddCT |
| 0H | ES | 1 | 16.28166375 | 0 | 0.063779971 |
| 6H | MCX | 1 | 17.167675 | 0 | 0.129679848 |
| | MCX + GDF8 | 1 | 18.7342185 | 0 | 0.343617126 |
| | GDF8 | 1 | 18.18648575 | 0 | 0.592686651 |
| | Neat | 1 | 18.7712783 | 0 | 0.120809901 |
| | AA + Wnt3A | 1 | 17.017828 | 0 | 0.320456551 |
| | Wnt3A | 1 | 18.310278 | 0 | 0.590436991 |
| 24H | MCX | 1 | 17.57825175 | 0 | 0.225765407 |
| | MCX + GDF8 | 1 | 17.4673155 | 0 | 0.1874731 |
| | GDF8 | 1 | 16.830046 | 0 | 0.191957571 |
| | Neat | 1 | 18.137209 | 0 | 0.172746894 |
| | AA + Wnt3A | 1 | 17.464121 | 0 | 0.048572579 |
| | Wnt3A | 1 | 17.842105 | 0 | 0.149329638 |
| 30H | MCX | 1 | 17.55899375 | 0 | 0.161380506 |
| | MCX + GDF8 | 1 | 18.367942 | 0 | 0.100658065 |
| | GDF8 | 1 | 17.879352 | 0 | 0.412868336 |
| | Neat | 1 | 17.94854725 | 0 | 0.249840271 |
| | AA + Wnt3A | 1 | 17.271180625 | 0 | 0.452296256 |
| | Wnt3A | 1 | 17.7675545 | 0 | 0.394262235 |
| 48H | MCX | 1 | 18.28386925 | 0 | 0.349895174 |
| | MCX + GDF8 | 1 | 18.804283 | 0 | 0.945447728 |
| | GDF8 | 1 | 17.450945 | 0 | 0.342614449 |
| | Neat | 1 | 17.95062605 | 0 | 0.32497567 |
| | AA + Wnt3A | 1 | 17.670651 | 0 | 0.049015228 |
| | Wnt3A | 1 | 17.688332 | 0 | 0.819963852 |
| 72H | MCX | 1 | 17.94318925 | 0 | 0.490391634 |
| | MCX + GDF8 | 1 | 19.19202475 | 0 | 0.40705415 |
| | GDF8 | 1 | 18.0303185 | 0 | 0.141377516 |
| | Neat | 1 | 18.2179935 | 0 | 0.601472099 |
| | AA + Wnt3A | 1 | 17.60177375 | 0 | 0.228450291 |

Figure 81

|  | Time (hours) | | | | | |
|---|---|---|---|---|---|---|
| G0/G1 | 0 | 6 | 24 | 30 | 48 | 72 |
| MCX + GDF8 | 24.6 | 33.9 | 33.4 | 19.2 | 71.9 | 40.1 |
| MCX | 24.6 | 38 | 34.4 | 18.6 | 75.5 | 35.8 |
| GDF8 | 24.6 | 20.9 | 35.3 | 32.7 | 48.5 | 36.8 |
| NEAT | 24.6 | 21.1 | 33.4 | 35.6 | 49 | 28.7 |
| WNT A/AA | 24.6 | 23.1 | 36.8 | 34.2 | 57.7 | 37.1 |
| WNT only | 24.6 | 20.4 | 32.7 | 27.9 | 55.8 | 37.1 |
| S | 0 | 6 | 24 | 30 | 48 | 72 |
| MCX + GDF8 | 39.2 | 24.4 | 28.7 | 48.3 | 12 | 23.9 |
| MCX | 39.2 | 28.3 | 27.8 | 55.6 | 11.8 | 27.6 |
| GDF8 | 39.2 | 31.3 | 20.9 | 41.9 | 27.7 | 19.8 |
| NEAT | 39.2 | 28.8 | 25.7 | 40.4 | 28 | 20.9 |
| WNT A/AA | 39.2 | 32.4 | 25.4 | 41.6 | 17.2 | 27.6 |
| WNT only | 39.2 | 28.6 | 16.9 | 36.1 | 23.3 | 31.6 |

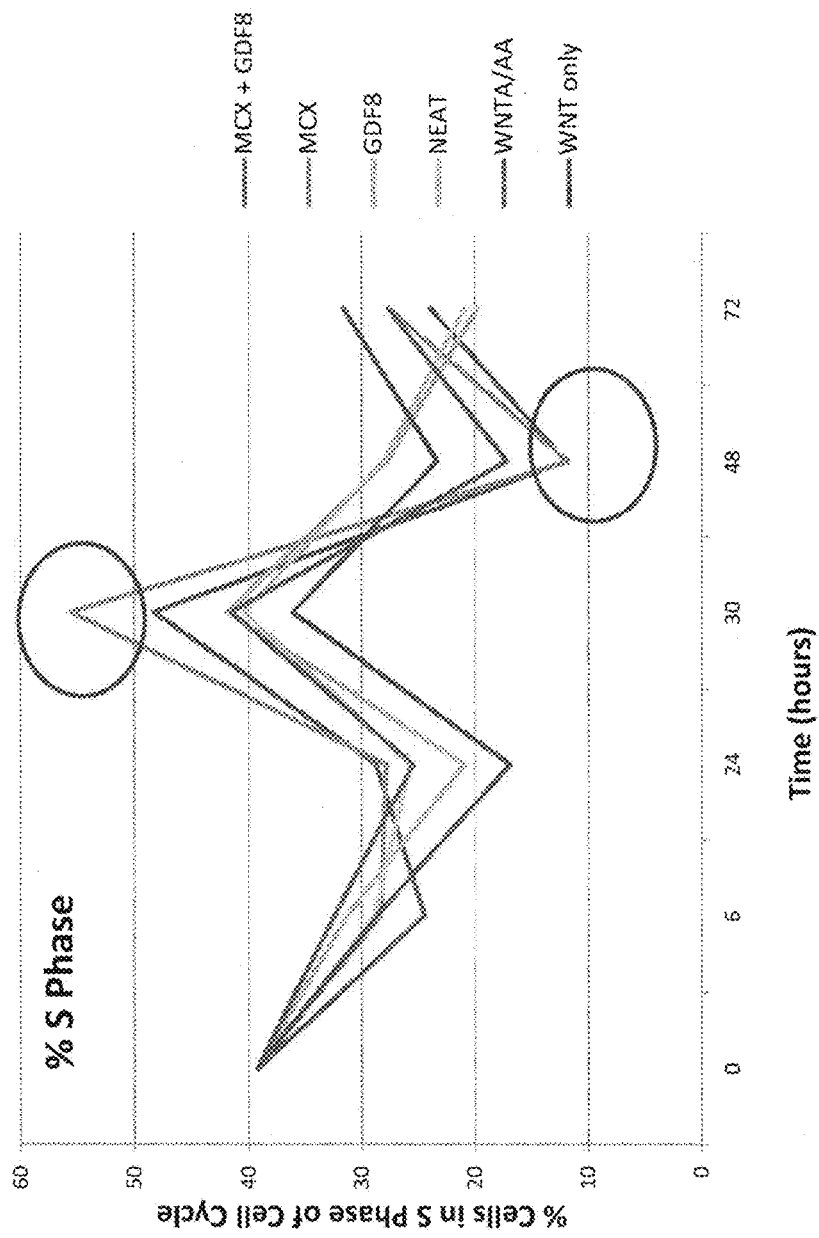

Figure 82

| M | 0 | 6 | 24 | Time (hours) 30 | 48 | 72 |
|---|---|---|---|---|---|---|
| MCX + GDF8 | 17.5 | 18 | 14 | 11.2 | 9.5 | 21.2 |
| MCX | 17.5 | 14.4 | 15.6 | 10.6 | 8.9 | 20.3 |
| GDF8 | 17.5 | 17.6 | 19.2 | 12.9 | 12.2 | 22 |
| NEAT | 17.5 | 18.6 | 18 | 11.7 | 11.7 | 22.4 |
| WNTA/AA | 17.5 | 17.2 | 18.4 | 12.3 | 12.3 | 19.5 |
| WNT only | 17.5 | 18.4 | 18 | 15.8 | 12.9 | 16.8 |
| EDU+ | 0 | 6 | 24 | 30 | 48 | 72 |
| MCX + GDF8 | 50.4 | 30 | 41.7 | 58.6 | 12.8 | 30.4 |
| MCX | 50.4 | 29.2 | 36.1 | 62.9 | 11.2 | 32.6 |
| GDF8 | 50.4 | 49.5 | 30 | 46.2 | 28.7 | 28 |
| NEAT | 50.4 | 46.7 | 35.1 | 47.2 | 28.9 | 32.6 |
| WNTA/AA | 50.4 | 48.4 | 32.5 | 49 | 20.3 | 30 |
| WNT only | 50.4 | 47.9 | 27.5 | 48.7 | 22.2 | 35.6 |
| DE @ 72hrs | CXCR4 | CD99 | CD9 | | | |
| MCX + GDF8 | 87.4 | 29.7 | 0.4 | | | |
| MCX | 96.9 | 31.7 | 0.7 | | | |
| GDF8 | 95.1 | 55.8 | 5.1 | | | |
| NEAT | 90.1 | 60.2 | 9.1 | | | |
| WNTA/AA | 98.1 | 22.1 | 3.3 | | | |
| WNT only | 87.8 | 6.2 | 31.7 | | | |

Figure 83

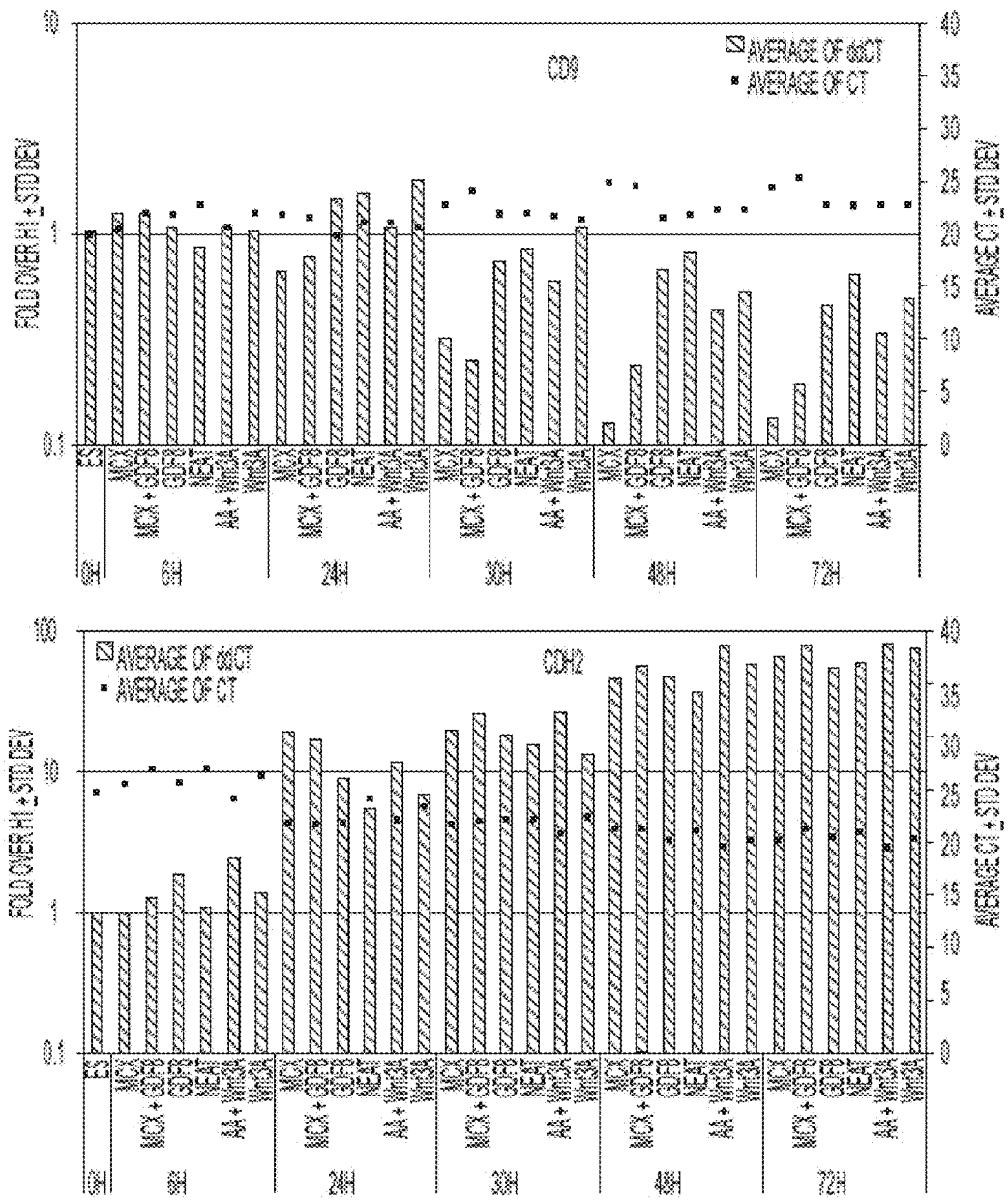

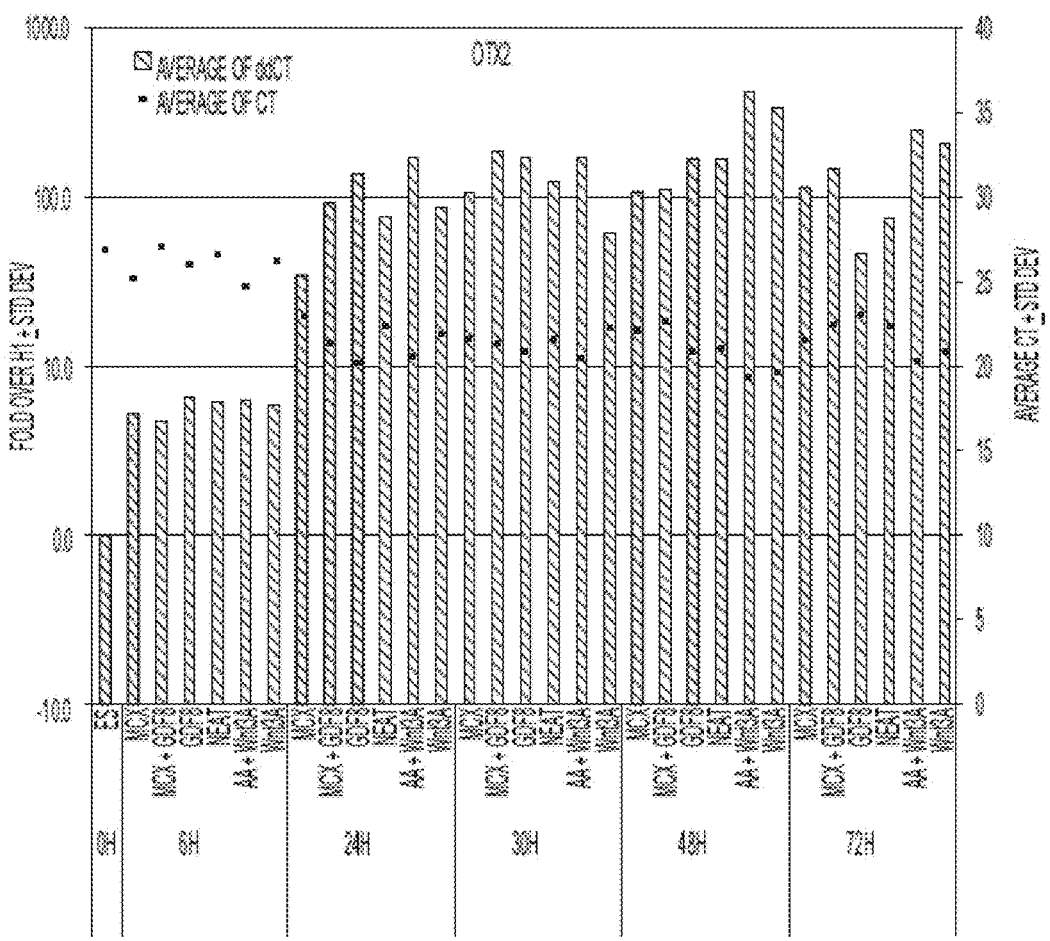

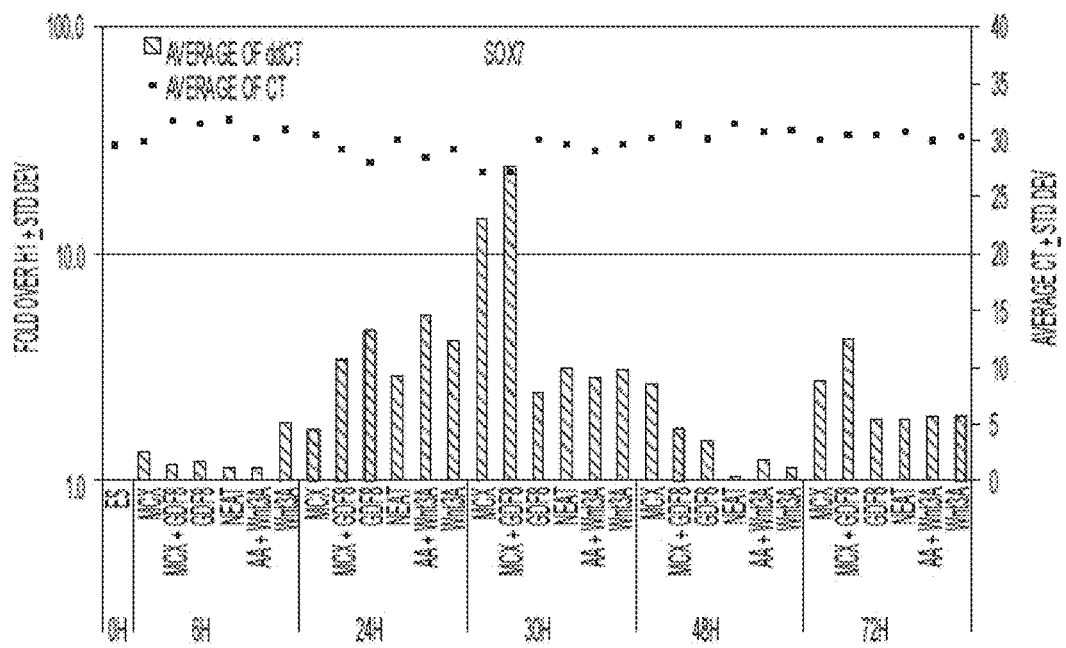

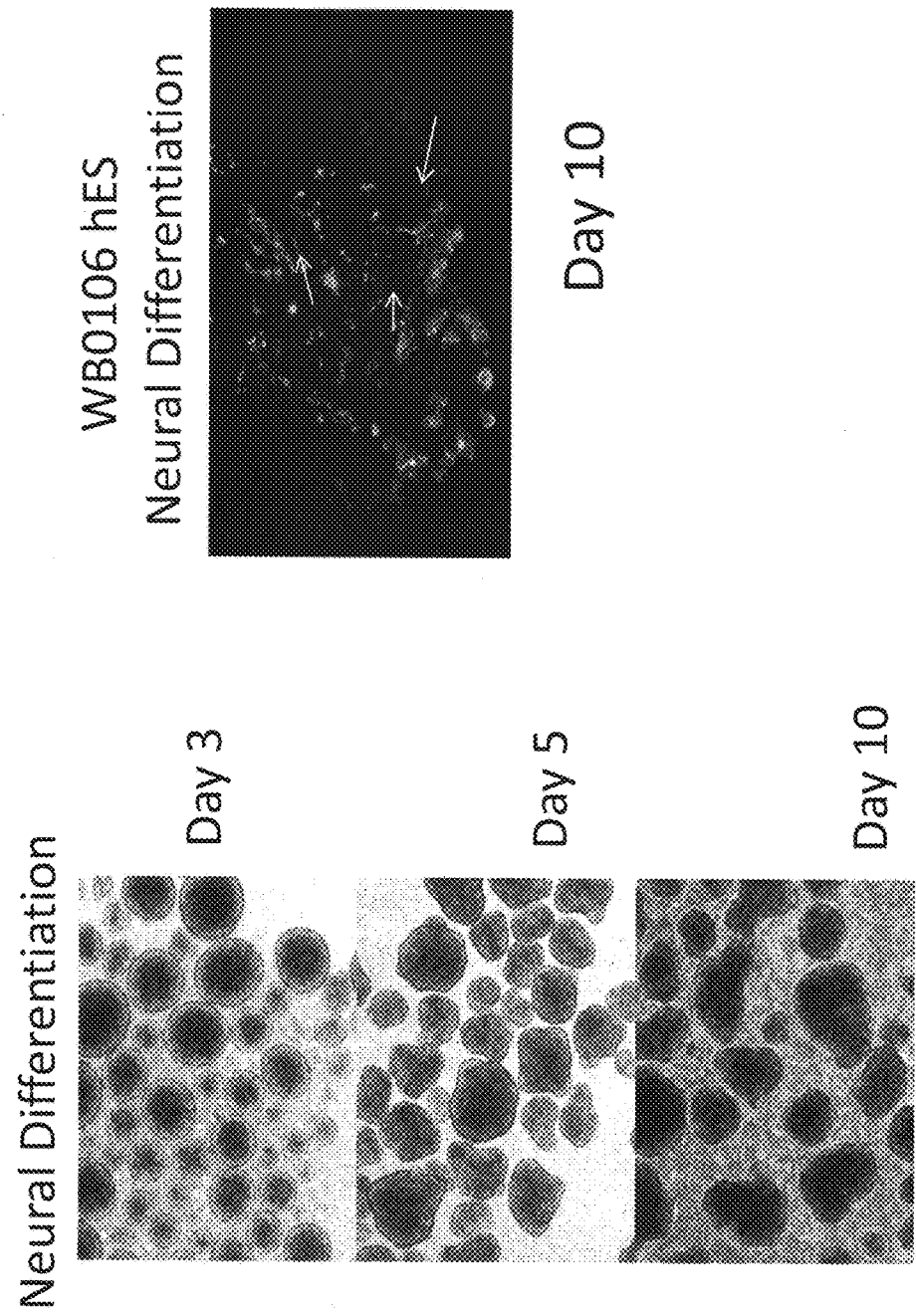

METHODS FOR SUSPENSION CULTURES OF HUMAN PLURIPOTENT STEM CELLS

CROSS-REFERENCE TO RELATED APPLICATIONS

This application claims priority to U.S. Provisional Application 61/747,799 (filed on Dec. 31, 2012) and U.S. Provisional Application 61/962,158 (filed on Nov. 1, 2013) both of which applications are incorporated by reference in their entireties.

FIELD OF THE INVENTION

The present invention is in the field of cell differentiation including preparing embryonic stem cells and other pluripotent cells that maintain pluripotency in aggregated cell cluster for differentiation to endoderm progenitor cells, pancreatic endocrine cells, mesoderm cells or ectoderm cells. In one aspect, the invention discloses a method of generating clusters of pluripotent stem cells and maintaining them in suspension culture for differentiation to pancreatic endoderm, pancreatic endocrine precursor cells, and single-hormone pancreatic endocrine cells.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, embryonic stem cells.

In vertebrate embryonic development, a pluripotent cell gives rise to a group of cells comprising three germ layers (ectoderm, mesoderm, and endoderm) in a process known as gastrulation. Tissues such as, thyroid, thymus, pancreas, gut, and liver, will develop from the endoderm, via an intermediate stage. The intermediate stage in this process is the formation of definitive endoderm.

By the end of gastrulation, the endoderm is partitioned into anterior-posterior domains that can be recognized by the expression of a panel of factors that uniquely mark anterior, mid, and posterior regions of the endoderm. For example, HHEX, and SOX2 identify the anterior region while CDX1, 2, and 4 identify the posterior region of the endoderm.

Migration of endoderm tissue brings the endoderm into close proximity with different mesodermal tissues that help in regionalization of the gut tube. This is accomplished by a plethora of secreted factors, such as FGFs, Wnts, TGF-ßs, retinoic acid ("RA"), and BMP ligands and their antagonists. For example, FGF4 and BMP are reported to promote CDX2 expression in the presumptive hindgut endoderm and repress expression of the anterior genes HHEX and SOX2 (2000 Development, 127:1563-1567). WNT signaling has also been shown to work in parallel to FGF signaling to promote hindgut development and inhibit foregut fate (2007 Development, 134:2207-2217). Lastly, secreted retinoic acid by mesenchyme regulates the foregut-hindgut boundary (2002 Curr Biol, 12:1215-1220).

The level of expression of specific transcription factors may be used to designate the identity of a tissue. During transformation of the definitive endoderm into a primitive gut tube, the gut tube becomes regionalized into broad domains that can be observed at the molecular level by restricted gene expression patterns. For example, the regionalized pancreas domain in the gut tube shows a very high expression of PDX1 and very low expression of CDX2 and SOX2. PDX1, NKX6.1, PTF1A, and NKX2.2 are highly expressed in pancreatic tissue; and expression of CDX2 is high in intestine tissue.

Formation of the pancreas arises from the differentiation of definitive endoderm into pancreatic endoderm. Dorsal and ventral pancreatic domains arise from the foregut epithelium. Foregut also gives rise to the esophagus, trachea, lungs, thyroid, stomach, liver, pancreas, and bile duct system.

Cells of the pancreatic endoderm express the pancreatic-duodenal homeobox gene PDX1. In the absence of PDX1, the pancreas fails to develop beyond the formation of ventral and dorsal buds. Thus, PDX1 expression marks a critical step in pancreatic organogenesis. The mature pancreas contains both, exocrine tissue and endocrine tissue arising from the differentiation of pancreatic endoderm.

D'Amour et al. describes the production of enriched cultures of human embryonic stem cell-derived definitive endoderm in the presence of a high concentration of activin and low serum (Nature Biotechnol 2005, 23:1534-1541; U.S. Pat. No. 7,704,738). Transplanting these cells under the kidney capsule of mice reportedly resulted in differentiation into more mature cells with characteristics of endodermal tissue (U.S. Pat. No. 7,704,738). Human embryonic stem cell-derived definitive endoderm cells can be further differentiated into PDX1 positive cells after addition of FGF10 and retinoic acid (U.S. Patent App. Pub. No. 2005/0266554A1). Subsequent transplantation of these pancreatic precursor cells in the fat pad of immune deficient mice resulted in the formation of functional pancreatic endocrine cells following a 3-4 month maturation phase (U.S. Pat. Nos. 7,993,920 and 7,534,608).

Fisk et al. report a system for producing pancreatic islet cells from human embryonic stem cells (U.S. Pat. No. 7,033,831). Small molecule inhibitors have also been used for induction of pancreatic endocrine precursor cells. For example, small molecule inhibitors of TGF-ß receptor and BMP receptors (Development 2011, 138:861-871; Diabetes 2011, 60:239-247) have been used to significantly enhance the number of pancreatic endocrine cells. In addition, small molecule activators have also been used to generate definitive endoderm cells or pancreatic precursor cells (Curr Opin Cell Biol 2009, 21:727-732; Nature Chem Biol 2009, 5:258-265).

Great strides have been made in improving protocols for culturing progenitor cells such as pluripotent stem cells. PCT Publication No. WO2007/026353 (Amit et al.) discloses maintaining human embryonic stem cells in an undifferentiated state in a two-dimensional culture system. Ludwig et al., 2006 (Nature Biotechnology, 24: 185-7) discloses a TeSR1 defined medium for culturing human embryonic stem cells on a matrix. U.S. Patent App. Pub. No. 2007/0155013 (Akaike et al.) discloses a method of growing pluripotent stem cells in suspension using a carrier that adheres to the pluripotent stem cells, and U.S. Patent App. Pub. No. 2009/0029462 (Beardsley et al.) discloses methods of expanding pluripotent stem cells in suspension using microcarriers or cell encapsulation. PCT Publication No. WO 2008/015682 (Amit et al.) discloses a method of expanding and maintaining human embryonic stem cells in a suspension culture under culturing conditions devoid of substrate adherence.

U.S. Patent App. Pub. No. 2008/0159994 (Mantalaris et al.) discloses a method of culturing human embryonic stem cells encapsulated within alginate beads in a three-dimensional culture system.

Despite these advances, a need still remains for a method to successfully culture pluripotent stem cells in a three-dimensional culture system that may differentiate to functional endocrine cells.

BRIEF DESCRIPTION OF THE DRAWINGS

The foregoing summary, as well as the following detailed description of the invention, will be better understood when read in conjunction with the appended figures. For the purpose of illustrating the invention, the figures demonstrate embodiments of the present invention. It should be understood, however, that the invention is not limited to the precise arrangements, examples, and instrumentalities shown.

FIG. 1b shows the results of flow cytometry for CD9, SSEA4, CXCR4, TRA-1-60 and TRA-1-81 for the Dispase®-treated cells of the human embryonic stem cell line H1 after culturing for 4 days in a 125 mL spinner flask containing 25 mL mTeSR®1 media according to Example 1. The cells exhibited high expression for markers of pluripotency (CD9, SSEA4, TRA-1-60 and TRA-1-81) with almost no expression of CXCR4, a marker for differentiation.

As shown in FIG. 1d, expression of CD9, a marker for pluripotency, was nearly eliminated, while the expression of markers of definitive endoderm differentiation CXCR4 (CD184) and CD99 were quite high.

FIG. 2b shows micrographs of the EDTA-treated cells of the human embryonic stem cell line H1 differentiated into stage 1, day 3 cells grown in spinner flask and stage 2 day 2, stage 4 day 1 and stage 4 day 3 cells grown in spinner flasks or Erlenmeyer flasks according to Example 2. Suspension differentiated cultures formed substantially uniform and homogenous populations of cells in spherical aggregates.

FIG. 2d shows qRT-PCR results for expression of selected genes associated with pluripotency and genes associated with definitive endoderm for the EDTA-treated cells of the human embryonic stem cell line H1 at the end of stage 1 compared to undifferentiated H1 (WA01) hES cells (see Example 2). FIG. 2d shows a decrease in the expression of pluripotency genes (CD9, Nanog, and POU5F1/OCT4) and a large increase in genes associated with definitive endoderm (CXCR4, CERBERUS ("CER1"), FOXA2, GATA4, GATA6, MNX1, and SOX17).

FIG. 2f shows qRT-PCR results for expression of selected genes associated with differentiation for the EDTA-treated cells of the human embryonic stem cell line H1 which were further differentiated from stage 1 to pancreatic endoderm cells by suspension in spinner flasks or Erlenmeyer flasks according to Example 2. The data is compared to expression in WA01 hES cells. The RT-PCR results show high levels of expression of pancreatic precursor genes.

As shown in FIG. 3a, the cells were removed from the surface as small aggregates.

FIG. 3b shows phase contrast micrographs of cells of the human embryonic stem cell line H1, which had been lifted from a static culture following treatment with Accutase® and which were then expanded in suspension culture for three days. Visible in FIG. 3b is the formation of a substantially uniform, spherical population of cell clusters.

FIG. 4a shows micrographs of suspension cultured human embryonic stem cells of the cell line H1 using a directed differentiation protocol at different stages of differentiation. Visible in FIG. 4a are micrographs of the cells at each stage of differentiation.

FIG. 4c shows the non-fasting blood glucose levels of SCID-Bg Mice transplanted with differentiated cells encapsulated in a TheraCyte™ device.

FIG. 5a shows flow cytometry data for the EDTA-treated cells of the human embryonic stem cell line H1 prior to transition to differentiation culture for markers associated with pluripotency and differentiation. As shown in FIG. 5a, high expression of the pluripotency markers CD9, SSEA4, TRA-1-60 and TRA-1-80 was observed.

FIG. 5b shows phase contrast images of the cells and flow cytometry data for CXCR4/CD184 and CD99 (markers of differentiation) and CD9 (a pluripotency marker) for three different feed settings during stage 1. The conditions tested were as follows: (A) media change 24 hours after initiation of differentiation, no media change at 48 hours; (B) media change 24 hours after initiation of differentiation and glucose bolus addition at 48 hours; and (C) no media change throughout stage 1 with glucose and GDF8 bolus added 24 hours after initiation of differentiation, then a glucose bolus added at 48 hours post initiation.

FIG. 5f shows the expression of C-peptide in SCID-Bg mice that were implanted with cells differentiated according to condition A (media change 24 hours after initiation of differentiation, no media change at 48 hours). Each SCID-Bg mouse was implanted with 5 million of the cells under the kidney capsule. As shown in FIG. 5f, by 12 weeks post implantation, human c-peptide was detectable at levels above 1 ng/mL, and at 16 weeks c-peptide levels were an average of 2.5 ng/mL.

As shown in FIG. 5g, glucose treatment induced a significant increase in circulating human c-peptide from an average of 0.93 ng/mL in a fasted state to 2.39 ng/mL in a fed state.

FIG. 6d shows the cell count (cells/ml) as a function of days of differentiation for cells of the human embryonic stem cell line H1 grown and differentiated on plates in media containing Activin A and WNT3A (WTN3A/AA plate), microcarriers in media containing Activin A and WNT3A (WTN3A/AA microcarrier), plates in media containing MCX and GDF8 (MCX/GDF8 plate) and microcarriers in media containing MCX and GDF8 (MCX/GDF8 microcarriers).

FIG. 7 shows the cell counts at various stages of differentiation in a Bioreactor from stage 1, day 1 to stage 4, day 3 for cells differentiated according to the protocol of Example 7. Cell counts are shown as million cells/ml as determined by an image-based cytometer (NucleoCounter®).

FIG. 8 shows the average daily bioreactor medium pH levels as a function of time (days of differentiation) during the differentiation protocol of Example 7. pH levels were determined by a NOVA BioProfile® FLEX (Nova Biomedical Corporation, Waltham, Mass.).

FIG. 9 shows the average daily bioreactor medium lactate levels as a function of time (days of differentiation) during the differentiation protocol of Example 7. Lactate levels were determined by a NOVA BioProfile® FLEX (Nova BiomedicalCorporation, Waltham, Mass.).

FIG. 10 shows the average daily bioreactor medium glucose levels as a function of time (days of differentiation) during the differentiation protocol of Example 7. Glucose levels were determined by a NOVA BioProfile® FLEX (Nova Biomedical Corporation, Waltham, Mass.).

FIG. 11 shows the undifferentiated gene expression, as determined by qRT-PCR, for stage 0, day 1 (i.e. twenty-four hours after inoculation) cells differentiated according to the protocol of Example 7 for the pluripotency array, which contains select genes associated with pluripotency.

FIG. 12 shows the undifferentiated gene expression, as determined by qRT-PCR, for stage 0, day 1 (i.e. twenty-four hours after inoculation) cells for the definitive endoderm ("DE") array, which contains select genes associated with definitive endoderm (see Example 7).

FIG. 13 shows the undifferentiated gene expression, as determined by qRT-PCR, for stage 0, day 3 (i.e. seventy-two hours after inoculation) cells for the pluripotency array, which contains select genes associated with pluripotency (see Example 7).

FIG. 14 shows the undifferentiated gene expression, as determined by qRT-PCR, for stage 0, day 3 (i.e. seventy-two hours after inoculation) cells for the DE array, which contains select genes associated with DE (see Example 7).

FIG. 15 shows the results of fluorescence-activated cell sorting (FACS) for CD9, CD184/CXCR4, SSEA4, TRA-1-60 and TRA-1-81 for undifferentiated stage 0, day 3 (i.e. seventy-two hours after inoculation) cells (see Example 7). The results are also shown in Table 8.

FIG. 16 shows the undifferentiated gene expression, as determined by qRT-PCR, for select genes of stage 0, day 1 (i.e. twenty-four hours after inoculation) and stage 0, day 3 (i.e. seventy-two hours after inoculation) cells differentiated according to the protocol of Example 7. Specifically, FIG. 16 shows a modest increase in gene expression for GATA4, GSC, MIXL1, and T and a ≥100× increase in GATA2 expression during the stage 0 process prior to directed differentiation.

FIG. 17 shows the undifferentiated gene expression, as determined by qRT-PCR, for the DE array, which contains select genes associated with DE, for stage 0, day 1 (i.e. twenty-four hours after inoculation) and stage 0, day 3 (i.e. seventy-two hours after inoculation) cells differentiated according to the protocol of Example 7. Specifically, FIG. 17 shows a ≥100× increase in CER1, FGF17, and FGF4 expression during the stage 0 process prior to directed differentiation.

FIGS. 18 and 19 show the gene expression for stage 1, day 1 cells differentiated according to the protocol of Example 7. FIG. 18 shows the gene expression, as determined by qRT-PCR, for the pluripotency array, which contains select genes associated with pluripotency, for stage 1, day 1 cells.

FIG. 19 shows the gene expression, as determined by qRT-PCR, for the DE array, which contains select genes associated with DE, for stage 1, day 1 cells. FIGS. 18 and 19 illustrate significant alterations in gene expression patterns such as a ~700× increase in FOXA2 expression and a 1000× increase in CER1, EOMES, FGF17, FGF4, GATA4, GATA6, GSC, MIXL1, and T expression.

FIGS. 20 and 21 show the gene expression for stage 1, day 3 cells differentiated according to the protocol of Example 7.

FIG. 20 shows the gene expression, as determined by qRT-PCR, for the pluripotency array, which contains select genes associated with pluripotency, for stage 1, day 3 cells.

FIG. 21 shows the gene expression, as determined by qRT-PCR, for the DE array, which contains select genes associated with DE, for stage 1, day 3 cells.

FIG. 22 shows the results of FACS for CD9, CD184 (also known as CXCR4) and CD99 for stage 1, day 3 cells differentiated according to the protocol of Example 7. A near complete transition from a CD9 expressing/CXCR4 negative pluripotent cell population at the initiation of differentiation (FIG. 15) to a homogeneous population of CXCR4 expressing cells (98.3% of cells CXCR4 positive, ±1.9SD) at the end of stage 1 (FIG. 22) was observed.

FIG. 23 shows the gene expression, as determined by qRT-PCR, for the DE array, which contains select genes associated with DE, for stage 1, day 3; stage 2, day 1; and stage 2, day 3 cells differentiated according to the protocol of Example 7. FIG. 23 shows that HNF4a and GATA6 expression levels at stage 2 days 1 and 3 increased, while genes expressed at high levels on day 3 of stage 1 (CXCR4, EOMES, FGF17, FGF4, MNX1, PRDM1, SOX17, and VWF) showed reduced expression by the end of stage 2.

FIG. 24 shows the gene expression of the foregut genes AFP, PDX1, and PROX1, as determined by qRT-PCR, for stage 2, day 1 cells and stage 2, day 3 cells differentiated according to the protocol of Example 7. As shown in FIG. 24, the expression of these genes increased.

FIG. 25 shows the results of FACS for PDX1, FOXA2, chromogranin, NKX2.2 and SOX2 for stage 3, day 3 cells grown in stage 3 medium (Table 7) differentiated according to the protocol of Example 7. As shown in FIG. 25, the cells expressed markers consistent with an endodermal pancreatic lineage as measured by PDX1 and FOXA2 expression (90.9%±11.9SD PDX1 positive and 99.2%±0.6SD FOXA2 positive).

FIG. 26 shows the gene expression, as determined by qRT-PCR, for the stage 4 array, which contains select genes associated with stage 4, for stage 3, day 1 and stage 3, day 3 cells differentiated according to the protocol of Example 7. FIG. 26 illustrates that these cells exhibit increased levels of a host of genes commonly expressed in the pancreas (ARX, GAST, GCG, INS, ISL1, NEUROD1, NGN3, NKX2.2, NKX6.1, PAX4, PAX6, PTF1A, and SST).

FIG. 27 shows the results of FACS for NKX6.1, chromagranin (CHGA), CDX2, SOX2, NKX2.2, PDX1, FOXA2 and NEUROD for stage 4, day 3 cells differentiated according to the protocol of Example 7. As shown in FIG. 27, stage 4 day 3 the cells retained high levels of PDX1 and FOXA2 expression and further developed an expression pattern consistent with a mix of pancreatic endocrine cells (28.1%±12.5SD chromogranin positive) and pancreatic progenitor cells (58.3%±9.7SD positive for NKX6.1).

FIG. 28 shows the gene expression, as determined by qRT-PCR, for the stage 4 array, which contains select genes associated with stage 4, for stage 3, day 3; stage 4, day 1 and stage 4, day 3 cells differentiated according to the protocol of Example 7. FIG. 28 shows an increased expression level of genes commonly expressed in the pancreas (ARX, GAST, GCG, IAPP, INS, ISL1, MAFB, NEUROD1, NGN3, NKX2.2, NKX6.1, PAX4, PAX6, PTF1A, and SST).

FIG. 29 shows the average results of FACS for NKX6.1, chromagranin (CHGA), CDX2, SOX2, NKX2.2, PDX1, FOXA2 and NEUROD for stage 4, day 3 cells differentiated according to the protocol of Example 7. Specifically, FIG. 29 shows the average FACS expression pattern of pancreatic precursors generated at a 3 L scale from different seed material lots.

FIG. 30 shows the average results of FACS for NKX6.1, chromagranin (CHGA), CDX2, SOX2, NKX2.2, PDX1, FOXA2 and NEUROD for stage 4, day 3 cells differentiated according to the protocol of Example 7. Prior to differentiation in stage 4, day 3 cells, the cells were expanded to form ISM and then grown at stage 0 in either a custom in-house medium "IH3" or Essential8™, both of which were supplemented with 2% BSA. The cells grown in the IH3 medium are the "IH3-P grown cells" and the cells grown in Essential8™ are the "EZ8 grown cells." No significant difference in expression patterns was observed between the cells grown in the different media.

FIG. 31 shows the average results of FACS for NKX6.1, chromagranin (CHGA), CDX2, SOX2, NKX2.2, PDX1, FOXA2 and NEUROD for stage 4, day 3 cells, which were previously grown at different pH levels in stage 0 (see Example 7). No significant change in the stage 4, day 3 cell profile was observed.

FIG. 32 compares the results of FACS for NKX6.1, chromogranin (CHGA), CDX2, SOX2, NKX2.2, PDX1, FOXA2 and NEUROD for stage 4, day 3 cells, which were not treated with Anti-Foam C, and stage 4, day 3 cells, which were treated with Anti-Foam C emulsion (94 ppm) (see Example 7). Anti-Foam C emulsion (Sigma Cat#A8011) was not observed to affect the profile of stage 4 day 3 cells.

FIGS. 33 to 35 show the gene expression, as determined by qRT-PCR, for select genes for cells differentiated according to the protocol of Example 8.

FIG. 33 shows the gene expression, as determined by qRT-PCR, for select genes of cells, twenty-four hours prior to the start of differentiation (see Example 8). As shown in FIG. 33, cells from the bioreactor retained expression for genes characteristic of pluripotency (POU5F1, NANOG, SOX2, and ZFP42) and showed minimal or no induction of genes characteristic of differentiation (AFP, and FOXA2: <50 fold increase; FOXD3, GATA2, GATA4, GSC, HAND2, MIXL1, and T: <10 fold increased expression).

FIG. 34 shows the gene expression, as determined by qRT-PCR, for select genes of cells twenty-four hours after the start of differentiation.

FIG. 35 shows the gene expression, as determined by qRT-PCR, for select genes of cells seventy-two hours after the start of differentiation.

FIG. 36(a) to 36(e) show the gene expression, as determined by qRT-PCR, for select genes for cells differentiated from stage 2 to stages 3 and 4 according to the protocol of Example 8. Specifically, these Figures show the gene expression of the cells at stage 2, day 1; stage 2, day 2; stage 2, day 3; stage 3, day 3; and, depending on the gene, stage 4, day 1. FIG. 36(a) shows the gene expression for AFP, ATOH1, and CDX2. FIG. 36(b) shows the gene expression for GAST, HAND1, HHEX, and HNF4a. FIG. 36(c) shows the gene expression for NKX2.2, NKX6.1, OSR1, and PDX1. FIG. 36(d) shows the gene expression for PROX1, PFT1a, SOX17, and SOX2. FIG. 36(e) shows the gene expression for SOX9. The data are shown as difference in expression versus undifferentiated H1 (WA01) hES cells (baseline expression of 1).

FIG. 37 show the gene expression, as determined by qRT-PCR, for select genes for cells at stage 4, day 3 of differentiation according to the protocol in Example 8. As shown in FIG. 37, at the end of differentiation at stage 3, day 3 the cells have differentiated into pancreatic progenitor cells characterized by high expression levels of PDX1 ($>1\times10^6$ fold induction) and other pancreatic genes (>1000 fold induction of ARX, GCG, GAST, INS, ISL, NEUROD1, NGN3, NKX2.2, NKX6.1, PAX4, PTF1a, and SST) and near total loss of OCT4/POU5F1 expression as compared to undifferentiated H1 human embryonic stem cells.

FIG. 38 shows the daily cell counts during the differentiation protocol according to Example 8. Specifically, FIG. 38 shows cell density as a function of the process day. FIG. 38 shows the cell counts for differentiation protocols of two reactor runs (PRD1205 and PRD1207) carried out at pH 6.8 and 7.2. For comparison, the cell counts for cell drift are also shown.

FIG. 39(a) to FIG. 39(d) illustrate the in vivo bioactivity of stage 4 day 3 cells, which were differentiated according to the protocol of Example 8 and were implanted into SCID-Bg mice. The cells were implanted subcutaneously via a TheraCyte™ device, under the kidney capsule or implanted after incubation in an ultra-low attachment dish. The mice were monitored for blood glucose and C-peptide levels every four weeks following graft implantation. FIG. 39(a) shows the C-peptide levels after implantation of 5M or 10M stage 4 day 3 cells in a TheraCyte™ device as a function of time. FIG. 39(b) shows the non-fasting glucose levels in animals after implantation of 5M or 10M stage 4 day 3 cells in a TheraCyte™ device. The mice in FIG. 39(b) were treated with STZ to ablate host β-cell function prior to implantation. FIG. 39(c) shows the C-peptide level produced after implantation of previously-cyropreserved stage 4 day 3 cells in a TheraCyte™ device as a function of time (weeks post implantation). FIG. 39(d) compares the C-peptide levels of mice treated by a kidney graft of never cryopreserved/fresh stage 4, day 3 cells or cryopreserved stage 4, day 3 cells implanted immediately after thaw (D0) or 1 day after thaw (D1).

FIG. 40A to FIG. 40D show FACS plots for CXCR4, CD99, and CD9 of cells differentiated for three days according to the protocol of Example 9 which were treated at stage 1, day 1 with: MCX compound and GDF-8 (FIG. 40A); MCX only (FIG. 40B); WNT3A and Activin A (FIG. 40C); and WNT3A only (FIG. 40D). These figures indicate that in suspension culture, addition of 3 μM MCX in the absence of a TGF-β family member on day one of differentiation generates definitive endoderm at levels comparable to that obtained when cells are treated with 3 μM MCX plus 100 ng/ml GDF-8 or 20 ng/ml WNT-3a plus 100 ng/ml Activin A on day one.

FIG. 42A shows FACS plots for CXCR4, CD99, and CD9 of cells differentiated for three days according to the protocol of Example 10 with full media exchange at stage 1. FIG. 42B shows FACS plots for CXCR4, CD99, and CD9 of cells differentiated for three days according to the protocol of Example 10 without a media exchange on day 3. The data suggest that in the suspension culture system, cultures which receive a media exchange on day three (FIG. 42A) of differentiation resulted in definitive endoderm with a comparable efficiency to cultures which did not receive a media exchange on day three (FIG. 42B).

FIG. 44A and FIG. 44B show FACS plots for CXCR4, CD99, and CD9 of cells differentiated for three days according to the protocol of Example 13 with either 3.64 g/l (FIG. 44A) or 2.49 g/l (FIG. 44B) added at stage 1.

FIG. 44C and FIG. 44D show phase contrast micrographs of cells differentiated for three days according to the protocol of Example 13 with either 3.64 g/l (FIG. 44C) or 2.49 g/l (FIG. 44D) added at stage 1.

FIG. 51 shows high expression of markers associated with pluripotency.

FIG. 53 shows an increase in expression of foregut genes (AFP, HHEX, PDX1, and PROX1).

As shown in FIG. 54, expression for PDX1 increased 60 fold from 12,000× over control at the end of stage 2 day 3 to 739,000× over control at the end of stage 3, day 3.

FIGS. 57 to 80 show the gene expression, as determined by qRT-PCR as a fold expression versus undifferentiated cells, for cells differentiated according to various embodiments of the protocol of Example 15 after 0 hours, 6 hours, 24 hours, 30 hours, 48 hours and 72 hours of differentiation for the following genes: AFP (FIG. 57); CD99 (FIG. 58); CD9 (FIG. 59); CDH1 (FIG. 60); CDH2 (FIG. 61); CDX2 (FIG. 62); CER1 (FIG. 63); CXCR4 (FIG. 64); FGF17 (FIG. 65); FGF4 (FIG. 66); FOXA (FIG. 67); GADPH (FIG. 68); GATA4 (FIG. 69); GATA6 (FIG. 70); GSC (FIG. 71); KIT (FIG. 72); MIXL1 (FIG. 73); MNX1 (FIG. 74); NANOG (FIG. 75); OTX2 (FIG. 76); POUF5F1 (FIG. 77); SOX17 (FIG. 78); SOX7 (FIG. 79) and T (FIG. 80).

FIG. 81 shows the results for clusters that were treated on the first day of differentiation with one of six conditions: (1) Neat, (2) 3 μM MCX plus 100 ng/ml GDF-8 (Catalog #120-00, Peprotech), (3) 3 μM MCX only, (4) 100 ng/ml GDF-8 only, (5) 20 ng/ml WNT-3A (Catalog #1324-WN-002, R&D Systems, MN) plus 100 ng/ml Activin A (Catalog #338-AC, R&D Systems, MN), or (6) 20 ng/ml WNT-3A only.

Figure 83:
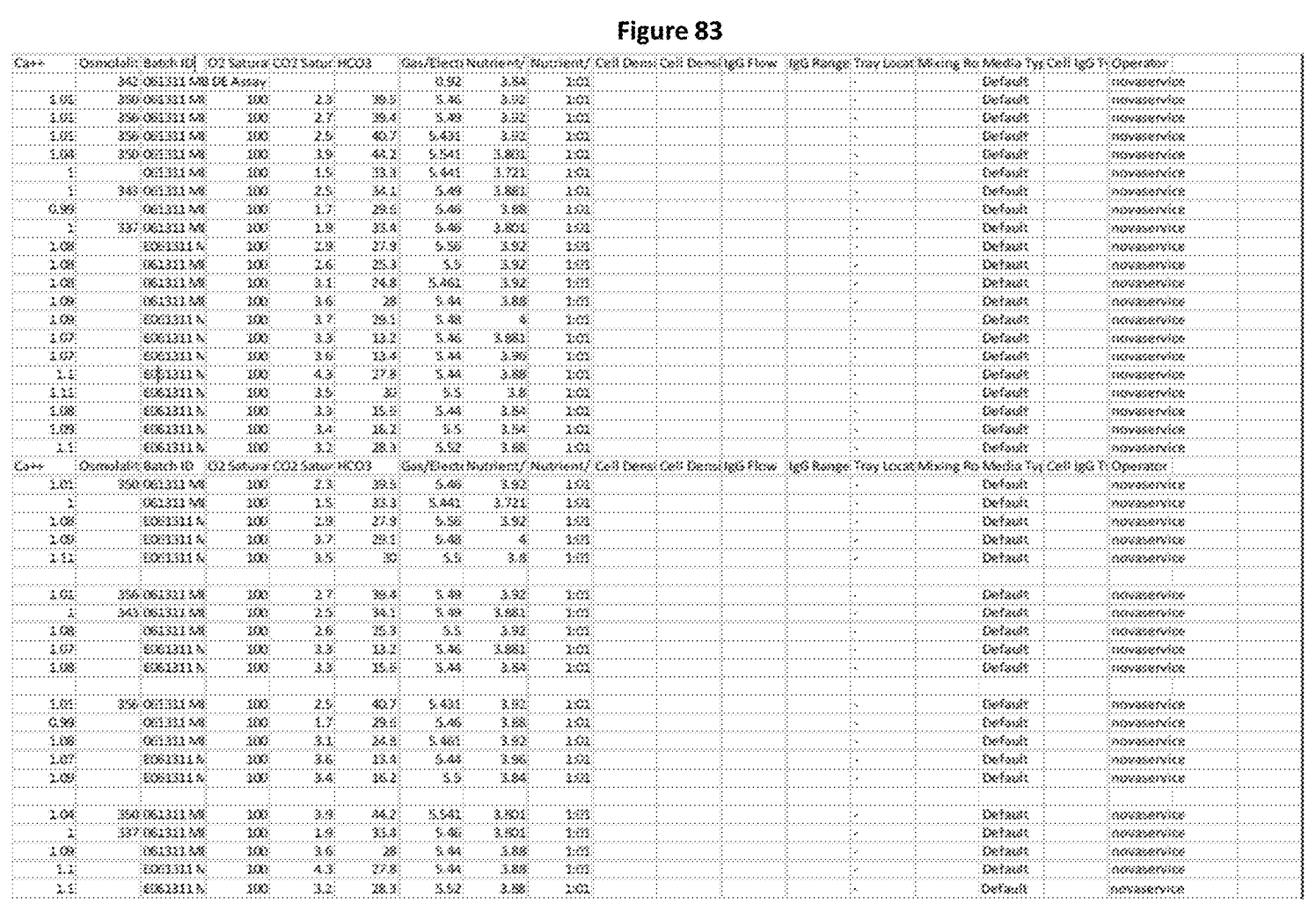

FIG. 83 shows the general operational parameters used in the protocols of Example 15.

Figure 84:
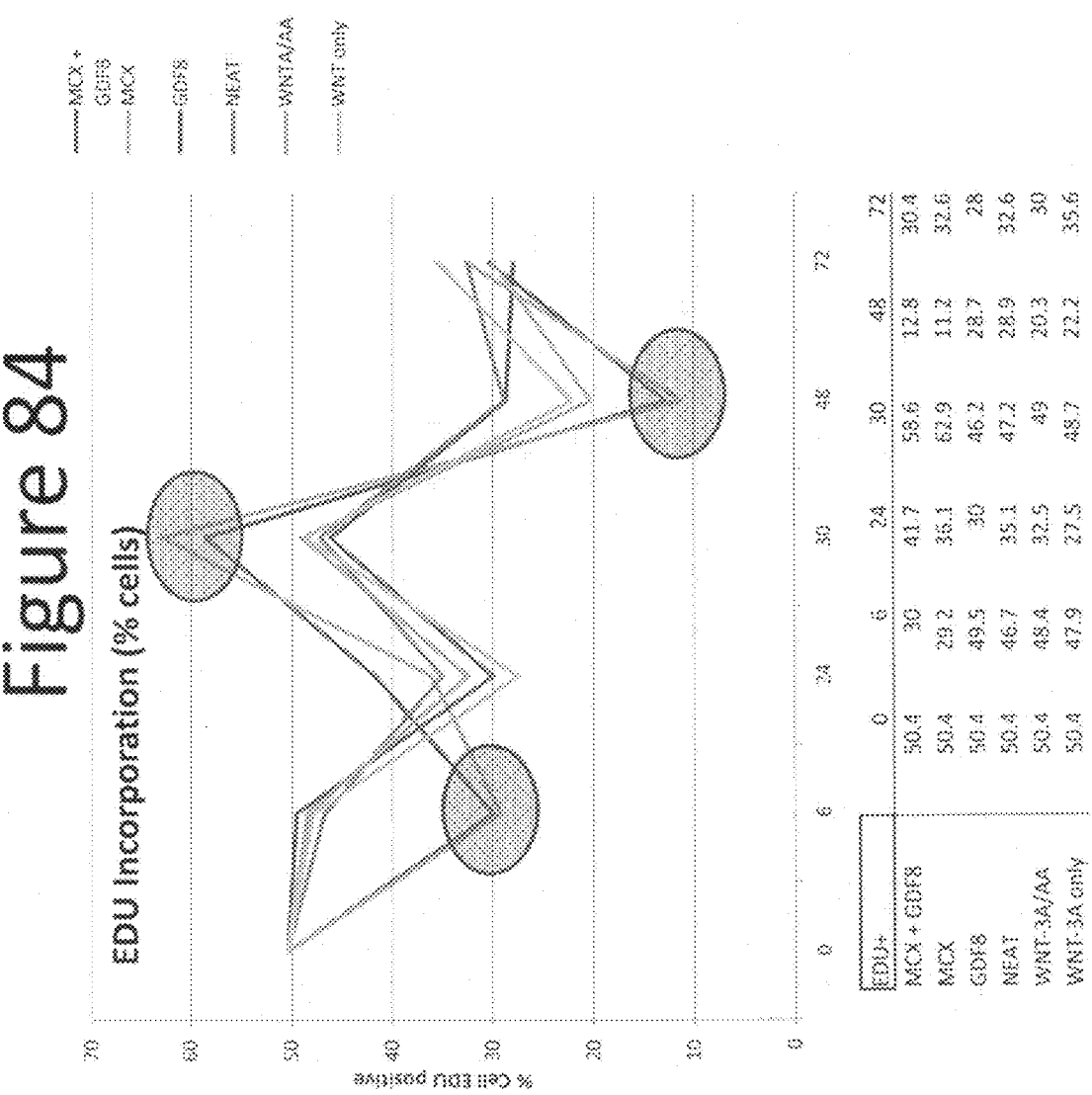

FIG. 84 shows the amount of EDU incorporation of cells after 6 hours, 24 hours, 30 hours, 48 hours, and 72 hours of differentiation according to various embodiments of the protocol of Example 15. Specifically, FIG. 84 shows the results for EDU incubated cells clusters that were treated on the first day of differentiation with one of six conditions: (1) Neat, (2) 3 µM MCX plus 100 ng/ml GDF-8 (Catalog #120-00, Peprotech), (3) 3 µM MCX only, (4) 100 ng/ml GDF-8 only, (5) 20 ng/ml WNT-3A (Catalog #1324-WN-002, R&D Systems, MN) plus 100 ng/ml Activin A (Catalog #338-AC, R&D Systems, MN), or (6) 20 ng/ml WNT-3A only.

Figure 85:
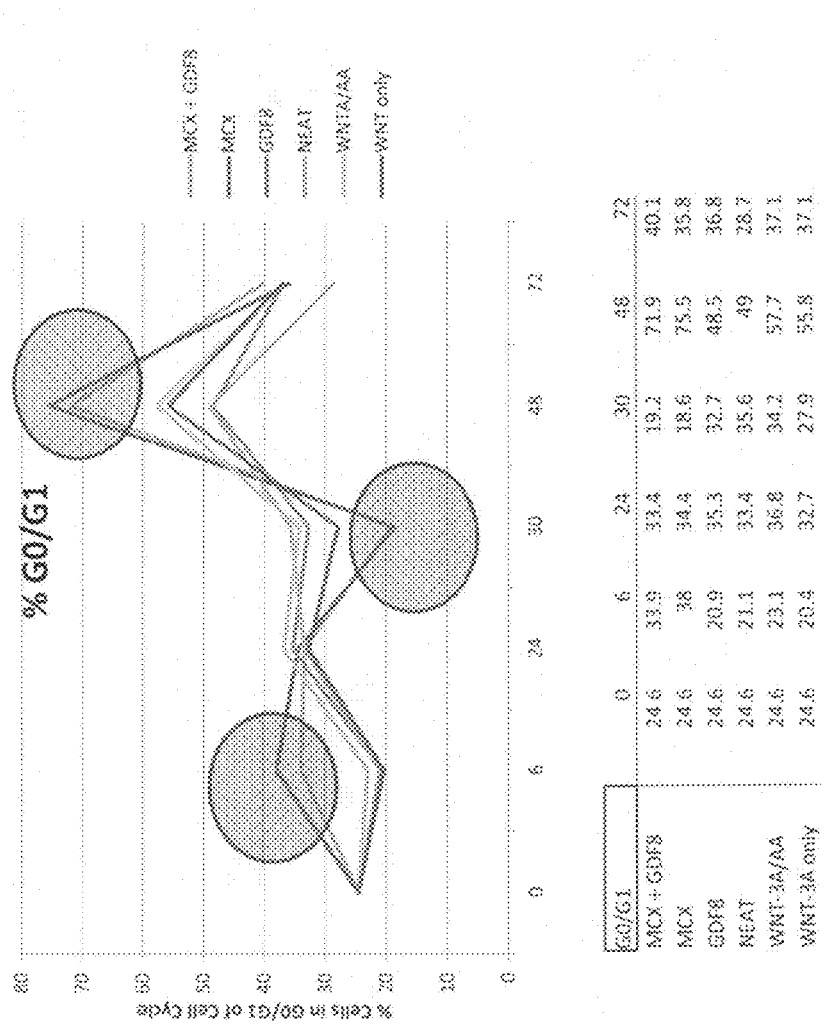

FIG. 85 shows the percentage of cells in G0/G1 of Cell Cycle for cells after 6 hours, 24 hours, 30 hours, 48 hours, and 72 hours of differentiation according to various embodiments of the protocol of Example 15. Specifically, FIG. 85 shows the results for clusters that were treated on the first day of differentiation with one of six conditions: (1) Neat, (2) 3µM MCX plus 100 ng/ml GDF-8 (Catalog #120-00, Peprotech), (3) 3 µM MCX only, (4) 100 ng/mlGDF-8 only, (5) 20 ng/ml WNT-3A (Catalog #1324-WN-002, R&D Systems, MN) plus 100 ng/ml Activin A (Catalog #338-AC, R&D Systems, MN), or (6) 20 ng/ml WNT-3A only.

Figure 86:
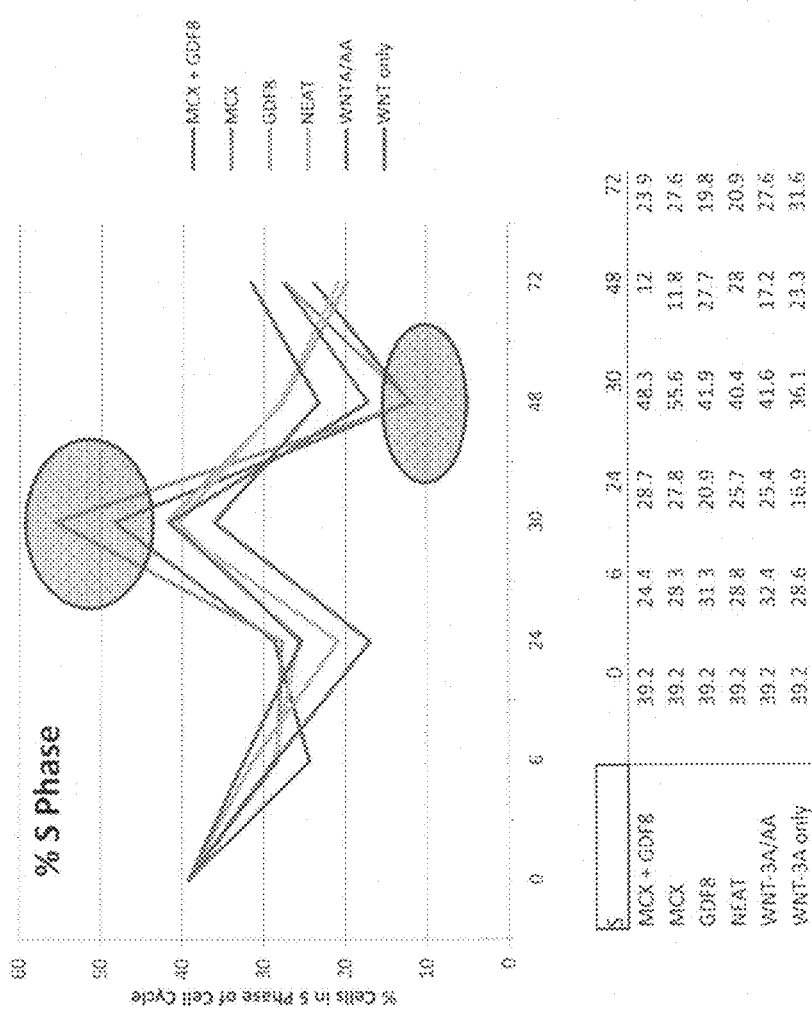

FIG. 86 shows the percentage of cells in S-phase of Cell Cycle for cells after 6 hours, 24 hours, 30 hours, 48 hours, and 72 hours of differentiation according to various embodiments of the protocol of Example 15. Specifically, FIG. 86 shows the results for clusters that were treated on the first day of differentiation with one of six conditions: (1) Neat, (2) 3 µM MCX plus 100 ng/ml GDF-8 (Catalog #120-00, Peprotech), (3) 3 µM MCX only, (4) 100 ng/ml GDF-8 only, (5) 20 ng/ml WNT-3A (Catalog #1324-WN-002, R&D Systems, MN) plus 100 ng/ml Activin A (Catalog #338-AC, R&D Systems, MN), or (6) 20 ng/ml WNT-3A only.

Figure 87:
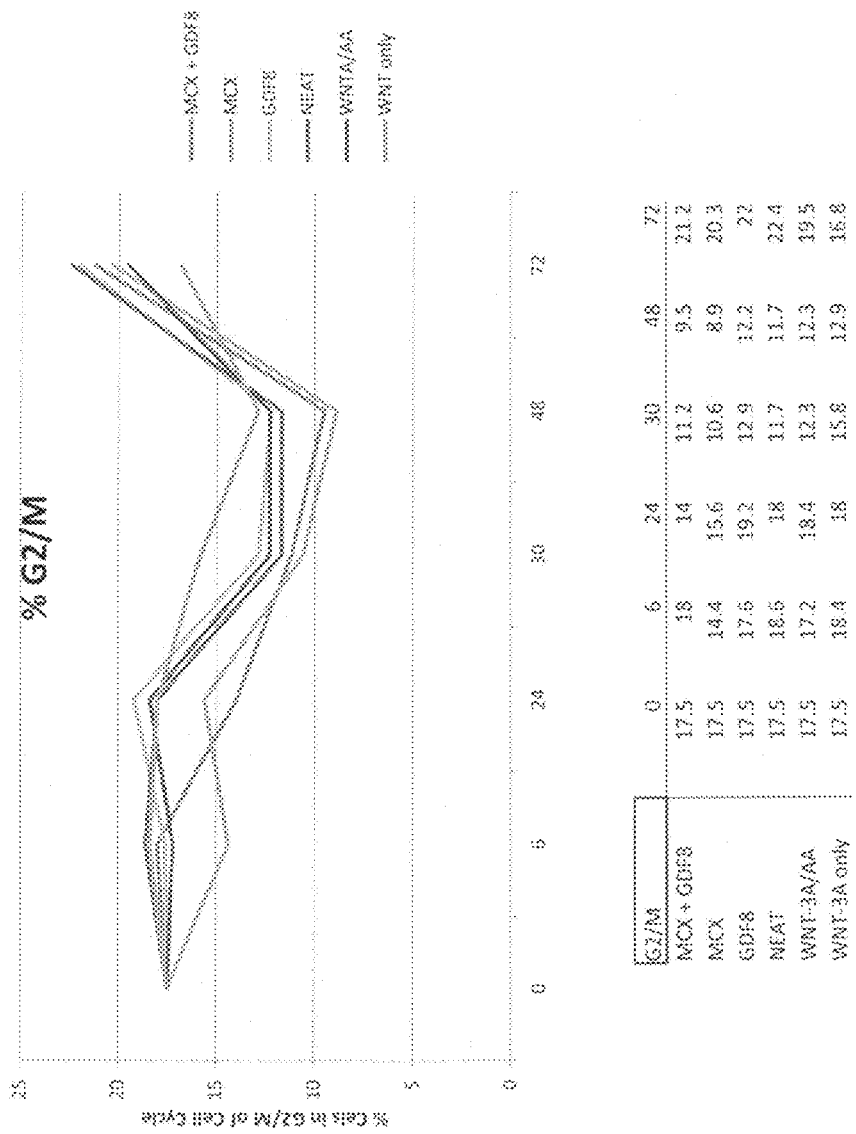

FIG. 87 shows the percentage of cells in S-phase of Cell Cycle for cells after hours, 6 hours, 24 hours, 30 hours, 48 hours, and 72 hours of differentiation according to various embodiments of the protocol of Example 15. Specifically, FIG. 87 shows the results for clusters that were treated on the first day of differentiation with one of six conditions: (1) Neat, (2) 3 µM MCX plus 100 ng/ml GDF-8 (Catalog #120-00, Peprotech), (3) 3 µM MCX only, (4) 100 ng/ml GDF-8 only, (5) 20 ng/ml WNT-3A (Catalog #1324-WN-002, R&D Systems, MN) plus 100 ng/ml Activin A (Catalog #338-AC, R&D Systems, MN), or (6) 20 ng/ml WNT-3A only.

Figure 88A:
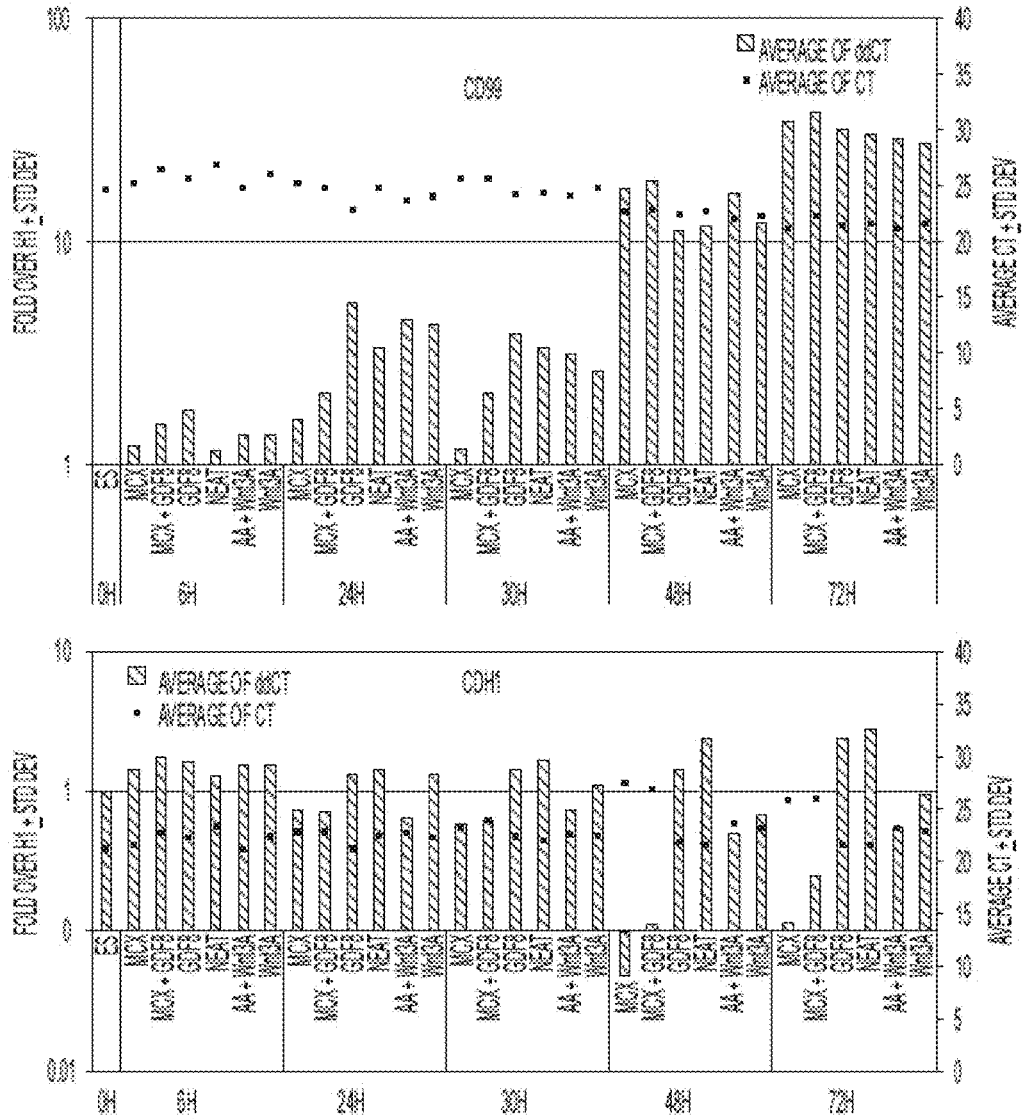
Figure 88C:
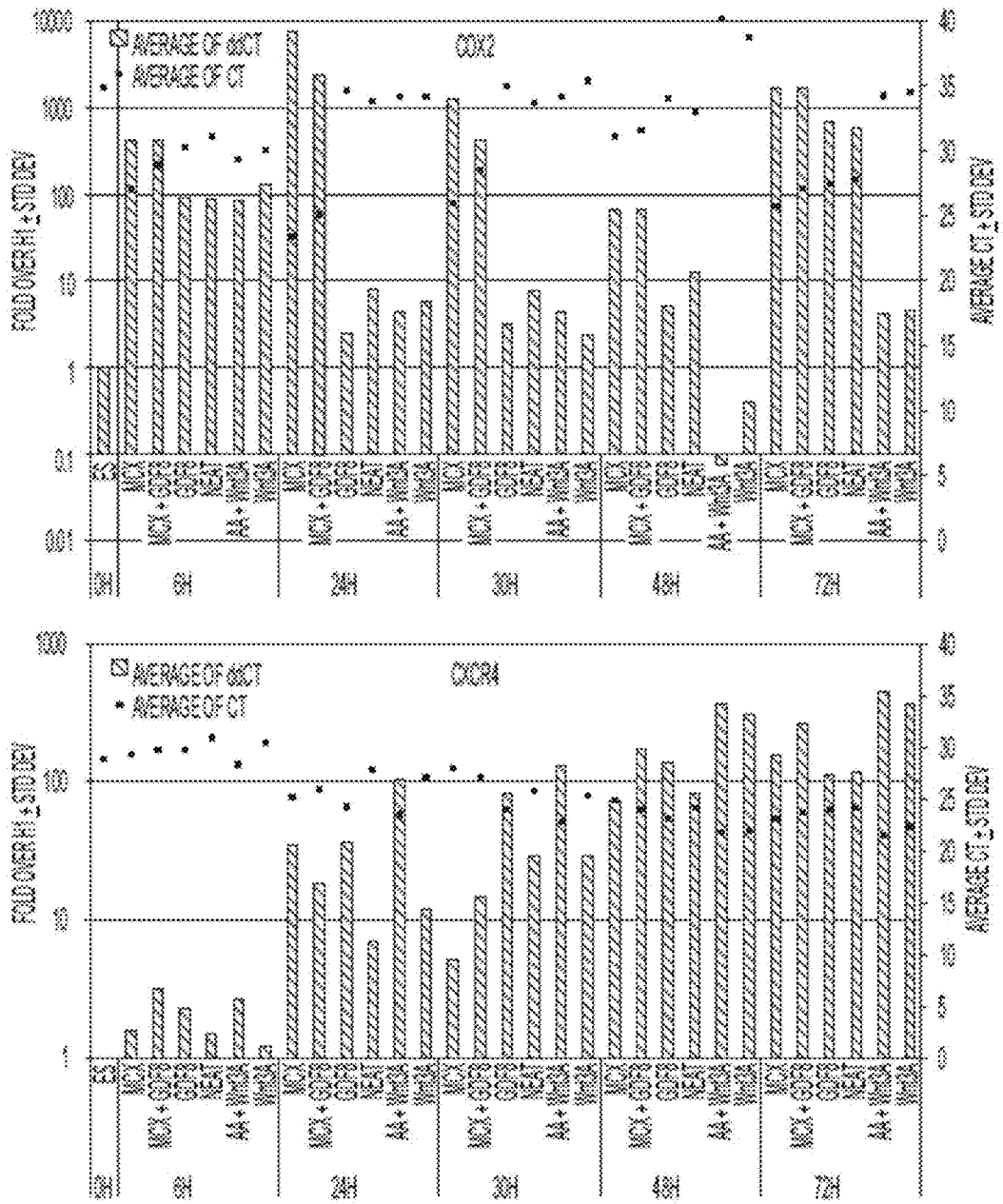
Figure 88D:
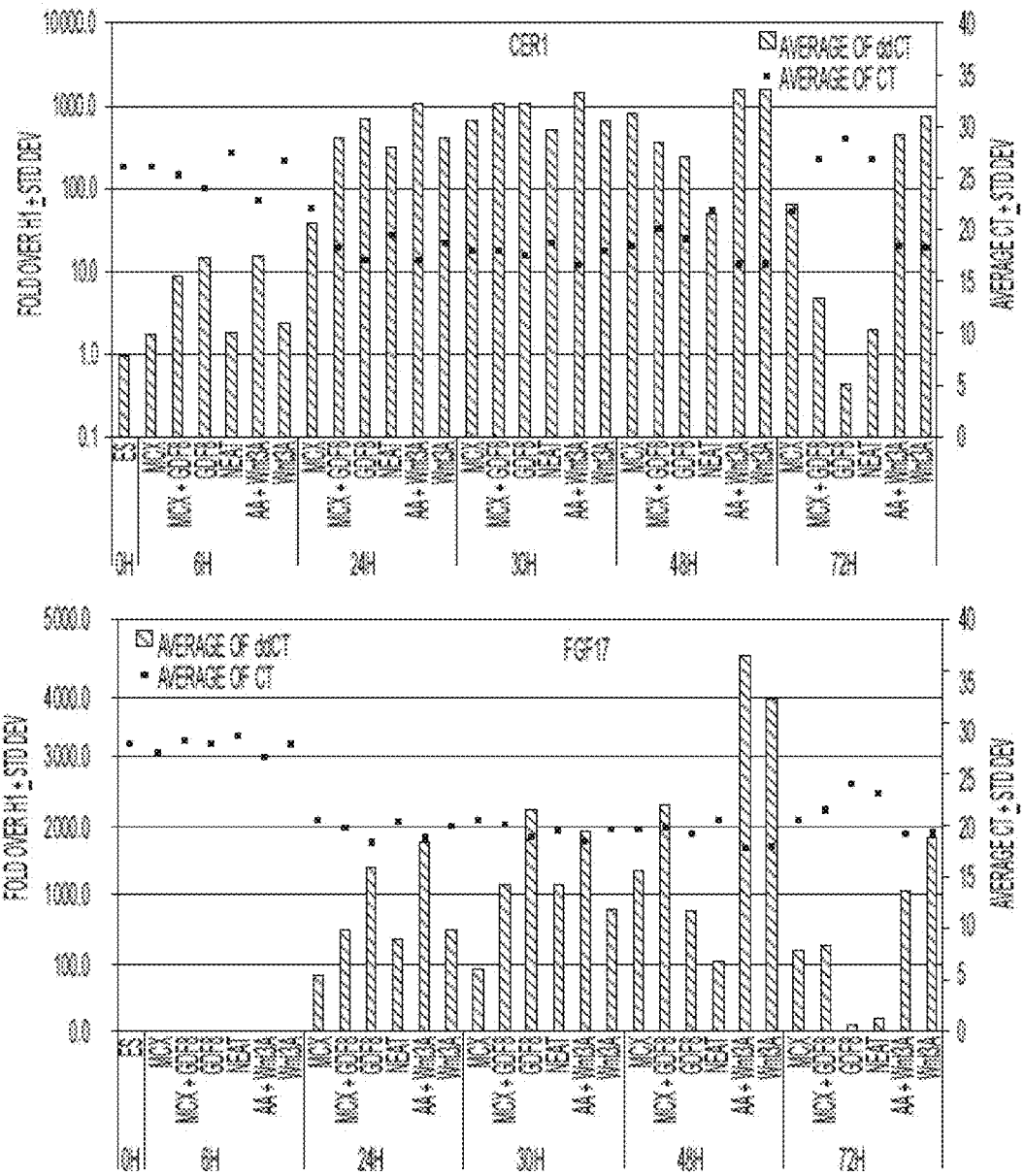
Figure 88E:
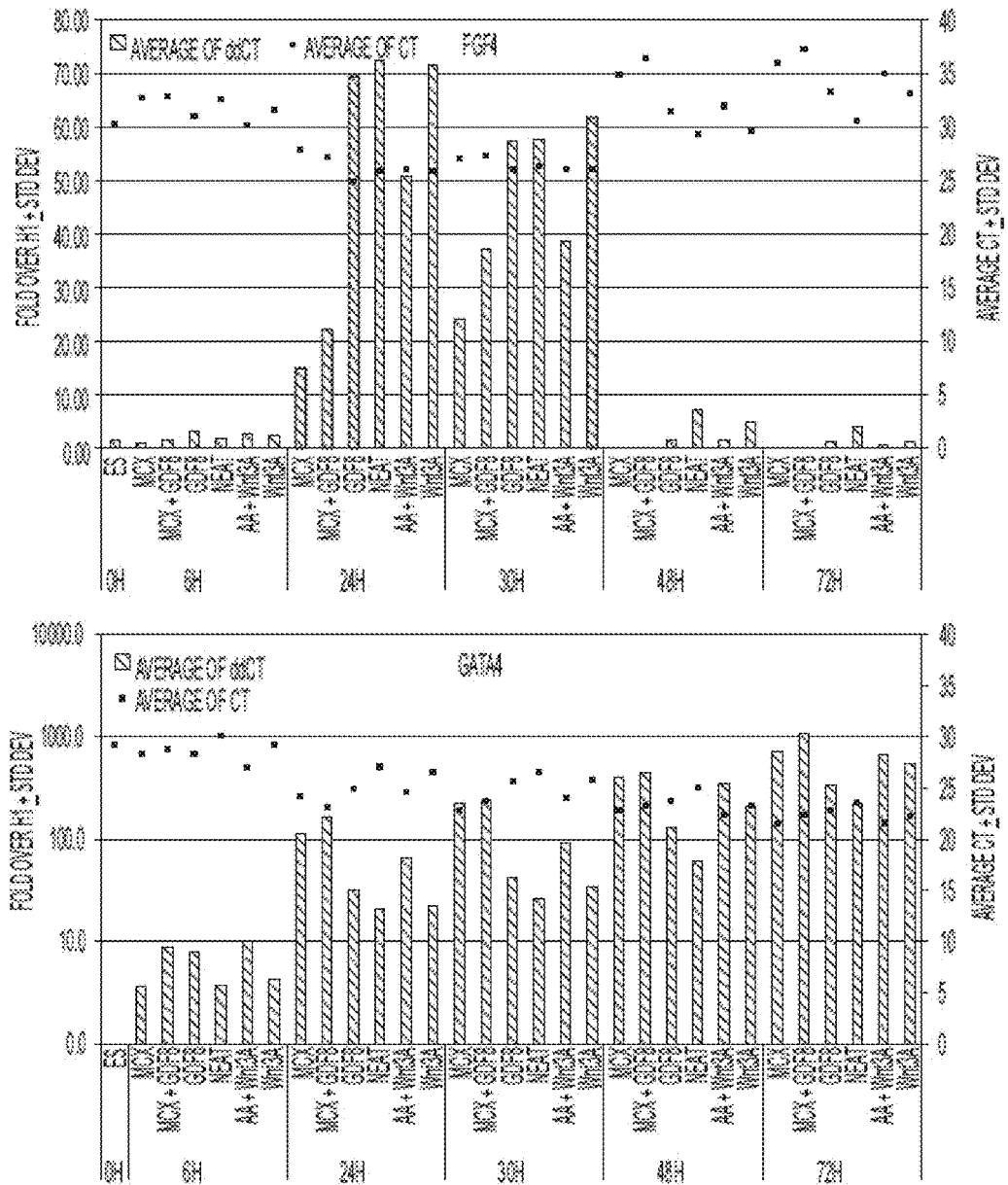
Figure 88F:
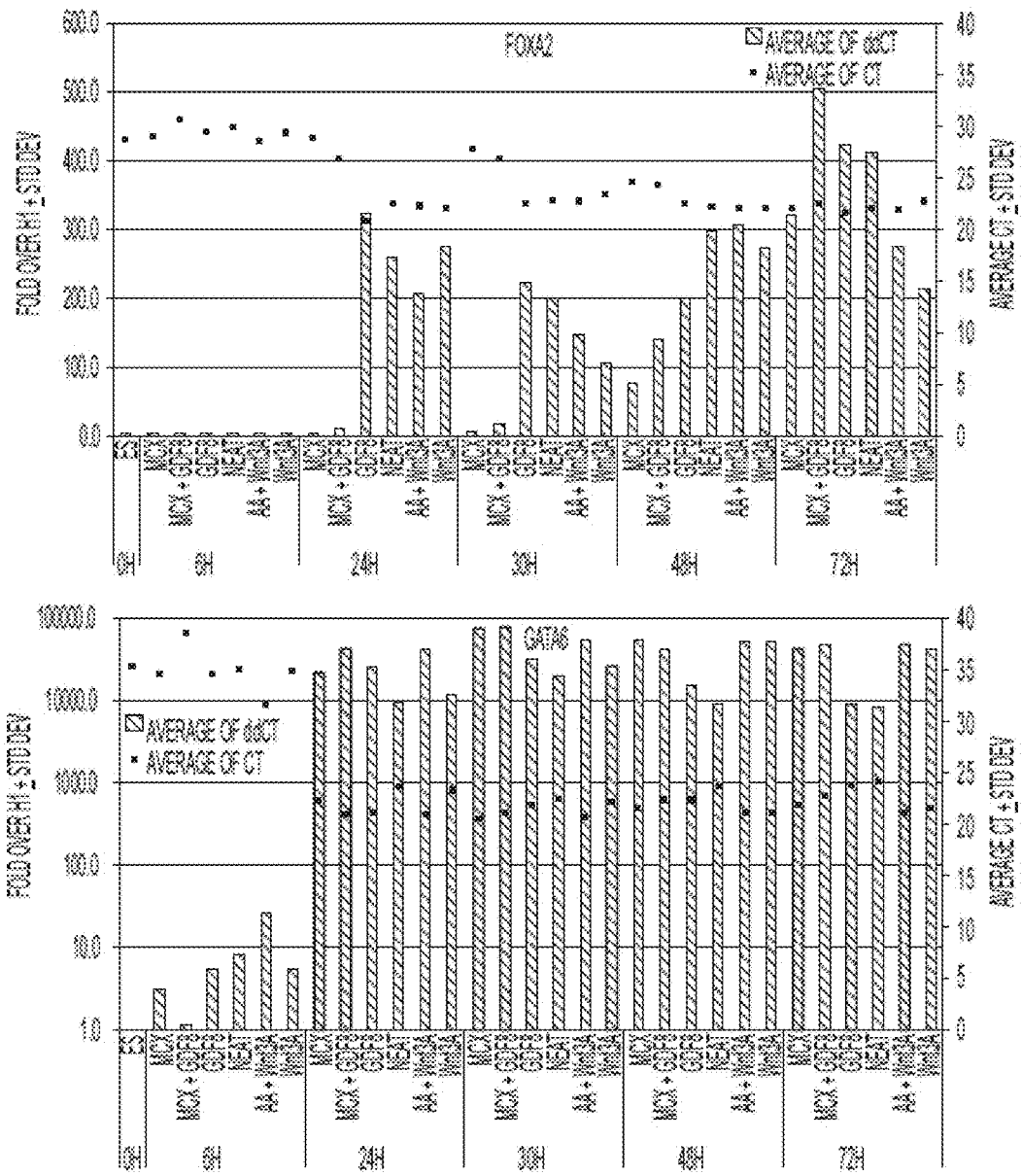
Figure 88G:
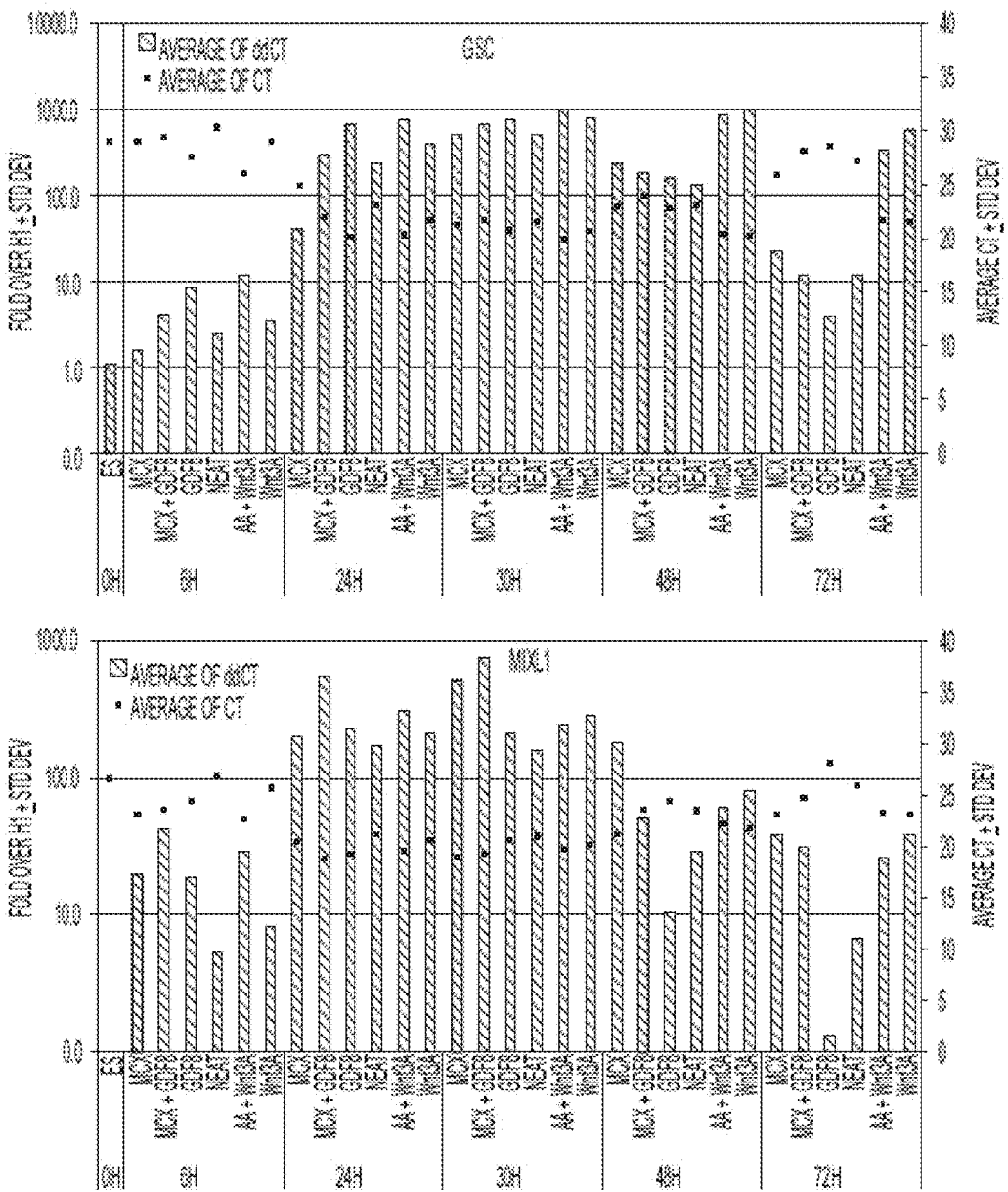
Figure 88H:
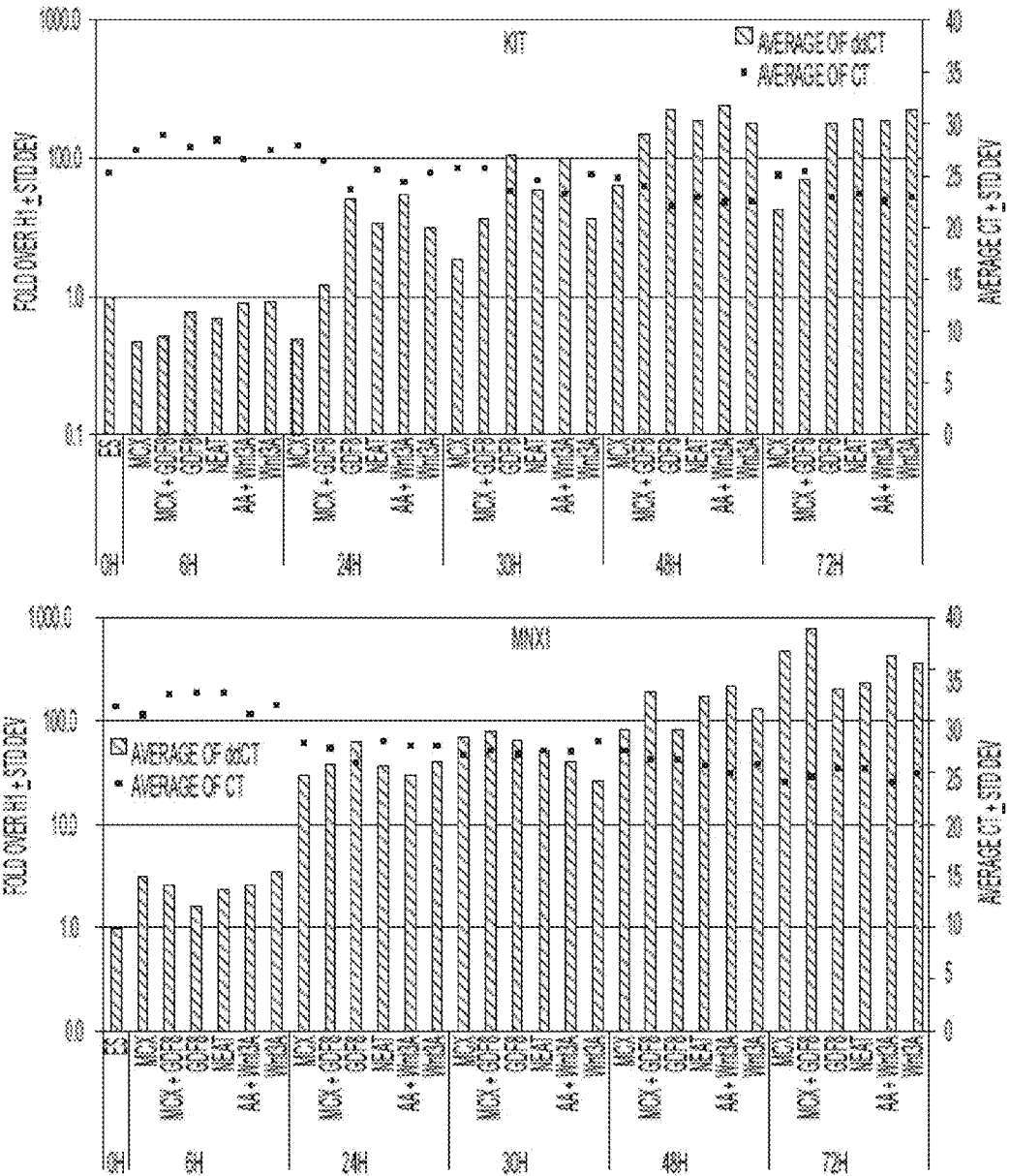
Figure 88I:
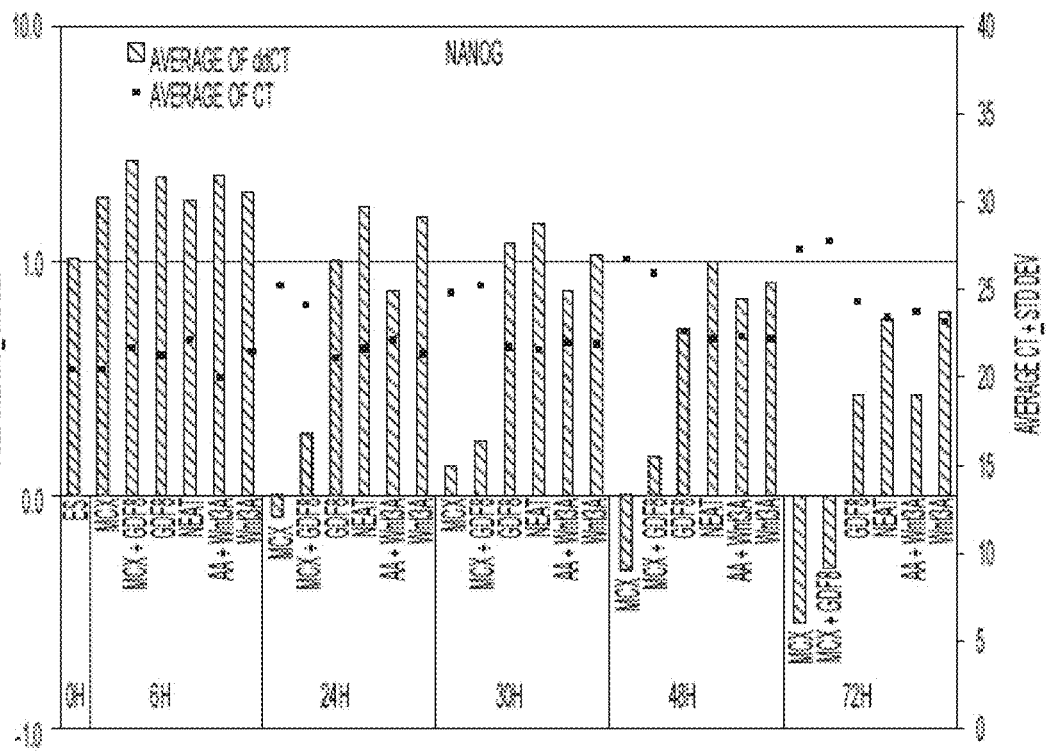
Figure 88K:
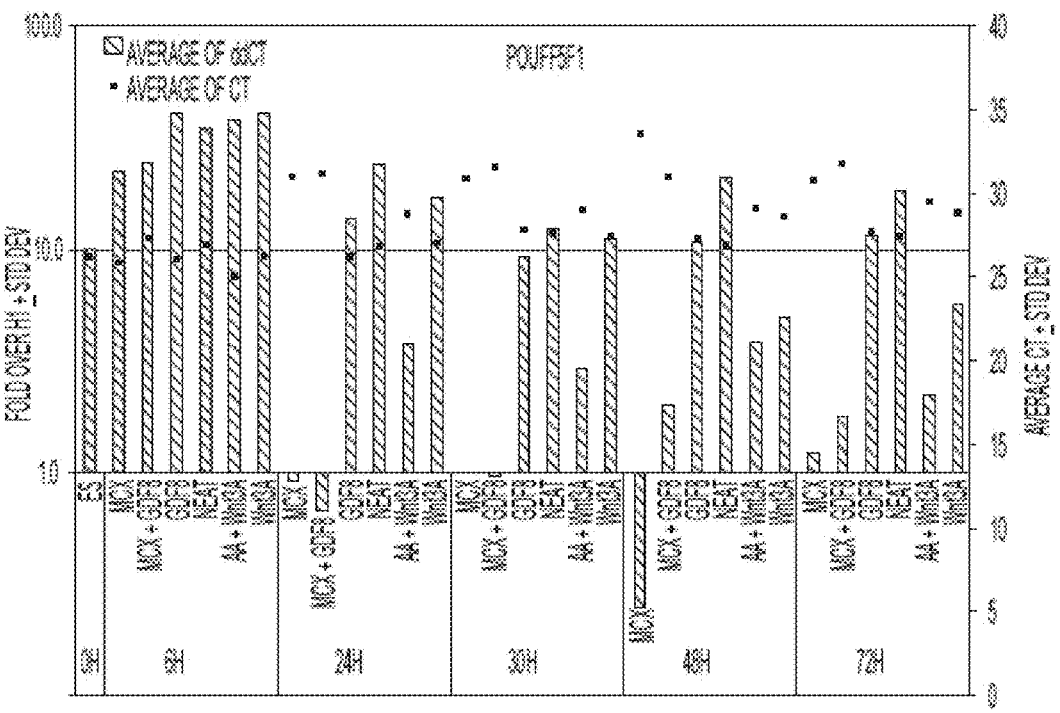
Figure 88I:
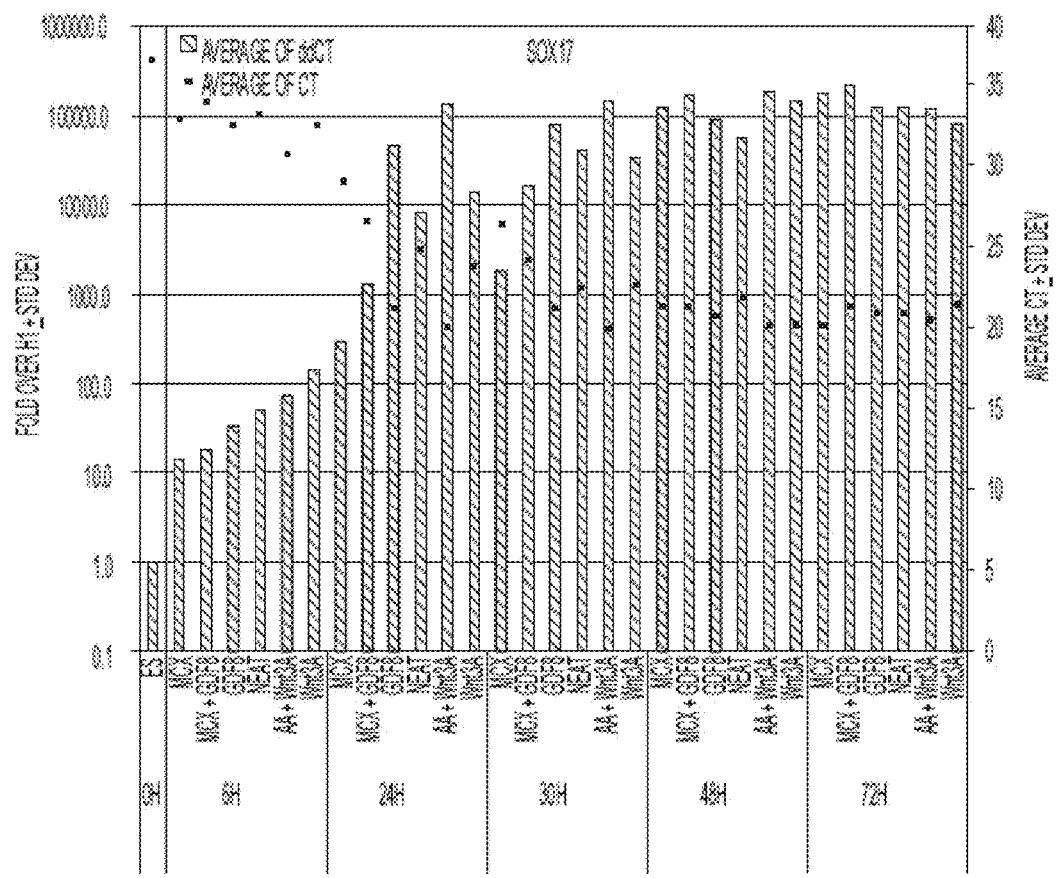
Figure 88N:
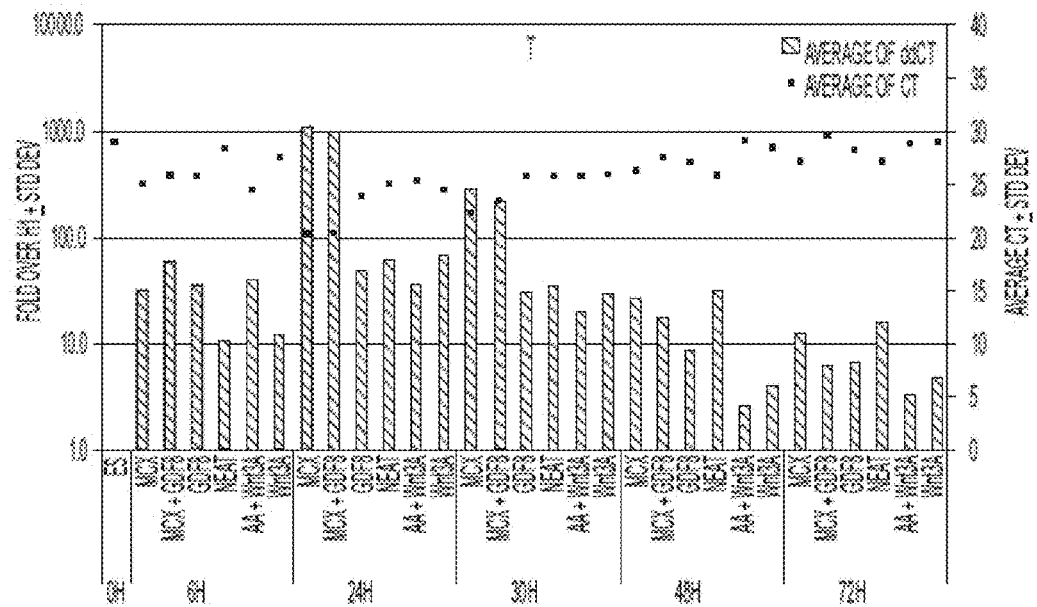

FIGS. 88*a* to 88*n* show the gene expression, as determined by qRT-PCR as a fold expression versus undifferentiated cells, for cells differentiated according to various embodiments of the protocol of Example 15 after 0 hours, 6 hours, 24 hours, 30 hours, 48 hours and 72 hours of differentiation. FIGS. 88*a*-88*b* show the gene expression, as determined by qRT-PCR as a fold expression versus undifferentiated cells, for CD99, CD9, CDH1, and CDH2. FIGS. 88*c*-88*d* show the gene expression, as determined by qRT-PCR as a fold expression versus undifferentiated cells, for CXD2, CER1, CXCR4, and FGF17. FIGS. 88*e*-88*f* shows the gene expression, as determined by qRT-PCR as a fold expression versus undifferentiated cells, for FGF4, FOXA, GATA4, and GATA6. FIGS. 88*g*-88*h* show the gene expression, as determined by qRT-PCR as a fold expression versus undifferentiated cells, for GSC, KIT, MIXL1 and MNX1. FIGS. 88*h*-88*l* show the gene expression, as determined by qRT-PCR as a fold expression versus undifferentiated cells, for NANOG, OTX2, POUF5F1, and SOX17. FIGS. 88*m*-88*n* show the gene expression, as determined by qRT-PCR as a fold expression versus undifferentiated cells, for SOX7 and T. The underlying data for FIGS. 88*a* to 88*n* is shown in FIGS. 58 to 67 and 69 to 80.

Figure 89:
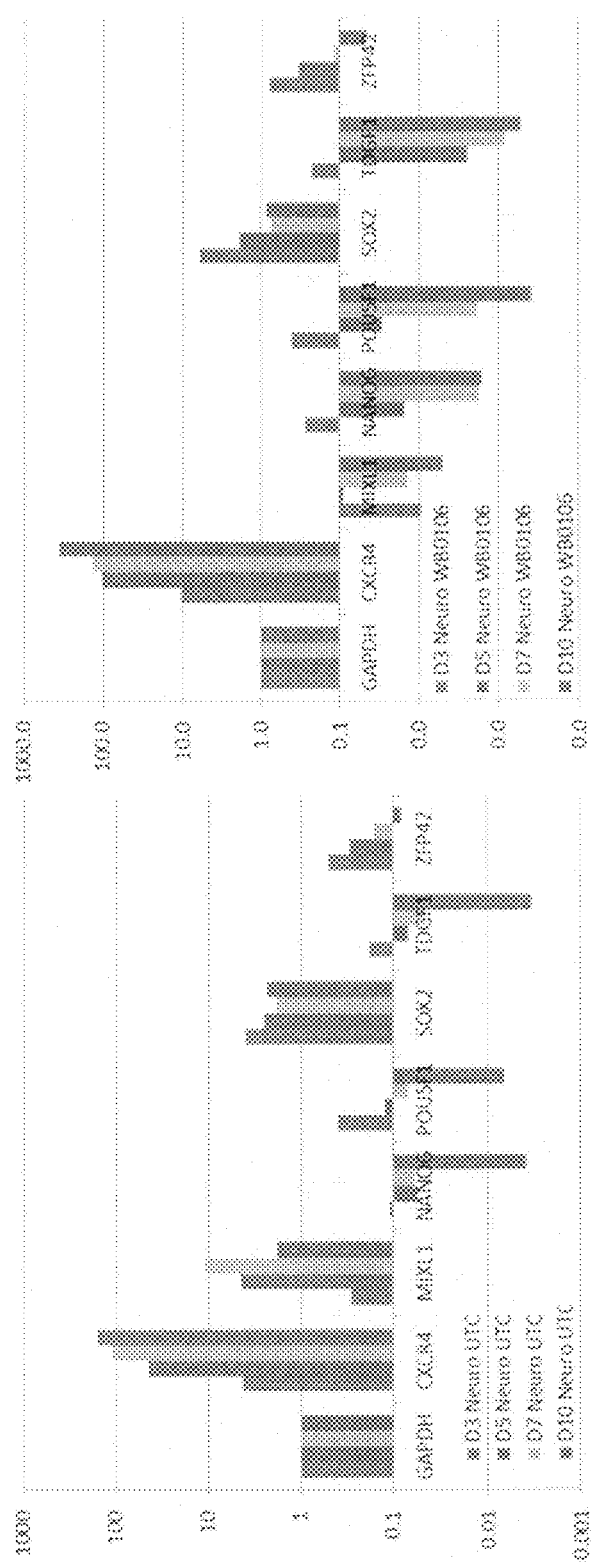

FIG. 89 shows the gene expression pattern, as determined by qRT-PCR, of pluripotent cells cultured in ectodermal differentiation medium according to the protocol of Example 16. As shown in FIG. 89, the cells differentiated towards the neural cell lineage. Specifically, the left panel of FIG. 89 shows the gene expression pattern for an induced pluripotent stem cell line generated from umbilical tissue cells (UTC). The right panel of FIG. 89 shows the gene expression pattern for the WB0106 sub-clone of the H1 hES cell line.

Figure 90:
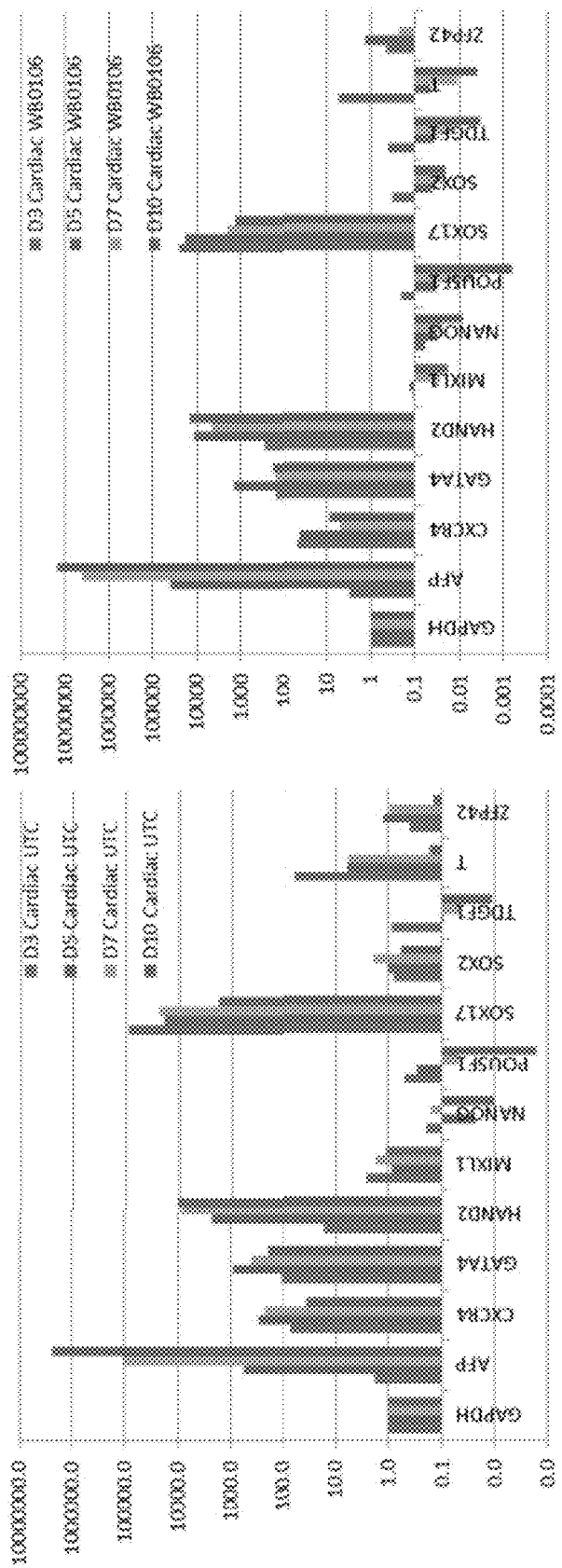

FIG. 90 shows the gene expression pattern, as determined by qRT-PCR, of pluripotent cells cultured in mesodermal differentiation medium according to the protocol of Example 16. As shown in FIG. 90, the cells differentiated towards cardiac cell lineage. Specifically, the left panel of FIG. 90 shows the gene expression pattern for an induced pluripotent stem cell line generated from umbilical tissue cells (UTC). The right panel of FIG. 90 shows the gene expression pattern for the WB0106 sub-clone of the H1 hES cell line.

Figure 91:
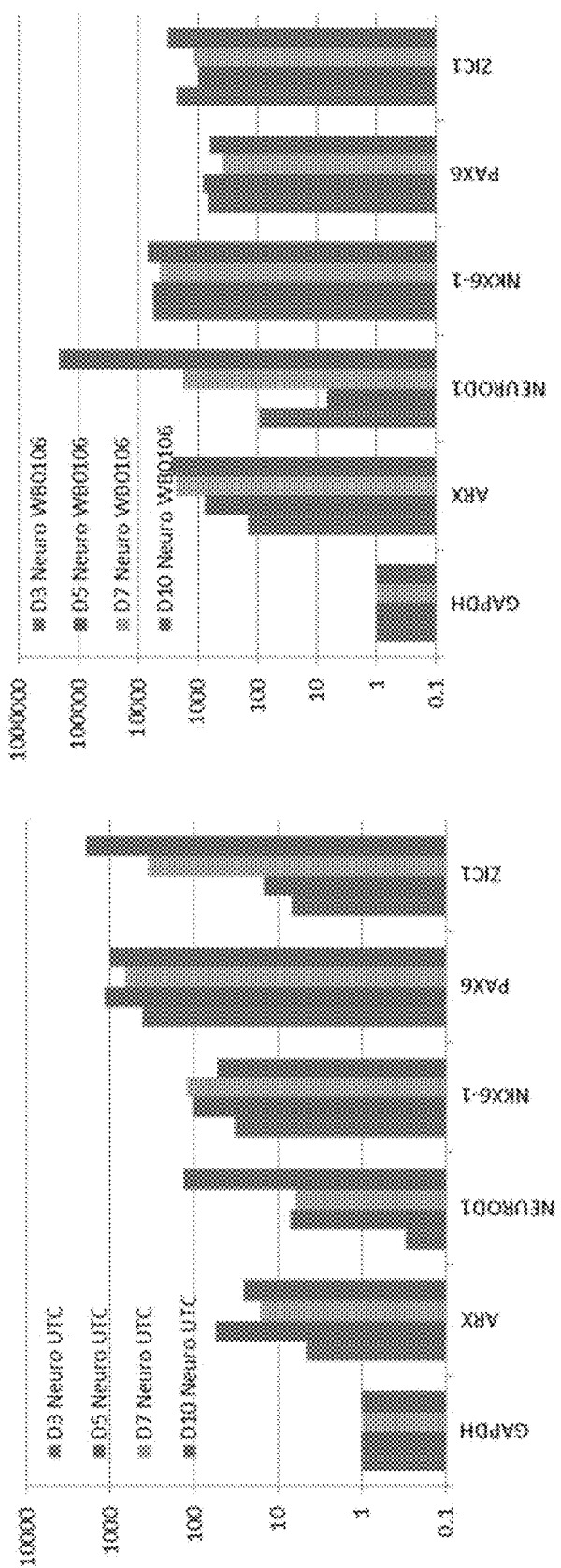

FIG. 91 shows the gene expression pattern, as determined by qRT-PCR, of pluripotent cells cultured in ectodermal differentiation medium according to the protocol of Example 16. As shown in FIG. 91, the cells differentiated towards neural cell lineage. Specifically, the left panel of FIG. 91 shows the gene expression pattern for an induced pluripotent stem cell line generated from umbilical tissue cells (UTC). The right panel of FIG. 91 shows the gene expression pattern for the WB0106 sub-clone of the H1 hES cell line.

Figure 92:
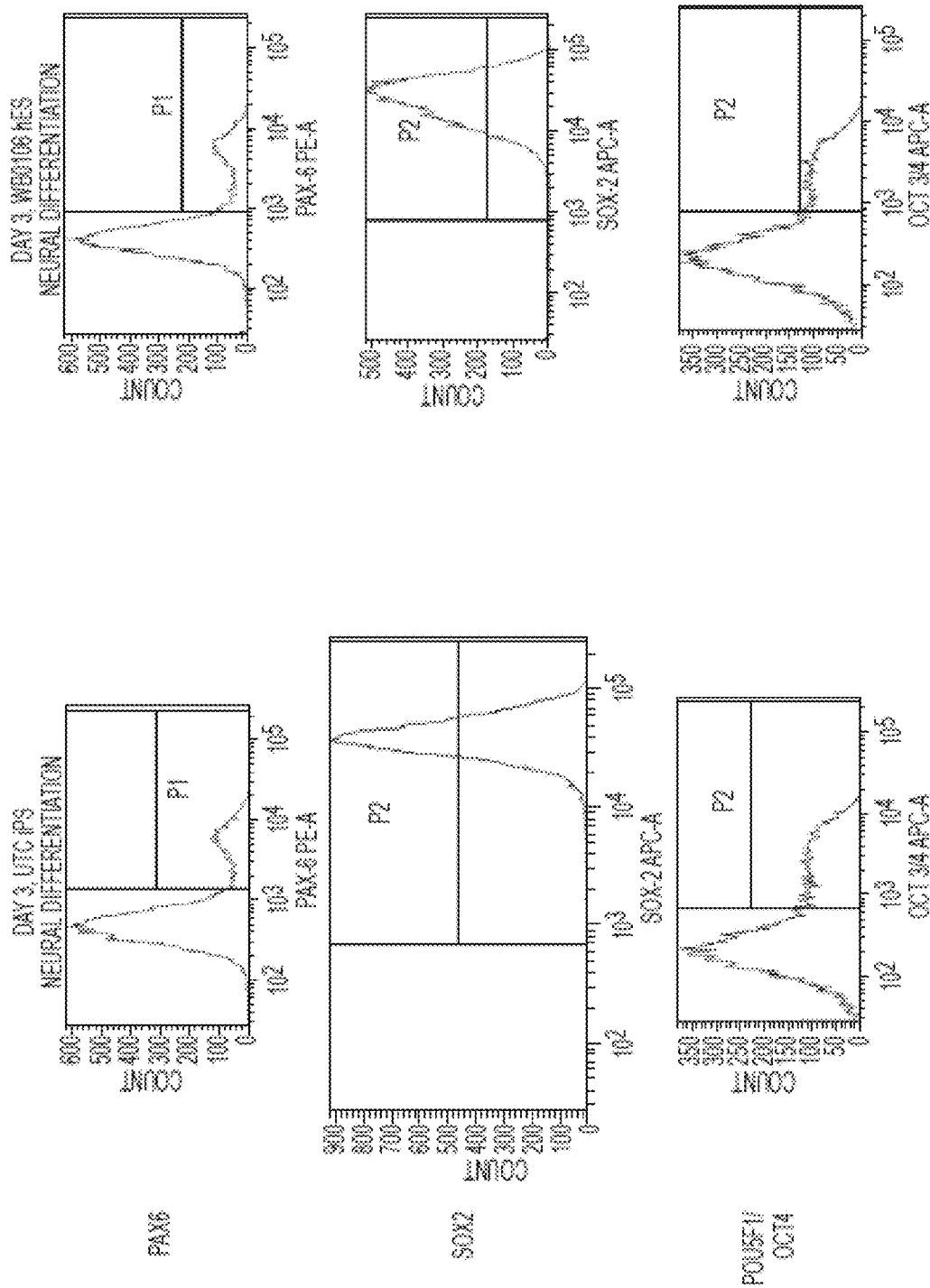

FIG. 92 shows the protein expression pattern for PAX6, SOX2, and POU5F1/OCT4, as determined by FACS, of pluripotent cells cultured for three days in ectodermal differentiation medium according to the protocol of Example 16. Specially, the left panels of FIG. 92 show the expression pattern for PAX6, SOX2, and POU5F1/OCT4 for an induced pluripotent stem cell line generated from umbilical tissue cells (UTC). The right panel of FIG. 92 shows the protein expression pattern for PAX6, SOX2, and POU5F1/OCT4 for the WB0106 sub-clone of the H1 hES cell line.

Figure 93:
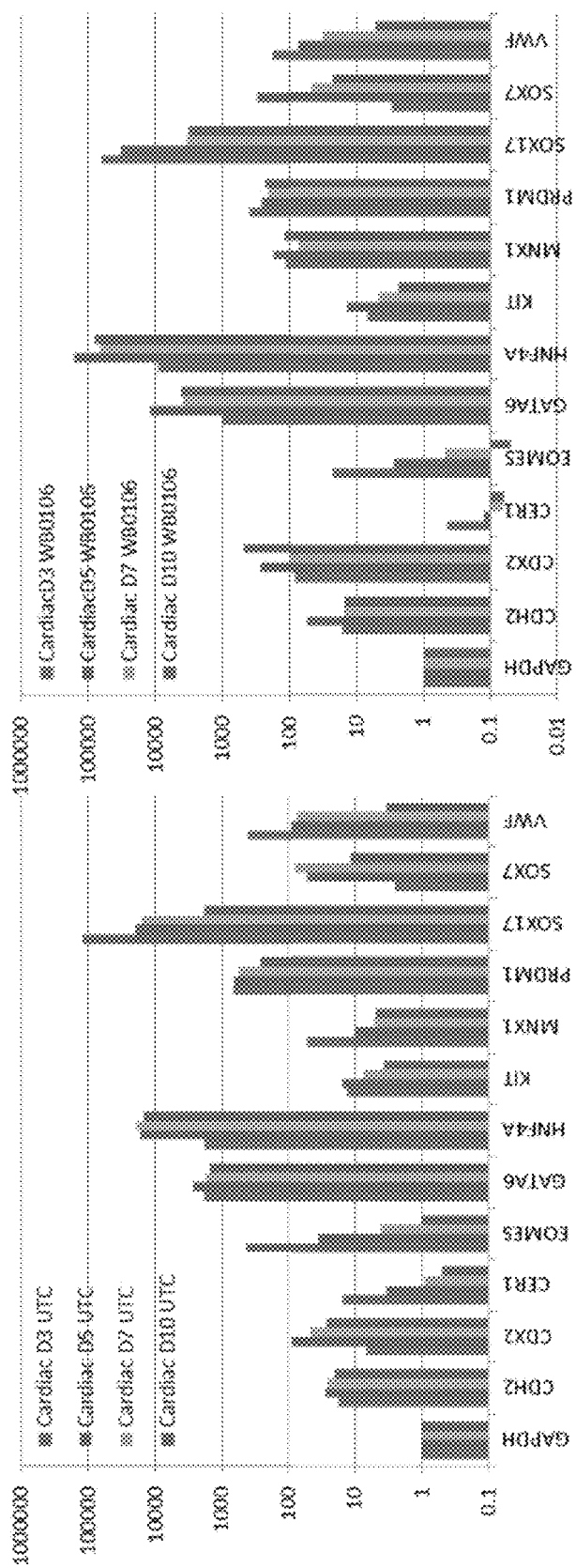

FIG. 93 shows the gene expression pattern, as determined by qRT-PCR, of pluripotent cells cultured in mesodermal differentiation medium according to the protocol of Example 16. As shown in FIG. 93, the cells differentiated towards cardiac cell lineage. Specifically, the left panel of FIG. 93 shows the gene expression pattern for an induced pluripotent stem cell line generated from umbilical tissue cells (UTC). The right panel of FIG. 93 shows the gene expression pattern for the WB0106 sub-clone of the H1 hES cell line.

Figure 94:
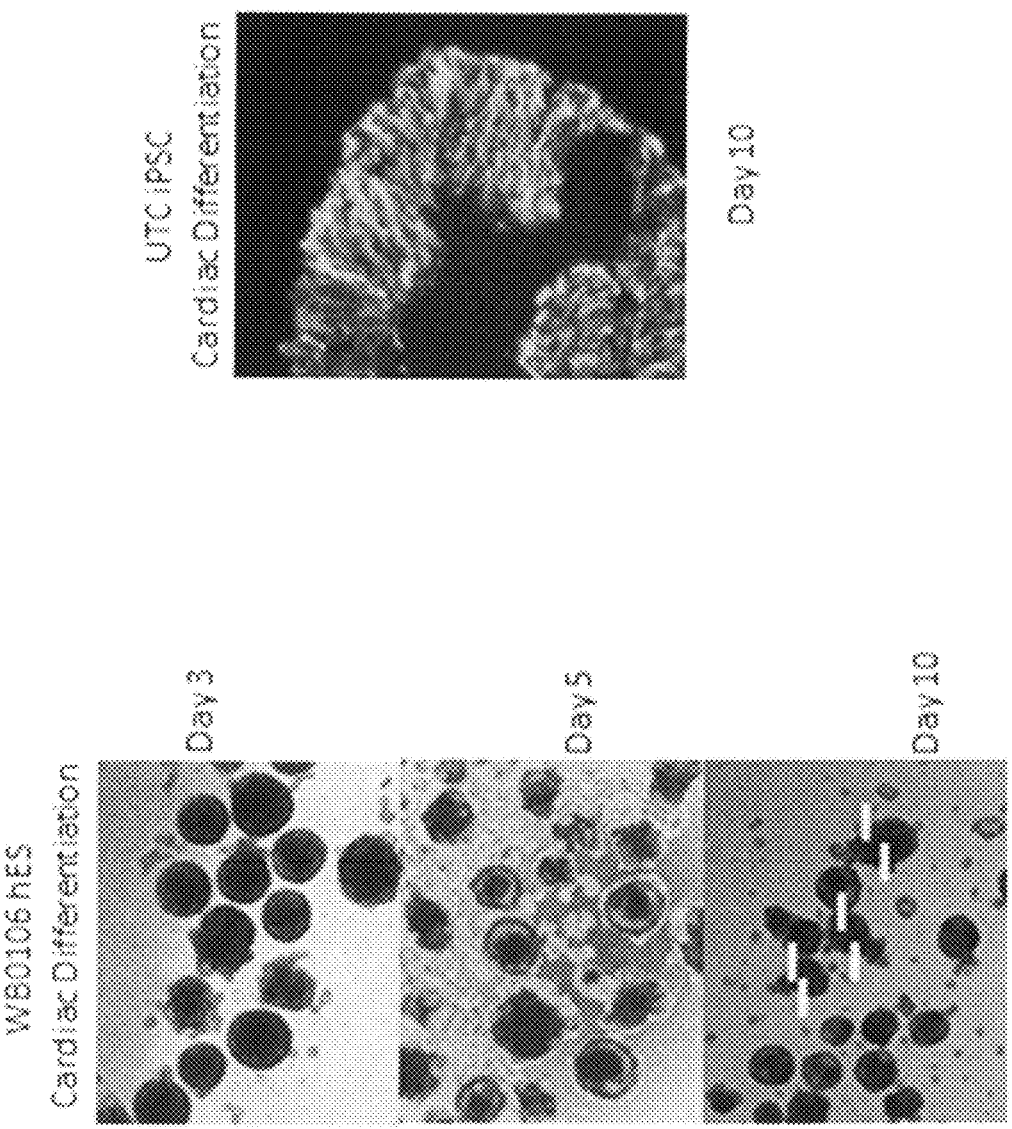

FIG. 94 shows micrographs for cells differentiated in mesodermal differentiation medium according to the protocol of Example 16. As shown in FIG. 94, the cells differentiated towards cardiac cell lineage. Specifically, the left hand panels of FIG. 94 show micrographs of cells of the WB0106 sub-clone of the H1 hES cell line at day 3, day 5 and day 10 of differentiation. The right hand panel of FIG. 94 shows a micrograph of induced pluripotent stem cell line generated from umbilical tissue cells (UTC IPSCs) after 10 days of differentiation.

FIG. 95 shows micrographs for cells differentiated in ectodermal differentiation medium according to the protocol of Example 16. As shown in FIG. 95, the cells differentiated towards the neural cell lineage. Specifically, the left hand panels of FIG. 95 show micrographs of cells of the WB0106 sub-clone of the H1 hES cell line at day 3, day 5 and day 10 of differentiation. The right hand panel of FIG. 95 shows a micrograph of induced pluripotent stem cell line generated from umbilical tissue cells (UTC iPCS) after 10 days of differentiation.

DETAILED DESCRIPTION

This application is directed to preparing embryonic stem cells and other pluripotent cells that maintain pluripotency in aggregated cell cluster for differentiation to endoderm progenitor cells; pancreatic endocrine cells, mesoderm cells or ectoderm cells. For clarity of disclosure, and not by way of limitation, the detailed description of the invention is divided into the following subsections that describe or illustrate certain features, embodiments or applications of the present invention.

Definitions

Stem cells are undifferentiated cells defined by their ability, at the single cell level, to both self-renew and differentiate. Stem cells may produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm, and ectoderm). Stem cells also give rise to tissues of multiple germ layers following transplantation and contribute substantially to most, if not all, tissues following injection into blastocysts.

Stem cells are classified by their developmental potential. "Cell culture" or "culturing" refer generally to cells taken from a living organism and grown under controlled conditions ("in culture" or "cultured"). A primary cell culture is a culture of cells, tissues, or organs taken directly from an organism before the first subculture. Cells are expanded in culture when they are placed in a growth medium under conditions that facilitate one or both of cell growth and division, resulting in a larger population of the cells. When cells are expanded in culture, the rate of cell proliferation is sometimes measured by the amount of time needed for the cells to double in number (referred to as doubling time).

"Expanding", as used herein is the process of increasing the number of pluripotent stem cells by culturing, such as by at least about 5%, 10%, 15%, 20%, 25%, 30%, 35%, 40%, 45%, 50%, 60%, 75%, 90%, 100%, 200%, 500%, 1000% or more, and levels within these percentages. It is appreciated that the number of pluripotent stem cells which can be obtained from a single pluripotent stem cell depends on the proliferation capacity of the pluripotent stem cell. The proliferation capacity of the pluripotent stem cell can be calculated by the doubling time of the cell, i.e., the time needed for a cell to undergo a mitotic division in the culture, and the period that the pluripotent stem cell can be maintained in the undifferentiated state, which is equivalent to the number of passages multiplied by the days between each passage.

Differentiation is the process by which an unspecialized ("uncommitted") or less specialized cell acquires the features of a specialized cell such as, a nerve cell or a muscle cell. A differentiated cell or a differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the lineage of a cell defines the heredity of the cell, i.e., which cells it came from and to what cells it can give rise. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Markers", as used herein, are nucleic acid or polypeptide molecules that are differentially expressed in a cell of interest. In this context, differential expression means an increased level for a positive marker and a decreased level for a negative marker as compared to an undifferentiated cell. The detectable level of the marker nucleic acid or polypeptide is sufficiently higher or lower in the cells of interest compared to other cells, such that the cell of interest can be identified and distinguished from other cells using any of a variety of methods known in the art.

As used herein, a cell is "positive for" a specific marker or "positive" when the specific marker is sufficiently detected in the cell. Similarly, the cell is "negative for" a specific marker, or "negative" when the specific marker is not sufficiently detected in the cell. In particular, positive by FACS is usually greater than 2%, whereas the negative threshold by FACS is usually less than 1%. Positive by PCR is usually less than 34 cycles (Cts); whereas negative by PCR is usually more than 34.5 cycles.

As used herein, "cell density" and "seeding density" are used interchangeably herein and refer to the number of cells seeded per unit area of a solid or semisolid planar or curved substrate.

As used herein, "suspension culture" refers to a culture of cells, single cells or clusters, suspended in medium rather than adhering to a surface.

As used herein, "serum free" refers to being devoid of human or animal serum. Accordingly, a serum free culture medium does not comprise serum or portions of serum.

In attempts to replicate the differentiation of pluripotent stem cells into functional pancreatic endocrine cells in cell culture, the differentiation process is often viewed as progressing through a number of consecutive stages. As used herein, the various stages are defined by the culturing times, and reagents set forth in the Examples included herein.

"Definitive endoderm", as used herein, refers to cells which bear the characteristics of cells arising from the epiblast during gastrulation and which form the gastrointestinal tract and its derivatives. Definitive endoderm cells express at least one of the following markers: FOXA2 (also known as hepatocyte nuclear factor 3-3 (HNF33)), GATA4, GATA6, MNX1, SOX17, CXCR4, Cerberus, OTX2, brachyury, goosecoid, C-Kit, CD99, and MIXL1. Markers characteristic of the definitive endoderm cells include CXCR4, FOXA2 and SOX17. Thus, definitive endoderm cells may be characterized by their expression of CXCR4, FOXA2, and SOX17. In addition, depending on the length of time cells are allowed to remain in stage 1, an increase in HNF4a may be observed.

"Pancreatic endocrine cells," as used herein, refer to cells capable of expressing at least one of the following hormones: insulin, glucagon, somatostatin, ghrelin, and pancreatic polypeptide. In addition to these hormones, markers characteristic of pancreatic endocrine cells include one or more of NGN3, NeuroD1, ISL1, PDX1, NKX6.1, PAX4, ARX, NKX2.2, and PAX6. Pancreatic endocrine cells expressing markers characteristic of β cells can be characterized by their expression of insulin and at least one of the following transcription factors: PDX1, NKX2.2, NKX6.1, NeuroD1, ISL1, HNF3β, MAFA, PAX4, and PAX6.

Used interchangeably herein are "d1", "d 1", and "day 1"; "d2", "d 2", and "day 2"; "d3", "d 3", and "day 3", and so on. These number letter combinations refer to a specific day of incubation in the different stages during the stepwise differentiation protocol of the instant application.

"Glucose" and "D-Glucose" are used interchangeably herein and refer to dextrose, a sugar commonly found in nature.

Used interchangeably herein are "NeuroD" and "NeuroD1" which identify a protein expressed in pancreatic endocrine progenitor cells and the gene encoding it.

"LDN" and "LDN-193189" refer ((6-(4-(2-(piperidin-1-yl)ethoxy)phenyl)-3-(pyridin-4-yl)pyrazolo[1,5-a]pyrimidine, hydrochloride; DM-3189)), a BMP receptor inhibitor available under the trademark STEMOLECULE™ from Stemgent, Inc., Cambridge, Mass., USA.

Isolation, Expansion and Culture of Pluripotent Stem Cells

Pluripotent stem cells may express one or more of the designated TRA-1-60 and TRA-1-81 antibodies (Thomson et al. 1998, *Science* 282:1145-1147). Differentiation of pluripotent stem cells in vitro results in the loss of TRA-1-60, and TRA-1-81 expression. Undifferentiated pluripotent stem cells typically have alkaline phosphatase activity, which can be detected by fixing the cells with 4% paraformaldehyde, and then developing with Vector® Red as a substrate, as described by the manufacturer (Vector Laboratories, Inc., Burlingame, Calif.). Undifferentiated pluripotent stem cells also typically express OCT4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of stem cells can be confirmed, for example, by injecting cells into severe combined immunedeficiency ("SCID") mice, fixing the teratomas that form using 4% paraformaldehyde, and then examining histologically for evidence of cell types from these three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered. Pluripotent cells may be readily expanded in culture using various feeder layers or by using matrix protein coated vessels. Alternatively, chemically defined surfaces in combination with defined media such as mTeSR®1 media (StemCell Technologies, Vancouver, BC, Canada) may be used for routine expansion of the cells.

Culturing in a suspension culture according to the method of some embodiments of the invention is effected by seeding the pluripotent stem cells in a culture vessel at a cell density that promotes cell survival and proliferation, but limits differentiation. Typically, a seeding density that maintains undifferentiation of cells is used. It will be appreciated that although single-cell suspensions of stem cells may be seeded, small clusters of cells may be advantageous.

To provide the pluripotent stem cells with a sufficient and constant supply of nutrients and growth factors while in the suspension culture, the culture medium can be replaced or replenished on a daily basis or at a pre-determined schedule such as every 1-5 days. Large clusters of pluripotent stem cells may cause cell differentiation, thus, measures may be taken to avoid large pluripotent stem cell aggregates. According to some embodiments of the invention, the formed pluripotent stem cell clusters are dissociated, for example, every 2-7 days and the single cells or small clumps of cells are either split into additional culture vessels (i.e., passaged) or retained in the same culture vessel and processed with replacement or additional culture medium.

Large pluripotent stem cell clumps, including a pellet of pluripotent stem cells resulting from centrifugation, can be subjected to one or both of enzymatic digestion and mechanical dissociation. Enzymatic digestion of pluripotent stem cell clumps can be performed by subjecting the clump to an enzyme, such as type IV Collagenase, Dispase® or Accutase®. Mechanical dissociation of large pluripotent stem cell clumps can be performed using a device designed to break the clumps to a predetermined size. Additionally, or alternatively, mechanical dissociation can be manually performed using a needle or pipette.

The culture vessel used for culturing the pluripotent stem cells in suspension according to the method of some embodiments of the invention can be any tissue culture vessel (e.g., with a purity grade suitable for culturing pluripotent stem cells) having an internal surface designed such that pluripotent stem cells cultured therein are unable to adhere or attach to such a surface (e.g., non-tissue culture treated vessel, to prevent attachment or adherence to the surface). Preferably to obtain a scalable culture, culturing according to some embodiments of the invention is effected using a controlled culturing system (preferably a computer-controlled culturing system) in which culture parameters such as temperature, agitation, pH, and oxygen are automatically monitored and controlled using a suitable device. Once the desired culture parameters are determined, the system may be set for automatic adjustment of culture parameters as needed to enhance pluripotent stem cell expansion and differentiation.

The pluripotent stem cells may be cultured under dynamic conditions (i.e., under conditions in which the pluripotent stem cells are subject to constant movement while in the suspension culture, e.g. a stirred suspension culture system) or under non-dynamic conditions (i.e., a static culture) while preserving their, proliferative, pluripotent capacity and karyotype stability over multiple passages.

For non-dynamic culturing of pluripotent stem cells, the pluripotent stem cells can be cultured in petri dishes, T-flasks, HyperFlasks® (Corning Incorporated, Corning, N.Y.), CellStacks® (Corning Incorporated, Corning, N.Y.) or Cell Factories (NUNC™ Cell Factory™ Systems (Thermo Fisher Scientific, Inc., Pittsburgh, Pa.)) coated or uncoated. For dynamic culturing of pluripotent stem cells, the pluripotent stem cells can be cultured in a suitable vessel, such as spinner flasks or Erlenmeyer flasks, stainless steel, glass or single use plastic shaker or stirred tank vessels. The culture vessel can be connected to a control unit and thus present a controlled culturing system. The culture vessel (e.g., spinner flask or Erlenmeyer flask) may be agitated continuously or intermittently. Preferably the cultured vessel is agitated sufficiently to maintain the pluripotent stem cells in suspension.

The pluripotent stem cells may be cultured in any medium that provides sufficient nutrients and environmental stimuli to promote growth and expansion. Suitable media include E8™, IH3 and mTeSR®1 or mTeSR®2. The media may be changed periodically to refresh the nutrient supply and remove cellular by-products. According to some embodiments of the invention, the culture medium is changed daily.

Sources of Pluripotent Stem Cell

Any pluripotent stem cell may be used in the methods of the invention. Exemplary types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily, before approximately 10 to 12 weeks gestation. Non-limiting examples are established lines of human embryonic stem cells (hESCs) or human embryonic germ cells, such as, for example the human embryonic stem cell lines H, H7, and H9 (WiCell Research Institute, Madison, Wis., USA). Also suitable are cells taken from a pluripotent stem cell population already cultured in the absence of feeder cells.

Also suitable are inducible pluripotent cells (IPS) or reprogrammed pluripotent cells that can be derived from adult somatic cells using forced expression of a number of pluripotent related transcription factors, such as OCT4, NANOG, Sox2, KLF4, and ZFP42 (*Annu Rev Genomics Hum Genet* 2011, 12:165-185). The human embryonic stem cells used in the methods of the invention may also be prepared as described by Thomson et al. (U.S. Pat. No. 5,843,780; Science, 1998, 282:1145-1147; *Curr Top Dev Biol* 1998, 38:133-165; *Proc Natl Acad Sci U.S.A.* 1995, 92:7844-7848). Also suitable are mutant human embryonic stem cell lines, such as, for example, BG01v (BresaGen, Athens, Ga.), or cells derived from adult human somatic cells, such as, for example, cells disclosed in Takahashi et al, Cell 131: 1-12 (2007). Pluripotent stem cells suitable for use in the present invention may be derived according to the methods described in Li et al. (*Cell Stem Cell* 4: 16-19, 2009); Maherali et al. (*Cell Stem Cell* 1: 55-70, 2007); Stadtfeld et al. (*Cell Stem Cell* 2: 230-240); Nakagawa et al. (*Nature Biotechnology* 26: 101-106, 2008); Takahashi et al. (*Cell* 131: 861-872, 2007); and U.S. Patent App. Pub. No. 2011-0104805. Other sources of pluripotent stem cells include induced pluripotent cells (IPS, Cell, 126(4): 663-676). Other sources of cells suitable for use in the methods of invention include human umbilical cord tissue-derived cells, human amniotic fluid-derived cells, human placental-derived cells, and human parthenotes. In one embodiment, the umbilical cord tissue-derived cells may be obtained using the methods of U.S. Pat. No. 7,510,873, the disclosure of which is incorporated by reference in its entirety as it pertains to the isolation and characterization of the cells. In another embodiment, the placental tissue-derived cells may be obtained using the methods of U.S. App. Pub. No. 2005/0058631, the disclosure of which is incorporated by reference in its entirety as it pertains to the isolation and characterization of the cells. In another embodiment, the amniotic fluid-derived cells may be obtained using the methods of U.S. App. Pub. No. 2007/0122903, the disclosure of which is incorporated by reference in its entirety as it pertains to the isolation and characterization of the cells Characteristics of pluripotent stem cells are well known to those skilled in the art, and additional characteristics of pluripotent stem cells continue to be identified. Pluripotent stem cell markers include, for example, the expression of one or more (e.g. 1, 2, 3, 4, 5, 6, 7, 8, 9, 10, 11, 12, 13, 14 or all) of the following: ABCG2, cripto, FOXD3, CONNEXIN43, CONNEXIN45, OCT4, SOX2, NANOG, hTERT, UTF1, ZFP42, SSEA-3, SSEA-4, TRA-1-60, TRA-1-81. In one embodiment, the pluripotent stem cells suitable for use in the methods of the invention express one or more (e.g. 1, 2, 3 or all) of CD9, SSEA4, TRA-1-60, and TRA-1-81, and lack expression of a marker for differentiation CXCR4 (also known as CD184) as detected by flow cytometry. In another embodiment, the pluripotent stem cells suitable for use in the methods of the invention express one or more (e.g. 1, 2 or all) of CD9, NANOG and POU5F1/OCT4 as detected by RT-PCR.

Exemplary pluripotent stem cells include the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). In one embodiment, the pluripotent stem cells are human embryonic stem cells, for example, H1 hES cells. In alternate embodiments, pluripotent stem cells of non-embryonic origin are used.

Differentiation of Cells Expressing Markers Characteristic of the Pancreatic Endoderm Lineage from Pluripotent Stem Cells Expansion of Pluripotent Stem Cells The present invention, in some of the embodiments as described below, relates to isolating and culturing stem cells, in particular culturing stem cell clusters, which retain pluripotency in a dynamic suspension culture system. Pluripotent cell clusters may be differentiated to produce functional β cells.

The pluripotent stem cells used in the methods of the present invention are preferably expanded in dynamic suspension culture prior to differentiation toward a desired end point. Advantageously, it has been found that the pluripotent stem cells can be cultured and expanded as clusters of cells in suspension in a suitable medium without loss of pluripotency. Such culturing may occur in a dynamic suspension culture system wherein the cells or cell clusters are kept moving sufficiently to prevent loss of pluripotency. Useful dynamic suspension culture systems include systems equipped with means to agitate the culture contents, such as via stirring, shaking, recirculation or the bubbling of gasses through the media. Such agitation may be intermittent or continuous, as long as sufficient motion of the cell clusters is maintained to facilitate expansion and prevent premature differentiation. Preferably, the agitation comprises continuous stirring such as via an impeller rotating at a particular rate. The impeller may have a rounded or flat bottom. The stir rate of the impeller should be such that the clusters are maintained in suspension and settling is minimized. Further, the angle of the impeller blade may be adjusted to aid in the upward movement of the cells and clusters to avoid settling. In addition, the impeller type, angle and rotation rate may all be coordinated such that the cells and clusters are in what appears as a uniform colloidal suspension.

Suspension culturing and expansion of pluripotent stem cell clusters may be accomplished by transfer of static cultured stem cells to an appropriate dynamic culture system such as a disposable plastic, reusable plastic, stainless steel or glass vessel, e.g. a spinner flask or an Erlenmeyer flask. For example, stem cells cultured in an adherent static environment, i.e., plate or dish surface, may first be removed from the surface by treatment with a chelating agent or enzyme. Suitable enzymes include, but are not limited to, type I Collagenase, Dispase® (Sigma Aldrich LLC, St. Louis, Mo.) or a commercially available formulation sold under the trade name Accutase® (Sigma Aldrich LLC, St. Louis, Mo.). Accutase® is a cell detachment solution comprising collagenolytic and proteolytic enzymes (isolated from crustaceans) and does not contain mammalian or bacterial derived products. Therefore, in one embodiment, the enzyme is a collagenolytic enzyme or a proteolytic enzyme or a cell detachment solution comprising collagenolytic and proteolytic enzymes. Suitable chelating agents include, but are not limited to, ethylenediaminetetraacetic acid EDTA. In some embodiments, the pluripotent stem cell cultures are incubated with the enzyme or chelating agent, preferably until colony edges began to curl and lift, but prior to full detachment of colonies from the culture surface. In one embodiment, the cell cultures are incubated at room temperature. In one embodiment, the cells are incubated at a temperature of more than 20° C., more than 25° C., more than 30° C. or more than 35° C., for example, at a temperature of between about 20° C. and about 40° C., between about 25° C. and about 40° C., between about 30° C. and about 40° C., for example, about 37° C. In one embodiment, the cells are incubated for at least about 1, at least about 5, at least about 10, at least about 15, at least about 20 minutes, for example between about 1 and about 30 minutes, between about 5 and about 30 minutes, between about 10 and about 25 minutes, between about 15 and about 25 minutes, for example, about 20 minutes. In one embodiment, the method involves the step of removing the enzyme or chelating agent from the cell culture after treatment. In one embodiment, the cell culture is washed once or twice or more, after removal of the enzyme or chelating agent. In one embodiment the cell culture is washed with an appropriate culture medium, such as mTeSR®1 (Stem Cell Technologies, Vancouver, BC, Canada). In one embodiment, a Rho-kinase inhibitor (for example, Y-27632, Axxora Catalog#ALX-270-333, San Diego, Calif.). The Rho-kinase inhibitor may be at a concentration of about 1 to about 100 µM, about 1 to about 90 µM, about 1 to about 80 µM, about 1 to about 70 µM, about 1 to about 60 µM, about 1 to about 50 µM, about 1 to about 40 µM, about 1 to about 30 µM, about 1 to about 20 µM, about 1 to about 15 µM, about 1 to about 10 µM, or about 10 µM. In one embodiment, the Rho-kinase inhibitor is added at least 1 µM, at least 5 µM or at least 10 µM. The cells may be lifted from the surface of the static culture system with a scraper or rubber policeman. Media and cells may be transferred to a dynamic culture system using a glass pipette or other suitable means. In a preferred embodiment, the media in the dynamic culture system is changed daily.

The invention provides, in one embodiment, methods of culturing and expanding pluripotent stem cells in a three-dimensional suspension culture. In particular, the methods provide for the culturing and expanding pluripotent stem cells by forming aggregated cell clusters of these pluripotent stem cells. The cell clusters may form as a result of treating pluripotent stem cell cultures with an enzyme (e.g. a neutral protease, for example Dispase®) or a chelating agent prior to culturing the cells. The cells may preferably be cultured in a stirred or shaken suspension culture system. In one embodiment, the invention further provides for formation of cells expressing markers characteristic of the pancreatic endoderm lineage from such clusters of pluripotent stem cells.

Preferably, the cell clusters are aggregated pluripotent stem cells. The aggregated stem cells express one or more markers of pluripotency, for example, one or more (e.g. 1, 2, 3 or all) of the markers CD9, SSEA4, TRA-1-60, and TRA-1-81, and lack expression of one or more markers for differentiation, for example, lack expression of CXCR4. In one embodiment, the aggregated stem cells express the markers for pluripotency CD9, SSEA4, TRA-1-60, and TRA-1-81, and lack expression of a marker for differentiation CXCR4.

One embodiment is a method of culturing pluripotent stem cells as cell clusters in suspension culture. The cell clusters are aggregated pluripotent stem cells, cultured in a dynamic stirred or shaken suspension culture system. The cell clusters may be transferred from a planar adherent culture using an enzyme, such as a neutral protease, for example Dispase, as a cell lifting agent to a stirred or shaken suspension culture system. Exemplary suitable enzymes include, but are not limited to, type IV Collagenase, Dispase® or Accutase®. The cells maintain pluripotency in a stirred or shaken suspension culture system, in particular a stirred suspension culture system.

Another embodiment of the invention is a method of culturing pluripotent stem cells as cell clusters in suspension culture, wherein the cell clusters are aggregated pluripotent stem cells transferred from a planar adherent culture using a chelating agent, for example EDTA, and cultured in a stirred or shaken suspension culture system. The cell clusters maintain pluripotency in a stirred or shaken suspension culture system, in particular a stirred (dynamically agitated) suspension culture system.

Another embodiment of the invention is a method of culturing pluripotent stem cells as cell clusters in suspension culture, wherein the cell clusters are aggregated pluripotent stem cells transferred from a planar adherent culture using the enzyme Accutase®, and cultured in a stirred or shaken suspension culture system. The cell clusters maintain pluripotency in the dynamically agitated suspension culture system.

The cell clusters of the invention may be differentiated into mesoderm cells, such as cardiac cells, ectoderm cells, such as neural cells, single hormone positive cells or pancreatic endoderm cells. The method may further include differentiation, for example differentiation of the pancreatic endoderm cells into pancreatic precursor cells and pancreatic hormone expressing cells. In another embodiment, pancreatic precursor cells are characterized by expression of β cell transcription factors PDX1 and NKX6.1.

In one embodiment, the step of differentiation is carried out after at least 12 hours, at least 24 hours, at least 36 hours, at least 48 hours, at least 72 hours, at least 96 hours, at least 120 hours, at least 144 hours, at least 168 hours, at least 196 hours or more, preferably about 48 hours to about 72 hours in the suspension culture system. Differentiation may be carried out using a stage-wise progression of media components, such as that described in the examples (e.g. see Table A and Tables 1a and 1c).

In a preferred embodiment, a three-dimensional cell cluster is produced by growing pluripotent stem cells in a planar adherent culture; expanding the pluripotent stem cells to aggregated cell clusters; and transferring the clusters of pluripotent stem cells from the planar adherent culture to a dynamic suspension culture using an enzyme or chelating agent. A further preferred embodiment is a method of expanding and differentiating pluripotent stem cells in a dynamically agitated suspension culture system by growing pluripotent stem cells in a planar adherent culture; expanding the pluripotent stem cells to aggregated cell clusters; and transferring the clusters of pluripotent stem cells from the planar adherent culture to a dynamic suspension culture using an enzyme or chelating agent; and differentiating the pluripotent cell clusters in a dynamic agitated suspension culture system to generate a pancreatic precursor cell population.

Another embodiment is a transplantable stem cell derived cell product comprising differentiated stem cells prepared from suspension of expanded pluripotent stem cell clusters that are differentiated to pancreatic precursor cells. More particularly, a transplantable stem cell derived product is produced by growing pluripotent stem cells in a planar adherent culture; expanding the pluripotent stem cells to aggregated cell clusters; and transferring the clusters of pluripotent stem cells from the planar adherent culture to a dynamic suspension culture using an enzyme or chelating agent; and differentiating the pluripotent cell clusters in a dynamically agitated suspension culture system. The transplantable stem cell derived cell product is preferably used to treat diabetes.

In another embodiment, the method includes transplantation into a diabetic animal for further in vivo maturation to functional pancreatic endocrine cells.

Another embodiment is a method of expanding and differentiating pluripotent stem cells in a suspension culture system comprising growing pluripotent stem cells in a planar adherent culture; removing the pluripotent stem cells from the planar adherent culture using an enzyme; adhering the pluripotent stem cells to microcarriers in static culture; expanding the pluripotent cells in a dynamically agitated suspension culture system; and differentiating the pluripotent cells in a dynamically agitated suspension culture system to generate a pancreatic precursor cell population.

The microcarriers may be of any form known in the art for adhering cells, in particular the microcarriers may be beads. The microcarrier can be comprised of natural or synthetically-derived materials. Examples include collagen-based microcarriers, dextran-based microcarriers, or cellulose-based microcarriers. For example, microcarrier beads may be modified polystyrene beads with cationic trimethyl ammonium attached to the surface to provide a positively charged surface to the microcarrier. The bead diameter may range from about 90 to about 200 µm, alternately from about 100 to about 190 µm, alternatively from about 110 to about 180 µm, alternatively from about 125 to 175 µm in diameter. Microcarrier beads may also be a thin layer of denatured collagen chemically coupled to a matrix of cross-linked dextran. Microcarrier beads may be glass, ceramics, polymers (such as polystyrene), or metals. Further, microcarriers may be uncoated, or coated, such as with silicon or a protein such as collagen. In a further aspect the microcarrier can be comprised of, or coated with, compounds that enhance binding of the cell to the microcarrier and enhance release of the cell from the microcarrier including, but not limited to, sodium hyaluronate, poly(monostearoylglyceride co-succinic acid), poly-D,L-lactide-co-glycolide, fibronectin, laminin, elastin, lysine, n-isopropyl acrylamide, vitronectin, and collagen. Examples further include microcarriers that possess a microcurrent, such as microcarriers with a particulate galvanic couple of zinc and copper that produces low levels of biologically relevant electricity; or microcarriers that are paramagnetic, such as paramagnetic calcium-alginate microcarriers.

In some embodiments, the population of pancreatic endoderm cells is obtained by a stepwise differentiation of pluripotent cell clusters. In some embodiments, the pluripotent cells are human embryonic pluripotent stem cells. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell.

In some embodiments, the present invention relates to a stepwise method of differentiating pluripotent cells comprising culturing stage 3-5 cells in a dynamic suspension culture. In some embodiments, the pancreatic endoderm population generated is transplanted into diabetic animals for further in vivo maturation to functional pancreatic endocrine cells. The invention also provides for systems or kits for use in the methods of the invention.

The invention also provides a cell or population of cells obtainable by a method of the invention. The invention also provides a cell or population of cells obtained by a method of the invention.

The invention provides methods of treatment. In particular, the invention provides methods for treating a patient suffering from, or at risk of developing, diabetes.

The invention also provides a cell or population of cells obtainable or obtained by a method of the invention for use in a method of treatment. In particular, the invention provides a cell or population of cells obtainable or obtained by a method of the invention for use in a method of treating a patient suffering from, or at risk of developing, diabetes. The diabetes may be Type 1 or Type 2 diabetes.

In one embodiment, the method of treatment comprises implanting cells obtained or obtainable by a method of the invention into a patient.

In one embodiment, the method of treatment comprises differentiating pluripotent stem cells in vitro into stage 1, stage 2, stage 3, stage 4, or stage 5 cells, for example as described herein, and implanting the differentiated cells into a patient.

In one embodiment, the method further comprises the step of culturing pluripotent stem cells, for example as described herein, prior to the step of differentiating the pluripotent stem cells.

In one embodiment, the method further comprises the step of differentiating the cells in vivo, after the step of implantation.

In one embodiment, the patient is a mammal, preferably a human.

In one embodiment, the cells may be implanted as dispersed cells or formed into clusters that may be infused into the hepatic portal vein. Alternatively, cells may be provided in biocompatible degradable polymeric supports, porous non-degradable devices or encapsulated to protect from host immune response. Cells may be implanted into an appropriate site in a recipient. The implantation sites include, for example, the liver, natural pancreas, renal subcapsular space, omentum, peritoneum, subserosal space, intestine, stomach, or a subcutaneous pocket.

To enhance further differentiation, survival or activity of the implanted cells in vivo, additional factors, such as growth factors, antioxidants or anti-inflammatory agents, can be administered before, simultaneously with, or after the administration of the cells. These factors can be secreted by endogenous cells and exposed to the administered cells in situ. Implanted cells can be induced to differentiate by any combination of endogenous growth factors known in the art and exogenously administered growth factors known in the art.

The amount of cells used in implantation depends on a number of various factors including the patient's condition and response to the therapy, and can be determined by one skilled in the art.

In one embodiment, the method of treatment further comprises incorporating the cells into a three-dimensional support prior to implantation. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells.

In certain embodiments of the invention, one or more of the following may be used in the methods of the invention.

TABLE A

| Component/ Condition | Stage | Suitable Amounts |
|---|---|---|
| Activin A (AA) | 1, 3 | Stage 1: about 100 mg/ml<br>Stage 3: about 5 ng/ml, from about 3 ng/ml to about 6 ng/ml |
| AlbuMAX ® | 3-5 | About 0.1% |
| ALK5 inhibitor | 4, 5 | About 1 µM, about 500 to about 1000 nM, about 600 to about 1000 nM, about 700 to about 1000 nM, about 800 to about 1000 nM, about 100 nM, about 500 nM or about 1 µM, from about 0.6 to about 1 µM |
| BSA | 1-5 | About 2%, 0.1% to about 2% |
| Cypi (Cyp26 inhibitor) | 4, 5 | About 100 nM, from about 80 nM to about 120 nM, from about 50 nM to about 150 nM |
| FGF7 ("F7") | 2, 3 | About 50 ng/mL, from about 30 ng/ml to about 60 ng/ml, from about 25 ng/ml to about 55 ng/ml |
| GDF8 | 1 | About 100 ng/mL, from about 80 ng/ml to about 150 ng/ml, from about 75 ng/ml to about 125 ng/ml, from about 75 ng/ml to about 150 ng/ml |
| Glucose | 1-5 | Stages 1 to 4:<br>About 8 mM, from about 1 m M to about 8 mM, from about 3 mM to about 5 mM<br>or<br>Stages 3 and 4<br>About 25 mM, from about 10 to about 25 mM<br>or<br>Stage 5<br>Less than about 11 mM, from about 1 mM to about 10 mM<br>or<br>Stage 5<br>More than about 25 mM, from about 25 mM to about 50 mM |
| ITS-X | 1-5 | About 1:50,000, about 1:200, about 1:1000, about 1:10,000 |
| LDN | 3 | About 100 nM, from about 80 nM to about 120 nM, from about 50 nM to about 150 nM |
| L-Glutamine | 1-5 | About 2 mM, from about 1 mM to about 3 mM, from about 2 mM to about 6 mM, from about 1 mM to about 6 mM |
| Lipid range | | From about 0.1% to about 0.2%, from about 0.05% to about 0.15%, from about 0.15% to about 0.2% |

TABLE A-continued

| Component/ Condition | Stage | Suitable Amounts |
|---|---|---|
| MCX | 1 | About 3 µM, about 2 µM, about 1 µM to about 5 µM, about 2 µM to about 4 µM, about 1 µM to about 3 µM, about 2 µM to about 3 µM |
| Oxygen Range | 1-5 | from hypoxia to about 30% of ambient, from about 10% to about 25% of ambient, from about 15% to about 30% of ambient |
| Retinoic Acid | 3 | About 2 µM, from about 1 µM to about 3 µM, form about 1.5 µM to about 2.5 µM |
| SANT | 3, 4 | About 0.25 µM, from about 0.1 µM to about 0.3 µM, from about 0.2 to about 0.3 µM. from about 0.1 µM to about 0.25 µM |
| SCIO | 4 | About 100 nM, about 2 µM |
| Time for differentiating from pluripotent to definitive endoderm | | Less than 48 hours, less than 30 hours, less than 24 hours, less than 18 hours, about 18 to 30 hours |
| TppB or TPB | 4 | About 500 nM, about 100 nM, from about 50 nM to about 550 nM, from about 50 nM to about 150 nM, from about 200 nM to about 500 nM, from about 300 nM to about 550 nM, about 50 nM, from about 25 nM to about 75 nM |
| Wnt3A | 1 | About 20 ng/ml, from about 10 ng/ml to about 25 ng/ml, from about 18 ng/ml to about 30 ng/ml, from about 18 ng/ml to about 22 ng/ml |
| Y-27632 | 0 | About 10 µM, from about 5 µM to about 15 µM, from about 5 µM to about 10 µM |

Publications cited throughout this document are hereby incorporated by reference in their entirety. The present invention is further illustrated, but not limited, by the following examples.

EXAMPLES

The present invention is further illustrated by the following non-limiting examples.

Example 1

Suspension and Clustering of Human Embryonic Stem Cells of the Cell Line H1 with Disease/Neutral Protease Cells of the human embryonic stem cell line H1, (WA01 cells, WiCell, Madison Wis.) at passage 41 were washed once with PBS (Catalog#14190, Invitrogen) and treated with a 1 mg/mL solution of Dispase® (Neutral Protease, Sigma Aldrich Co LLC, Catalog# D4818, St. Louis, Mo.) in DMEM/F12 (Invitrogen Catalog#11330, Grand Island, N.Y.). Cells were incubated at 37° C. for 15-25 minutes until colony edges began to curl and lift, but prior to full detachment of colonies from the culture surface. Dispase® was then removed and the culture dish was washed twice with mTeSR®1 (Stem Cell Technologies, Vancouver, BC, Canada) media containing 10 µM Y-27632 (Axxora Catalog#ALX-270-333, San Diego, Calif.). The mTeSR®1 media containing 10 µM Y-27632 was then added to the culture dish at 5 mL/60 cm² and the cells were lifted from the surface with a scrapper or rubber policeman. Media and cells were then transferred to a 50 mL conical tube using a glass pipette and clusters were centrifuged at 90 g (rcf) for 3 minutes.

Figure 1A:
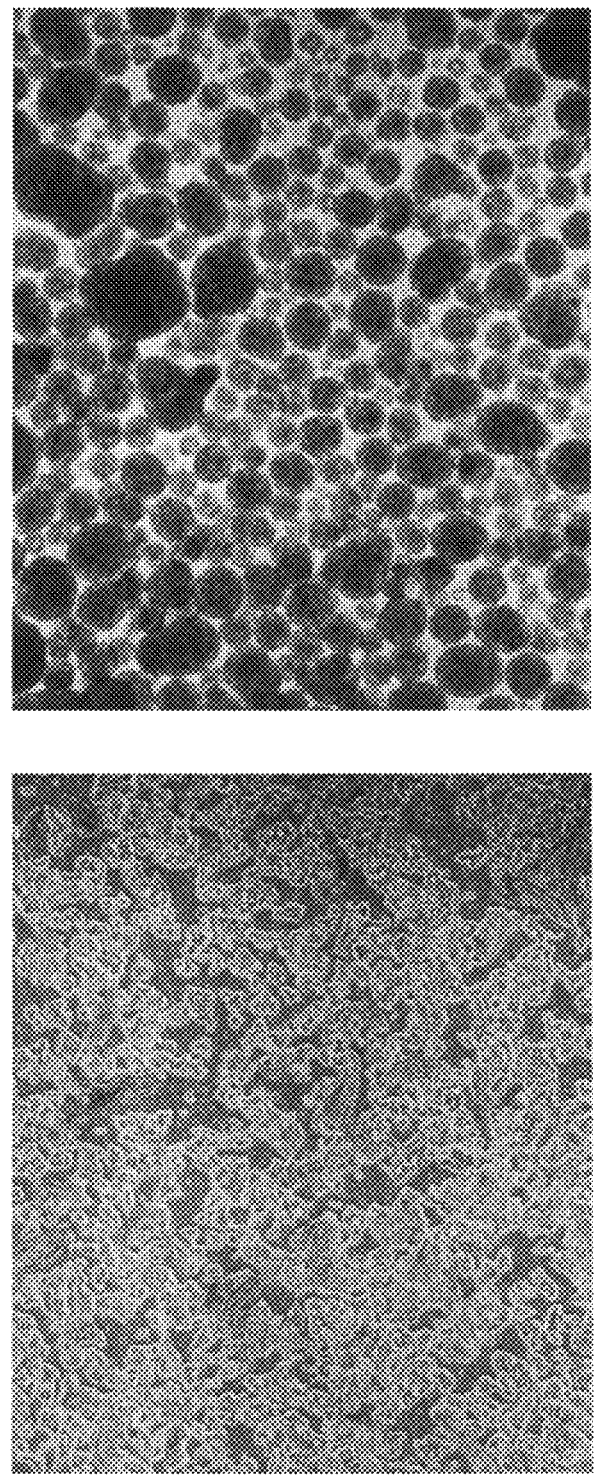
FIG. 1a shows micrographs of Dispase®-treated cells of the human embryonic stem ("hES") cell line H1 immediately after lifting (left hand panel) and after 24 hours in non-adherent static culture (right hand panel) according to Example 1. The cells after lifting (left hand panel) resembled fragments of monolayer with an average fragment diameter of about 20-30 microns each fragment consisting of clumps of cells. After 24 hours in non-adherent static culture, the cells assumed a cluster-like configuration.

After centrifugation, media was aspirated and cells were gently re-suspended and briefly triturated in 12 mL mTeSR®1 media containing 10 µM Y-27632 per 225-240 cm² of total planar culture (equivalent to one T225 flask or four 10 cm dishes, approximately 90 million cells). The cell suspension was then transferred (1 mL/well) to Ultra Low Binding Culture 6 well dishes (Corning Incorporated, Catalog#3471, Corning, N.Y.) containing 2 mL/well of fresh mTeSR®1 media with 10 μM Y-27632. Cells lifted in this manner resembled fragments of monolayer, with the average diameter of lifted fragments around 20-30 microns (FIG. 1a) each consisting of clumps of cells. These monolayer fragments were incubated in suspension for 2 hours, (incubation time can range from 0.5-4 hours) at which point aggregates of fragments were observed. The aggregates were then triturated briefly with a glass 10 ml pipette, and incubated overnight (the aggregates can proceed directly into suspension) in the low binding plate (aggregates can also be incubated in non-treated cell culture plastic and standard tissue culture treated plastic).

After overnight incubation (18-24 hours), cells and media were transferred directly to a 125 mL spinner flask (Corning Incorporated, Catalog#4500-125, Corning N.Y.) containing 25 mL mTeSR®1 media stirred at 50 rpm (can range from 30-80+ rpm) to make a final volume of approximately 75 mL. Media was changed daily for 4 days. Pluripotency was determined after 4 days in culture and flow cytometry results showed high expression for the markers of pluripotency (CD9, SSEA4, TRA-1-60, and TRA-1-81) with almost no expression of a marker for differentiation (CXCR4). See FIG. 1b. These data demonstrate that H1 hES cells can be successfully transferred as cell clusters to suspension culture from a planar adherent culture format with Dispase® as a cell lifting agent and maintain pluripotency in a stirred (dynamic) suspension culture system. This example can also be carried out in shaken rather than stirred suspension systems with plates and Erlenmeyer flasks with comparable results.

After 4 days in suspension culture (differentiation can also begin 24-120 hours after formation of aggregates, preferably culture for 2-3 days before beginning differentiation), the pluripotent cell aggregates were differentiated with a stagewise progression of media components to induce the cells to form a pancreatic fate. The spinner agitation was turned up for differentiation of the aggregates to a speed of 65 rpm. The media and components are shown in Table 1a.

Figure 1C:
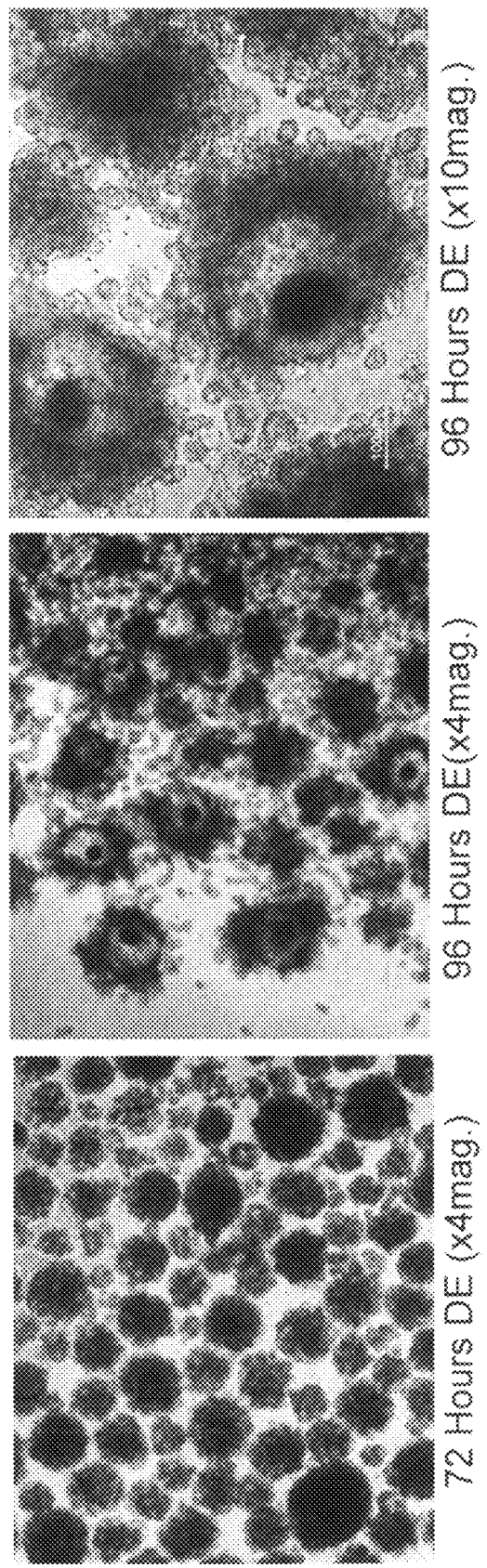
FIG. 1c shows micrographs of the Dispase®-treated cells of the human embryonic stem cell line H1 after 72 and 96 hours of differentiation at the end of stage 1. Visible in FIG. 1c are loose cell aggregates after 72 hours at 4× magnification (left hand panel), 96 hours at 4× magnification (center panel) and 96 hours at 10× magnification (right hand panel).
Figure 1D:
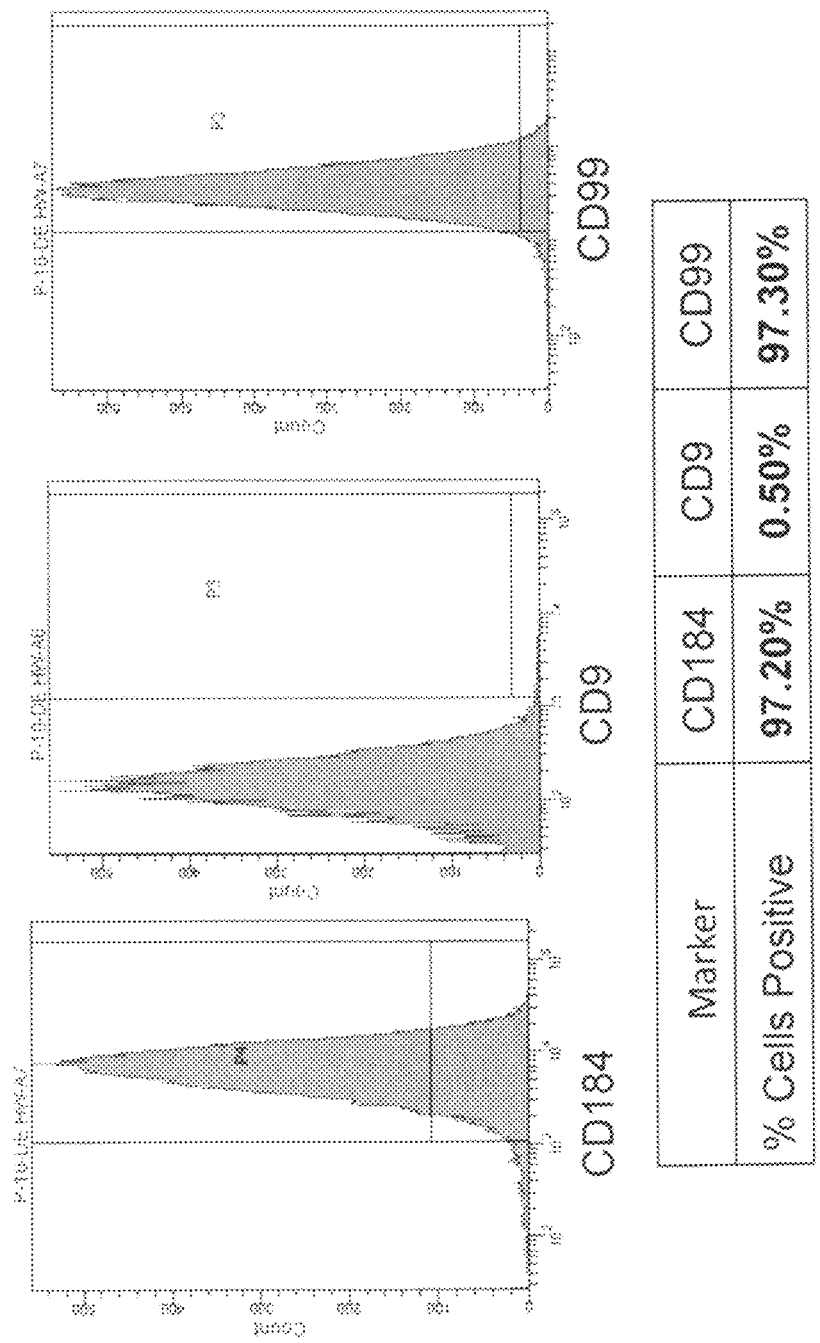
FIG. 1d shows flow cytometry results for the Dispase®-treated cells of the human embryonic stem cell line H1 at the end of stage 1 differentiation for the markers CD9, CD184 (CXCR4) and CD99 (see Example 1).
Figure 1E:
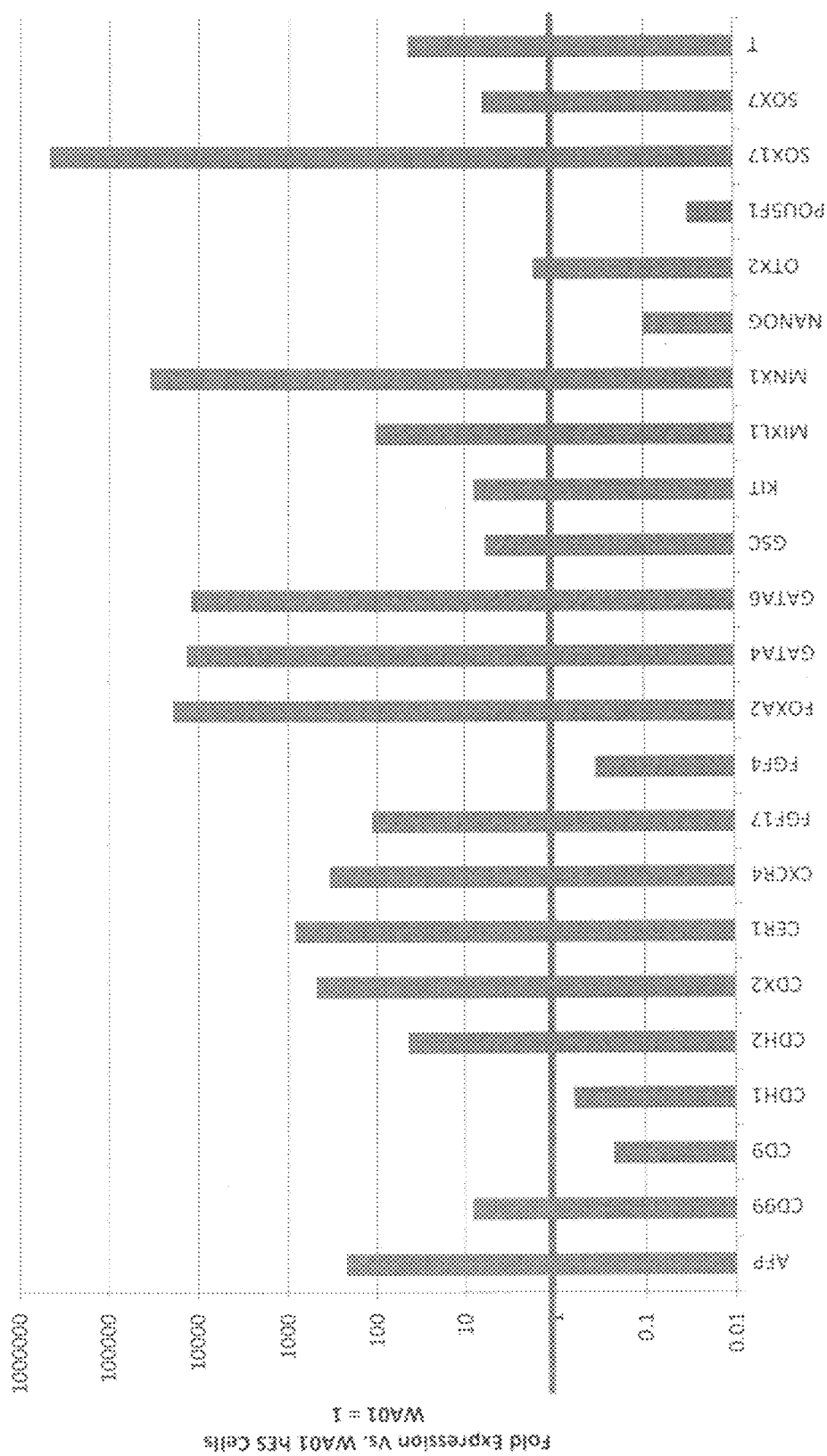
FIG. 1e shows quantitative reverse transcription polymerase chain reaction (qRT-PCR) results for expression of selected genes associated with pluripotency and genes associated with definitive endoderm for the Dispase®-treated cells of the human embryonic stem cell line H1 at the end of stage 1 compared to undifferentiated H1 (WA01) hES cells (see Example 1). The cells at the end of stage 1 showed a dramatic decrease in the expression of pluripotency genes (CD9, NANOG, and POU5F1/OCT4) and a large increase in genes associated with definitive endoderm (CXCR4, CERBERUS (CER1), GSC, FOXA2, GATA4, GATA6, MNX1, and SOX17) versus undifferentiated WA01 hES cells.

At the end of stage 1 samples were run for flow cytometry and PCR. Suspension differentiated cultures formed a uniform and homogeneous population of cells in loose aggregates at the end of stage 1 (FIG. 1c), with expression of a marker for pluripotency (CD9) nearly eliminated, while the markers for definitive endoderm differentiation were quite high, 97.2% positive for CXCR4 (CD184) and 97.3% positive for CD99 (FIG. 1d). These results correlated with qRT-PCR results which showed a dramatic decrease in the expression of pluripotency genes (CD9, NANOG, and POU5F1/OCT4) and a large increase in genes associated with definitive endoderm (CXCR4, CERBERUS, GSC, FOXA2, GATA4, GATA6, MNX1, and SOX17) versus undifferentiated WA01 hES cells (FIG. 1e).

The definitive endoderm clusters were then further differentiated toward a primitive foregut by removing the TGF-3 family member, GDF8, and adding FGF7 to the media. After three days culture with FGF7, the clusters were differentiated to a pancreatic PDX1 expressing fate by addition of all-trans-retinoic acid to either a media containing high glucose (25 mM) and low concentration of lipid rich bovine serum albumin (AlbuMAX® (Life Technologies Corporation, Carlsbad, Calif.) or a media containing a relatively low glucose concentration (8 mM) and 2% fatty acid free bovine serum albumin. The detailed addition of components to these media is listed in Table 1a. At the end of the differentiation the samples were analyzed for expression of markers of pancreatic precursor cells. It was observed that the clusters differentiated with either condition—low glucose+2% FAF-BSA (A) or high glucose+0.1% AlbuMAX® (B)—as measured by flow cytometry expressed high levels of NKX6.1, a transcription factor required for functional β cells, and high levels of endocrine pancreas markers such as synaptophysin and chromogranin (Table 1b). These results were consistent with RT-PCR results which showed high levels of multiple pancreatic precursor genes expressed in samples from both condition A and B (data not shown).

Figure 1F:
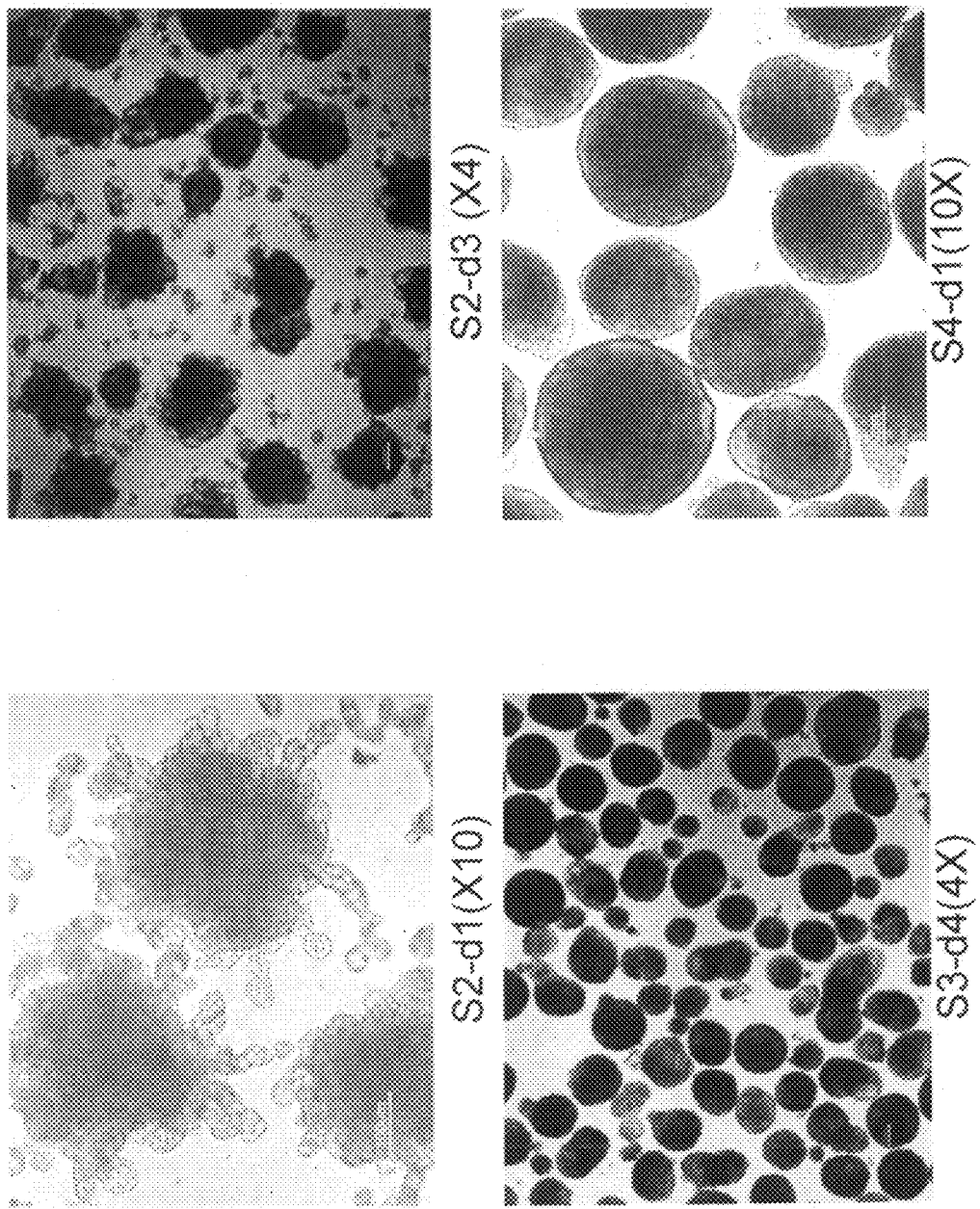
FIG. 1f shows micrographs of the Dispase®-treated cells of the human embryonic stem cell line H1 as the cells further differentiated from definitive endoderm toward the pancreatic endoderm (see Example 1). Clear morphological changes to cells and cell clusters are visible as differentiation progresses from stage 2, day 1 (top left hand panel) to stage 2, day 3 (top right hand panel) to stage 3, day 4 (lower left hand panel) and stage 4, day 1 (lower right hand panel).

Typical morphologies of cell clusters as they progressed through differentiation from definitive endoderm (DE) (FIG. 1c) to primitive foregut and onto pancreatic endoderm (FIG. 1f) demonstrated visible morphological changes to cells and cell clusters. Typically, pluripotent clusters appear dense and dark by phase contrast microscopy, then become looser in appearance as cells progress to primitive foregut in stage 2. This morphology reverses following all-trans-retinoic acid treatment and the clusters again become more dense and uniform with a smooth cluster border.

Cells differentiated according to condition B through stage 4 were held for an additional 5 days in stage 5 media containing an ALK5 inhibitor (see Table 1c). This additional maturation in culture resulted in a significant increase in endocrine marker expression: INS, GCG, SST, PPY, and PCSK1. The cell clusters were then implanted into the kidney capsule of SCID-Bg mice according to IACUC approved study protocol, and the mice were followed for 20 weeks with fasted/fed c-peptide measured every 2 to 4 weeks. After 4 weeks post implantation, following a 20 hour fast and then glucose stimulation, c-peptide was not detectable. By 6 weeks, 2 of 5 mice positive showed some (0.087 & 0.137 ng/mL) human c-peptide, and by 10 weeks, 5 of 5 mice were positive (0.085-0.291 ng/mL) for c-peptide. At 16 weeks, following 20 hour fast and glucose stimulation, all 4 mice (4/4) were positive (0.377-3.627 ng/mL) for c-peptide expression.

These results indicate that a pluripotent cell aggregate can be formed and then differentiated in suspension culture to generate a pancreatic precursor cell population characterized by expression of β cell transcription factors like PDX1 and NKX6.1. Furthermore, differentiated cell clusters that were implanted and allowed to mature in vivo expressed insulin in response to glucose challenge at physiologically appropriate levels.

Table 1a: Differentiation Protocol

TABLE 1a

| | Differentiation Protocol | | | |
| --- | --- | --- | --- | --- |
| | Stage 1 | Stage 2 | Stage 3 | Stage 4 |
| Basal Media (final glucose concentration) | | MCDB131 8 mM glucose | | MCDB131 8 mM (A) or 25 mM glucose (B) |

TABLE 1a-continued

Differentiation Protocol

| | Stage 1 | Stage 2 | Stage 3 | Stage 4 |
|---|---|---|---|---|
| Protein Supplement | 2% Fatty Acid Free Bovine Serum Albumin (FAF-BSA) and 2 mM L-Glutamine | | 2% Fatty Acid Free Bovine Serum Albumin (FAF-BSA) and 2 mM L-Glutamine (A) or 0.1% Albumax (Bovine Serum Albumin) and 2 mM L-Glutamine (B) | |
| Growth factors AND/OR Small molecules | MCX (3 µM) For 0-24 hours GDF8 (100 ng/mL)for 0-96 hours ITS-X (1:50,000) | FGF7 (50 ng/ml) ITS-X (1:50,000) | FGF7 (50 ng/ml) ITS-X (1:200) RA (2µM) SANT (0.25 µM) AA (5 ng/mL) LDN (100 nM) | ITS-X (1:200) SANT (0.25 µM) Cypi (100 nM) TppB (500 nM) LDN (100 nM) |
| Total Days | 4 | 3 | 4 | 5 |
| Media Exchanges | Every 24 hours | Every 24 hours | Every 24 hours | Every 24 hours |

TABLE 1b

Flow Cytometry Results for Selected Markers of Differentiation

| Glucose (sample) | BSA | % NKX6.1 | % CDX2 | % Insulin | % Synaptophysin | % Chromogranin |
|---|---|---|---|---|---|---|
| Low (A) | 2% FAF BSA | 55 | 7 | 5.5 | 34.5 | 26.5 |
| High (B) | 0.1% Albumax | 48 | 7 | 0.5 | 26.9 | 30 |

TABLE 1c

Differentiation Protocol

| | Stage 5 |
|---|---|
| Basal Media (final glucose concentration) | MCDB131 (25 mM glucose) |
| Protein Supplement | 0.1% AlbuMAX ® (Bovine Serum Albumin) and 2 mM L-Glutamine |
| Growth factors AND/OR Small molecules | ITS-X (1:200) Cypi (100 nM) LDN (100 nM) ALKVi (10 mM) |
| Total Days | 5 |
| Media Exchanges | Every 24 hours |

Example 2

Suspension and Clustering of Human Embryonic Stem Cells of the Cell Line H1 with EDTA Cells of the human embryonic stem cell line H1, (WA01 cells, WiCell, Madison Wis.) at passage 41 were washed once with PBS (Catalog#14190, Invitrogen) and treated with EDTA, a non-enzymatic cell lifting/passaging agent (Lonza, Catalog#17-7-11E). Cells were incubated at room temperature for 8 minutes. EDTA was then removed and after 1 or 2 more minutes (9-10 minutes total EDTA exposure) the plate was rinsed with mTeSR®1 media containing 10 µM Y-27632 (Axxora Catalog#ALX-270-333, San Diego, Calif.) and dislodged cells were collected in a 50 ml conical tube using a glass pipet. One additional rinse of the platwith mTeSR®1 media containing 10 µM Y-27632 was e performed and pooled with dislodged cells. Note that some cells remained on the plate after 9-10 minutes of exposure to EDTA at room temperature, and lifted cells were not completely disaggregated to a single cell suspension. Instead, the cells were removed from the surface as small aggregates. Media and cells were then transferred to a 50 ml conical tube using a glass pipet and a cell count was performed (Nucleo-Counter®-ChemoMetec A/S, Cat#YC-T100, Denmark). Additional mTeSR®1 media containing 10 µM Y-27632 was added as needed to make a concentration of cells at 1.0 to 1.5 million cells/ml.

Cells were not centrifuged, as the clusters were loosely aggregated and would disassociate to single cells if centrifuged to a pellet and re-suspended by pipette. Instead, media and cells in the tube were gently swirled until a uniform suspension was formed. If desired, one can also lengthen the period of EDTA treatment and take cells to near a single cell suspension. The cell suspension was then transferred to two non-tissue culture treated 6 well dishes (Becton Dickinson, Catalog# Falcon 351146, Franklin Lakes, N.J.) in a 37° C. humidified 5% $CO_2$ incubator at 3 ml/well with a glass pipette. Cells were incubated in suspension for 2 hours at which point aggregates were observed. The aggregates were then triturated by gentle pipetting with a glass pipette to disrupt large aggregates and create a homogeneous, uniform cluster suspension, then incubated undisturbed overnight.

Figure 2A:
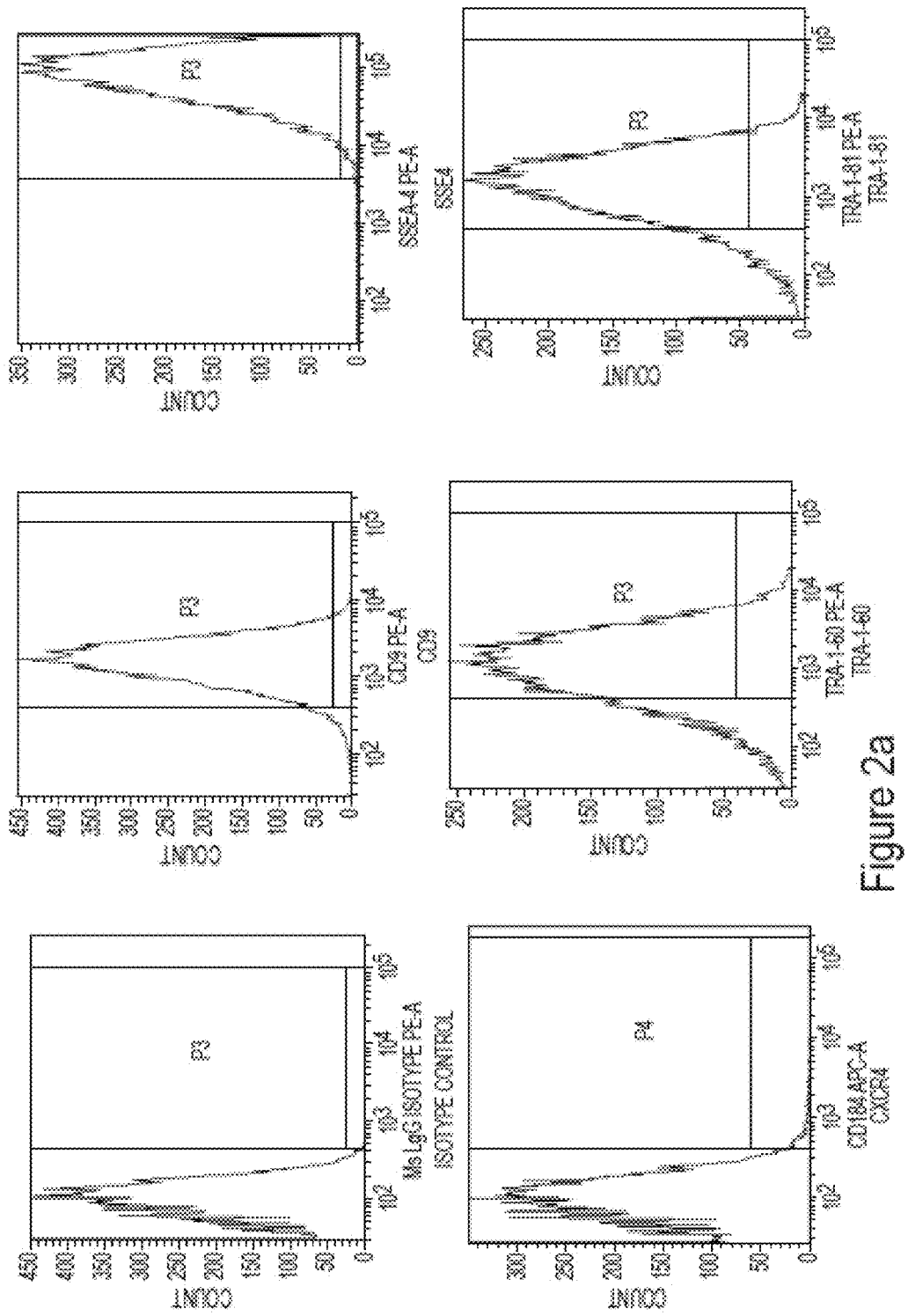
FIG. 2a shows flow cytometry data for EDTA-treated cells of the human embryonic stem cell line H1 after 2 days of culture in stirred suspension culture post-EDTA treatment, and prior to transition to differentiation culture, for markers associated with pluripotency and differentiation according to Example 2. The data showed high expression for the markers of pluripotency (CD9, SSEA4, TRA-1-60, and TRA-1-81) with almost no expression of a marker for differentiation (CXCR4).

Then 18-24 hours later, cells and media were spun down in 50 mL conical tubes at 90 g (rcf) for 3 minutes. The spent media supernatant was discarded, the cell aggregates were suspended in fresh mTeSR®1 and the suspension was transferred to a spinner flask (Corning Incorporated, Catalog#4500-125, Corning N.Y.) stirred at 55 rpm in a 37° C. humidified 5% $CO_2$ incubator. Media was changed daily for 2 days. Pluripotency was determined after 2 days in stirred suspension culture before transition to differentiation culture. The flow cytometry results for CD9, SSEA4, TRA-1-60, TRA-1-81, and CXCR4 expression are shown in scatter plot format in FIG. 2a. These data show high expression for the markers of pluripotency (CD9, SSEA4, TRA-1-60, TRA-1-81) and low or no expression of a marker for differentiation (CXCR4). These results indicate that H1 hES cells can be transferred to suspension culture from a planar adherent culture format using a non-enzymatic lifting method and maintain pluripotency in a dynamic agitated suspension culture system.

After 2 days in suspension culture, the pluripotent cell aggregates were differentiated with a stage-wise progression of media components to induce the cells to form a pancreatic fate. The spinner agitation was maintained at a speed of 55 rpm. The media and components are shown in Table 2a.

Figure 2C:
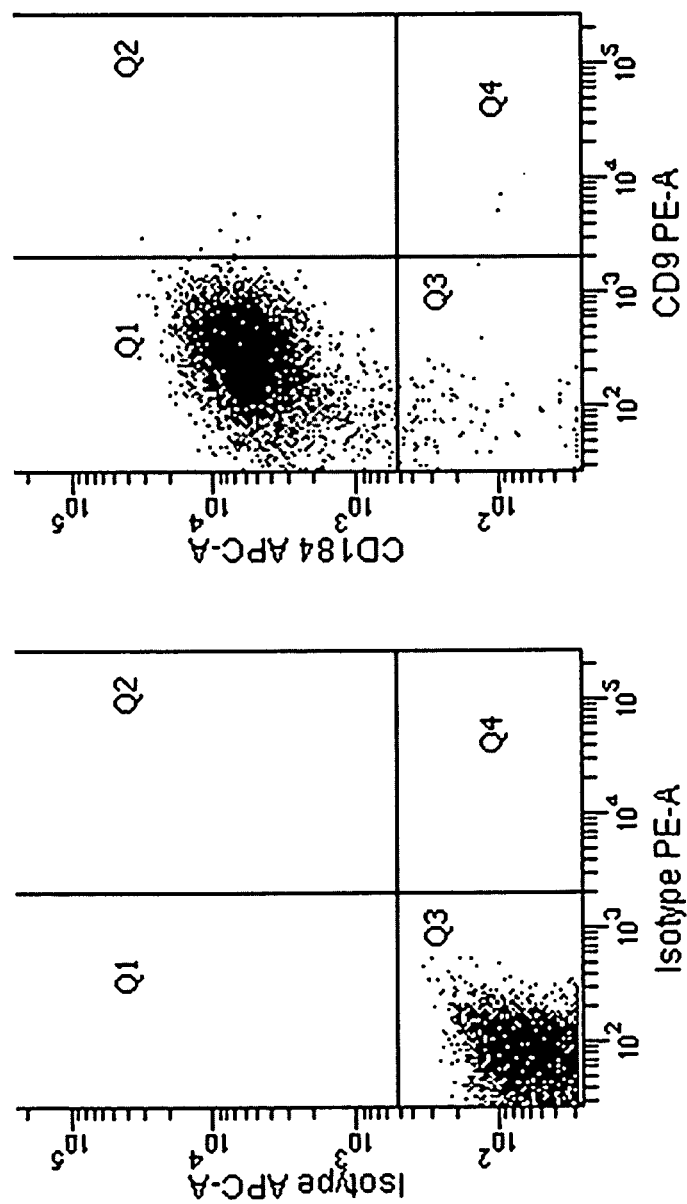
FIG. 2c shows flow cytometry data for the EDTA-treated cells of the human embryonic stem cell line H1 at the end of stage 1 for cell surface markers of pluripotency and endoderm differentiation. As visible in FIG. 2c, expression of CD9, a marker for pluripotency, was nearly eliminated while expression for CXCR4 (CD184), a marker for definitive endoderm differentiation was quite high.

At the end of stage 1 samples were run for flow cytometry and PCR. Suspension differentiated cultures formed a uniform and homogeneous population of cells in loose aggregates at the end of stage 1 (FIG. 2b), with expression of a marker for pluripotency (CD9) nearly eliminated, while CXCR4 (CD184), a marker for definitive endoderm differentiation, was quite high, 95.9%±1.8sd (FIG. 2c) across three spinner flasks. These results correlated with qRT-PCR results which showed a dramatic decrease in the expression of pluripotency genes (CD9, NANOG, and POU5F1/OCT4) and a large increase in genes associated with definitive endoderm (CXCR4, CERBERUS, GSC, FOXA2, GATA4, GATA6, MNX1, and SOX17) versus undifferentiated WA01 hES cells (FIG. 2d).

Figure 2E:
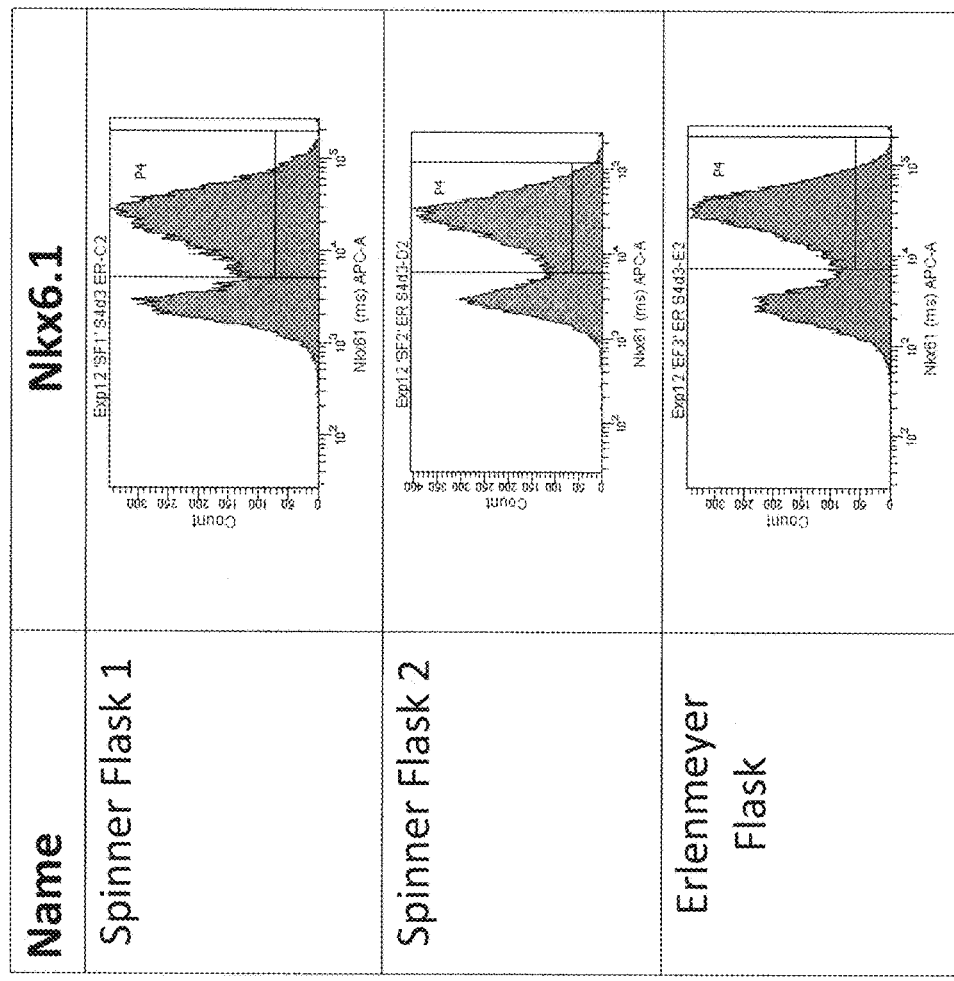
FIG. 2e shows flow cytometry data for markers indicative of differentiation (NKX6.1, CDX2, SOX2, and Chromagranin) for the EDTA-treated cells of the human embryonic stem cell line H1 which were differentiated from stage 1 to pancreatic endoderm cells by suspension in spinner flasks or Erlenmeyer flasks according to Example 2. The flow cytometry data shows high levels of NKX6.1, a transcription factor required for functional β cells, and high levels of endocrine pancreas markers such as synaptophysin (data not shown) and chromogranin with both suspension formats.
Figure 2E:
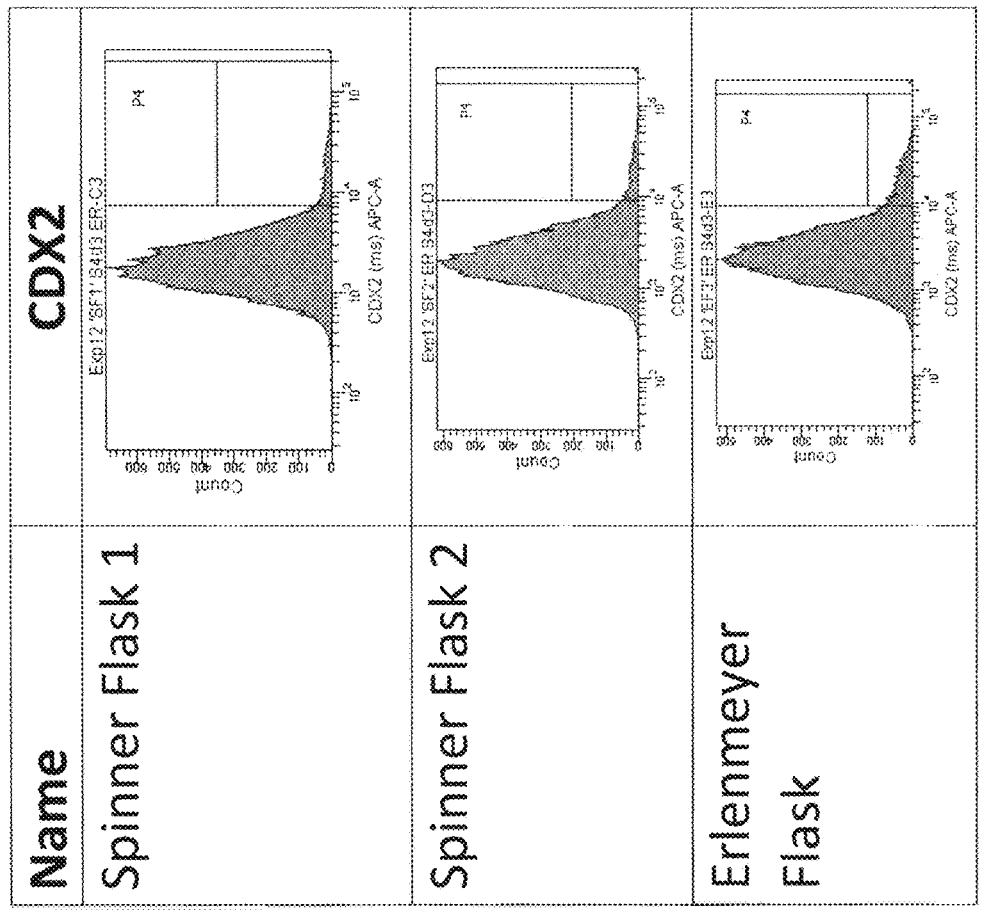
Figure 2E:
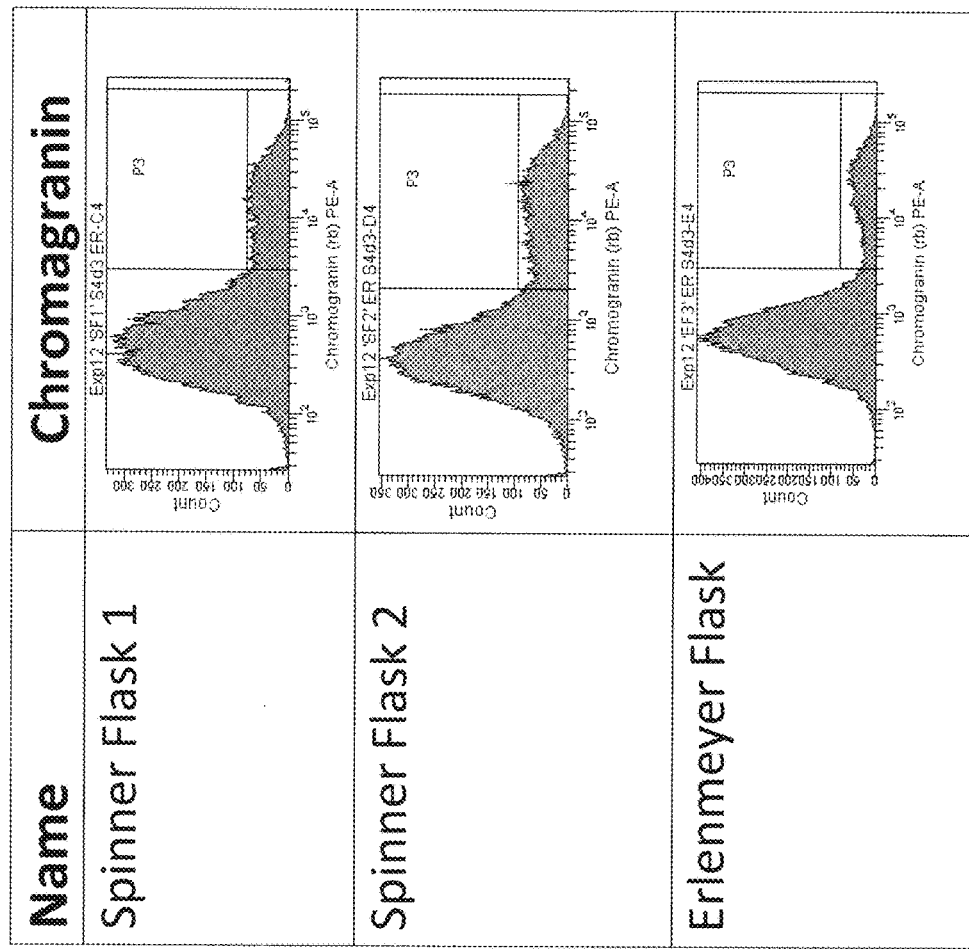

The definitive endoderm clusters from spinner flasks were then pooled and distributed to either another spinner flask or an Erlenmeyer flask (shaken agitation system) and directed for further differentiation toward a primitive foregut by removing GDF8, and adding FGF7 to the media. After three days culture with FGF7, the clusters were differentiated to a pancreatic PDX1 expressing fate by addition of all-trans-retinoic acid to a media containing a relatively low glucose concentration (8 mM) and 2% fatty acid free bovine serum albumin. The detailed addition of components to these media is listed in Table 2a. At the end of the differentiation the samples were analyzed for expression of markers of pancreatic precursor cells. Using flow cytometry, high levels of NKX6.1, a transcription factor required for functional β cells, and high levels of endocrine pancreas markers such as synaptophysin and chromogranin (Table 2b and FIG. 2e) were observed with both suspension formats. These results were consistent with RT-PCR results which showed very similar high levels of multiple pancreatic precursor genes expressed in samples generated in spinner flask format or Erlenmeyer flask format (FIG. 2f).

These results demonstrate that a pluripotent cell aggregate can be formed and then differentiated in suspension culture in multiple suspension culture formats, including a stirred system or a shaken suspension system, to generate a pancreatic precursor cell population characterized by expression of β cell transcription factors like PDX1 and NKX6.1.

TABLE 2a

Media Components and Differentiation Protocol

|  | Stage 0 | Stage 1 | Stage 2 | Stage 3 | Stage 4 |
| --- | --- | --- | --- | --- | --- |
| Basal Media | mTeSR1 | MCDB131 (8 mM Glucose) 3.64 g/L NaCO$_3$ | | MCDB131 (8 mM Glucose) 2.41 g/L NaCO$_3$ | |
| Supplement | mTeSR1 | 2% FAF-BSA 1:50,000 ITS-X 1x GlutaMax | | 2% FAF-BSA 1:200 ITS-X 1x GlutaMax | |
| Growth factors | | GDF8 (d 2 only) 100 ng/ml | FGF7 50 ng/ml | FGF7 50 ng/ml | |
| Small molecules | Y-27632 (day 1 only) [10 µM] | MCX (0-24 hours) [2 µM] | | RA [2 µM] SANT [0.25 µM] TPPB [100 nM] LDN (Day one only) [100 nM] | SANT [0.25 µM] Cypi [100 nM] ALK5 inh [1 µM] TPPB [100 nM] |
| Days | 3 | 3 | 3 | 3 | 3 |
| NOTES: | 1 d NTCT 2 days SF | Media change Day 1 and 2, No change d 3 | Media change Day 1 and 3, No change d 2 | Media change Day 1 and 2, No change d 3 | Media change d 1 And d 2, No change d 3 |

TABLE 2b

Flow Cytometry Results for Selected Markers of Differentiation

| Sample | % NKX6.1 | % CDX2 | % SOX2 | % NKX2.2 | % Synaptophysin | % Chromogranin |
| --- | --- | --- | --- | --- | --- | --- |
| Spinner Flask (avg) | 68.1 | 4.0 | 31.3 | 36.2 | 27.0 | 25.3 |
| Erlenmeyer Flask | 65.8 | 7.69 | 28.1 | 30.0 | 30.7 | 17.0 |

Example 3

Suspension Clustering and Serial Suspension Passage of Human Embryonic Stem Cells of the Cell Line H1

Figure 3A:
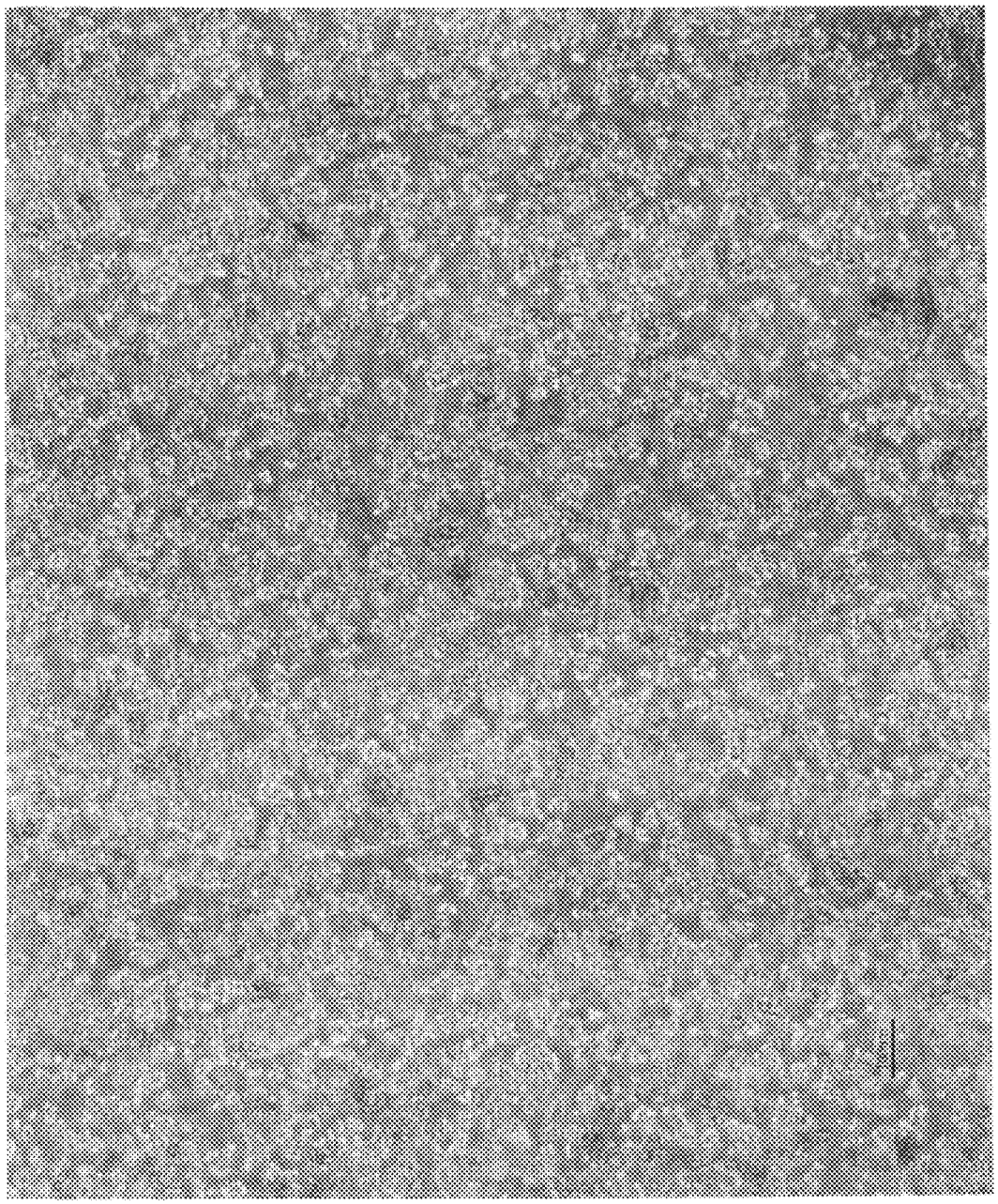
FIG. 3a shows a micrograph of cells of the human embryonic stem cell line H1, which had been lifted from a static culture following treatment with Accutase®.

Cells of the human embryonic stem cell line H1, (WA01 cells, WiCell, Madison Wis.) at passage 40 grown on tissue culture treated polystyrene coated with Matrigel® (Corning Incorporated, Corning N.Y.) were washed twice with PBS (Catalog#14190, Invitrogen) and treated with a half strength solution of Accutase® (one part PBS to one part Accutase®, Sigma-Aldrich, Catalog# A-6964, St. Louis, Mo.). Cells were incubated at room temperature for 3½ minutes. (Accutase® is a cell detachment solution comprised of collagenolytic and proteolytic enzymes (isolated from crustaceans) and does not contain mammalian or bacterial derived products.) Accutase® was then removed and after 3 more minutes (6½ minutes total Accutase® exposure), the plate was rinsed with mTeSR®1 media containing 10 µM Y-27632 and dislodged cells were collected in a 50 ml conical tube using a glass pipet. One additional rinse of the plate with mTeSR®1 media containing 10 µM Y-27632 was performed and pooled with dislodged cells. Some cells remained on the plate after the exposure to Accutase® and lifted cells were not completely disaggregated to a single cell suspension. Rather the cells were removed from the surface as small aggregates (FIG. 3a). Media and cells were then transferred to a 50 ml conical tube using a glass pipette and a cell count was performed. Additional mTeSR®1 media containing 10 µM Y-27632 was added as needed to make a concentration of cells at 1.0 to 1.5 million cells/ml.

Cells were not centrifuged, as the clusters were loosely aggregated and would disassociate to single cells if centrifuged to a pellet and resuspended by pipette. Instead, media and cells in the tube were gently swirled until a uniform suspension was formed. The cell suspension was then transferred to two ultra-low binding culture 6 well dishes in a 37° C. humidified 5% $CO_2$ incubator at 3 ml/well with a glass pipette. Cells were incubated in suspension for 90 minutes at which point aggregates were observed. The aggregates were then triturated briefly, and transferred directly to a 125 ml spinner flask containing 25 ml mTeSR®1 media stirred at 55 rpm (total final volume was approximately 75 mL). Media was changed daily for 3 days, and pluripotency was determined on the $3^{rd}$ day in culture. Phase contrast microscope images of the clusters show a uniform, spherical population of clusters that formed after 90 minutes in static suspension culture and expanded over three days in culture (FIG. 3b). At the end of three days in suspension culture, the cells were assayed for pluripotency by flow cytometry results for the markers CD9, SSEA4, TRA-1-60, TRA-1-81, and CXCR4. The cells maintained high expression of markers for pluripotency (CD9, SSEA4, TRA-1-60, TRA-1-81) and almost no expression for CXCR4, a marker of differentiation (Table 3). These data show that H1 hES cells can be transferred to suspension culture from a planar adherent culture format using an enzymatic lifting method, such as Accutase®, and will maintain pluripotency in a dynamic agitated suspension culture system.

The pluripotent clusters were then serially passaged using Accutase® dissociation for an additional 20 passages. At each passage, 50 million cells were gravity settled for 2 minutes in a 50 ml conical tube, washed twice with PBS and treated with a half strength solution of Accutase® in a 37° C. water bath with gentle swirling of the tube at two and four minutes after addition of Accutase®. After six minutes incubation Accutase® was aspirated from the tube without disturbing the cell pellet. The cells were then incubated 3 more minutes (9 minutes total Accutase® exposure). The tube was then rinsed with mTeSR®1 media containing 10 µM Y-27632, triturated twice using a glass pipet, and the suspended cells passed through a 70 micron cell strainer (BD Falcon, Cat#352350, Franklin Lakes, N.J.). Two additional rinses of the tube with mTeSR®1 media containing 10 µM Y-27632 were performed and passed through the cell strainer.

Figure 3C:
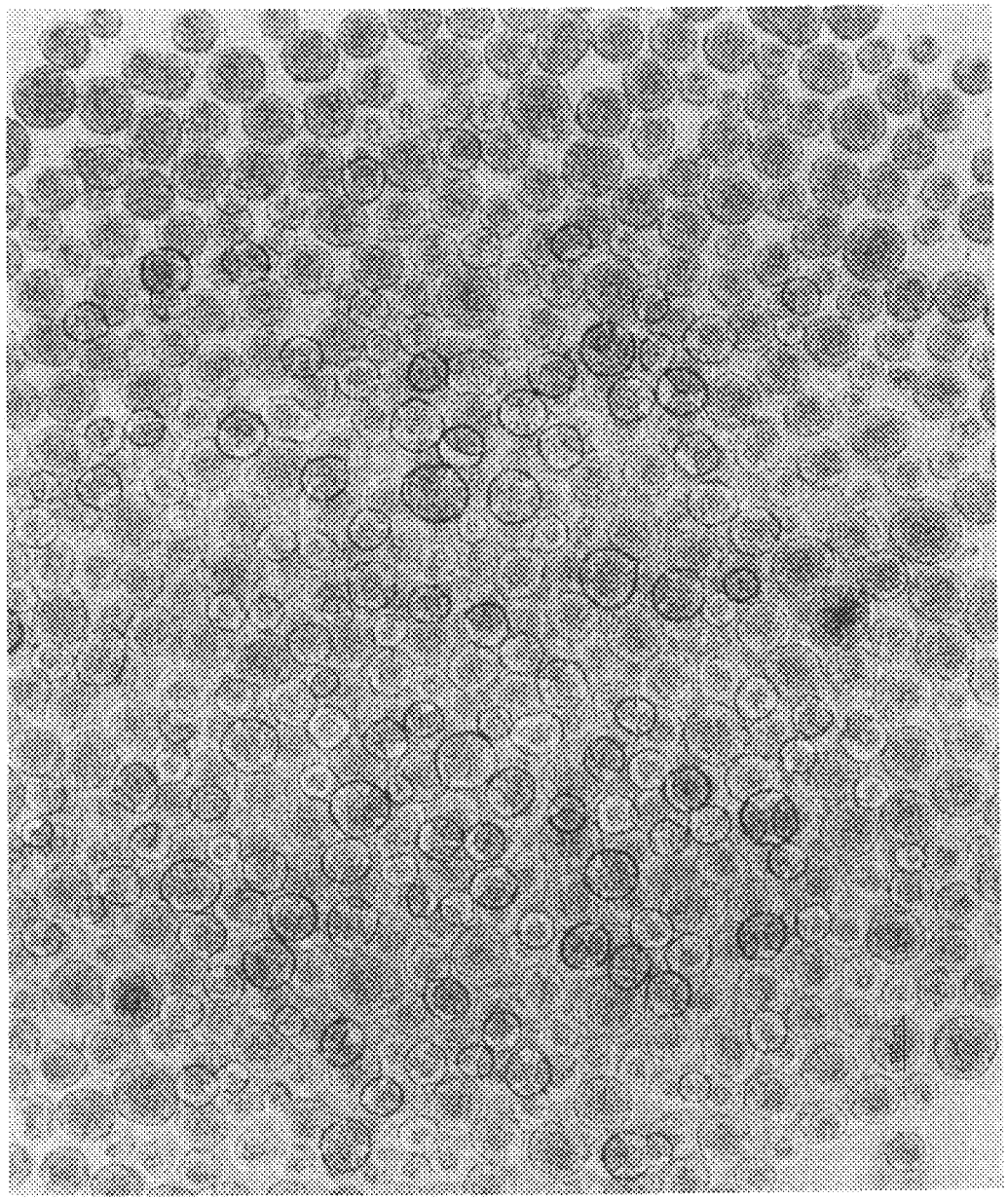
FIG. 3c shows a micrograph of clusters of cells of the human embryonic stem cell line H1, which had been lifted from a static culture following treatment with Accutase®, which were then expanded in suspension culture for three days, and which were then serially passaged using Accutase® dissociation.

Media and cells in the tube were gently swirled until a uniform suspension was formed. The cell suspension was then transferred to ultra-low binding culture 6 well dishes in a 37° C. humidified 5% $CO_2$ incubator at 3 ml/well with a glass pipette and incubated in suspension for 2 hours (tested 0-28 hrs) at which point aggregates were transferred to a glass spinner flask with a final volume of 80 ml of media. Alternatively, the cell suspension could be directly placed into a spinner flask agitated at 55 rpm or an Erlenmeyer flask shaken at 40 rpm, and clusters formed in the stirred suspension (FIG. 3c) in a final volume of 80 ml of media.

Using this serial passage method, the cells were passaged 20 times, with an approximate split ratio of 1:3 at each passage. Pluripotency was measured at each passage by flow cytometry and karyotype was determined using a florescent in-situ hybridization (FISH) assay for chromosomes 12 and 17; two chromosomes identified as potentially unstable in hES cells. The flow cytometry results for CD9, SSEA4, TRA-1-60, TRA-1-81, and CXCR4 expression are shown in scatter plot format and show high expression for the markers of pluripotency and low or no expression of a marker for differentiation (CXCR4), while FISH assays for chromosomes 12 and 17 showed normal copy number. These data indicate that H1 hES cells can be maintained in suspension culture with routine serial passage using Accutase®, a non-mammalian, enzymatic cell dissociation method, and will maintain pluripotency and stable karyotype in a dynamic agitated suspension culture system, generating $1 \times 10^9$ cells per original input cell over the course of 20 passages. (EDTA can also be used for this serial suspension for 6 passages.)

TABLE 3

Flow Cytometry for Pluripotency of the Cells as a Function of Time based on Results for the Markers CD9, SSEA4, TRA-1-60, TRA-1-81, and CD184 (CXCR4)

| Passage (culture day) | CD9 | SSEA4 | TRA-1-60 | TRA-1-81 | CD184 |
|---|---|---|---|---|---|
| 1 (3) | 92.0% | 100.0% | 57.4% | 58.6% | 0.2% |
| 2 (4) | 73.3% | 99.9% | 63.5% | 54.3% | 0.1% |
| 3 (3) | 87.5% | 99.7% s | 65.8% | 63.6% | 0.1% |
| 4 (4) | 86.7% | 99.8% s | 60.9% | 68.2% | 0.1% |
| 5 (3) | 79.3% | 99.7% | 67.6% | 69.9% | 0.3% |
| 6 (3) | 79.3% | 99.7% | 67.6% | 69.9% | 0.3% |
| 7 (3) | 93.7% | 100.0% | 60.1% | 58.8% | 0.2% |
| 8 (3) | 83.0% | 99.0% | 73.0% | 68.0% | 0.5% |
| 9 (4) | 94.6% | 100.0% | 65.5% | 64.2% | 0.1% |
| 10 (4) | 96.3% | 100.0% | 77.3% | 75.0% | 0.2% |
| 11 (4) | 97.3% | 100.0% | 69.1% | 61.3% | 0.2% |
| 12 (4) | 91.6% | 100.0% | 56.9% | 62.7% | 0.6% |
| 13 (4) | 97.3% | 99.9% | 62.9% | 63.2% | 0.2% |
| 14 (4) | 97.1% | 100.0% | 71.1% | 82.4% | 1.0% |
| 15 (4) | 96.1% | 99.6%* | 79.0% | 74.2% | 0.2% |
| 16 (4) | 87.7% | 99.9% | 77.1% | 72.5% | 0.3% |
| 17 (4) | 98.6% | 99.7% | 69.9% | 57.7% | 0.3% |
| 18 (4) | 97.7% | 100.0% | 68.6% | 56.6% | 0.2% |
| 19 (4) | 97.1% | 100.0% | 79.4% | 70.4% | 0.1% |
| 20 (4) | 96.9% | 100.0% | 57.4% | 55.7% | 0.4% |

Example 4

Directed Differentiation of Suspension Cultured Human Embryonic Stem Cells of the Cell Line H1

Cells of the human embryonic stem cell line H1, (WA01 cells, WiCell, Madison Wis.) at passage 40 were lifted from a planar adherent culture using Accutase® and transferred to suspension culture format. The cells were maintained in a dynamic agitated suspension culture system for 30 passages using the method described in Example 3.

Pluripotency was confirmed through the first 20 passages as shown in Table 3, with stable high levels of pluripotency markers maintained throughout the culture, as measured by flow cytometry. To confirm pluripotency and demonstrate their ability to provide a cell source for treatment of diabetes, cells were differentiated to a pancreatic precursor in a dynamic agitated suspension culture system through a step-wise progression of different media containing morphogens or growth factors intended to recapitulate normal pancreatic development. This process gives rise to a pancreatic precursor cell population characterized by a high PDX1 and NKX6.1 co-expression. When these cells were transplanted, they matured further to functional glucose stimulated insulin secreting tissue able to secrete insulin in response to glucose and maintain normal blood glucose in a streptozotocin induced model of diabetes. See FIG. 4C and Table 4c.

In order to generate these pancreatic precursor cells, H1 human embryonic stem cells that had been expanded and maintained in a dynamic agitated suspension culture system for 16 passages were differentiated using the method described in Example 3. In summary, the cells were expanded for 30 passages, tested for pluripotency for the first 20 of these passages; the cells were differentiated on the $16^{th}$ passage. Pluripotent cells in cluster format were transferred from mTeSR®1 media to FBC solution (Table 4a) at 4° C. for 3 hours. Cell clusters were then moved to a 3 liter glass suspension bioreactor regulated by a Sartorius Stedim Biostat B-DCU (Goettingen, Germany) control unit and suspended in differentiation media at 0.55 million cells/mL according to Table 4b. The cells were maintained 14 days in the closed sterile suspension bioreactor regulated for temperature, pH, and dissolved oxygen (DO) (FermProbe® pH electrode 225 mm, Model # F-635, and dissolved oxygen OxyProbe® 12 mm Sensor, model number D-145 from Broadley-James Corporation, Irvine Calif.).

Figure 4B:
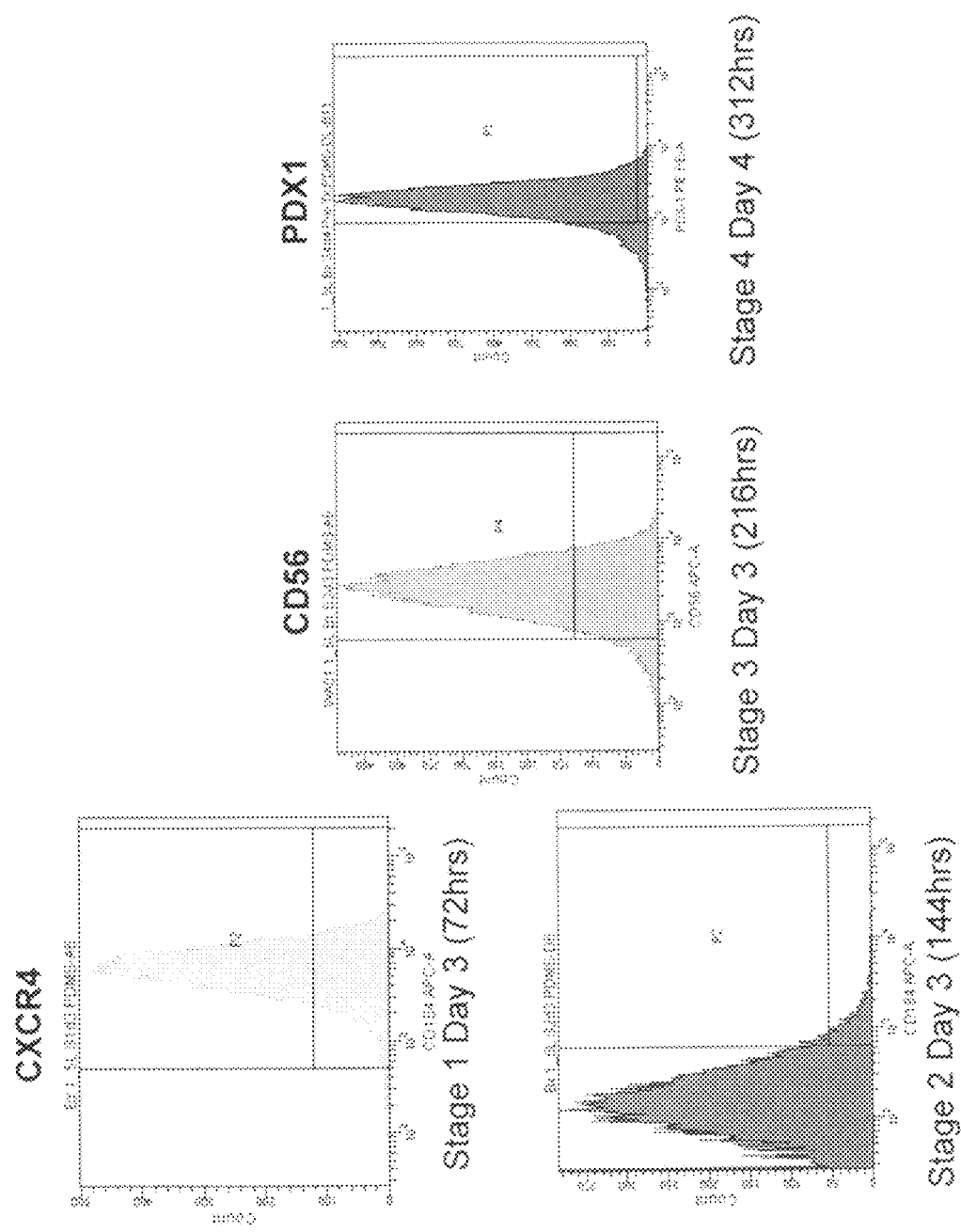
FIG. 4b shows the results of flow cytometry for markers of differentiation (CXCR4, CD56 and PDX1) for suspension cultured human embryonic stem cells of the cell line H1 using a directed differentiation protocol at different stages of differentiation (hours after beginning differentiation). At the end of the differentiation process on day 4 of stage 4, a high percentage of the cells were positive for PDX1 expression.

Throughout the run, media bicarbonate levels were maintained at 3.64 g/L with pH maintained at pH 7.4 by regulation of $CO_2$ flow in a total media volume of ≤1.6 liters. The bioreactor head space was continuously perfused with $CO_2$, air, and 02, under control of the Sartorious control system with a 20% dissolved oxygen set-point for stage 1 and a 30% dissolved oxygen set-point for stage 2 onward with a constant gas flow of 150 cc/minute. Oxygen flow was regulated in response to dissolved oxygen content and $CO_2$ flow was regulated in response to pH. Temperature was maintained at 37° C. throughout the run by an electric heated jacket. At the initiation of the run and for each media exchange (93% of media removed per exchange) the impeller (3" stainless steel pitch blade impeller operated at 70 rpm) was stopped and media was removed or added by peristaltic pump through a dip tube in the bioreactor connected to C-Flex® tubing using a Terumo™ tube welder to maintain a closed system. Images of cells/clusters were taken at the end of each stage of differentiation, and flow cytometry samples were collected and assayed for CXCR4 expression at stage 1 day 3 and 3 days later at the end of stage 2 (FIG. 4a). A near total population transition from a CXCR4 negative pluripotent cell population at the initiation of differentiation (Table 3, passage 16) to a population of CXCR4 expressing (98.5% of cells CXCR4 positive, FIG. 4b) cells was observed. These cells then transitioned to a nearly CXCR4 negative state 3 days later at the end of stage 2 (7.0% of cells CXCR4 positive), and by the end of stage 3 the cells had almost completely transitioned to a CD56 positive state. At the end of the differentiation process on day 4 of stage 4, the cells were 88.5% positive for PDX1 expression (FIG. 4b) and showed an expression pattern consistent with a mix of pancreatic endocrine cells (33.5% chromogranin positive) and pancreatic progenitor cells (65.7% positive for NKX6.1). This stage specific marker expression pattern indicated an efficient stage-wise differentiation from a pluripotent population to pancreatic cells. At the end of the differentiation process 2.77 million cells/mL were generated (4.1 billion cells in 1.5 Liter), indicating a total mass expansion of 5 differentiated cells per each input hES cell.

At the end of the run, 500 mL were removed for centrifugation and washing and were tested in an animal model of engraftment, maturation, and function. The remaining 1000 mL of cell suspension was processed in a kSep®400 system (KBI Biosystems, Durham N.C.) to wash, filter, and concentrate the cell product in a fully closed loop system. The cell product was concentrated from a starting volume of 1 liter to 50 mL of concentrated cells at a final concentration of 41 million cells/mL. These concentrated cells were then dispensed into 24 vials with 1.2 ml fill volume using an automated vial fill machine (Fill-It, TAP, Hertfordshire UK) and frozen by placing into a liquid nitrogen freezer.

The 500 mL differentiated cells that were washed and concentrated by standard centrifugation were transplanted at a dose of 5 million cells per SCID-Bg mouse placed either directly under the kidney capsule, or placed inside an immune-protective macro encapsulation device (TheraCyte™, Irvine Calif.) that was implanted subcutaneously (6 animals per condition). By 12 weeks post implantation, the implanted cells expressed significant levels of circulating human C-peptide (>0.1 ng/mL) as detected by ELISA (human c-peptide custom ELISA Mercodia cat#10-1141-01) in response to fasting and then feeding and by 16-20 weeks animals had over 1 ng/mL of circulating c-peptide (Table 4c).

At 27 weeks (190 days) post implantation, two animals with device encapsulated immune-protected grafts were each treated with a single high dose of streptozoticin (STZ) to selectively kill all endogenous mouse β islet cells and induce diabetes (250 mg/Kg). For the next two weeks after an STZ treatment sufficient to induce frank diabetes in a control animal the engrafted animals' blood glucose levels remained within normal range (<150 mg/dL). At 29 weeks post implantation and two weeks after STZ administration the two animals were then tested for glucose stimulated insulin secretion (GSIS) and showed a marked increase in circulating human c-peptide in response to glucose administration. Furthermore, when each of the grafts were removed at day 209 (29.5 weeks) post implantation, the animals' blood glucose levels increased dramatically to >500 mg/dL.

These results demonstrate that a human embryonic stem cell derived cell product to treat diabetes can be prepared from suspension of expanded and differentiated stem cells. The product can be generated in a scalable, stirred, closed loop bioreactor system and the cell product can be processed with a closed loop wash and concentration as required for commercial cGMP manufacturing. This human embryonic stem cell derived cell product can treat diabetes in a widely used animal model of diabetes as shown by GSIS competence, ability to regulate blood glucose, and the return to a diabetic state upon removal of the cell therapy.

TABLE 4a

Composition of FBC solution

| Component | Amount (mg/L) | Function | Grade |
|---|---|---|---|
| Dextrose, Anhydrous | 901 | Sugar | USP |
| Potassium Chloride | 559 | Salt | USP |
| Sodium Bicarbonate | 2000 | Buffer | USP |
| Sucrose | 6846 | Sugar | USP |
| Mannitol | 3644 | Sugar Alcohol | USP |
| Calcium Chloride Dihydrate ($CaCl_2 \cdot 2H_2O$) | 70 | Salt | USP |
| Magnesium Chloride ($MgCl_2 \cdot 6H_2O$) | 1017 | Salt | USP |
| Potassium Bicarbonate ($KHCO_3$) | 500 | Buffer | USP |
| Potassium Monophosphate ($KH_2PO_4$) | 1361 | Buffer | $NF^b/FCC^c$ |
| Lactobionic Acid | 35830 | Cell Stabilizer | $NA^d$ |
| L-Glutathione | 922 | Anti-oxidant | NA |
| HCl | To adjust pH | Acid | $ACS^e$ |
| Sodium Hydroxide | To adjust pH | Base | NF/FCC |
| Water for Injection (WFI) | To prepare the solutions | To prepare the solutions | USP |

[a] USP = United States Pharmacopeia
[b] NF = National Formulary
[c] FCC = Food Chemicals Codex
[d] NA = Not applicable
[e] ACS = American Chemical Society TABLE 4b Media Components and Differentiation Protocol

| | Stage 1 | Stage 2 | Stage 3 | Stage 4 |
|---|---|---|---|---|
| Basal Media (final glucose conc.) | MCDB131 3.64 g/l NaCO3 (8 mM glucose) | | | |
| Protein/Amino Acid Supplement | 2% Fatty Acid Free Bovine Serum Albumin (FAF-BSA) and 2 mM L-Glutamine | | | |
| Growth factors AND/OR Small molecules | MCX (3 μM) For 0-24 hours GDF8 (100 ng/mL) for 24-72 hours ITS-X (1:50,000) | FGF7 (50 ng/ml) ITS-X (1:50,000) | FGF7 (50 ng/ml) ITS-X (1:200) RA (2 μM) SANT (0.25 μM) AA (5 ng/mL) TppB (200 nM) LDN (100 nM) for 0-24 hours stage3 | ITS-X (1:200) SANT (0.25 μM) Cypi (100 nM) SCIO (2 uM) TppB (100 nM) |
| Total Days | 3 | 3 | 3 | 5 |
| Media Exchanges | Time 0 and 24 hours | Time 0 and 48 hours | Time 0 and 24 hours | Time 0 and 48 and 96 hours |

(Nomenclature: Time 0 = first feeding of the new stage; Time 24, 48 or 96 hours = time after new stage media)

TABLE 4c

C-peptide expression (ng/mL)

| C-Peptide (ng/mL) | 4 wk | 8 wk | 12 wk | 16 wk | 20 wk | 24 wk | 29 wk |
|---|---|---|---|---|---|---|---|
| Kidney Capsule Implant (N = 6) | 0.00 | 0.03 | 0.19 | 0.95 | 2.56 | | |
| STDEV | 0.00 | 0.03 | 0.17 | 0.71 | 1.33 | | |
| Theracyte Device Implant (N = 6) | 0.00 | 0.02 | 0.35 | 0.58 | 1.45 | 2.49 | 2.85 |
| STDEV | 0.01 | 0.01 | 0.54 | 0.51 | 1.02 | 0.75 | 0.21 |

Example 5

Directed Differentiation in Suspension Format of Adherent Cultured Human Embryonic Stem Cells of the Cell Line H1

Cells of the human embryonic stem cell line H1, (WA01 cells, WiCell, Madison Wis.) at passage 41 were lifted from a planar adherent culture using EDTA and transferred to suspension culture format using the method described in Example 2.

Pluripotency of the cellular aggregates was measured by flow cytometry as shown in FIG. 5a and high expression of the pluripotency markers CD9, SSEA4, TRA-1-61, and TRA-1-80, indicating the cells were highly pluripotent, was observed. These pluripotent cells were then differentiated to a pancreatic precursor in a dynamically agitated suspension culture system through a step-wise progression of different media containing small molecules and growth factors intended to recapitulate morphogen drivers of normal pancreatic development. This process produces a pancreatic precursor cell population characterized by co-expression of the pancreatic cell transcription factors, PDX1 and NKX6.1. When these cells are transplanted they mature further to functional glucose stimulated insulin secreting tissue which can correct high blood glucose in a streptozotocin induced model of diabetes.

In order to generate the pancreatic precursor cell population, pluripotent cells in cluster format maintained in mTeSR®1 media were transferred to a 0.2 liter glass stirred suspension bioreactor (Dasgip, Catalog#DS0200 TBSC, Shrewsbury, Mass.) with controller regulated temperature, pH, and dissolved oxygen. Pluripotent cell clusters were cultured in the bioreactor for two days. At that time (stage 1, day 0) the media was exchanged and differentiation was initiated as the cell aggregates were suspended at approximately 0.7 million cells/mL in differentiation media according to Table 5a. The cells were then maintained in this closed sterile suspension bioreactor for 14 days. Throughout differentiation, media bicarbonate levels were maintained at 3.64 g/L with pH maintained at 7.4 by regulation of $CO_2$ flow in a total volume of 0.3 liter. The bioreactor head space was sparged with $CO_2$ and air under control of the Dasgip control system with a 30% dissolved oxygen set-point under a constant gas flow of 5 liters/hour. Air flow was regulated in response to dissolved oxygen content and CO$_2$ flow was regulated in response to pH.

TABLE 5a

Media Components and Differentiation Protocol

| | Stage 1 | Stage 2 | Stage 3 | Stage 4 |
|---|---|---|---|---|
| Basal Media (final glucose concentration) | MCDB131 3.64 g/l NaCO$_3$ (8 mM glucose) | MCDB131 3.64 g/l NaCO$_3$ (8 mM glucose) | MCDB131 3.64 g/l NaCO$_3$ (8 mM glucose) | MCDB131 3.64 g/l NaCO$_3$ (8 mM glucose) |
| Protein Supplement | | 2% Fatty Acid Free Bovine Serum Albumin (FAF-BSA) and 2 mM L-Glutamine | | |
| Growth factors AND/OR Small molecules | MCX (3 μM) As specified GDF8 (100 ng/mL) As specified ITS-X (1:50,000) | FGF7 (50 ng/ml) ITS-X (1:50,000) | FGF7 (50 ng/ml) ITS-X (1:200) RA (2 μM) SANT (0.25 μM) AA (5 ng/mL) TppB (200 nM) LDN (100 nM) for 0-24 hours stages | ITS-X (1:200) SANT (0.25 μM) Cypi (100 nM) SCIO (2 uM) TppB (100 nM) |
| Total Days | 3 | 3 | 3 | 5 |
| Media Exchanges | As specified | Time 0 and 48 hours | Time 0 and 24 hours | Time 0 and 48 and 96 hours |

Temperature was maintained at 37° C. throughout the run. At the initiation of the run and for each media exchange (95% of media removed per exchange) the impeller was stopped and media was removed and then added by peristaltic pump through a bioreactor dip tube connected to C-Flex® tubing using a Terumo™ tube welder to maintain a closed system.

Several different feed settings were tested during stage 1: (a) media change 24 hours after initiation of differentiation, no media change at 48 hours; (b) media change 24 hours after initiation of differentiation and glucose bolus addition at 48 hours; and (c) no media change throughout stage 1 with glucose and GDF8 bolus added 24 hours after initiation of differentiation, then a glucose bolus added at 48 hours post initiation.

Figure 5C:
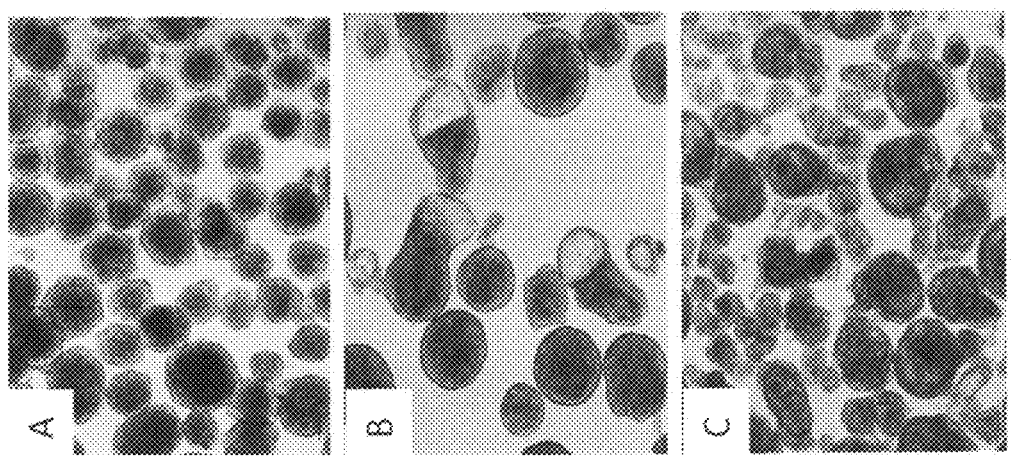
FIG. 5c shows phase contrast images of the differentiated cells exhibiting pancreatic endoderm morphology, which were differentiated using the following feed settings during the formation of definitive endoderm: (A) media change 24 hours after initiation of differentiation, no media change at 48 hours; (B) media change 24 hours after initiation of differentiation and glucose bolus addition at 48 hours; and (C) no media change throughout stage 1 with glucose and GDF8 bolus added 24 hours after initiation of differentiation, then a glucose bolus added at 48 hours post initiation.
Figure 5D:
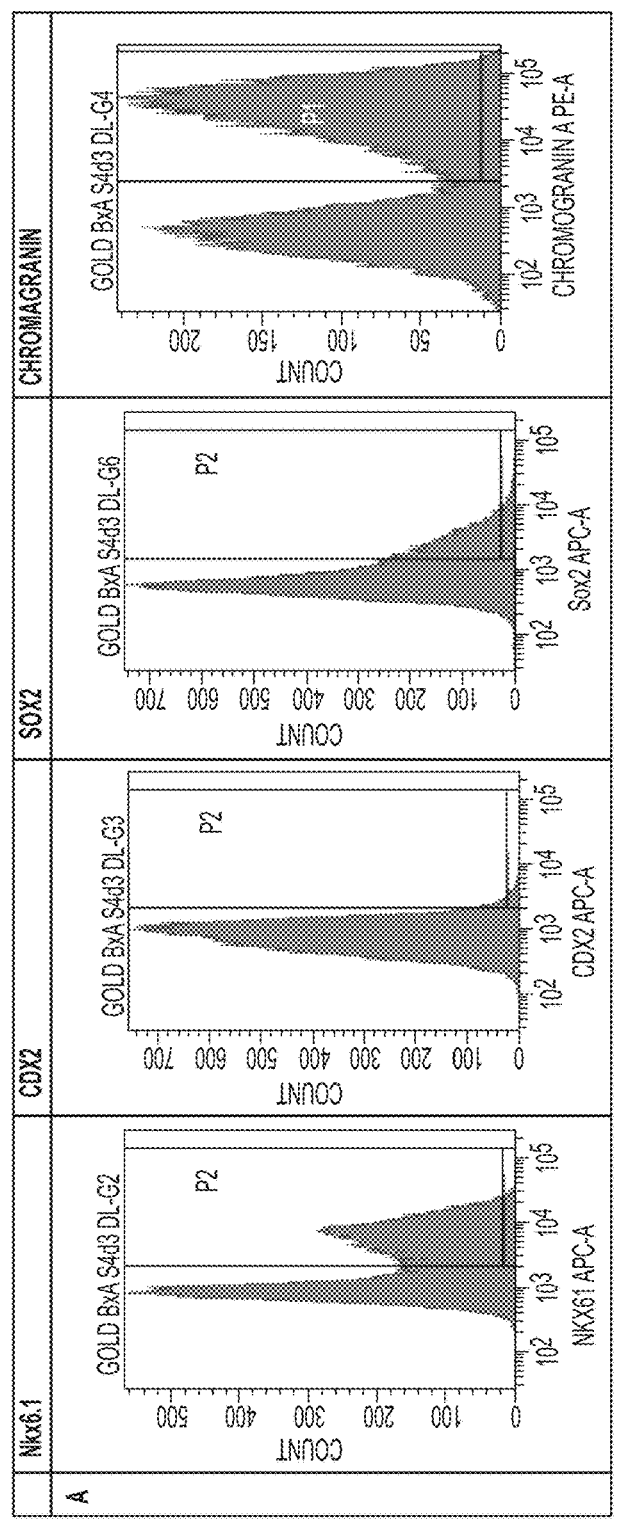
FIG. 5d shows the results of flow cytometry for select markers of pancreatic gene expression (NKX6.1 and chromogranin) and select non-pancreatic genes (CDX2 and SOX2) for differentiated cell as the end of stage 4, which were differentiated using the following feed settings during formation of definitive endoderm: (A) media change 24 hours after initiation of differentiation, no media change at 48 hours; (B) media change 24 hours after initiation of differentiation and glucose bolus addition at 48 hours; and (C) no media change throughout stage 1 with glucose and GDF8 bolus added 24 hours after initiation of differentiation, then a glucose bolus added at 48 hours post initiation.
Figure 5D:
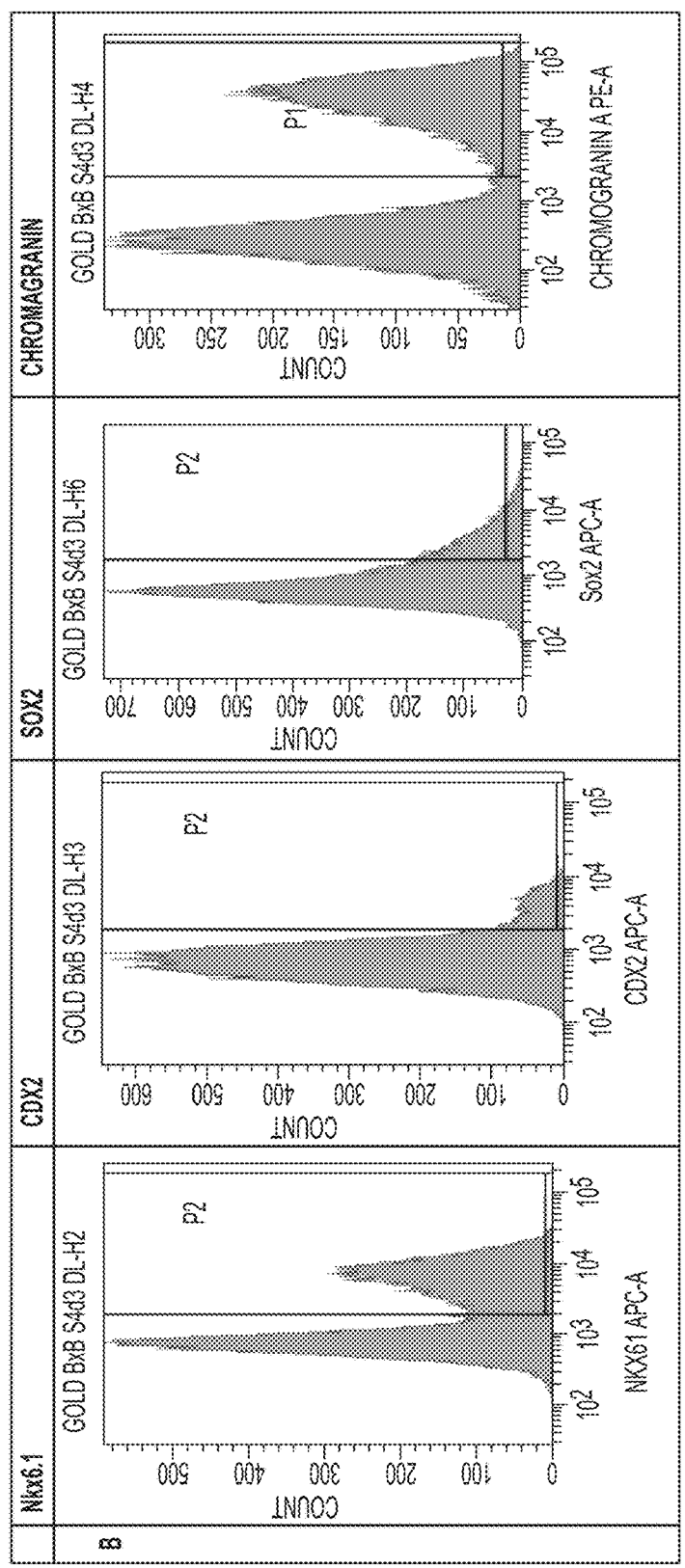
Figure 5D:
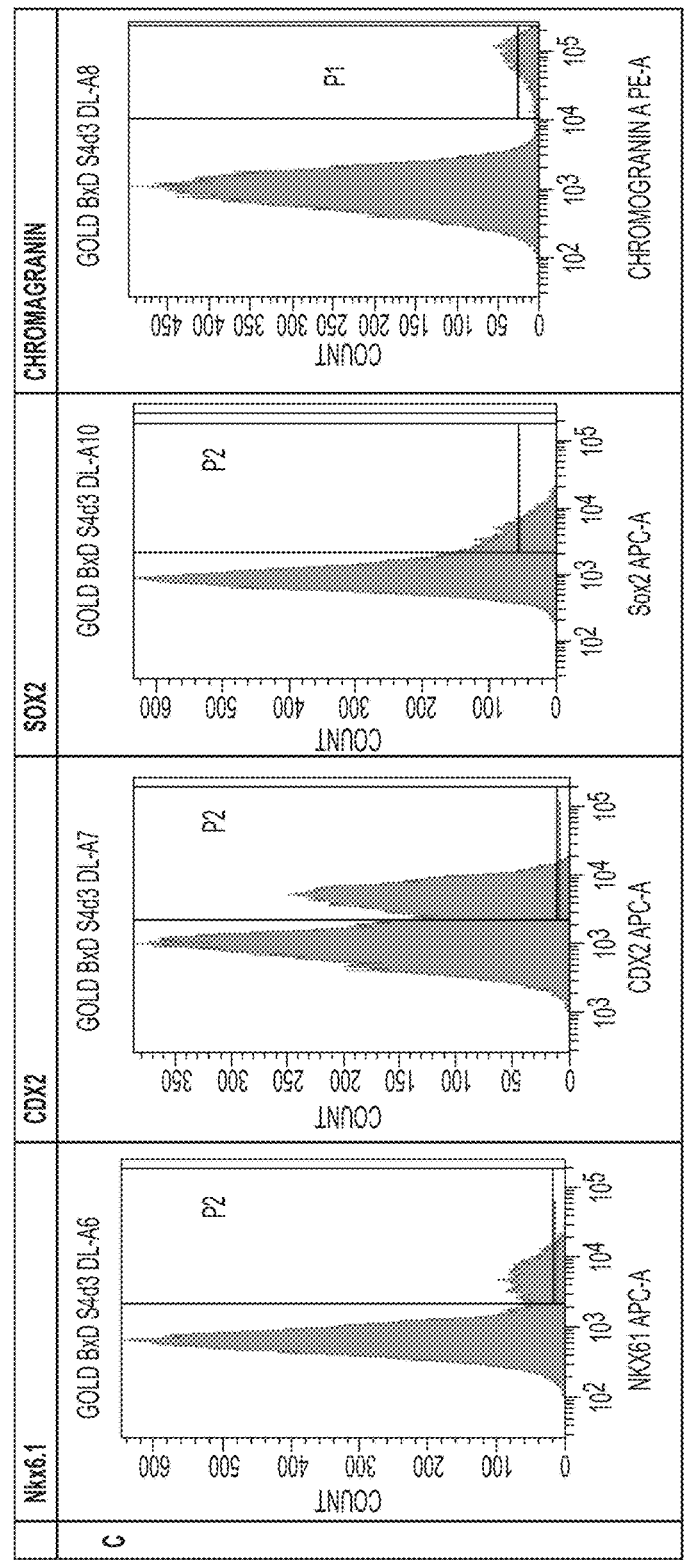
Figure 5E:
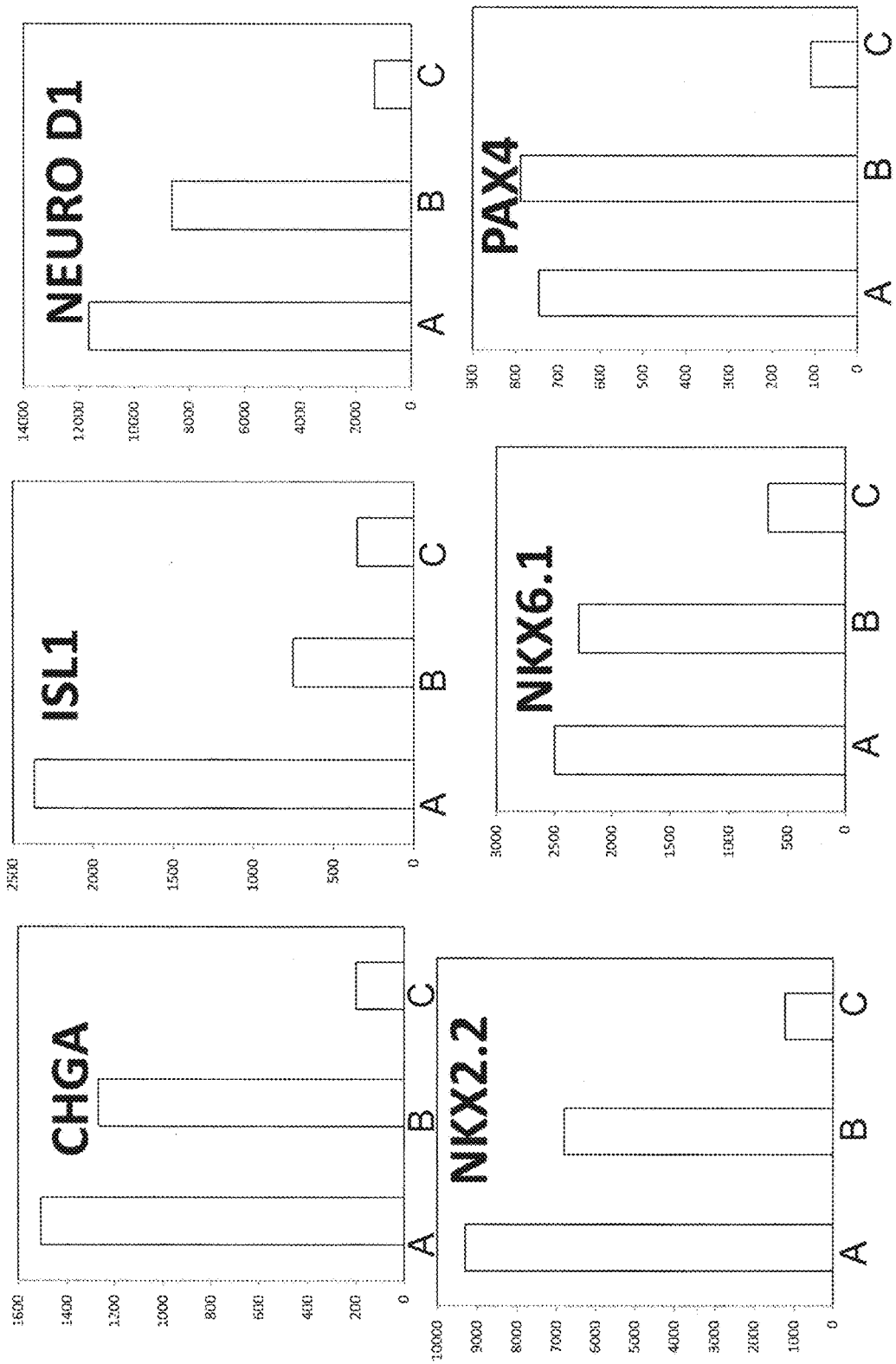
FIG. 5e shows qRT-PCR results for select pancreatic and non-pancreatic gene expression for differentiated cells as the end of stage 4, which were differentiated using the following feed settings during formation of definitive endoderm: (A) media change 24 hours after initiation of differentiation, no media change at 48 hours; (B) media change 24 hours after initiation of differentiation and glucose bolus addition at 48 hours; and (C) no media change throughout stage 1 with glucose and GDF8 bolus added 24 hours after initiation of differentiation, then a glucose bolus added at 48 hours post initiation. The data are shown as fold difference in expression versus undifferentiated H1 (WA01) hES cells (baseline expression of 1).
Figure 5E:
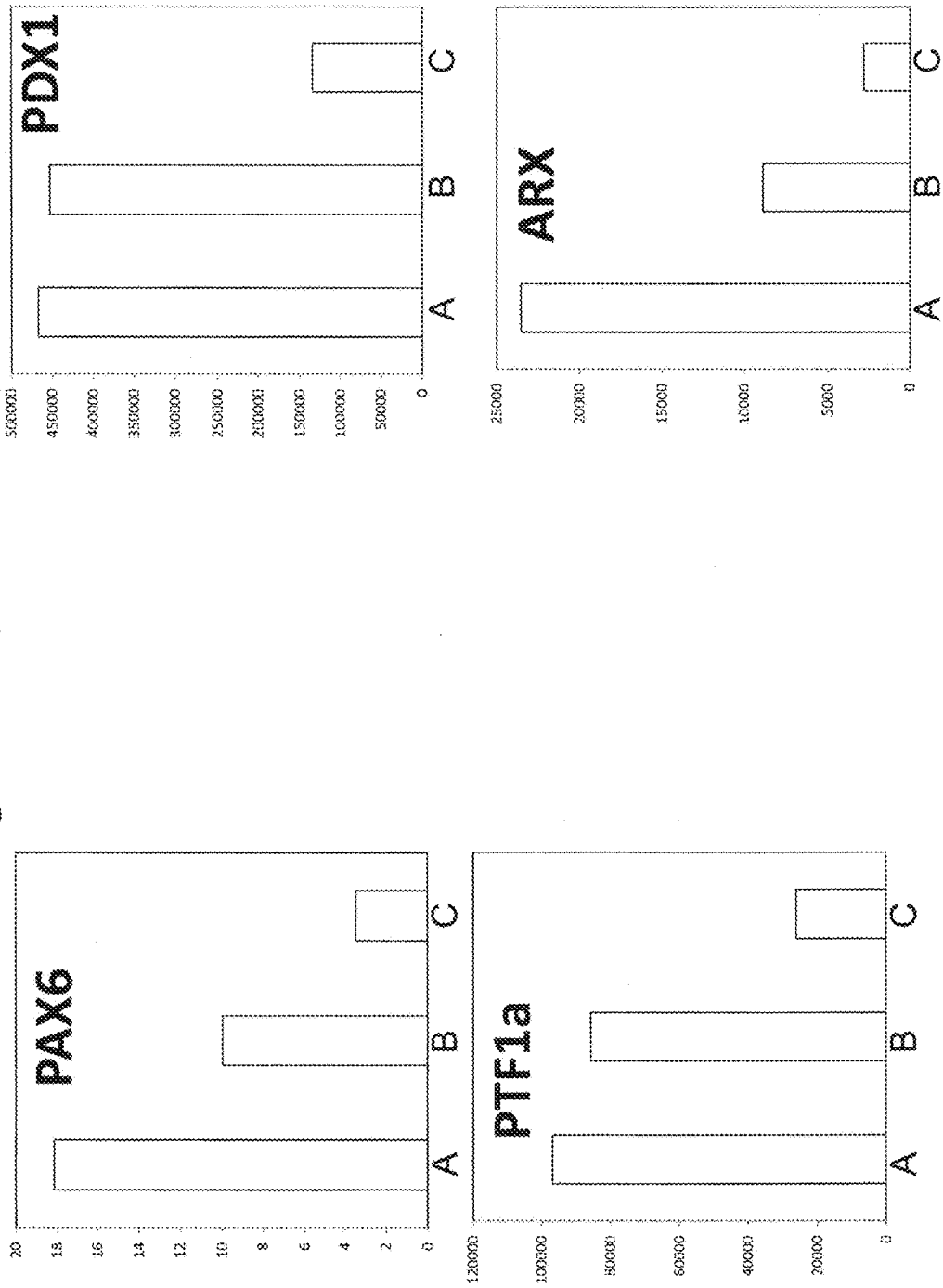
Figure 5E:
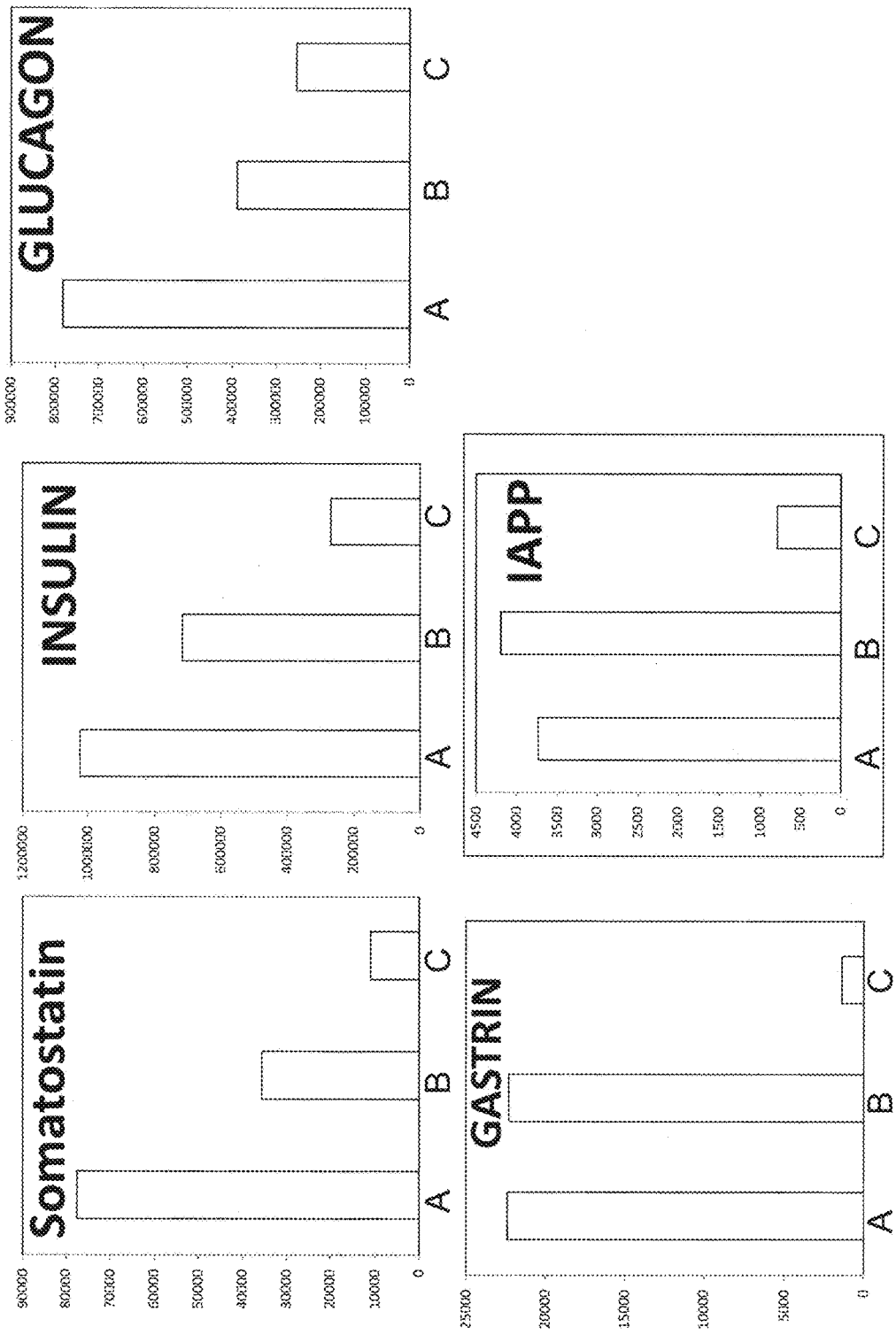
Figure 5E:
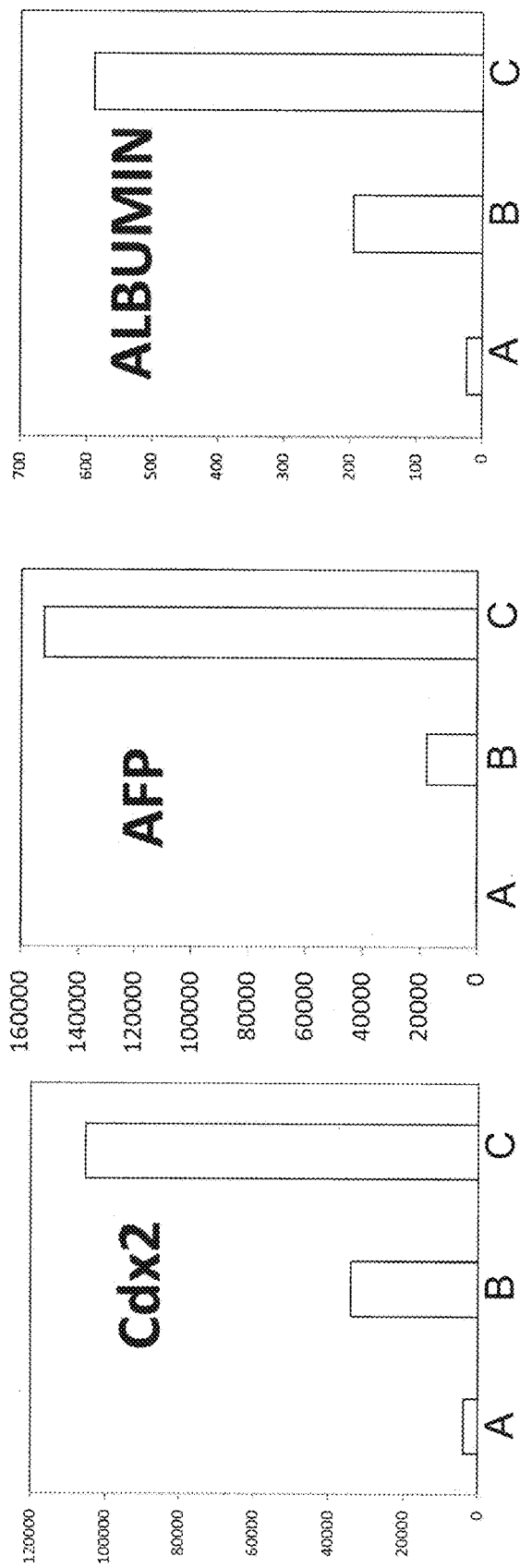

Cell counts at the initiation, middle, and end of the process were taken for each reactor as listed in Table 5b. At the end of stage 1, cells were sampled for protein expression patterns by flow cytometry. Cells differentiated in condition A—media change 24 hours after initiation of differentiation to definitive endoderm, then no media change for next 48 hours—showed the best results as measured by induction of markers of differentiation (CD99 and CXCR4) and reduction in pluripotency marker expression (CD9) (FIG. 5b). The higher expression of CXCR4 and CD99 in combination with lower expression of CD9 at the end of definitive endoderm formation correlated with the higher expression of pancreatic genes and lower expression of genes indicative of alternate organ fates later in differentiation (FIGS. 5d and 5e). Specifically, one or both of not changing media throughout the first stage of differentiation or adding glucose to the media in stage 1 in a bulk feeding format resulted in lower CXCR4 levels at the end of stage 1 which correlated with very different aggregate morphologies at the end of the four stage differentiation (FIG. 5c). Specifically, conditions B and C had lower pancreatic gene expression (NKX6.1 and CHGA) and higher expression of non-pancreatic genes (CDX2 and SOX2) at the end of stage 4 as measured by flow cytometry (FIG. 5d and Table 5b). These findings were borne out by qRT-PCR (FIG. 5e), as condition A showed significantly higher expression of pancreatic genes than condition C, with condition B intermediate to A and C. Furthermore, Condition C expressed significantly higher levels of genes indicative of an alternative non-pancreatic fate, e.g. CDX2, AFP, and Albumin (FIG. 5e). These data indicate that a homogeneous, high CXCR4 expressing definitive endoderm (DE) generated without a media change for the last 48 hours of DE formation is able to convert later to a pure pancreatic endoderm population.

Figure 5G:
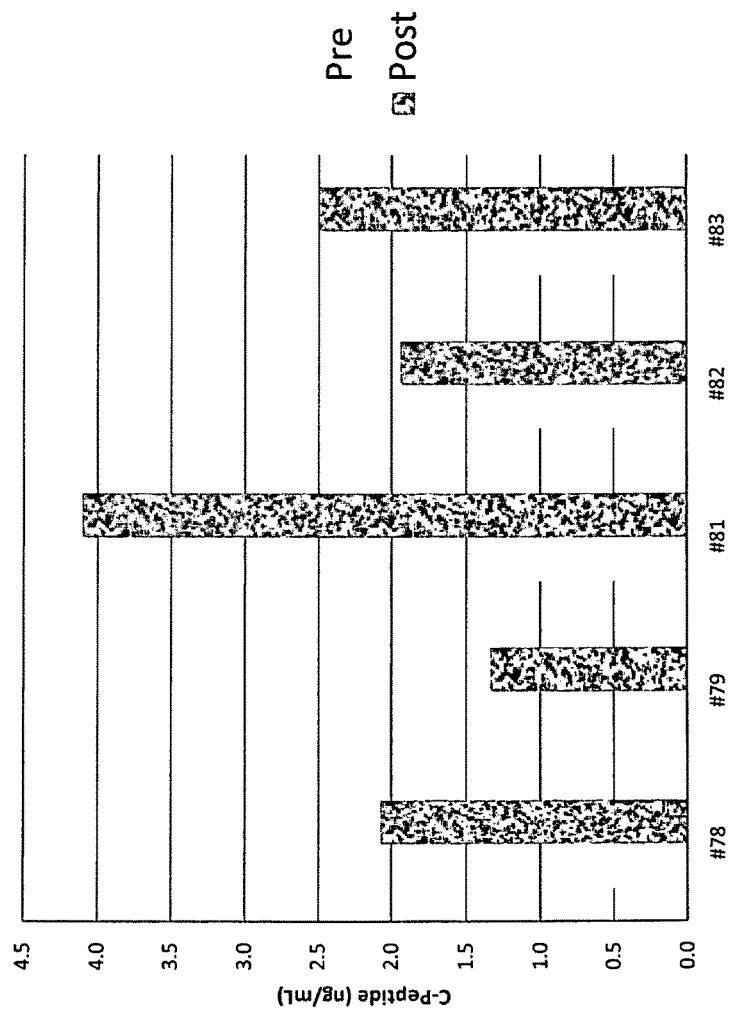
FIG. 5g shows the effect of glucose treatment for selected SCID-Bg mice pre- and post-administration (e.g. implantation) of cells differentiated according to condition A (media change 24 hours after initiation of differentiation, no media change at 48 hours).
Figure 5H:
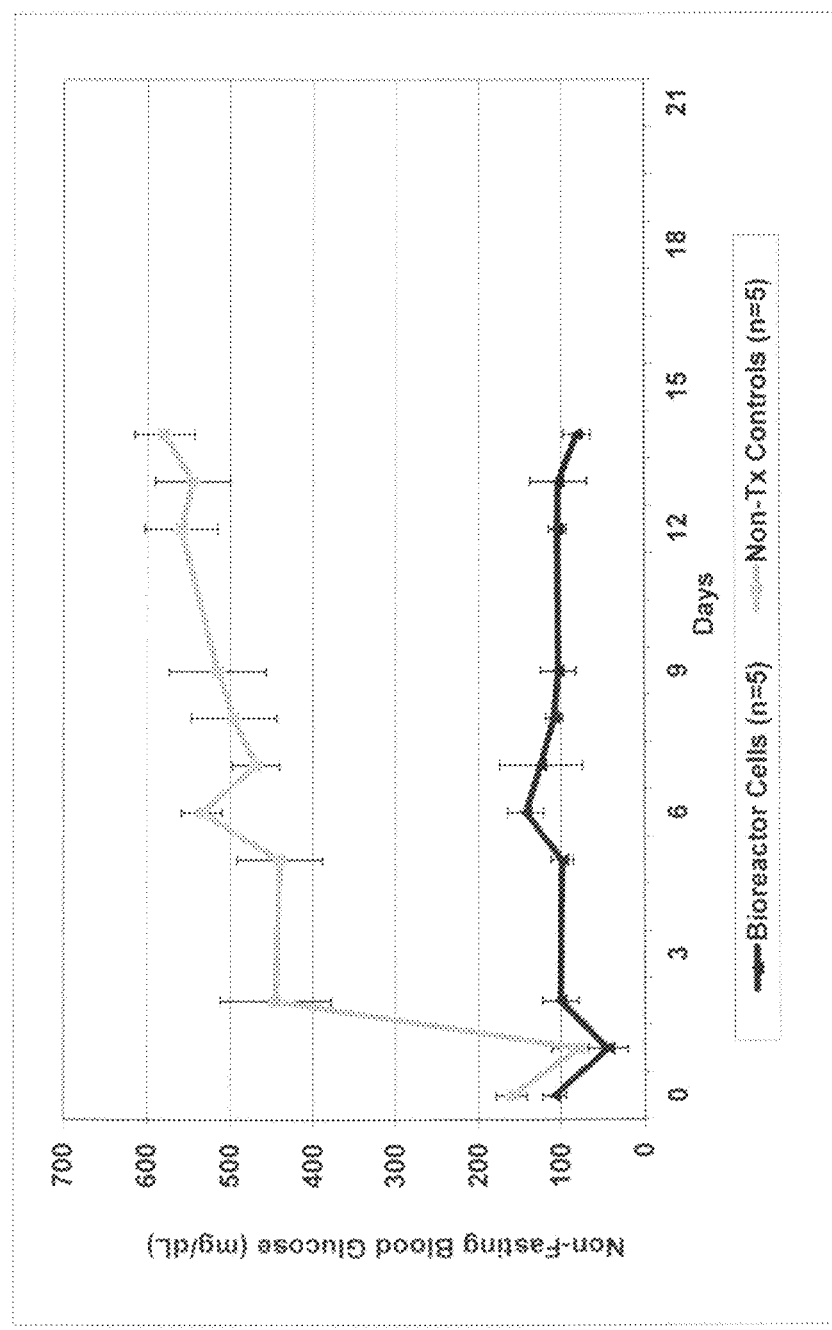
FIG. 5h shows the effect of streptozotocin (STZ) administration (i.e. STZ-induced diabetes) on SCID-Bg mice that had been administered cells differentiated according to condition A (media change 24 hours after initiation of differentiation, no media change at 48 hours). As evident from FIG. 5h, animals with a graft of functional GSIS competent tissue (i.e. those that had been administered the cells) maintained normal blood glucose levels unlike the untreated controls which developed frank diabetes.

At the end of the four stage differentiation, the cells differentiated according to condition A were removed from the bioreactor, washed with MCDB131 media containing 0.1% FAF-BSA and implanted in SCID-Bg mice. Each mouse was transplanted with 5 million cells directly under the kidney capsule. Every 4 weeks after implantation blood draws were performed and blood glucose and c-peptide were measured. By 12 weeks post implantation, human c-peptide was detectable by ELISA at levels above 1 ng/mL, and at 16 weeks c-peptide levels were an average of 2.5 ng/mL (FIG. 5f). At 20 weeks post-implantation c-peptide was measured in the animals in a fasted and then fed state. Glucose treatment induced a significant increase in circulating human c-peptide from 0.93 ng/mL in a fasted state to 2.39 ng/mL in a fed state (FIG. 5g) indicating that the transplanted cells had matured to functional GSIS competent tissue. Furthermore, when the animals were given a streptozotocin (STZ) administration (mouse β cells are more sensitive to and preferentially destroyed by STZ compared to human β cells) to induce a diabetic state, the animals with a graft of functional GSIS competent tissue maintained normal blood glucose levels unlike the untreated controls which developed frank diabetes (FIG. 5h). These results demonstrate that animals with a hES differentiated cell graft were protected from STZ induced diabetes by a functional pancreatic tissue graft.

TABLE 5b

Cell Counts and Flow Cytometry Data

| Pluripotency (Condition) | Viable Cell density (Million cells/mL) | CD9 | CD184 | SSEA4 | TRA-1-60 | TRA-1-81 |
|---|---|---|---|---|---|---|
| (A) | 0.723 | 93.8 | 0.2 | 100 | 74.3 | 67.3 |
| (B) | 0.677 | 92.3 | 0.2 | 100 | 71.7 | 71 |
| (C) | 0.738 | 89.9 | 0.1 | 100 | 75.3 | 72.1 |

| DE (Condition) | Viable Cell density Million cells/mL | CD9 | CD184 | CD99 |
|---|---|---|---|---|
| (A) | 0.965 | 1.7 | 99.6 | 84.3 |
| (B) | 1.22 | 4.8 | 93.1 | 81.2 |
| (C) | 1.2 | 8.3 | 68 | 34.1 |

| PE (Condition | Viable Cell density (Million cells/mL | NKX6.1 | Synaptophysin | CDX2 | SOX2 | NKX2.2 | CHGA |
|---|---|---|---|---|---|---|---|
| (A) | 0.795 | 47.5 | 48.4 | 2.9 | 23.8 | 61.7 | 55.7 |
| (B) | 0.98 | 44.4 | 38.5 | 10.3 | 21.4 | 45.4 | 41.5 |
| (C) | 1.33 | 15.4 | 5.8 | 37 | 18.4 | 9.6 | 6.7 |

Example 6

Directed Differentiation in Suspension Format of Microcarrier Adherent Cultured Human Embryonic Stem Cells of the Cell Line H1

Cytodex® 3 Microcarrier beads (C3) (Sigma-Aldrich Co LLC, St. Louis, Mo., Catalog # C3275) were prepared for culture by soaking 400 mg of the beads in 20 ml volume silicon coated glass scintillation vials containing 15 ml Dulbecco's PBS (DPBS), for 4-24 hours. Cytodex® 3 consists of a thin layer of denatured collagen chemically coupled to a matrix of cross-linked dextran. The denatured collagen layer on Cytodex® 3 is susceptible to digestion by a variety of proteases, including trypsin and collagenase, and provides the ability to remove cells from the microcarriers while maintaining maximum cell viability, function, and integrity.

After soaking, the beads were autoclaved and rinsed with sterile DPBS and re-suspended in mouse embryonic fibroblast conditioned media (MEF-CM) supplemented with 10 µM Y-27632. The beads were then transferred to 125 ml Corning® glass spinner flasks (Corning Incorporated, Corning, N.Y.) at a density of 100 mg beads/flask. The spinner containing beads and MEF-CM with Y-27632 was equilibrated in a humidified 5% $CO_2$ incubator at 37° C. for at least 60 min.

Cells of the human embryonic stem cell line H1, (WA01 cells, WiCell, Madison Wis.) at passage 44 were lifted from a planar adherent culture using TrypLE™ (Life Technologies Corporation, Grand Island, N.Y.) (8 minute incubation at 37° C. to form a single cell suspension). The cells were then washed and suspended in MEF-CM with Y-27632 and 11 million hES cells were allowed to adhere to the beads for 6 hours in a static (still) incubation period. MEF-CM with Y-27632 was then added to a spinner flask to make a final media volume of 75 mL, and the cells and beads were agitated in the glass spinner flask at an impeller speed of 50 rpm. The cells were grown in this manner for 5 days with a daily 50 mL media exchange of MEF-CM. After 5 days in culture, the flasks contained $53 \times 10^6$ cells ($\pm 12 \times 10^6$ SD). As a control, one million H1 hES cells were also seeded to 6 well tissue culture polystyrene dishes coated with a 1:30 dilution of Matrigel™ and maintained with a daily media change of MEF-CM.

Figure 6A:
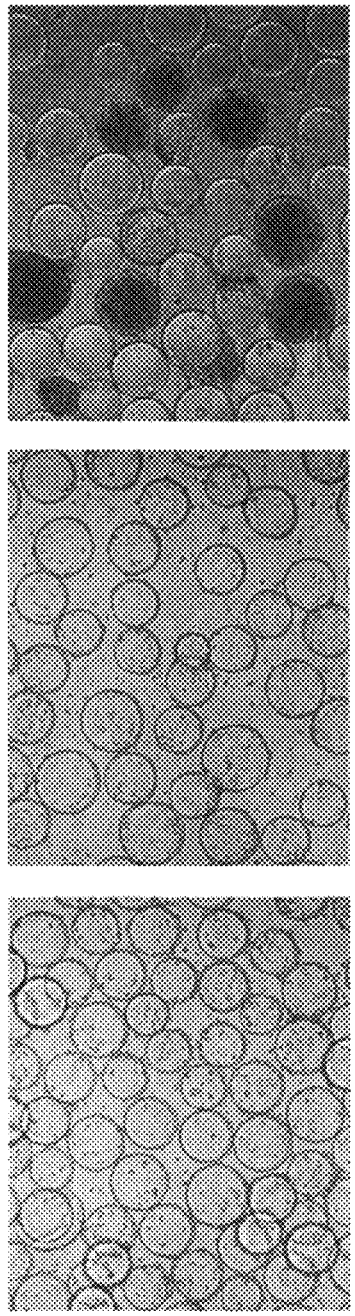
FIG. 6a shows micrographs of cells of the human embryonic stem cell line H1 grown on Cytodex® 3 microcarrier beads prior to differentiation.
Figure 6B:
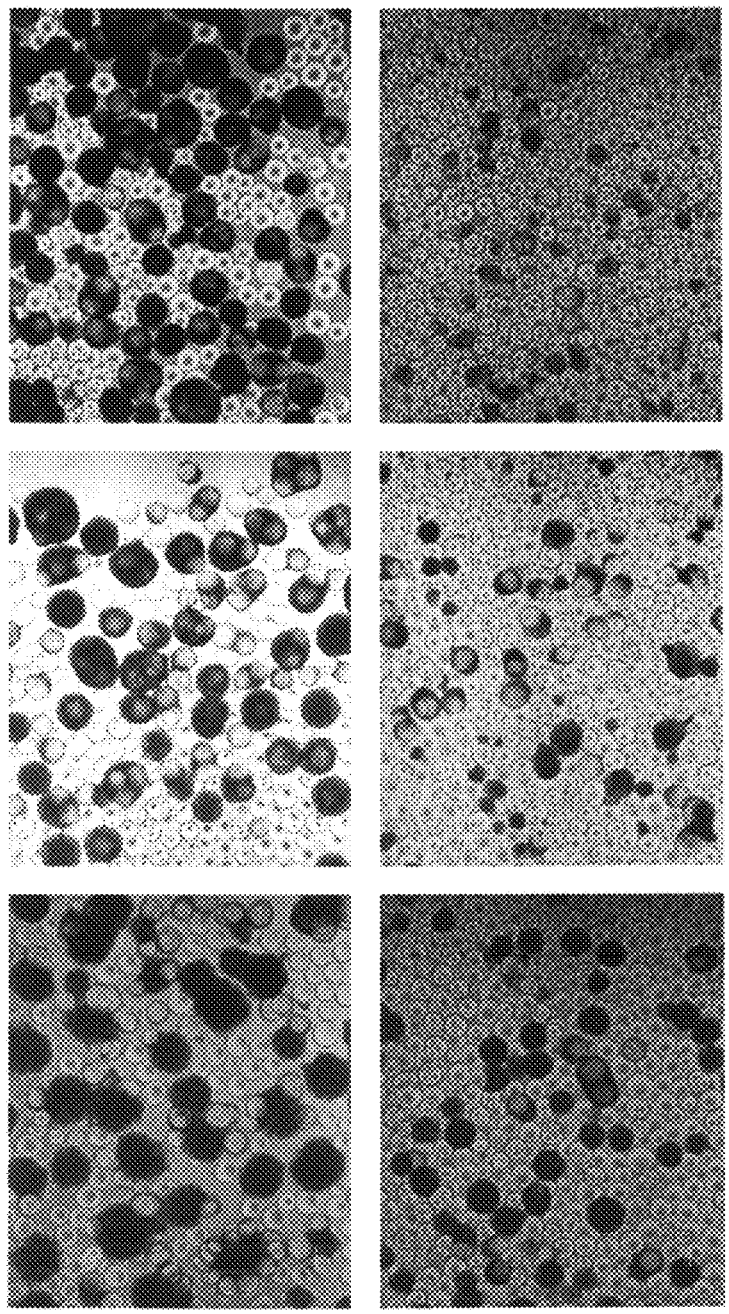
FIG. 6b shows micrographs of cells of the human embryonic stem cell line H1 grown on Cytodex® 3 microcarrier beads at various stages of differentiation.
Figure 6C:
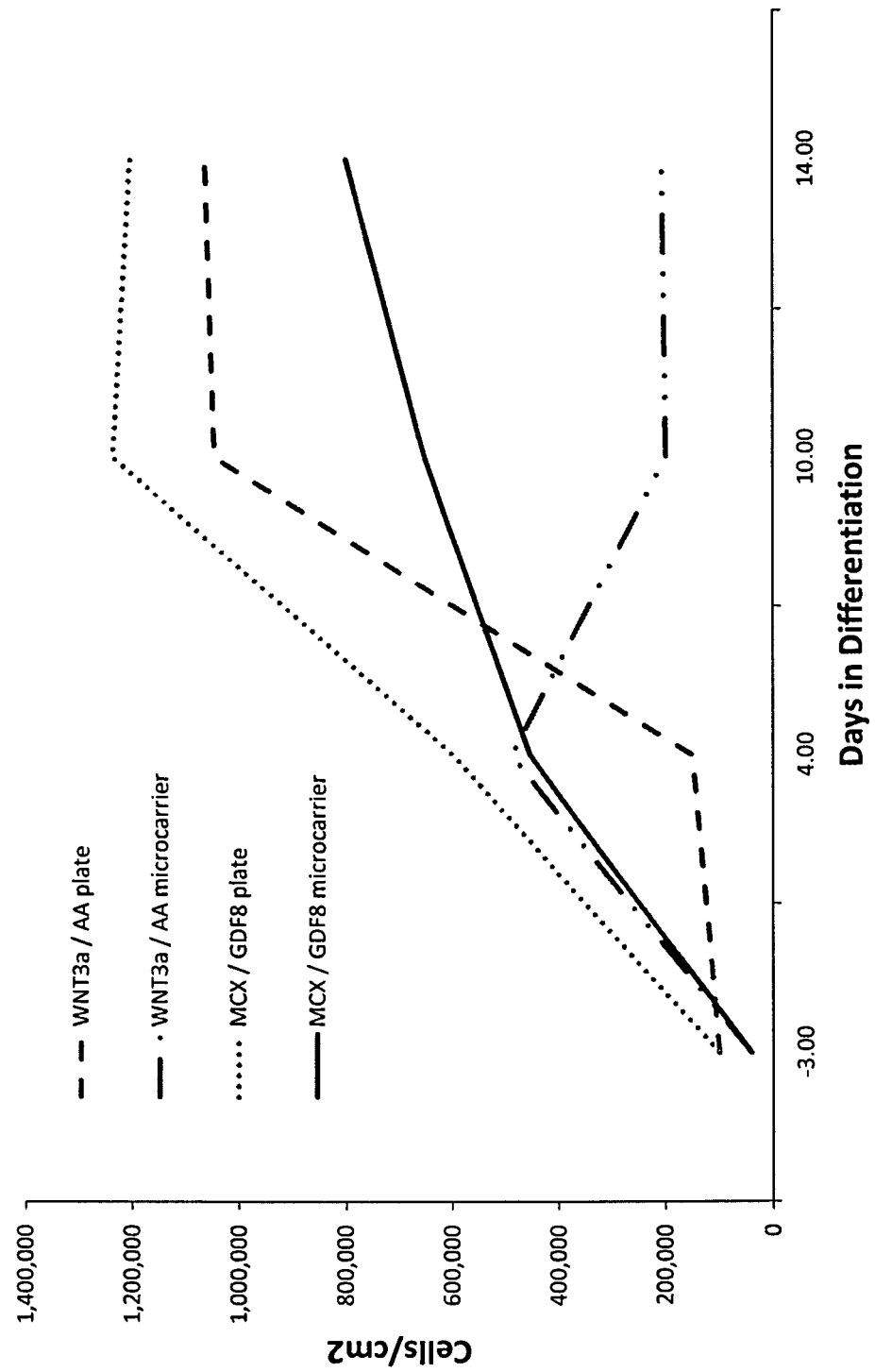
FIG. 6c shows the cell count (cells/cm$^2$) as a function of days of differentiation for cells of the human embryonic stem cell line H1 grown and differentiated on plates in media containing Activin A (AA) and WNT3A (WTN3A/AA plate), microcarriers in media containing Activin A and WNT3A (WTN3A/AA microcarriers), plates in media containing MCX and GDF8 (MCX/GDF8 plate) and microcarriers in media containing MCX and GDF8 (MCX/GDF8 microcarriers).

After 5 days in pluripotent culture, these cells were then differentiated to a pancreatic precursor in a dynamic agitated suspension culture system through a step-wise progression of different media containing one or both of small molecules and growth factors intended to recapitulate normal pancreatic development morphogens. Two media formulations were tested-as a method to recapitulate normal pancreatic development; one which used Activin A and Wnt3A to form DE, and another that used the MCX compound with GDF8 to form DE (Tables 6a and 6b, respectively). Media was changed daily, and samples were characterized by RT-PCR and flow cytometry to determine the cell properties. Phase contrast images of the cells on microcarriers were taken and a time course of the cell morphology as pluripotent culture before differentiation of the cells was initiated is shown in FIG. 6a. A time course showing the culture differentiating is shown in FIG. 6b. A cell count was also taken at various time points through the experiment, and the results are presented as a function of surface area (cells/$cm^2$ in FIG. 6c) or media volume (cells/mL in FIG. 6d) for the media formulations in either a planar culture or a suspended microcarrier culture.

Figure 6E:
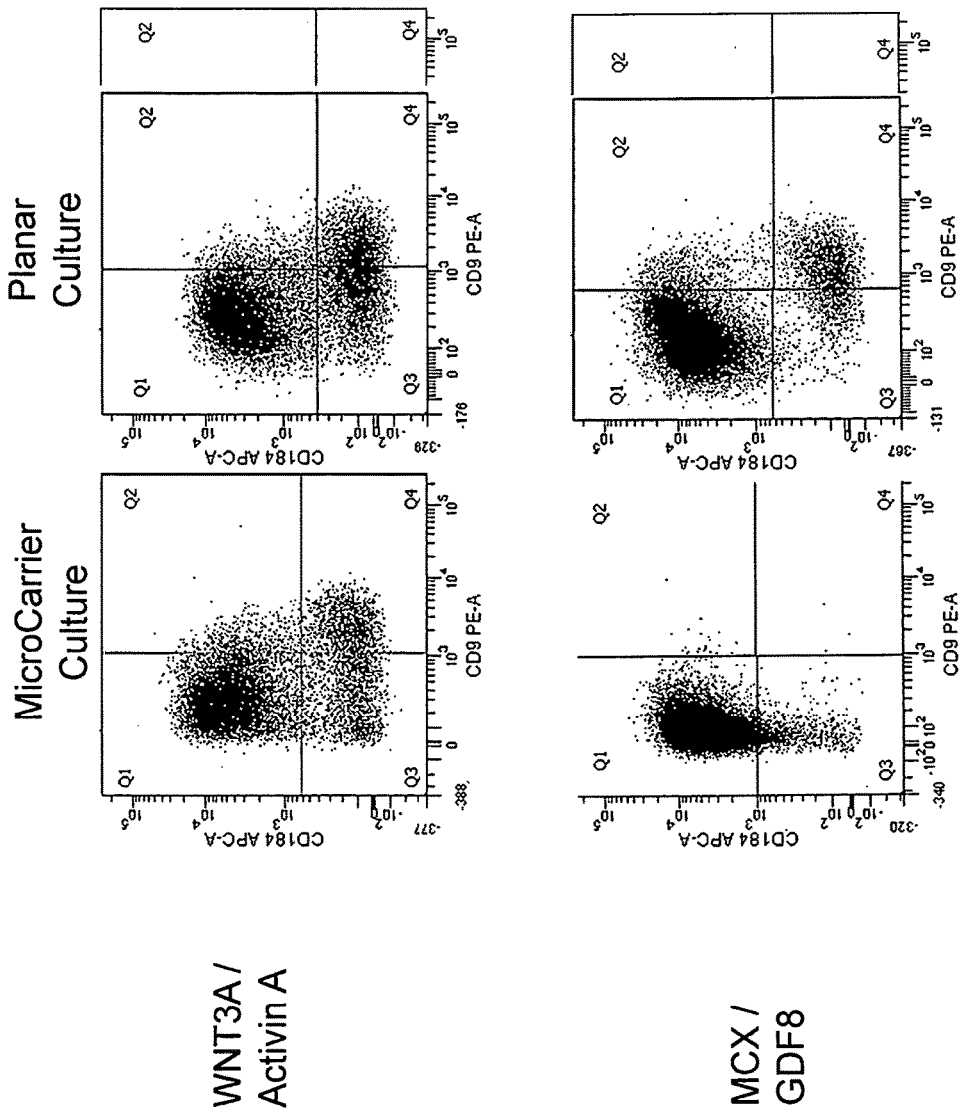
FIG. 6e shows flow cytometry results for the first stage of differentiation of cells grown on a microcarrier culture or planar culture in the presence of: (a) WNT3A and AA; or (2) MCX and GDF8 as a dot plot of cell expression of CXCR4/CD184 (Y-axis) and CD9 (X-axis).
Figure 6F:
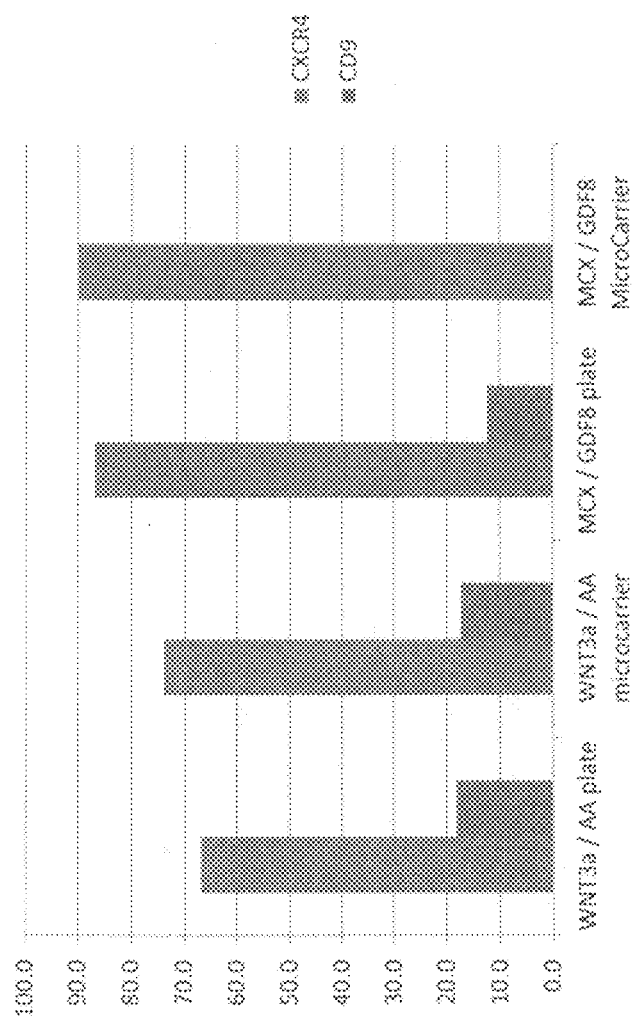
FIG. 6f shows flow cytometry results for the first stage of differentiation of cells grown on a microcarrier culture or planar culture in the presence of: (a) WNT3A and AA; or (2) MCX and GDF8 as total expression of each of the markers (CXCR4 and CD9).
Figure 6G:
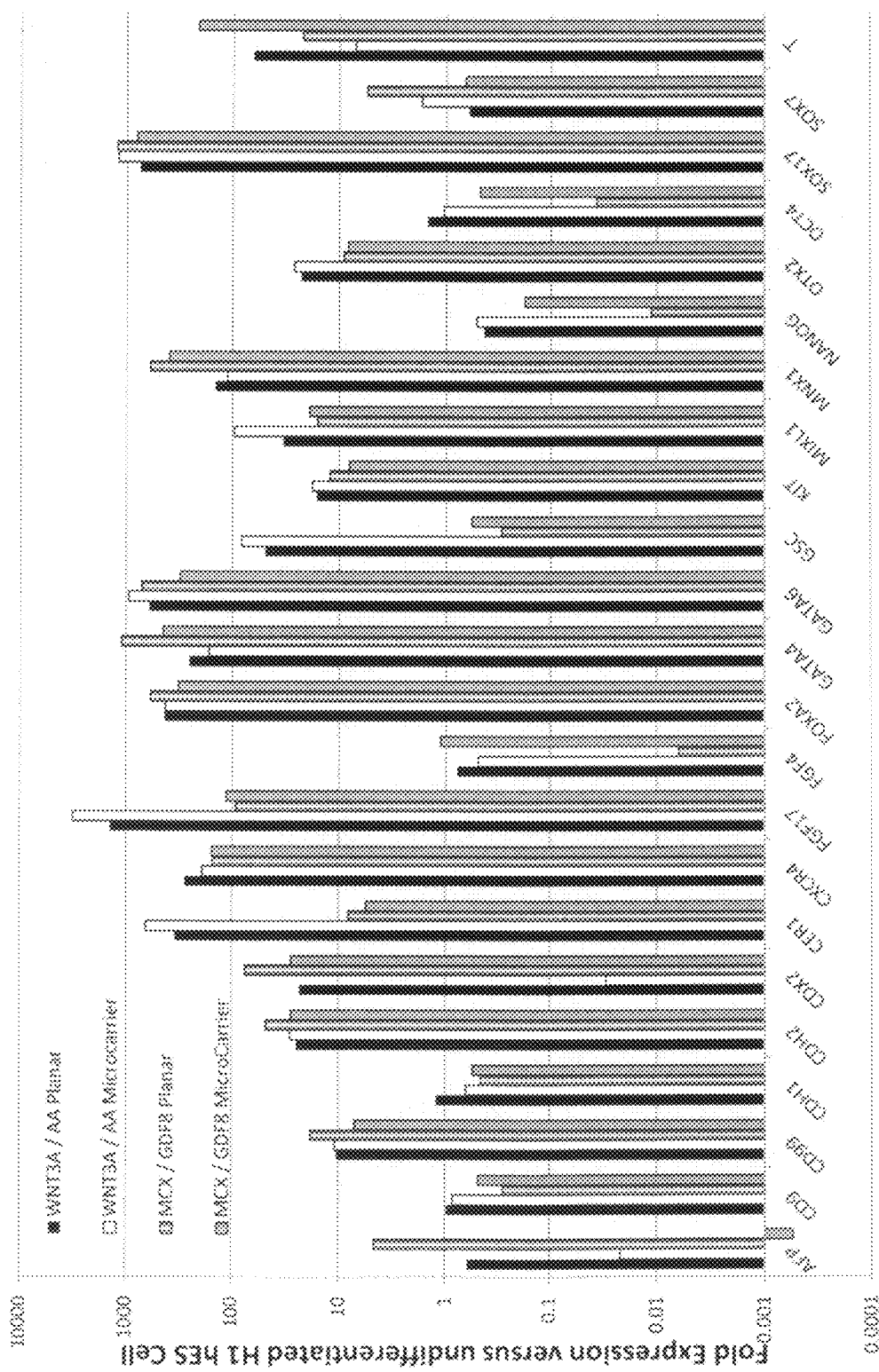
FIG. 6g shows qRT-PCR results for expression of selected genes associated with differentiation for cells of the human embryonic stem cell line H1, which were differentiated by growth on planar culture or on microcarrier beads in suspension culture in the presence of: (a) WNT3A and AA; or (2) MCX and GDF8.
Figure 41:
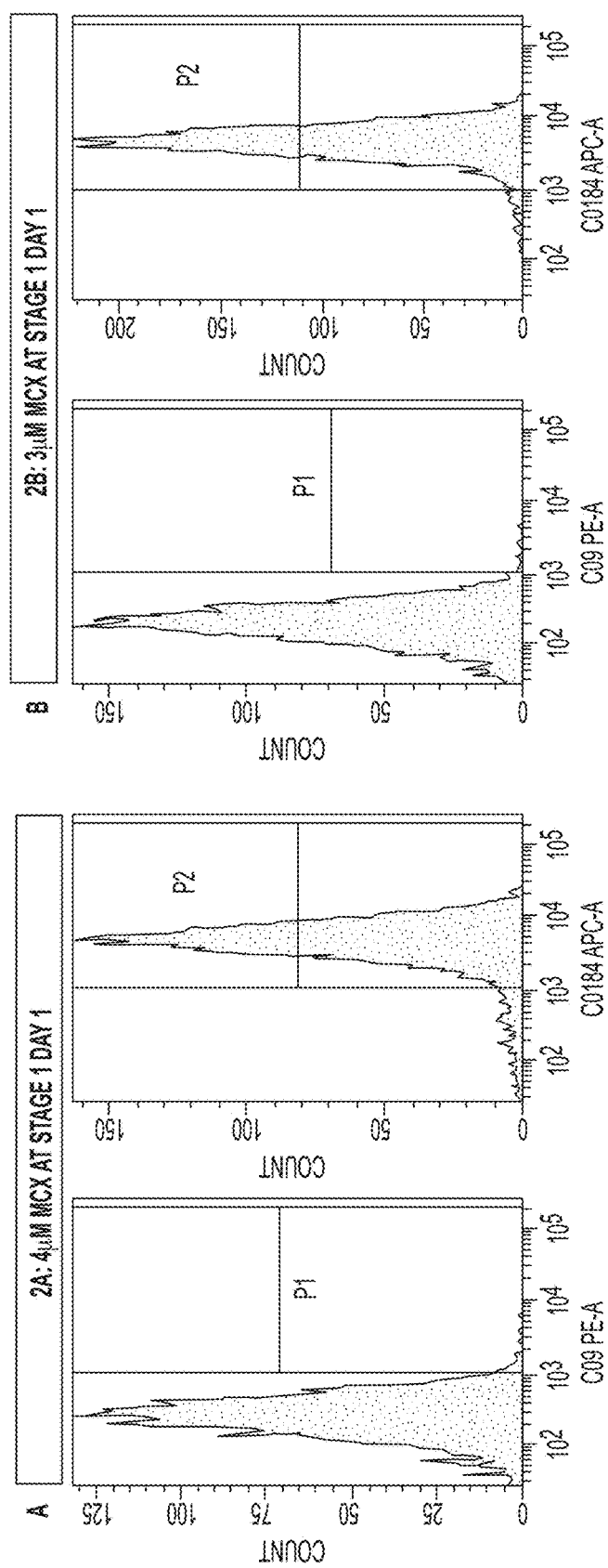
FIGS. 41A to 41D show FACS plots for CXCR4, CD99, and CD9 of cells differentiated for three days according to the protocol of Example 10, which were treated with various amounts of MCX at stage 1, day 1. Specifically, the cells at stage 1, day 1 were treated with: 4 μM of MCX (FIG. 41A); 3 μM of MCX (FIG. 41B); 2 μM of MCX (FIG. 41C); and 1.5 μM of MCX (FIG. 41D).
Figure 41:
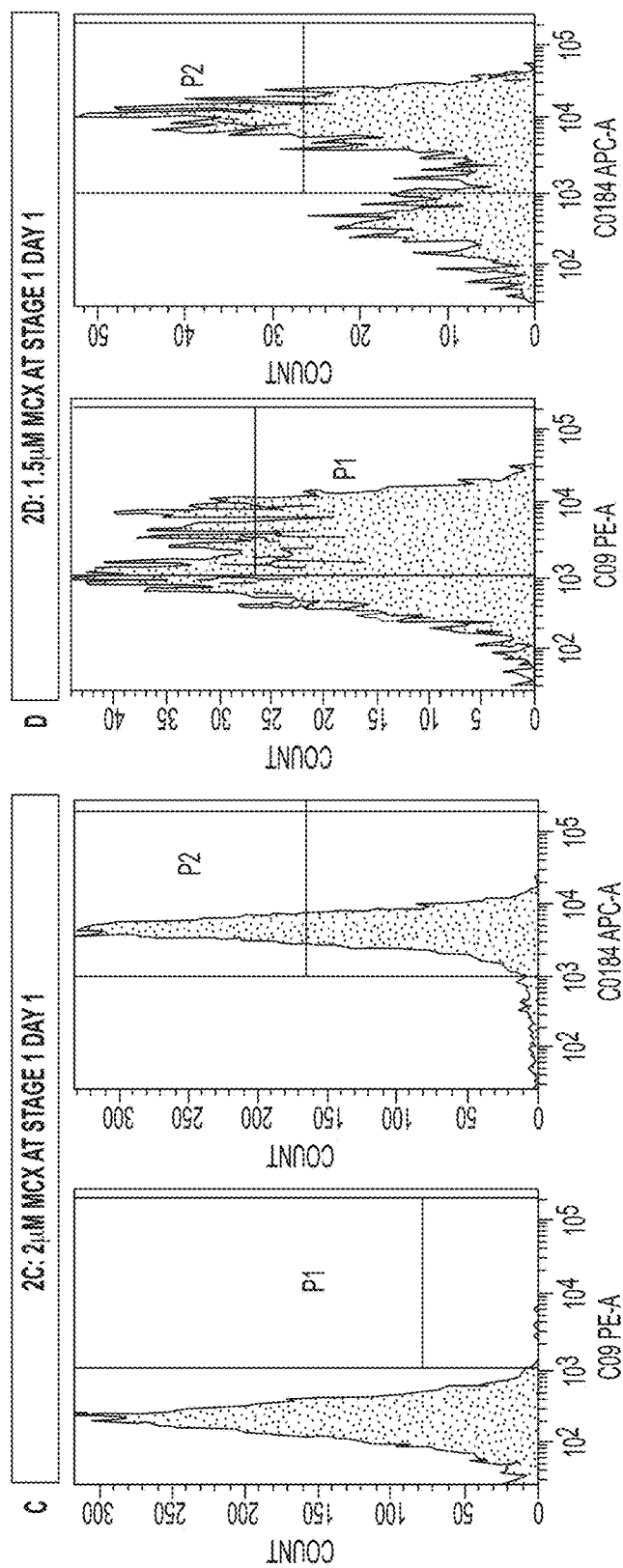

The cells were characterized at various points throughout the process by both flow cytometry and RT-PCR. Flow cytometry results for the first stage of differentiation, the formation of definitive endoderm, are shown as a dot plot of cell expression of CXCR4 (Y-axis) and CD9 (X-axis) in FIG. 6e and the results are also expressed as total expression of each marker in FIG. 6f. The results indicate that in all conditions a substantial majority of the cells form definitive endoderm, as defined by gain of CXCR4 expression and loss of the pluripotency surface marker, CD9. Furthermore, the more efficient formation of definitive endoderm occurs in rank order of treatment from MCX/GDF8 MicroCarriers >MCX/GDF8 Planar >WNT3A/AA MicroCarriers >WNT3A/AA Planar. There does appear to be a media specific effect on the cells, as cells treated with MCX/GDF8 show lower expression of CERBERUS (Cer 1), GOOSE-COID, and FGF17 (FIG. 6g) However, all treatment conditions show similar expression levels of definitive endoderm genes; CD99, CXCR4, FOXA2, KIT, and SOX17 (FIG. 6g and Table 6c). These processes generate a pancreatic precursor cell population characterized by co-expression of the pancreatic cell transcription factors, PDX1 and NKX6.1. When these cells are transplanted they mature further to functional glucose stimulated insulin secreting tissue which can correct high blood glucose in a streptozotocin induced model of diabetes.

As used in this example, the MCX compound is 14-Prop-2-en-1-yl-3,5,7,14,17,23,27-heptaazatetracyclo[19.3.1.1~2,6~.1~8,12.~]heptacosa-1 (25),2(27),3,5,8(26),9,11,21,23-non-aen-16-one, which has the following formula (Formula 1):

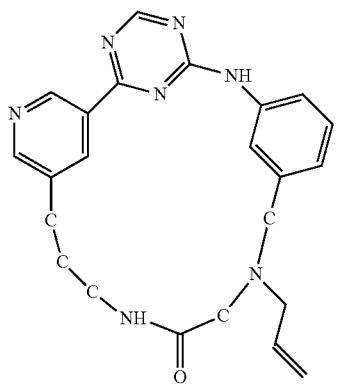 [SMILES: C=CCN1CC(=O)NCCCc2cncc(c2)-c2ncnc(n2)Nc2cccc(c2)C1]

Other cyclic aniline-pyridinotriazines may also be used instead of the above-described MCX compound. Such compounds include but are not limited to 14-Methyl-3,5,7,14,18,24,28-heptaazatetracyclo[20.3.1.1~2,6~.-1~8,12~]octacosa-1 (26),2(28),3,5,8(27),9,11,22,24-nonaen-17-on-e and 5-Chloro-1,8,10,12,16,22,26,32-octaazapentacyclo [24.2.2.1~3,7~-1~9,13~.1~14,18-]tritriaconta-3(33),4,6,9 (32), 10-,12,14(31),15,17-nonaen-23-one. These compounds are shown below (Formula 2 and Formula 3):

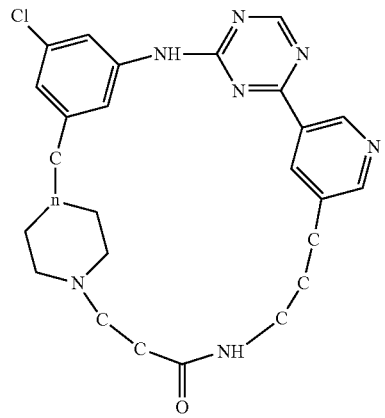

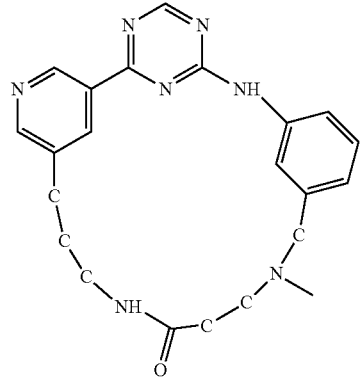

Exemplary suitable compounds are disclosed in U.S. Patent App. Pub. No. 2010/0015711, the disclosure of which is incorporated in its entirety as it pertains to the MCX compounds, related cyclic aniline-pyridinotriazines, and their synthesis.

TABLE 6a

Media Formulations and Differentiation Protocol

|  | Stage 1 | | Stage 2 | Stage 3 | Stage 4 | | |
| --- | --- | --- | --- | --- | --- | --- | --- |
| Basal Media | RPMI | | DMEM/F12 | | DMEM | | |
|  | 11 mM Glucose | | 17.5 mM Glucose | | 25 mM Glucose | | |
| Supplement | +0.2% FBS | +0.5% FBS | +2% FBS | | +1% B27 | | |
| Growth | AA | AA | FGF7 | Noggin | Noggin | Noggin | |
| Factors | (100 ng/ml) | (100 ng/ml) | (50 ng/ml) | (100 ng/ml) | (100 ng/ml) | (100 ng/ml) | |
| And/Or | Wnt3a | | | RA | ALK5i | ALK5i | |
| Small | (20 ng/ml) | | | (2 μM) | (1 μM) | (1 μM) | |
| Molecules | | | | SANT1 | TPB | | |
|  | | | | (250 nM) | (50 nM) | | |
| Days | 1 d | 2 d | 3 d | 4 d | 4 d | 2 d | |

TABLE 6b

Media Formulations and Differentiation Protocol

|  | Stage 1 | Stage 2 | Stage 3 | Stage 4 |
| --- | --- | --- | --- | --- |
| Basal media | MCDB131 8 mM Glucose | MCDB131 10.5 mM Glucose | MCDB131 25 mM Glucose | MCDB131 25 mM Glucose |
| Supplement | 2% FAF-BSA | 2% FAF-BSA | 0.1% AlbuMAX ® | 0.1% AlbuMAX ® |
| Growth factors | GDF8 100 ng/ml | FGF7 50 ng/ml | FGF7 (50 ng/ml) AA (5 ng/ml) | PKC activator SANT |
| Small molecule agonist/ antagonist | MCX (day 1only) 3 μM 1:50000 ITS-X | 1:50000 ITS-X | RA (2 μM) SANT (250 μM) LDN 193189 1:200 ITS:X | LDN 193189 MCX 1:200 ITS:X |
| Days | 4 | 3 | 4 | 6 |

TABLE 6c

| Description | H1 hES Calibrator | WNT3A/AA PLANAR | WNT3A/AA MicroCarrier | MCX/GDF8 PLANAR | MCX/GDF8 MicroCarrier |
| --- | --- | --- | --- | --- | --- |
| GAPDH Control | 1 | 1 | 1 | 1 | 1 |
| AFP | 1 | 0.6 | 0.0 | 4.7 | 0.0 |
| CD9 | 1 | 1.0 | 0.9 | 0.3 | 0.5 |
| CD99 | 1 | 10.5 | 10.9 | 18.5 | 7.1 |
| CDH1 | 1 | 1.2 | 0.6 | 0.5 | 0.6 |
| CDH2 | 1 | 24.8 | 28.4 | 47.8 | 27.8 |
| CDX2 | 1 | 23.2 | 0.0 | 74.9 | 27.8 |
| CER1 | 1 | 346.2 | 649.7 | 8.1 | 5.6 |
| CXCR4 | 1 | 280.3 | 190.1 | 153.9 | 154.7 |
| FGF17 | 1 | 1406.4 | 3174.5 | 92.0 | 112.9 |
| FGF4 | 1 | 0.8 | 0.5 | 0.0 | 1.1 |
| FOXA2 | 1 | 432.5 | 424.3 | 588.5 | 321.2 |
| GATA4 | 1 | 252.4 | 165.3 | 1100.1 | 444.9 |
| GATA6 | 1 | 607.1 | 939.9 | 709.4 | 312.0 |
| GSC | 1 | 49.0 | 81.6 | 0.3 | 0.6 |
| KIT | 1 | 16.3 | 17.9 | 12.3 | 8.0 |
| MIXL1 | 1 | 33.2 | 95.6 | 16.0 | 19.1 |
| MNX1 | 1 | 146.3 | 111.4 | 595.8 | 392.6 |
| NANOG | 1 | 0.4 | 0.5 | 0.0 | 0.2 |
| OTX2 | 1 | 22.9 | 26.4 | 9.1 | 8.3 |
| OCT4 | 1 | 1.5 | 1.1 | 0.0 | 0.5 |
| SOX17 | 1 | 751.1 | 1198.2 | 1235.0 | 796.3 |
| SOX7 | 1 | 0.6 | 1.7 | 5.5 | 0.7 |
| T | 1 | 64.1 | 7.1 | 22.3 | 212.9 |

Example 7

A sub-clone of the H1 (WA01) hES cell line—WB0106 was used for this example. WB0106 was derived at the WiCell Research Institute (Madison, Wis.) from H1 line seed material termed DDL-13. The WB0106 sub-clone of the H1 line was derived from a DDL-13 vial thawed at passage 23 into mTeSR®1 medium on a Matrigel™ substrate, and was subsequently passaged using EDTA. WB0106 was frozen at passage 28 and was selected for these studies on the basis of a normal karyotype (FISH and G-band), ability to differentiate to pancreatic progenitor cells, and competency to form clusters and expand in suspension culture.

A WB0106 WCB vial was then thawed into medium on a substrate of Matrigel™ in a T225 flask (Corning Incorporated, Corning, N.Y.) and at the first passage the cells were expanded into additional T225 flasks. At the second passage the cells from multiple T225 flasks were combined and used to seed a single 2-Layer Cell Stack™ (CS2). Once the CS2 was 70% confluent, C-Flex® tubing assembly caps with adjacent pump tubing were attached to the media ports to close the system. After the system was closed with C-Flex® tubing bags or bottle were welded on via Terumo welder and liquid volumes (medium, PBS$^{-/-}$, Accutase®, or suspended cells) were transferred using a peristaltic pump.

To lift the cells from the CS2, cells were washed once with PBS$^{-/-}$, then treated with a half strength solution of Accutase® diluted with PBS$^{-/-}$ and incubated for 4 to 5 minutes. The Accutase® was then removed, and 3 minutes after application of the enzyme solution, the CS2 was tapped to encourage cell lifting. A bottle of medium supplemented with 2% BSA and containing 10 micromolar of the Rho Kinase inhibitor, Y-27632, was pumped into the CS2 to rinse and inactivate the residual Accutase® and the rinse was then collected. A second rinse volume was added, collected, and pooled with the first rinse. Then 2.0-2.5×10$^8$ cells in 200 mL were transferred into a 1 layer CellSTACK® and incubated at 37° for 2 hours in a humidified 5% CO$_2$ incubator. Using a closed loop of C-Flex® tubing with pump tubing attached between the two CellSTACK® media ports the cell suspension was triturated for 5 minutes at 75 rpm by peristaltic pump to homogenize the aggregates. The closed loop tubing was replaced with sterile 0.2 micron filters to allow gas exchange and the CellSTACK® was incubated overnight at 37° in a humidified 5% $CO_2$ incubator. After overnight incubation (12-22 hours, 18 hours optimal) the cells in the CellSTACK® formed rounded spherical aggregates (clusters) of pluripotent cells.

The medium supplemented with 2% BSA containing the suspended cell clusters were transferred from the CellSTACK® to a 1 liter disposable spinner flask (Corning; Corning, N.Y.) along with 0.4 liter of fresh medium supplemented with 2% BSA and maintained at 55-65 rpm. Twenty four hours after transfer, the 1 liter disposable spinner flask was removed from the humidified 5% $CO_2$ incubator and the clusters allowed to settle for 5-10 minutes. The medium was then aspirated until 200 mL remained in the vessel and 400 mL of additional fresh culture medium was then added to the spinner flask. This process was repeated at the end of day 2 (48 hours after transfer).

At the end of day 3 (72 hours after transfer to the spinner flask from the CS2), the cell clusters were disassociated with Accutase® treatment for passaging and further expansion. The passage process was initiated by removing the 1 liter disposable spinner flask from the humidified 5% CO2 incubator. The flask was placed on a spinner plate inside of a biosafety cabinet to maintain a homogeneous suspension of cells. The cell suspension was removed from the spinner flask by 100 mL pipette and distributed evenly between four 175 mL conical polycarbonate tubes (ThermoFisher-Nalgene; Buffalo, N.Y.) and centrifuged for 5 minutes at 80-200 rcf. The spent medium was aspirated without disturbing the cell pellets. Then 25 mL of DPBS without calcium or magnesium ($DPBS^{-/-}$) was added to each tube, and the cells were combined into one conical tube and centrifuged for 5 minutes at 80-200 rcf. The $DPBS^{-/-}$ was aspirated from the conical tube and 30 mL of a 50% Accutase®/50% $DPBS^{-/-}$ solution was added to the tube. The cell clusters were pipetted up and down 1-3 times, and then intermittently swirled for 4 minutes, then centrifuged for 5 minutes at 80-200 rcf. The Accutase® was then aspirated as completely as possible without disturbing the cell pellet and the conical tube was continuously and gently tapped for 3-5 minutes until the cell suspension appeared a uniform milky white. 10 mL of medium supplemented with 2% BSA containing 10 micromolar Rho Kinase inhibitor, Y-27632, was added to the cell suspension and triturated 2-4 times to inactivate the residual Accutase®. 90 mL of medium supplemented with 2% BSA containing 10 micromolar Rho Kinase inhibitor, Y-27632, was added to the cells and the suspension passed through a 40 micron cell strainer (BD Falcon; Franklin Lakes, N.J.).

The cell density in the 100 mL volume of the filtered cell suspension was determined with a NC-100 NucleoCounter® (ChemoMetec A/S, Allerod, Denmark) and additional medium was added to give a final cell concentration of $1 \times 10^6$ cells/mL in medium supplemented with 2% BSA containing 10 micromolar Rho Kinase inhibitor, Y-27632. Then 225 mL (225 million cells) of the cell suspension was transferred to a 1 liter disposable spinner flask and incubated for 1 hour without agitation in a humidified 5% $CO_2$ incubator. The flask was then removed from the incubator and agitated at 100 rpm on a spinner plate in a biosafety cabinet for 1-3 minutes. While the cell suspension was mixing, an additional 225 mL of medium supplemented with 2% BSA containing 10 micromolar Rho Kinase inhibitor, Y-27632, was added to the cell suspension. The spinner flask was then returned to the humidified 5% $CO_2$ incubator for 30 minutes. The flask was then removed from the incubator and agitated at 100 rpm on a spinner plate in a biosafety cabinet for 1-3 minutes. While the cell suspension was mixing, an additional 150 mL of medium supplemented with 2% BSA containing 10 micromolar of the Rho Kinase inhibitor, Y-27632, was added to the cell suspension to make a final volume of 600 mL and the flask returned to stirred suspension in the incubator. At both 24 and 48 hours after Accutase® dissociation cell clusters were allowed to settle to the bottom of the flask for 5-10 minutes. Being sure to minimize any cluster loss, 400 mL of spent medium was removed from the flask by aspiration and was replaced with fresh medium. Using this process, H1 cells were converted from adherent culture on a substrate to suspension culture as cell clusters.

72 hours after initial Accutase® treatment the process of cell cluster dissociation and spinner flask seeding (passaging) was repeated to maintain the cells in suspension for multiple passages (tested range: 1-10 passages). The above process was followed with the exception that after the first 24 hours no medium was removed, and 200 mL of fresh medium was added. At 48 hours after Accutase® dissociation clusters were allowed to settle to the bottom of the flask for 5-10 minutes, 600 mL was aspirated, and 400 mL of fresh medium was added to the flask.

These suspension passaged and cultured cells could then be cryopreserved and stored for future use. In order to prepare the suspension expanded cell for cryopreservation the cell clusters were dissociated with Accutase® as described above for suspension passaging, except cells were not passed through a 40 micron cell strainer. The cell count for the 100 mL cell suspension generated from each 1 liter disposable flask was determined. The cell suspensions were then combined and centrifuged for 5 minutes at 80-200 rcf. The medium from the centrifuge tube was then removed as completely as possible without disturbing the cell pellet. Cold (<4° C.) CryoStor®10 (Stem Cell Technologies, Inc., Vancouver, BC, Canada) was then added in a drop-wise manner to achieve a final concentration of 150 million cells per mL and the cell solution was held in an ice bath during transfer to a 1.8 mL Corning® cryo vial (Corning Incorporated, Corning, N.Y.) or 15 mL Miltenyi cryo bag (Miltenyi Biotec Inc. Auburn, Calif.).

The suspension expanded cells were then frozen in a vial at high density in a controlled rate freezer as follows. The chamber was pre-cooled to 4° C. and the temperature was held until sample vial temperature reached 6° C. The chamber temperature was then lowered 2° C./min until the sample reached −7° C. Once the sample vial reached −7° C., the chamber was cooled 20° C./min until the chamber reached −45° C. The chamber temperature was then allowed to briefly rise at 10° C./min until the chamber temperature reached −25° C., and the chamber was then further cooled at 0.8° C./min until the sample vial reached −45° C. The chamber temperature was then cooled at 35° C./min until the chamber reached −160° C. The chamber temperature was then held at −160° C. for at least 10 minutes, after which the vials were transferred to gas phase liquid nitrogen storage.

In order to inoculate a stirred tank bioreactor the high density cryo-preserved cells were removed from the liquid nitrogen storage, thawed and used to seed a closed 3 liter glass bioreactor (DASGIP; Julich, Germany). Four or five vials were removed from gas phase liquid nitrogen storage and placed directly in a 37° C. water bath for 105 seconds. The thawed vial contents were then transferred via 2 ml glass pipette to a 50 ml conical tube. Then 9 ml of medium (IH3 or E8™) containing 2% BSA and supplemented with 10 micromolar Rho Kinase inhibitor, Y-27632 was added to the tube in a drop wise manner. The cells were then centrifuged at 80-200 rcf for 5 minutes. The supernatant from the tube was aspirated, 10 ml fresh medium (IH3 or E8™) containing 2% BSA and supplemented with 10 micromolar Rho Kinase inhibitor, Y-27632 was added and the volume containing the cells was pipetted into a media transfer bottle (Cap2V8®, SaniSure, Moorpark, Calif.). The bottle contents were then pumped directly into the bioreactor via a sterile C-flex tubing weld by peristaltic pump. In preparation for pluripotent stem cell inoculation the bioreactor was prepared with 1.5 L of medium (IH3 or E8™ supplemented with 2% BSA and containing 10 micromolar Rho Kinase inhibitor, Y-27632), pre-warmed to 37°, stirred at 70 rpm, regulated to 6.8-7.1 pH by $CO_2$, with a dissolved oxygen set-point of 30% ($CO_2$, air, $O_2$, and $N_2$ regulated). Immediately post-inoculation the bioreactor was sampled for cell count, and medium volume was adjusted as needed to give a final cell concentration of $0.225 \times 10^6$ cells/mL.

The cells inoculated into the stirred tank bioreactor formed cell clusters in the continuously stirred tank, and were maintained in pluripotency medium (IH3 or E8™, supplemented with 2% BSA) in the reactor for three days total. Medium was changed daily, with a partial media exchange performed 24 hours after inoculation as 1-1.3 liter of spent medium was removed and 1.5 liters of fresh medium added. Forty-eight hours after inoculation, 1.5-1.8 liters of spent medium was removed and 1.5 liters of fresh medium was added. At 72 hours after inoculation, pluripotent cell differentiation was initiated by removing >90% of the spent medium and adding differentiation medium (Table 7).

Once the staged differentiation process was initiated the cells were maintained for 12 or more days in the closed sterile suspension bioreactor regulated for temperature (37°), pH (7.4 for differentiation), and dissolved oxygen (10% DO set-point for stage 1 and 30% DO set-point all other times, $CO_2$, $O_2$, $N_2$, and air regulated). Throughout the differentiation process, at each media exchange, the impeller was stopped 5-20 minutes prior to medium removal via dip-tube to allow clusters to settle. Medium in the bioreactor was removed or added to/from a closed bottle or bag by peristaltic pump through a dip tube connected to C-Flex® tubing using a Terumo™ tube welder to maintain a closed system. The impeller and heater were re-energized once sufficient medium was added to the vessel to fully submerge the impeller.

In order to monitor the bioreactor process, samples of medium containing cell clusters were drawn daily to determine cell number and viability (NucleoCounter®) as shown in FIG. 7. A general expansion of cells was observed during the process, as the inoculum of $0.225 \times 10^6$ viable cells/mL expanded to generate an average of $0.92 \times 10^6$ viable cells/mL at stage 4 day 3. By maintaining the cells at an acidic set-point (pH 7.0-6.8) during bioreactor inoculation and pluripotent cell clustering and culture, the average cell output at stage 4 day 3 increased to an average of $1.3 \times 10^6$ cells/mL (FIG. 7).

In addition to daily counts, bioreactor medium samples were analyzed by NOVA BioProfile® FLEX (Nova Biomedical Corporation, Waltham, Mass.). It was observed that, per the reactor set-points, the pH of the medium in stage 0 was acidic relative to a homeostatic standard pH of 7.4 common to most culture media and the reactor medium pH declined through stage 0 as a result of cellular metabolism (FIG. 8). These results correlated with a trend of increasing lactic acid concentrations and decreasing glucose levels through the end of the $6^{th}$ day of differentiation (FIGS. 9 and 10). Together, these data indicated the cells in the reactor were most rapidly growing and glucose consumptive through stage 0 and the first two stages of differentiation (day 1-6). However, from stage 3 onward, cell metabolism (reduced lactate levels and increased glucose levels) in the reactor declined correlating with a peak in cell numbers at stage 3 followed by a decline in cell density over the course of stage 4.

In order to determine if stage specific changes in pH and metabolism matched stage changes in mRNA expression patterns. A test of bioreactor cell samples was carried out using four Applied Biosystems®Low Density Arrays (Life Technologies Corporation, Carlsbad, Calif.) designated Pluripotency, Definitive Endoderm (DE), Gut Tube (GT), or stage 4 (S4) the results were compared to a historical undifferentiated H1 (WB0106) hES cell sample as control to standardize expression across all runs and arrays.

Using these arrays gene expression was determined for each stage of differentiation. It was also observed that seed material cells thawed into the bioreactor showed an undifferentiated gene expression pattern at stage 0 day 1 and stage 0 day 3 (24 and 72 hours after bioreactor inoculation: FIGS. 11, 12, 13, and 14). These results correlated well with flow cytometry results which showed high expression levels of CD9, SSEA4, TRA-1-60, and TRA-1-81, and the absence of CXCR4/CD184 (FIG. 15 and Table 8). Although flow cytometry and qRT-PCR assays for genes expression showed robust and stable expression patterns for genes of pluripotency (CD9, NANOG, POU5F1, SOX2, TDGF, and ZFP42) consistent with a stable pluripotent state that was also noted a modest but variable increase in gene expression for GATA4, GSC, MIXL1, and T; and a ≥100× increase in CER1, FGF17, FGF4 and GATA2 expression in some samples during the stage 0 process prior to directed differentiation (FIGS. 16 and 17).

At the completion of stage 0 (72 hours after reactor inoculation), the cells were moved into differentiation medium (Table 7) containing MCX and GDF8. Twenty-four hours after this media change significant alterations in gene expression patterns were noted (FIGS. 18 and 19), such as a ~700× increase in FOXA2 expression and a 1000× increase in CER1, EOMES, FGF17, FGF4, GATA4, GATA6, GSC, MIXL1, and T expression. These increased expression levels indicated the cells were transitioning through a mesendodermal fate. It was also noted that CDX2 levels were elevated at stage 1 day 1 versus undifferentiated cells (470× increase in expression vs. control), however this was a transient increase in expression and CDX2 levels dropped 94% from stage 1, day 1 to stage 1 day 3 returning to levels comparable to those observed prior to induction of differentiation (FIGS. 14, 19, and 21).

At 72 hours after exposure to the DE differentiation medium, the cells expressed a profile consistent with specification to definitive endoderm, as CXCR4 levels peaked and FOXA2 and SOX17 were expressed at >1000× over historical control. Consistent with definitive endoderm, it was also noted that the genes CER1, EOMES, FGF17, FGF4, GATA4, GATA6, GSC, MIXL1, and T dropped from elevated levels observed at stage 1 day 1 (FIGS. 20 and 21).

The changes in gene expression observed by qRT-PCR correlated with results observed by flow cytometry. A near complete transition was also seen from a CD9 expressing/CXCR4 negative pluripotent cell population at the initiation of differentiation (FIG. 15) to a homogeneous population of CXCR4 expressing cells (98.3% of cells CXCR4 positive, ±1.9SD) at the end of stage 1 (FIG. 22).

Following the completion of definitive endoderm formation (stage 1) the medium was changed to one containing FGF7, a morphogen used to induce primitive foregut formation (stage 2). Consistent with formation of primitive foregut, HNF4a and GATA6 expression levels at stage 2 days 1 and 3 were increased, while genes expressed at high levels on day 3 of stage 1 (CXCR4, EOMES, FGF17, FGF4, MNX1, PRDM1, SOX17, and VWF) showed reduced expression by the end of stage 2 (FIG. 23). The expression of foregut genes (AFP, PDX1, and PROX1) was increased (FIG. 24).

After the cells had been cultured in stage 2 medium for 72 hours, the culture was switched to a stage 3 medium (Table 7). Once in this medium the cells expressed markers consistent with an endodermal pancreatic lineage as measured by PDX1 and FOXA2 expression (90.9%±11.9SD PDX1 positive and 99.2%±0.6SD FOXA2 positive) shown in FIG. 25. These results were confirmed by data from samples analyzed by qRT-PCR for gene expression. Gene expression for PDX1 increased 5 fold in 24 hours from the end of stage 2 day 3 (38,000× vs. H1) to the end of stage 3 day 1 (200,000× vs. H1) and doubled again 48 hours later on stage 3 day 3 (435,000× vs. H1). These data show the cells were specifying to a pancreatic fate (FIG. 26). This observation was further supported by the increased levels of a host of genes commonly expressed in pancreas (ARX, GAST, GCG, INS, ISL1, NEUROD1, NGN3, NKX2.2, NKX6.1, PAX4, PAX6, PTF1A, and SST) as shown in FIG. 26. In addition, very low or no OCT4/POU5F1 expression (2-10% of control or 32-37 sample Cts by qRT-PCR) and high expression levels for other markers of endodermal lineages AFP, ALB, and CDX2– was also seen, further indicating the specification and transition of the cell population in the bioreactor from a relatively plastic gut tube fate to a pancreatic fate.

At the end of the differentiation process on stage 4 day 3, the cells retained high levels of PDX1 and FOXA2 expression and further developed an expression pattern consistent with a mix of pancreatic endocrine cells (28.1%±12.5SD chromogranin positive) and pancreatic progenitor cells (58.3%±9.7SD positive for NKX6.1) as shown in FIG. 27. This stage specific marker expression pattern indicated an efficient stage-wise differentiation from a pluripotent population to pancreatic precursor cells. The results observed with flow cytometry, were further confirmed with data from qRT-PCR. A host of genes commonly expressed in pancreas (ARX, GAST, GCG, IAPP, INS, ISL1, MAFB, NEUROD1, NGN3, NKX2.2, NKX6.1, PAX4, PAX6, PTF1A, and SST) all showed increased expression levels. (FIG. 28).

The expression pattern observed in FIG. 27 held consistent across multiple runs as multiple process variables, such as different seed materials, stage 0 medium, pH of stage 0 medium and the use of anti-foam, were tested. Multiple sources of seed material were tested and each efficiently generated a pancreatic endodermal fate with >90% FOXA2, >75% PDX1, and >50% NKX6.1 (FIG. 29). Furthermore, it was noted that was no significant difference in expression patterns of bioreactor product when the cells were grown at stage 0 in a custom in-house medium called "IH3" supplemented with 2% BSA or a commercially available medium: Essential8™, supplemented with 2% BSA (FIG. 30). When the role of pH in stage 0 culture was examined, it was noted that cells grown in stage 0 at a relatively low pH (6.8) had increased expansion in the bioreactor relative to the average run (FIG. 7), but no significant change in the stage 4 day 3 cell profile (FIG. 31). Additionally, the use of Anti-Foam C emulsion (Sigma Cat#A8011) at 94 parts per million was seen to reduce bubbles produced by sparging but did not appear to affect the profile of cells from the end of stage 0 through stage 4 day 3 cell (Table 9 and FIG. 32).

At the end of each bioreactor differentiation the product cells were cryopreserved. The cells were washed in MCDB131 with 3.63 g/L sodium bicarbonate or MCDB131 with 3.63 g/L sodium bicarbonate, glucose (8 mM final), and 1× Glutamax, and then transferred to cold (<4° C.) cryopreservation media comprised of 57.5% MCDB131 with 2.43 g/L sodium bicarbonate, 30% Xeno-free KSR, 10% DMSO, and 2.5% HEPES (final concentration 25 mM). The cells were then frozen in a controlled rate freezer (CRF) using a cooling profile that maintained the cell clusters in cryopreservation media at ambient temperature for a maximum of 15 minutes, reduced to a temperature of 4° C. for 45 min, and further reduced by 2.00° C./min to −7.0° C. (sample). The sample was then quickly cooled, reducing the temperature of the chamber at a rate of 25.0° C./min to −45.0° C. A compensation increase was then provided by increasing the chamber temp ° C./min to −25.0° C. (chamber). The sample was then cooled at 0.2° C./min until the temperature reached −40.0° C. The chamber was then cooled to −160° C. at a rate of 35.0° C./min and held at that temperature for 15 minutes. The samples were moved to a gas phase liquid nitrogen storage container at the termination of the CRF run.

The cells could be thawed by removal from vapor phase liquid nitrogen storage and transferring the vial to a 37° C. water bath. The vial was gently swirled in the water bath for less than 2 minutes until a small ice crystal remained in the vial. The vial contents were then transferred to a 50 ml conical and diluted drop-wise over two minutes using MCDB131 media with 2.43 g/L sodium bicarbonate and 2% BSA to a final volume of 20 ml total. The total cell number was then determined by NucleoCounter® and the cell suspension transferred to an ultra-low attachment culture dish for 1 hour. The cells were then isolated from the media in a 50 ml conical, the supernatant removed and cells re-suspended in stage 4 media for analysis or in vivo study.

Alternatively after thawing, vialed cells were transferred to an empty 125 mL glass Corning® spinner flask (Corning, Incorporated, Corning, N.Y.) and 10 mL MCDB131 medium containing 2.43 g/L sodium bicarbonate and 2% BSA was added to the flask in a drop-wise manner. The final volume was then adjusted to 80 mL of the same medium. The total cell number was determined by NucleoCounter® and the cell suspension stirred at 40-65 rpm overnight (12-28 hours). The cells were then characterized or used for in vivo study.

TABLE 7

| Starting Day/Date: | Stage 1 | Stage 2 | Stage 3 | Stage 4 |
|---|---|---|---|---|
| Basal Media | MCDB131 Cust (3.64 g/LNaCO₃) | MCDB131 Cust (3.64 g/LNaCO₃) | MCDB131 Cust (3.64 g/LNaCO₃) | MCDB131 Cust (3.64 g/LNaCO₃) |

TABLE 7-continued

| Starting Day/Date: | Stage 1 | Stage 2 | Stage 3 | Stage 4 |
|---|---|---|---|---|
| Supplement | 2% FAF-BSA 2.5 mM glucose 1:50,000 ITS-X Glutamax 1:100 | 2% FAF-BSA 2.5 mM glucose 1:50,000 ITS-X Glutamax 1:100 | 2% FAF-BSA 2.5 mM glucose 1:200 ITS-X Glutamax 1:100 | 2% FAF-BSA 2.5 mM glucose 1:200 ITS-X Glutamax 1:100 |
| Growth factors | Day 1 and 2 only: GDF8 100 ng/mL | FGF7 50 ng/mL | FGF7 50 ng/mL | None |
| Small molecules | Day 1 only: MCX [2 μM] | | RA [2 μM] SANT [0.25 μM] TPPB [100 nM] Day 1 only LDN [100 nM] | SANT [0.25 μM] TPPB [100 nM] |
| Days | 3 | 3 | 3 | 3 |
| NOTES: All Days refer to 0 H | Media change Days 1 and 2, No change Day 3 | Media change Days 1 and 3, No change Day 2 | Media change Days 1 and 2, No change Day 3 | Media change Day 1 and end of Day 3 if S4 is extended |

TABLE 8

| BX replicate | Seed Material | CD9 | CD184 | SSEA4 | TRA-1-60 | TRA-1-81 |
|---|---|---|---|---|---|---|
| 1 | KC | 83.3 | 0.1 | 99.9 | 94.5 | 85.8 |
| 2 | HW | 95.5 | 0.2 | 100 | 91 | 84 |
| 3 | ISM (Pink) | 95.8 | 0.1 | 100 | 76.1 | 36.5 |
| 4 | ISM (Pink) | 93.2 | 0 | 99.9 | 78.5 | 64.5 |
| 5 | ISM 1 | 97.8 | 0.2 | 99 | 74.8 | 66.4 |
| 6 | ISM 2 | 98.6 | 0.2 | 100 | 92.2 | 86 |
| 7 | ISM 1 | 98.1 | 0.1 | 99.9 | 88.8 | 80.3 |
| 8 | ISM 1 | 99.1 | 0.1 | 99.9 | 93.8 | 83.3 |
| 9 | ISM 2 | 97.2 | 0.1 | 99.9 | 88.3 | 81 |
| 10 | ISM5 | 98 | 0.1 | 99.3 | 93.1 | 85.7 |
| 11 | ISM6 | 72.6 | 0.2 | 99.9 | 94.7 | 88.9 |
| 12 | ISM6 | 85.9 | 0.7 | 99.4 | 71.9 | 54.1 |
| | Average | 93.6 | 0.1 | 99.8 | 87.8 | 76.6 |
| | St. Deviation | 8.3 | 0.1 | 0.3 | 7.6 | 15.5 |

TABLE 9

| Stage-Day-Time | Viable Cell density (M cells/mL) | CD9 | CD184 | SSEA4 | TRA-1-60 | TRA-1-81 | | | |
|---|---|---|---|---|---|---|---|---|---|
| S0D3-24H | 0.626 | 95.8 | 0.1 | 99.8 | 87.9 | 74 | | | |

| Stage-Day-Time | Viable Cell density (M cells/mL) | CD9 | CD184 | CD99 |
|---|---|---|---|---|
| S1D3-24H | 0.9 | 50.7 | 98.9 | 99 |

| Stage-Day-Time | Viable Cell density (M cells/mL) | NKX6.1 | CHROMG. | NKX2.2 | PDX1 | FOXA2 |
|---|---|---|---|---|---|---|
| S4D1-24H | 0.943 | 69.3 | 14.2 | 23.6 | 98.8 | 99.7 |

| Stage-Day-Time | Viable Cell density (M cells/mL) | NKX6.1 | CHROMG. | CDX2 | SOX2 | NKX2.2 | PDX1 | FOXA2 | NEUROD |
|---|---|---|---|---|---|---|---|---|---|
| S4D3-24H | 1.002 | 66.2 | 35.6 | 0.3 | 15.8 | 38.1 | 99 | 99 | 45.6 |

Materials:
  human embryonic stem (hES) cell line H1, (WA01 cells, WiCell, Madison Wis.)
  PBS (Catalog#14190, Invitrogen)
  Y-27632 (Axxora Catalog#ALX-270-333, San Diego, Calif.)
  EDTA, (Lonza, Catalog#17-7-11E)
  NucleoCounter®—(ChemoMetec A/S, Cat#YC-T100, Allerod, Denmark)
  Non-Tissue Culture Treated 6 well dishes (Becton Dickinson, Catalog# Falcon 351146, Franklin Lakes, N.J.)
  Accutase®, (Sigma, Catalog# A-6964, St. Louis, Mo.)
  pH, and dissolved oxygen (DO) bioreactor probes (FermProbe® pH electrode 225 mm, Model # F-635, and DO OxyProbe® 12 mm Sensor, Model # D-145 from Broadley-James Corporation, Irvine Calif.)
  Immune-protective macro encapsulation device (TheraCyte™, Irvine Calif.)
  Mm HUMAN C-PEPTIDE ELISA (MERCODIA CAT#10-1141-01)
  GlutaMAX™, MCDB131, and ITS-X Invitrogen
  FAF-BSA (Proliant)
  Retinoic Acid, Glucose 45% (2.5M), SANT (Shh inhibitor) (Sigma)
  GDF8 (Peprotech)
  MCX
  FGF7 (R & D Systems)
  LDN-193189 (BMP receptor antagonist) (Stemgent)
  TPPB (PKC activator) (ChemPartner)
  MCDB131 Cust

Example 8

Maturation and Function of Cryo-Preserved Bioreactor Generated Pancreatic Progenitor Clusters In order to generate sufficient cells for each bioreactor study one passage 31 master cell bank vial of H1 hES (WB0106) cells was thawed. The cells were expanded under adherent conditions in mTeSR®1 media for several passages on Matrigel™ using EDTA passaging until sufficient cells were generated to seed five Matrigel™ coated 2-Layer CellSTACKs® (CS2). Once the adherent cells growing in the CS2 were 70% confluent, C-Flex® tubing assembly caps with adjacent pump tubing were attached to the media ports to close the system. After the system was closed bags or bottle were welded on with C-Flex® via Terumo welder and all liquid volumes (medium, PBS$^{-/-}$, Accutase®, or suspended cells) were transferred using a peristaltic pump.

To lift the cells from the CS2s, cells were washed once with Dulbecco's Phosphate Buffered Saline without calcium or magnesium (PBS$^{-/-}$), then treated with a half strength solution of Accutase® diluted with an equal part of PBS$^{-/-}$ and incubated for 4-5 minutes. The Accutase® solution was then removed, and 3 minutes after application of the enzyme solution, the CS2s were tapped to encourage cell lifting. A bottle of mTeSR®1™ containing 10 micromolar Rho Kinase inhibitor, Y-27632, was pumped into the CS2s to rinse and inactivate the residual Accutase® and the rinse was then collected. A second rinse volume was added, collected, and pooled with the first rinse. $1.6$-$2.0 \times 10^9$ cells were recovered from the CS2s in a final volume of 2 liters. $2.0$-$2.5 \times 10^8$ cells per layer, were transferred into four CS2s or eight 1 layer Cell Stacks™ and incubated at 37° for 2 hours in a humidified 5% CO2 incubator in a volume of 200 mL per layer.

Using a closed loop of C-Flex® tubing with adjacent pump tubing attached between CellSTACK® media ports the cell suspension was triturated for 5 minutes at 75 rpm by peristaltic pump to homogenize the aggregates. The CellSTACKs® were then incubated overnight at 37° for 18 hours in a humidified 5% CO2 incubator. The 2 liters of cells and media from the Cell Stacks were then pooled and transferred, 1 liter each, into two 3 liter DASGIP bioreactors along with 1.5 liter of fresh mTeSR® medium per bioreactor. The cells were maintained for two additional days with mTeSR® medium before initiating differentiation, with a full media exchange 24 hours after bioreactor inoculation. Differentiation was then initiated and directed as described in Table 10. The cells were maintained 14 or 15 days total (2 days mTeSR®+12 or 13 days of staged differentiation) in the closed sterile suspension bioreactor regulated for temperature (37°), pH (drift, or regulated by CO2 to 6.8 or 7.2 for pluripotent cells and 7.4 for differentiation), and dissolved oxygen (30% DO set-point, CO2/air regulated). The impeller was stopped for 5-20 minutes prior to each media exchange to allow clusters to settle. Medium was removed or added by peristaltic pump through a dip tube connected to C-Flex® tubing (Cole-Parmer North America, Vernon Hills, Ill.) using a Terumo™ tube welder to maintain a closed system. The impeller and heat jacket were re-energized once sufficient medium was added to submerge the impeller.

Two production runs were initiated in 3 liter reactors using these methods. In the first reactor run two different pH set points were tested over the first two days of pluripotent culture medium. Reactor 1 was set to pH 7.2 with a fixed CO2 gas infusion rate of 5%, so the pH would "drift" lower as the reactor environment acidified over time due to metabolic activity of the cells. Reactor 2 was set to a pH of 7.2 regulated by CO2 gas levels. In the second reactor run the pH was set to 6.8 for reactor 1 and 7.2 for reactor 2, both regulated by CO2 gas levels.

In order to monitor the bioreactor process cell clusters were taken at the end of each stage of differentiation and assayed by flow cytometry (Table 11; Table 12). A near complete transition was observed from a CD9 expressing/CXCR4 negative pluripotent cell population at the initiation of differentiation to a homogeneous population of CXCR4 expressing cells (96.9-98.1% of cells CXCR4 positive) at the completion of definitive endoderm formation.

The results observed by flow cytometry correlated with results from paired samples analyzed by rt-PCR. Samples were tested throughout the process for gene expression characteristic of staged differentiation from pluripotency to a pancreatic fate. Prior to the initiation of directed differentiation, mRNA was tested from bioreactor cell clusters on a low density array for a panel of genes associated with pluripotency or early differentiation fates.

It was observed that cells from the bioreactor retained expression for genes characteristic of pluripotency (POU5F1, NANOG, SOX2, and ZFP42) and showed minimal or no induction of genes characteristic of differentiation (AFP, and FOXA2: <50 fold increase; FOXD3, GATA2, GATA4, GSC, HAND2, MIXL1, and T: <10 fold increased expression) as compared to undifferentiated H1 controls (FIG. 33). However once the cells were contacted with stage 1 day 1 differentiation media gene expression patterns changed dramatically as levels of CDX2, CER1, FGF17, FGF4, FOXA2, GATA4, GATA6, GSC, MIXL1, MNX1, and Brachyury (T) expression increased to 100 to 1000 fold greater than undifferentiated H1 hES cells (FIG. 34). By the end of stage 1 day 3 (formation of definitive endoderm), CD9, CDX2, FGF4, MIXL1, NANOG, POU5F1, and Brachyury (T) had decreased expression relative to stage 1-day 1 while xpression of characteristic definitive endoderm genes such as CD99, CER1, CXCR4, FGF17, GATA4, GATA6, KIT, OTX, or SOX17 peaked (FIG. 35).

At the end of stage 1 the cell culture medium was changed from one containing GDF8 to a medium containing FGF7. Several different gene expression patterns were noted: an increase in expression of certain genes over the course of stage 2 (AFP, ATOH1, HHEX, OSR1, PDX1, PROX1, SOX2, and SOX9), a decrease in expression (HAND1 and SOX17), stable high expression throughout (HNF4a), or low/no expression (CDX2, GAST, NKX2.2, NKX6.1, and PTF1a) (FIG. 36a-e). These patterns indicated that the cells in the reactor were becoming foregut (AFP, ATOH1, HHEX, HNF4a, OSR1, PDX1, PROX1, SOX2, and SOX9) expression for markers of mesoderm (HAND1 and SOX17) decreased. However, by the end of stage 2, the cells had not yet specified to a more mature gut or pancreatic fates (CDX2, GAST, NKX2.2, NKX6.1, and PTF1a).

By the end of stage 3 the cells had specified to a pancreatic lineage as measured by PDX1 expression demonstrated by >100,000 fold increase in mRNA vs. undifferentiated control (FIG. 36) and 76-98% of the cells expressing PDX1 by flow cytometry (Table 11). Also observed was induction of other genes of the pancreas (GAST, NKX2.2, NKX6.1, PROX1, PTF1a, and SOX9) and gut such as AFP and CDX2; indicating the cells had begun to specify to a more mature fate.

By the end of the differentiation process on day 3 or 4 of stage 4, the cells showed an expression pattern consistent with a mix of pancreatic endocrine cells (47-54% Chromogranin positive) and pancreatic progenitor cells (33-52% positive for NKX6.1) as shown in Tables 11 and 12. This stage specific marker expression pattern indicated an efficient stage-wise differentiation from a pluripotent population to pancreatic progenitor cells characterized by high expression levels of PDX1 (>1×10$^6$ fold induction) and other pancreatic genes (>1000 fold induction of ARX, GCG, GAST, INS, ISL, NEUROD1, NGN3, NKX2.2, NKX6.1, PAX4, PTF1a, and SST) and near total loss of OCT4/POU5F1 expression as compared to undifferentiated H1 human embryonic stem cells (FIG. 37).

At the end of the differentiation process 0.08-0.45×10$^6$ cells/mL were generated (FIG. 38: daily cell counts). The cells generated in this process were then cryo-preserved or directly implanted into an animal subcutaneously via a TheraCyte™ device or placed under the kidney capsule. In order to cryopreserve the cells, they were transferred to cryopreservation media comprised of 57.5% MCDB131 with 2.43 g/L sodium bicarbonate, 30% Xeno-free KSR, 10% DMSO, and 2.5% HEPES (final concentration 25 mM). Once the cell clusters were suspended in cryopreservation media at ambient temperature the cryo-vials were moved to the controlled rate freezer (CRF) within 15 minutes. The chamber temperature was then reduced to 4° C. for 45 min, and further reduced by 2.00° C./min to −7.0° C. (sample). The sample was then quickly cooled, reducing the temperature of the chamber at a rate of 25.0° C./min to −45.0° C. A compensation increase was then provided by increasing the chamber temp 10.0° C./min to −25.0° C. (chamber). The sample was then cooled at 0.2° C./min until the temperature reached −40.0° C. The chamber was then cooled to −160° C. at a rate of 35.0° C./min and held at that temperature for 15 minutes. The samples were moved to a gas phase liquid nitrogen storage container at the termination of the CRF run.

After the cells had been stored in gas phase liquid nitrogen the cells were thawed by removal from storage and transferred to a 37° C. water bath. The vial was gently swirled in the water bath for less than 2 minutes until a small ice crystal remained in the vial. The vial contents were then transferred to a 50 ml conical and diluted drop-wise over two minutes using MCDB131 media with 2.43 g/L sodium bicarbonate and 2% BSA to a final volume of 20 ml total. The total cell number was then determined by NucleoCounter® and the cell suspension transferred to an ultra-low attachment culture dish for 1 hour. The cells were then isolated from the media in a 50 ml conical, the supernatant removed and cells re-suspended in stage 4 media. The cells were then either implanted into an animal subcutaneously via TheraCyte™ device or under the kidney capsule or the cells were incubated in an ultra-low attachment culture dish overnight and then implanted into an animal.

The animals were monitored for blood glucose and C-peptide levels every four weeks following graft implantation. Animals treated with non-cryopreserved pancreatic precursor cells inside a TheraCyte™ device or by direct placement of the cells under the kidney capsule matured to express over 1 ng/mL C-peptide by 16 weeks and reached 2 ng/mL C-peptide by 20 weeks post-implantation (FIGS. 39a and 39d). Furthermore, when treated with STZ to ablate host β-cell function, the engrafted animals maintained normoglycemia until the grafts were removed, indicating that the grafts were competent to protect the animals from diabetes induced by a single high dose of STZ (FIG. 39b).

This pattern was also observed in animals treated with cryopreserved cells. Animals treated by kidney capsule graft with cryopreserved pancreatic precursor cells that had been cultured for 1 hour after thaw (1207B) had an average of 0.56 ng/mL and 1.09 ng/mL of C-peptide at 16 and 20 weeks, respectively, while cells cultured overnight after thaw (1207C) had an average of 0.81 ng/mL and 1.35 ng/mL of C-peptide at 16 and 20 weeks, respectively (FIG. 39d). Animals treated with cryopreserved pancreatic precursor cells inside a TheraCyte™ device had over 1 ng/mL C-peptide by 16 weeks, and similar to the non-cryopreserved controls, were able to express therapeutic levels of C-peptide one week after STZ treatment (0.98 ng/mL, FIG. 39c). These results indicate that cryopreserved pancreatic precursor cells can function comparably to non-cryopreserved controls when tested in an animal model.

TABLE 10

| Starting | Stage 0 | Stage 1 | Stage 2 | Stage 3 | Stage 4 |
| --- | --- | --- | --- | --- | --- |
| Basal Media Supplement | mTeSR1 | MCDB131 (3.64 g NaCO3) 2% FAF-BSA 2.5 mM glucose 1:50,000 ITS-X Glutamax 1:100 | MCDB131 (3.64 g NaCO3) 2% FAF-BSA 2.5 mM glucose 1:50,000 ITS-X Glutamax 1:100 | MCDB131 (3.64 g NaCO3) 2% FAF-BSA 2.5 mM glucose 1:200 ITS-X Glutamax 1:100 | MCDB131 (3.64 g NaCO3) 2% FAF-BSA 2.5 mM glucose 1:200 ITS-X Glutamax 1:100 |
| Growth factors | | Day 2 only: GDF8 100 ng/mL | FGF7 50 ng/mL | FGF7 50 ng/mL | None |
| Small molecules | Y-27632 (day 0 only) [1:1000, 10 uM] | Day 1 only: MCX [3 uM] | | RA [2 uM] SANT [0.25 uM] TPPB [100 nM] Day 1 only LDN [100 nM] | SANT [0.25 uM] TPPB [100 nM] |
| Days | | 3 | 3 | 3 | 3 | 3 |
| NOTES: | | | Media change Days 1 and 2, No change D3 | Media change Days 1 and 3, No change Day 2 | Media change Days 1 and 2, No change D3 | Media change Day 1 only Glucose bolus Day 3 |

Note:
Basal media in Table 10 above may optionally include 5 mM glucose at stages 1-5 when Glutamax is not used in supplement.
Cypi ([100 nM]) may optionally be added at stage 4 in Table 10 shown above.

TABLE 11

| | Process Day | Name | CD9 | CD184 | SSEA4 | TRA-1-60 | TRA-1-81 |
|---|---|---|---|---|---|---|---|
| Pluripotency | 2 | Bx1 | 78.9 | 0.1 | 100 | 54.5 | 51.1 |
| | | Bx2 | 66.5 | 0.0 | 100 | 63.5 | 72.3 |

| | | Name | CD9 | CD184 | | | |
|---|---|---|---|---|---|---|---|
| DE (S1D2) | 4 | BX1 | 9.9 | 87.9 | | | |
| | | BX2 | 19.7 | 83.1 | | | |
| DE (S1D3) | 5 | BX1 | 17.4 | 98.1 | | | |
| | | BX2 | 25.4 | 96.9 | | | |

| | | Name | Nkx6.1 | Nkx2.2 | PDX1 | | |
|---|---|---|---|---|---|---|---|
| PE(S3D3) | 11 | BX1 | 4.4 | 25.2 | 98.6 | | |
| | | BX2 | 4.8 | 28.9 | 76.2 | | |

| | | Name | Nkx6.1 | Synaptophysin | CDX2 | Sox2 | Nkx2.2 | Chrom. |
|---|---|---|---|---|---|---|---|---|
| PPC (S4d3) | 14 | BX1 | 33.2 | 67.4 | 2.1 | 13.0 | 69.3 | 51.1 |
| | | BX2 | 35.1 | 56.9 | 1.9 | 11.5 | 64.4 | 51.2 |

TABLE 12

| | Process Day | Name | CD9 | CD184 | SSEA4 | TRA-1-60 | TRA-1-81 |
|---|---|---|---|---|---|---|---|
| Pluripotency | 2 | BX1 | 99.8 | 0.3 | 100.0 | 88.6 | 85.8 |
| | | BX2 | 99.8 | 0.3 | 100.0 | 86.8 | 85.9 |

| | | Name | CD9 | CD184 | CD99 | | |
|---|---|---|---|---|---|---|---|
| DE (S1d3) | 5 | BX1 | 88.3 | 99.2 | 97.0 | | |
| | | BX2 | 78.3 | 99.3 | 96.9 | | |

| | | Name | Nkx6.1 | | | Nkx2.2 | Chrom. |
|---|---|---|---|---|---|---|---|
| PE(S3d3) | 11 | BX1 | 6.3 | | | 23.2 | 8.5 |
| | | BX2 | 1.2 | | | 24.6 | 11.5 |

| | | Name | Nkx6.1 | Synaptophysin | CDX2 | Sox2 | Nkx2.2 | Chrom. |
|---|---|---|---|---|---|---|---|---|
| PPC (S4d3) | 14 | BX1 | 49.0 | | 7.3 | 13.1 | 56.1 | 49.2 |
| | | BX2 | 52.6 | | 3.1 | 19.9 | 54.5 | 47.4 |
| PPC (S4d4) | 15 | BX1 | 48.4 | 53.1 | 0.4 | 4.9 | 60.3 | 44.3 |
| | | BX2 | 45.7 | 66.5 | 0.2 | 4.5 | 63.7 | 54.3 |

Calculation of Shear Stress Experienced by Cell Aggregates in a Stirred Tank Bioreactor The shear stress experienced by cell aggregates in a 2.7 liter DASGIP stirred suspension bioreactor mixed at an agitation rate of 70 rpm in a 3l DASGIP bioreactor was determined. In order to calculate the shear stress values, the following stated assumptions were made.

Assumptions:

1. Max shear stress imposed on cell aggregates is not a result of turbulent eddies
2. Max shear stress imposed on cell aggregates is not a result of aggregate-aggregate or aggregate-impeller collision
3. Baffles (i.e. diptubes and probes) imposed shear stress are not addressed in these calculations For the purposes of the calculations herein, the nomenclature and physical parameters listed below were used.

Nomenclature

| Abbreviation | | units |
|---|---|---|
| $P$ | Fluid Density | kg/m$^3$ |
| $\mu$ | Fluid viscosity | Pa s |
| $\vartheta$ | Kinematic Viscosity | m$^2$/s |
| $\tau_{max}$ | Maximum Shear Stress | dyn/cm2 |
| N | Agitation | rev/sec |
| P | Power consumed | kg m$^2$/s$^3$ |
| $P_N$ | Power Number | dimensionless |
| Re | Reynold's Number | dimensionless |
| $\varepsilon$ | Power Dissipated per unit mass | m$^2$/s$^3$ |
| $D_i$ | Impeller Diameter | M |
| $D_t$ | Tank Diameter | M |
| W | Impeller Widtch | M |
| $V_L$ | Liquid volume | m$^3$ |
| $K_1$-$K_4$ | Calculated values based on Nagata Empirical Correlations | |

Parameters:

| Bioreactor Parameters | |
| --- | --- |
| $D_i$ | 0.08 m |
| $D_t$ | 0.13 m |
| W | 0.04 m |
| $V_L$ | 0.0024 m3 |
| Medium Parameters | |
| Density (ρ) | 1000 kg/m³ |
| Viscosity (μ) | 8.50E-04 Pa s |
| kinematic viscosity (ϑ) | 8.50E-07 m²/s |

The listed medium and bioreactor parameters were applied to the equations below.

Equations:

Reynolds numbers:

$$Re = \frac{\rho N D_i^2}{\mu}$$

Maximum Shear Stress on aggregate (Cherry and Kwon 1990)

$$\tau_{max} = 5.33 \rho \sqrt{\varepsilon \vartheta}$$

Power Dissipated (ε) per unit mass $$\varepsilon = \frac{P}{V_L \rho}$$

Power Consumed (P)

$$P = P_N N^3 D_i^5 \rho$$

Power Number calculation was based on the empirical correlation derived by Nagata (1975) for an unbaffled stirred tank.

$$P_N = \frac{K_1}{Re} + K_2 \left[ \frac{10 + 1.2 Re^{0.66}}{10 + 3.2 Re^{0.66}} \right]^{K_4}$$

Where $$K_1 = 14 + \frac{W}{D_t} \left[ 670 \left( \frac{D_i}{D_t} - 0.6 \right)^2 + 185 \right]$$

$$K_2 = 10^{K_3}$$

$$K_3 = 1.3 - 4 \left[ \frac{W}{D_t} - 0.5 \right]^2 - 1.14 \frac{D_i}{D_t}$$

$$K_4 = 1.1 + 4 \left( \frac{W}{D_t} \right) - 2.5 \left[ \frac{D_i}{D_t} - 0.5 \right]^2 - 7 \left[ \frac{W}{D_t} \right]^4$$

A maximum shear of at least 2.5 dyn/cm² imposed on cell aggregates at an agitation rate of 70 rpm in a 2.7 L DASGIP bioreactor was calculated. The cells comprising the outermost layer of the clusters experience the highest levels of shear stress. These shear stress values are highly dependent on the assumptions stated.

Example 9

Differentiation of Human Embryonic Stem Cells from Cell Line WA01 into Definitive Endoderm: Role of MCX/GDF8 in Suspension Culture Clusters from pluripotent human embryonic stem cell line H1 (NIH code: WA01) were seeded at cell densities ranging from 0.25×10⁶ to 2×10⁶ cells/ml in Erlenmeyer/Shaker flasks, spinner flasks, or uncoated ultra low-binding or non-tissue culture treated 6-well plates in MCDB-131 medium containing 3.64 g/ml sodium bicarbonate and 5.5 mM glucose (Catalog #A13051 DJ, Invitrogen, CA), which was supplemented with 2% fatty acid free BSA (Catalog #68700, Proliant, IA), 1× GlutaMAX™ (Catalog #35050-079, Invitrogen, CA), an additional 2.5 mM glucose (Catalog # G8769, Sigma) and ITS-X at 1:50,000 stock concentration (Catalog #51500056, Invitrogen, CA). MCDB-131 medium supplemented in this manner will be referred to as "stage 1 basal medium" for the purposes of this application. Clusters in this medium were treated on the first day of differentiation with either 3 μM MCX (a GSK3B inhibitor, 14-Prop-2-en-1-yl-3,5,7,14,17,23,27-heptaazatetracyclo [19.3.1.1~2,6~.1~8,12~]heptacosa-1(25),2(27),3,5,8(26),9,11,21,23-nonaen-16-one, U.S. patent application Ser. No. 12/494,789; incorporated herein by reference in its entirety) and 100 ng/ml GDF-8 (Catalog #120-00, Peprotech), or 3 μM MCX only, or 20 ng/ml WNT-3A (Catalog #1324-WN-002, R&D Systems, MN) plus 100 ng/ml Activin A (Catalog #338-AC, R&D Systems, MN) or 20 ng/ml WNT-3A only. On day two, cells were transferred to fresh stage 1 basal media supplemented with either 100 ng/ml GDF8 or 100 ng/ml Activin A. Samples were collected for flow cytometry, PCR and Western Blot analysis at various time points ranging from time zero (immediately before addition of basal media plus supplements) up to 72 hours after beginning differentiation.

The efficiency with which definitive endoderm was generated was determined after 3 days of differentiation under each condition by measuring the percentage of cells expressing the cells surface markers CXCR4, CD99 and CD9 using flow cytometry. The data (as shown in FACS plots in FIG. 40a-d and summarized in Table 13) indicates that in suspension culture, addition of 3 μM MCX in the absence of a TGF-3 family member on day one of differentiation generates definitive endoderm at levels comparable to that obtained when cells are treated with 3 μM MCX plus 100 ng/ml GDF-8 or 20 ng/ml WNT-3A plus 100 ng/ml Activin A on day one.

TABLE 13

| Treatment (Day 1 → Day 2 and 3) | CD9 (% by FACS) | CD99(% by FACS) | CD184(% of Parent) |
| --- | --- | --- | --- |
| MCX + GDF8 → GDF8 | 1.5 | 0.0 | 95.3/95.4 |
| MCX only → GDF8 | 6.4 | 0.0 | 93.6/93.6 |
| WNT3a + Activin A → Activin A | 3.3 | 22.1 | 98.1/97.5 |
| WNT3a only → Activin A | 31.7 | 6.2 | 87.8/86.1 |

Example 10

Differentiation of Human Embryonic Stem Cells from Cell Line WA01 into Definitive Endoderm: Dose Response of MCX Compound Concentration in Suspension Culture Clusters from pluripotent human embryonic stem cell line H1 (NIH code: WA01) were seeded at cell densities ranging from 0.25×10⁶ to 2×10⁶ cells/ml in Erlenmeyer/shaker flasks or spinner flasks in stage 1 basal media as described in Example 9. Clusters were treated with stage 1 basal medium containing 1.5, 2, 3, or 4 µM MCX on day one of differentiation and with fresh stage 1 basal medium containing 100 ng/ml GDF-8 on day 2. No media exchange was performed on day three. Samples were collected for flow cytometry and PCR analysis at the end of day three of differentiation.

The efficiency with which definitive endoderm was generated was then determined by measuring the percentage of cells expressing the cells surface markers CXCR4, CD99 and CD9 using flow cytometry. The data (as shown in FACS plots in FIG. 41A-D and summarized in Table 14) indicate that in suspension cultures, addition of MCX at concentrations less than 2 µM results in progressively fewer definitive endoderm positive cells (as evidenced by a lower percentage of CXCR4 positive and a higher percentage of CD9 positive cells). Further, at concentrations above 4 µM, MCX exhibits a deleterious effect on the cells, which results in decreased cell viability. However, by increasing BSA concentrations, the effects of MCX can be modulated such that concentrations ≥4 micromolar may be used. Conversely, concentrations ≤1.5 micromolar may be used to generate definitive endoderm when used with lower BSA concentrations.

TABLE 14

| Treatment | CD9 (% by FACS) | CD184 (% by FACS) |
|---|---|---|
| 4 µM MCX | 1.0 | 95.1 |
| 3 µM MCX | 0.2 | 96.0 |
| 2 µM MCX | 0.2 | 96.5 |
| 1.5 µM MCX | 68.4 | 67.8 |

Example 11

Differentiation of Human Embryonic Stem Cells from Cell Line WA01 into Definitive Endoderm: Role of Media Exchange Frequency in Suspension Culture Clusters from pluripotent human embryonic stem cell line H1 (NIH code: WA01) were seeded at cell densities ranging from 0.25×10⁶ to 2×10⁶ cells/ml in Erlenmeyer/shaker flasks or spinner flasks in stage 1 basal media as described in Example 9. Clusters were treated with stage 1 basal medium containing 3 µM MCX on day one of differentiation and with fresh stage 1 basal medium containing 100 ng/ml GDF-8 on day 2. Control cultures received a media exchange on day three; to a separate vessel, no media exchange was performed on day three. Samples were collected for flow cytometry and PCR analysis at the end of day three of differentiation.

Figure 42:
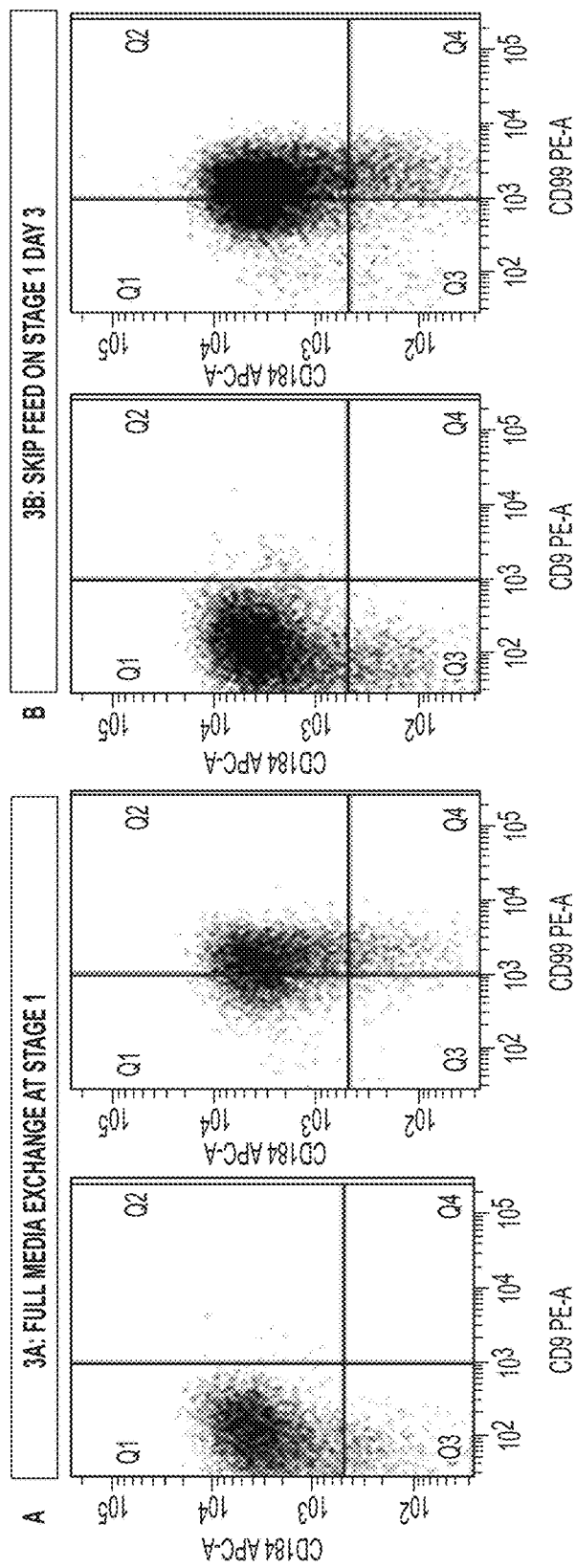
FIG. 42A and FIG. 42B show FACS plots for CXCR4, CD99, and CD9 of cells differentiated for three days according to the protocol of Example 11. Specifically, these Figures show the role of media exchange frequency in suspension culture.

The efficiency with which definitive endoderm was generated was then determined under each condition by measuring the percentage of cells expressing the cells surface markers CXCR4, CD99 and CD9 using flow cytometry. The results are shown in FACS plots in FIGS. 42A&B and summarized in Table 15.

TABLE 15

| Treatment | CD9 (% by FACS) | CD99(% by FACS) | CD184(% by FACS) |
|---|---|---|---|
| Full Media Exchange at stage 1 | 0.2 | 72.4 | 90.2/89.6 |
| Skip Feed at stage 1 day 3 | 0.9 | 68.3 | 89.2/89.8 |

Example 12

Differentiation of Human Embryonic Stem Cells from Cell Line WA01 into Definitive Endoderm: Use of GlutaMAX™ in Suspension Culture Clusters from pluripotent human embryonic stem cell line H1 (NIH code: WA01) were seeded at cell densities ranging from 0.25×10⁶ to 2×10⁶ cells/ml in Erlenmeyer/shaker flasks or spinner flasks.

The example was carried out to determine whether Glutamax™ supplementation was required for generation of definitive endoderm by suspending clusters in stage 1 basal media (described in Example 9) plus or minus GlutaMAX™, which was supplemented with 3 µM MCX on day one of differentiation and with fresh stage 1 basal medium containing 100 ng/ml GDF-8 on day 2. No media exchange was performed on day three. Samples were collected for flow cytometry and PCR analysis at the end of day three of differentiation.

Figure 43:
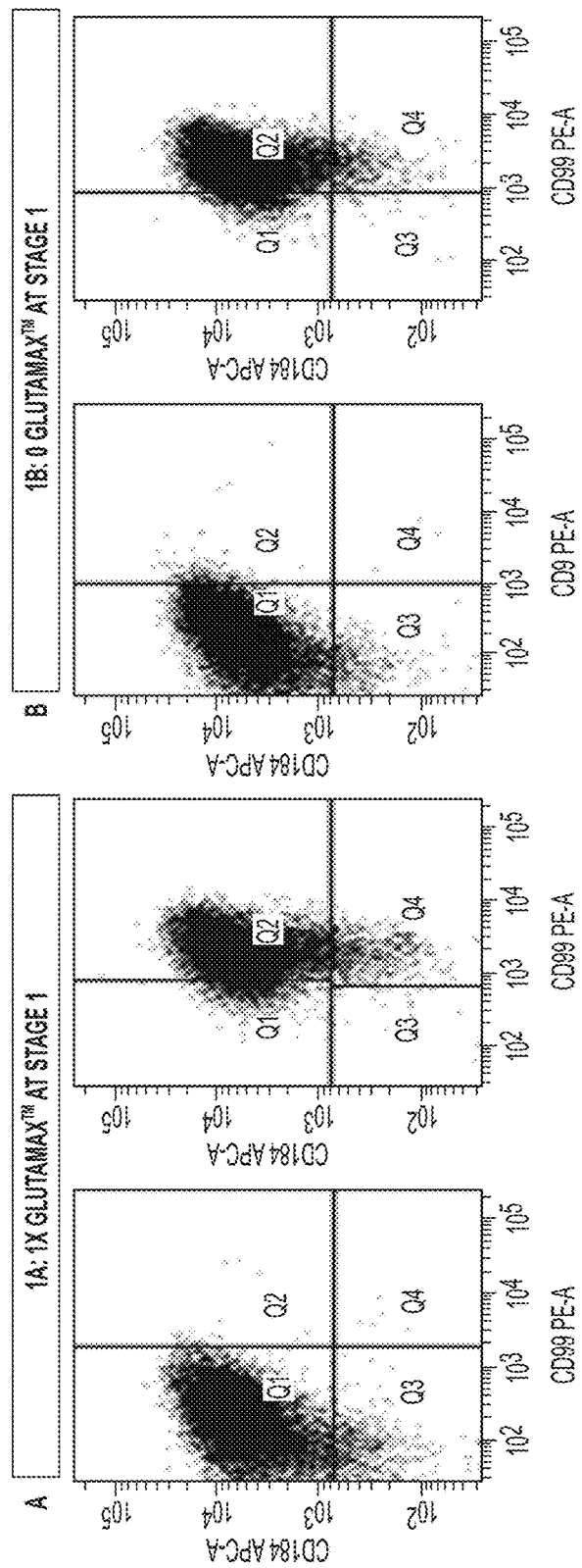
FIG. 43A and FIG. 43B show FACS plots for CXCR4, CD99, and CD9 of cells differentiated for three days according to the protocol of Example 12. Specifically, these Figures show the role of GlutaMAX™ in suspension culture. The cells were cultured at stage 1 in a medium supplemented with 1× GlutaMAX™ (FIG. 43A) or free of GlutaMAX™ or any glutamine (0 M GlutaMAX™) (FIG. 43B). The data suggest that in the suspension culture system, addition of GlutaMAX™ does not appear to influence the efficiency with which definitive endoderm is generated

The efficiency with which definitive endoderm was generated was determined under each condition by measuring the percentage of cells expressing the cells surface markers CXCR4, CD99 and CD9 using flow cytometry. The data and results are shown in FACS plots in FIGS. 43A&B and summarized in Table 16.

TABLE 16

| Treatment | CD9 (% by FACS) | CD99(% by FACS) | CD184(% by FACS) |
|---|---|---|---|
| X GlutaMAX ™ | 0.2 | 93.7 | 96.8/96.7 |
| 0 GlutaMAX ™ | 1.3 | 95.6 | 97.7/97.3 |

Example 13

Differentiation of Human Embryonic Stem Cells from Cell Line WA01 into Definitive Endoderm: Role of Sodium Bicarbonate Concentration in Suspension Culture Clusters from pluripotent human embryonic stem cell line H1 (NIH code: WA01) were seeded at cell densities ranging from 0.25×10⁶ to 2×10⁶ cells/ml in Erlenmeyer/shaker flasks or spinner flasks in either stage 1 basal media as described in Example 9 (containing 3.64 g/l sodium bicarbonate), or in a modified stage 1 basal media which contained 2.43 g/l sodium bicarbonate. Clusters were treated with stage 1 basal medium containing MCX and GDF-8 as described in Example 12. Samples were collected for flow cytometry at the end of day three of differentiation. Phase contrast images were also captured on each day of differentiation.

Figure 44:
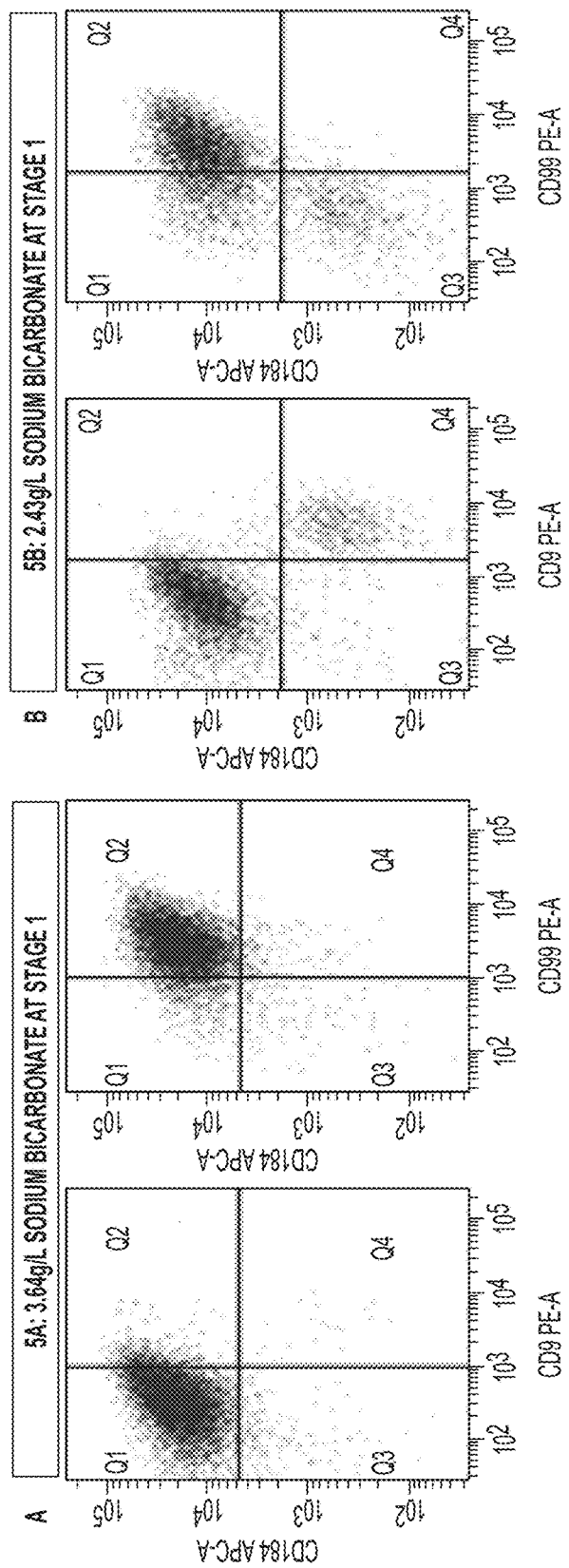
FIGS. 44A to 44D show the effects of various amounts of sodium bicarbonate on cells differentiated according to the protocol of Example 13.
Figure 44:
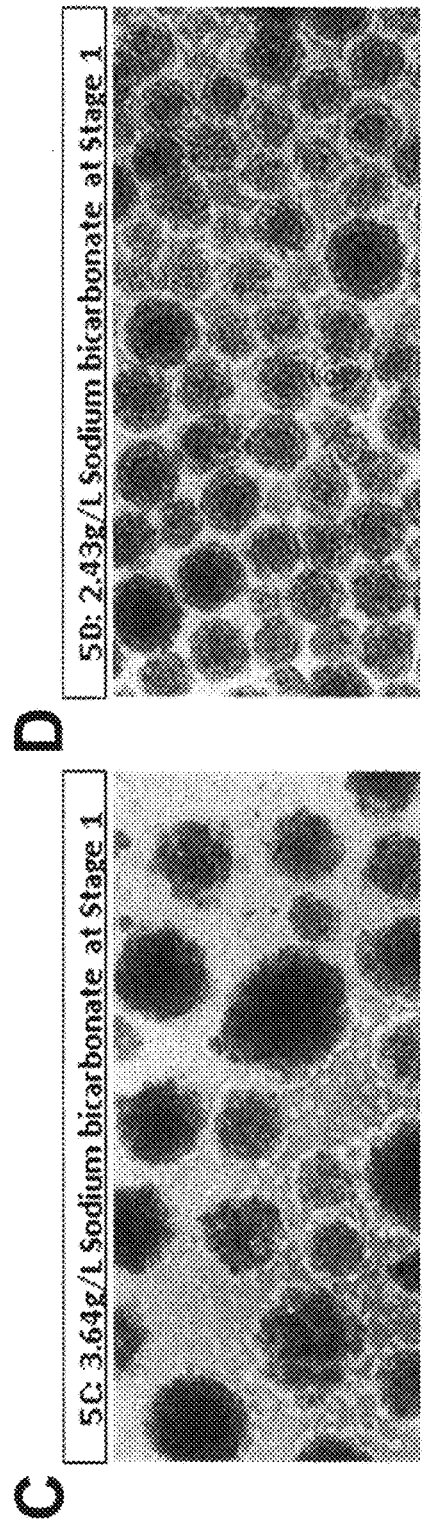

The efficiency with which definitive endoderm was generated was then determined by measuring the percentage of cells expressing the cells surface markers CXCR4, CD99 and CD9 using flow cytometry. The data is shown in FACS plots in FIGS. 44 A&B and summarized in Table 17. In suspension cultures, sodium bicarbonate levels, as low as 2.43 g/L, appear to generate definitive endoderm less efficiently (on average, 87.4% of cells express CXCR4) than when the cells were differentiated in medium containing 3.64 g/L (on average, 97.35% of cells express CXCR4). In addition, it was observed that differences in bicarbonate levels correlated with differences in cluster morphologies at the end of stage 1, as observed by phase contrast microscopy (FIGS. 44 C&D). Also, cells differentiated under high bicarbonate levels were noted to form looser clusters than cells differentiated in 2.43 g/L of bicarbonate.

TABLE 17

| Treatment | CD9 (% by FACS) | CD99 (% by FACS) | CD184 (% by FACS) |
|---|---|---|---|
| 3.64 g/L Sodium bicarbonate | 5.5 | 92.7 | 97.7/97.0 |
| 2.43 g/L Sodium bicarbonate | 12.3 | 66.7 | 86.4/88.4 |

Example 14

Generating Pancreatic Progenitor Clusters from Human Induced Pluripotent Stem Cells in a Scalable Bioreactor Process Cell therapies will require large numbers (>$10^8$) of cells per dose. This example demonstrates a process capable of differentiating induced pluripotent stem cell (iPS cell) masses at 3 to 5 orders of magnitude greater than possible with current cell therapy manufacturing practices.

In this example, an iPS cell line was used—UTC (derived from umbilical tissue cells previously described in U.S. patent application Ser. No. 13/330,931). The cells were derived on mouse embryonic feeder cells using plasmid transfection in a "foot-print" free manner and cryo-preserved at passage 15.

From these cryopreserved cells, a series of cell banks were generated by thawing a source material vial directly onto human recombinant laminin (hrLaminin, Catalog# LN-521 from Biolamina, Stockholm, Sweden) in Essential8™ medium (E8™) from Life Technologies Corporation (Grand Island, N.Y.) to generate an in-house seed material. This thawed and expanded material was called a "Pre-Pre Master Cell Bank" (Pre-Pre MCB) which served as seed material for future banks. Using the pre-pre MCB 3 sequential cell banks were then generated—a Pre-MCB, a MCB, and a working cell bank (WCB). One WCB vial was then thawed, expanded on hrLaminin using EDTA passaging for three passages in E8™. The cells were first seeded from thaw into a T225 flask (Corning; Corning, N.Y.) and then passaged into multiple T225 flasks. The multiple T225 flasks were then passaged and combined to seed a single 1-Layer Cell Stack™ (CS1). Once the cells in the CS1 were confluent, cells were washed once with PBS$^{-/-}$, treated with a half strength solution of Accutase® diluted with PBS$^{-/-}$ and incubated for 4 to 5 minutes. The Accutase® was then removed, and 3 minutes after application of the enzyme solution, the CS1 was tapped to encourage cell lifting. E8™ supplemented with 2% BSA and containing 10 micromolar of the Rho Kinase inhibitor, Y-27632, was added to the CS1 to rinse and inactivate the residual Accutase®. The rinse was then collected and a second rinse volume was added, collected, and pooled with the first rinse.

The cells were transferred in medium supplemented with 2% BSA and containing 10 micromolar of the Rho Kinase inhibitor, Y-27632, to a 1 liter disposable spinner flask (Corning; Corning, N.Y.) at a concentration of $1 \times 10^6$ cells/mL in 225 mL liter. The cells were allowed to cluster in static suspension for 60 minutes in a humidified 5% $CO_2$ incubator, then agitated for 5 minutes at 55-65 rpm and 225 mL additional medium supplemented with 2% BSA and containing 10 micromolar of the Rho Kinase inhibitor, Y-27632 was added. The cells were allowed to settle in static culture for 30 additional minutes, and then 150 mL additional medium supplemented with 2% BSA and containing 10 micromolar of the Rho Kinase inhibitor, Y-27632, was added to the spinner flask. Thereafter the cells were continuously stirred at 50-70 rpm in a humidified 5% CO2 incubator. Twenty-four hours later the spinner flask was removed from the incubator and the clusters allowed to settle for 5-10 minutes. The medium was then aspirated until 200 mL remained in the vessel and 400 mL of additional fresh culture medium was then added to the spinner flask. This process was repeated at the end of day 2 (48 hours after transfer).

Then 72 hours after initial Accutase® treatment the process of cell cluster dissociation and spinner flask seeding (passaging) was repeated to maintain the cells in suspension for multiple passages (tested range: 1-10 passages).

Using this process UTC iPS cells were converted from adherent culture on a substrate to suspension culture as cell clusters and then expanded in suspension. These suspension passaged and cultured cells were then cryopreserved and stored for later use. In order to prepare the suspension expanded cell clusters for cryopreservation the cell clusters were dissociated with Accutase® as described above, except cells were not passed through a 40 micron cell strainer. The cells from each 1 liter disposable flask were then counted, combined as needed and centrifuged for 5 minutes at 80-200 rcf. The supernatant was then removed as completely as possible without disturbing the cell pellet. Cold (<4° C.) CryoStor®10 was then added in a drop-wise manner to achieve a final concentration of 150 million cells per mL and the cell solution was held in an ice bath during transfer to a 1.8 mL corning cryo vial (Corning; Corning, N.Y.) or 15 mL Miltenyi cryo bag (Miltenyi Biotec Inc. Auburn, Calif.).

The suspension expanded cells were then frozen in a vial at high density in a controlled rate freezer as follows. The chamber was pre-cooled to 4° C. and the temperature was held until sample vial temperature reached 6° C. The chamber temp was then ramped down at 2° C./min until the sample reached −7° C. Once the sample vial reached −7° C., the chamber was cooled 20° C./min until the chamber reached −45° C. The chamber temperature was then allowed to briefly rise at 10° C./min until the chamber temperature reached −25° C., and the chamber was then further cooled at 0.8° C./min until the sample vial reached −45° C. The chamber temperature was then cooled at 35° C./min until the chamber reached −160° C. The chamber temperature was then held at −160° C. for at least 10 minutes, after which the vials were transferred to gas phase liquid nitrogen storage.

In order to inoculate a stirred tank bioreactor the high density cryo-preserved cells were removed from the liquid nitrogen storage, thawed and used to seed a closed 0.2 liter glass bioreactor (DASGIP; Julich, Germany). Cryo-vials were removed from gas phase liquid nitrogen storage and placed directly in a 37° C. water bath for 105 seconds. The thawed vial contents were then transferred via 2 mL glass pipette to a 50 mL conical tube. Then 9 mL of E8™ containing 2% BSA supplemented with 10 micromolar Rho Kinase inhibitor, Y-27632 was then added to the tube in a drop wise manner. The cells were then centrifuged at 80-200 rcf for 5 minutes. Afterwards, the supernatant was aspirated from the tube and, 10 ml of fresh E8 containing 2% BSA and supplemented with 10 micromolar Rho Kinase inhibitor, Y-27632 was added. This volume containing the cells was pipetted into a media transfer bottle (Cap2V8®, SaniSure, Moorpark, Calif.) and the bottle contents were pumped directly into the bioreactor via a sterile C-flex tubing weld by peristaltic pump. In preparation for pluripotent stem cell inoculation the bioreactor was prepared with 0.15 L of E8™ supplemented with 2% BSA and 10 micromolar Rho Kinase inhibitor, Y-27632, pre-warmed to 37°, stirred at 70 rpm, regulated to 6.8-7.1 pH by $CO_2$, with a dissolved oxygen set-point of 30% ($CO_2$, air, $O_2$, and $N_2$ regulated). Immediately post-inoculation the bioreactor was sampled for cell count, and medium volume was adjusted as needed to give a final cell concentration of $0.225 \times 10^6$ cells/mL.

The cells inoculated into the stirred tank bioreactor formed cell clusters in the continuously stirred tank. After inoculation, the cell clusters were maintained in E8™ medium, supplemented with 2% BSA, in the reactor for three days. The medium was changed daily; 24 hours after inoculation 90% of spent medium was removed and 0.15 liters of fresh medium added. Forty-eight hours after inoculation, 90% of spent medium was removed and 0.15 liters of fresh medium was added. At 72 hours after inoculation, pluripotent cell differentiation was initiated by removing >90% of the spent medium and adding differentiation medium (Table 18).

Once the staged differentiation process was initiated the cells were maintained for 12 or more days in the closed sterile suspension bioreactor regulated for temperature (37°), pH (7.4 for differentiation), and dissolved oxygen (10% DO set-point for stage 1 and 30% DO set-point all other times, $CO_2$, $O_2$, $N_2$, and air regulated). Throughout the differentiation process, at each media exchange, the impeller was stopped 5-20 minutes prior to medium removal via dip-tube to allow clusters to settle. Medium in the bioreactor was removed or added to/from a closed bottle or bag by peristaltic pump through a dip tube connected to C-Flex® tubing using a Terumo™ tube welder to maintain a closed system. The impeller and heater were re-energized once sufficient medium was added to the vessel to fully submerge the impeller.

Figure 45:
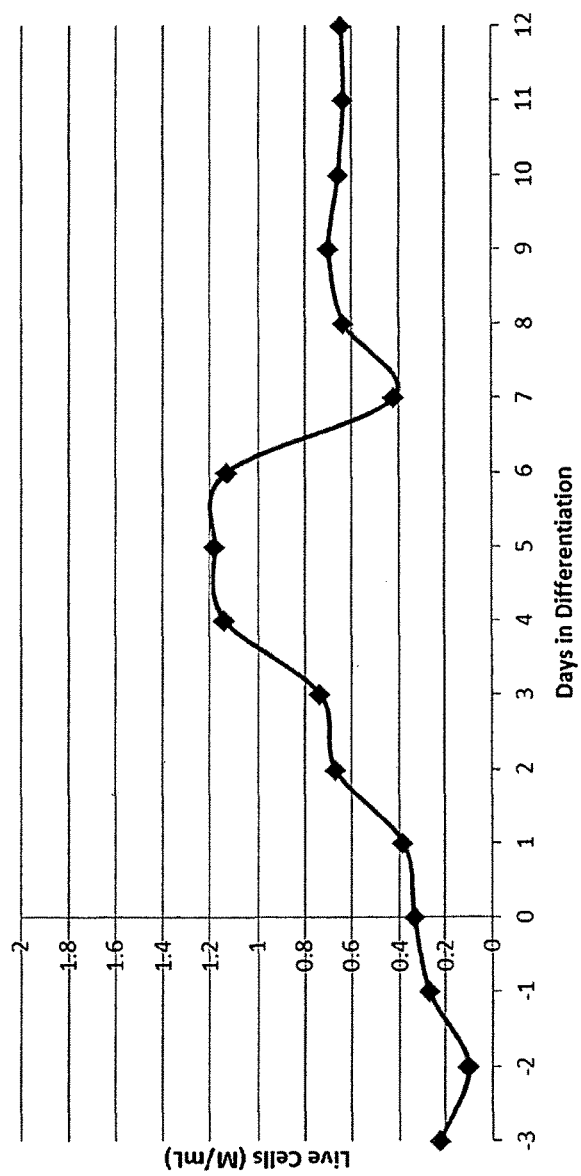
FIG. 45 shows daily cell counts for cell density as a function of differentiation for cells differentiated according to the protocol of Example 14. The cells counts were obtained using an image-based cytometer (NucleoCounter®).

In order to monitor the bioreactor process samples of medium containing cell clusters were drawn daily to determine cell number and viability (NucleoCounter®) as shown in FIG. 45. A general expansion of cells was observed during the process, as the inoculum of $0.225 \times 10^6$ viable cells/mL expanded to generate $0.65 \times 10^6$ viable cells/mL at stage 4 day 3 (FIG. 45).

Figure 46:
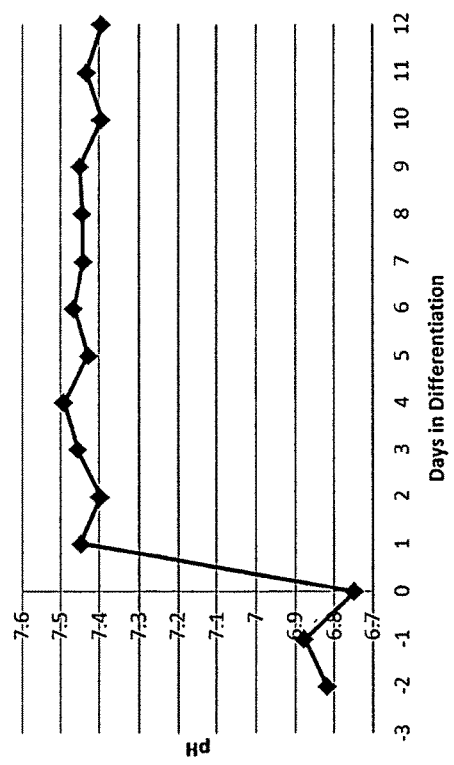
FIG. 46 shows the average daily bioreactor medium pH levels as a function of time (days of differentiation) during the differentiation protocol of Example 14. pH levels were determined by a NOVA BioProfile® FLEX (Nova Biomedical Corporation, Waltham, Mass.).
Figure 47:
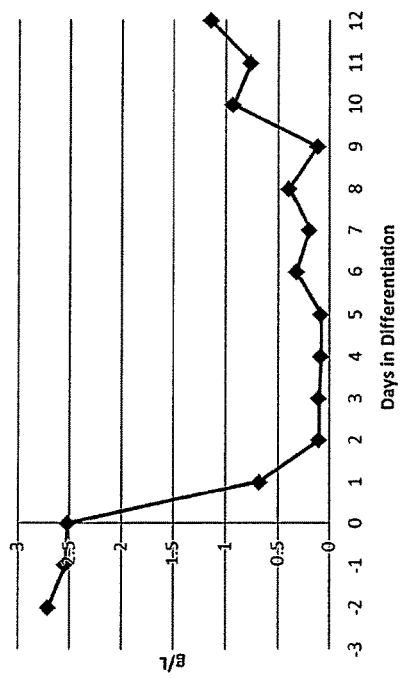
FIG. 47 shows the average daily bioreactor medium glucose levels as a function of time (days of differentiation) during the differentiation protocol of Example 14. Glucose levels were determined by a NOVA BioProfile® FLEX (Nova Biomedical Corporation, Waltham, Mass.).
Figure 48:
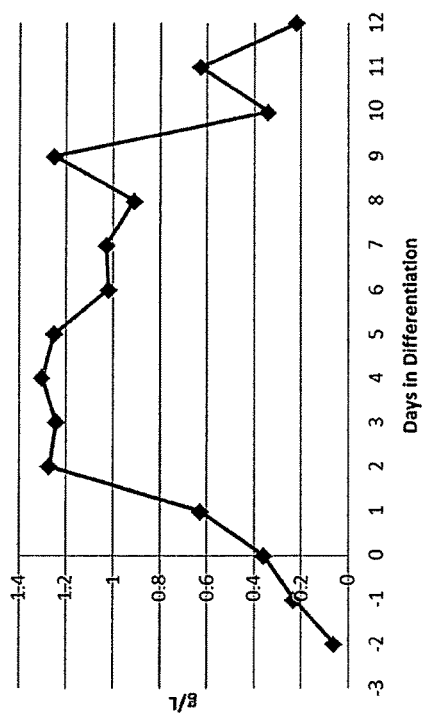
FIG. 48 shows the average daily bioreactor medium lactate levels as a function of time (days of differentiation) during the differentiation protocol of Example 14. Lactate levels were determined by a NOVA BioProfile® FLEX (Nova BiomedicalCorporation, Waltham, Mass.).

In addition to daily counts, bioreactor medium samples were analyzed by NOVA BioProfile® FLEX (Nova Biomedical Corporation, Waltham, Mass.). It was observed that, per the reactor set-point at stage 0 (pH 6.8), the pH of the medium in stage 0 was acidic (pH 6.8) through stage 0 (FIG. 46). The acidic set-point at stage 0 appeared to reduce the metabolic activity of the cells, at a relatively low lactic acid and high glucose levels in stage 0 media were observed. Once the cells began differentiation through to the end of stage 3, the cells consumed almost all of the glucose (FIG. 47) in the media and generated high levels of lactic acid (FIG. 48). Additionally increases in cell density were observed over the course of stages 1 and 2 (FIG. 45).

In order to determine if stage specific changes in pH and metabolism matched stage changes in mRNA expression patterns as measured by qRT-PCR the following was done. Four Applied Biosystems Low Density Arrays were used (Life™, Carlsbad, Calif.) designated Pluripotency, Definitive Endoderm (DE), Gut Tube (GT), or stage 4 (S4). Results are presented as fold differences versus undifferentiated UTCiPS cell sample as control to standardize expression across all runs and arrays.

Figure 49:
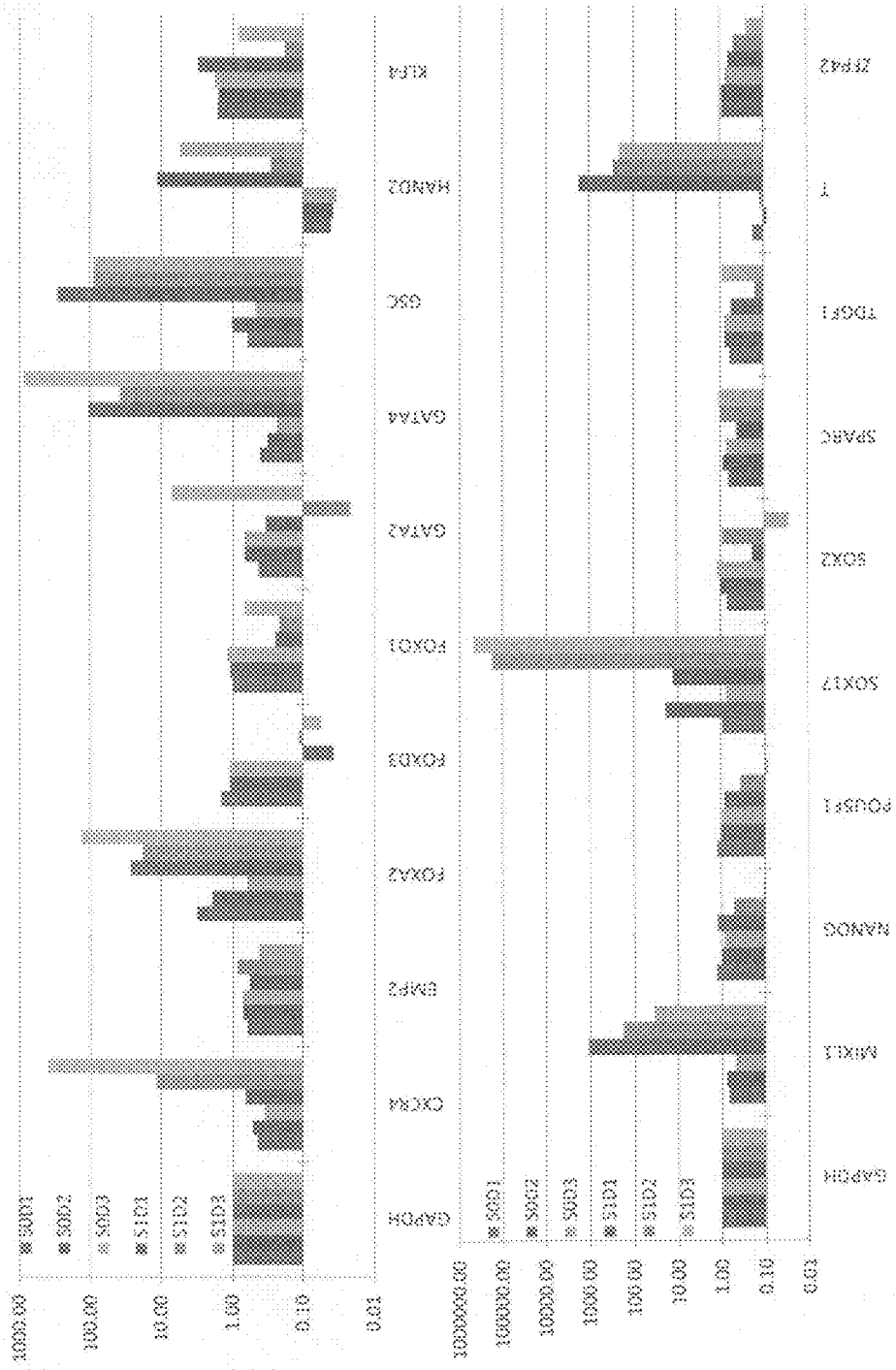
FIG. 49 shows the gene expression, as determined by qRT-PCR as a fold expression versus undifferentiated cells, for the pluripotency array, which contains select genes associated with pluripotency, for stage 0, day 1 to 3 and stage 1, day 1 to day 3 cells differentiated according to the protocol of Example 14.
Figure 50:
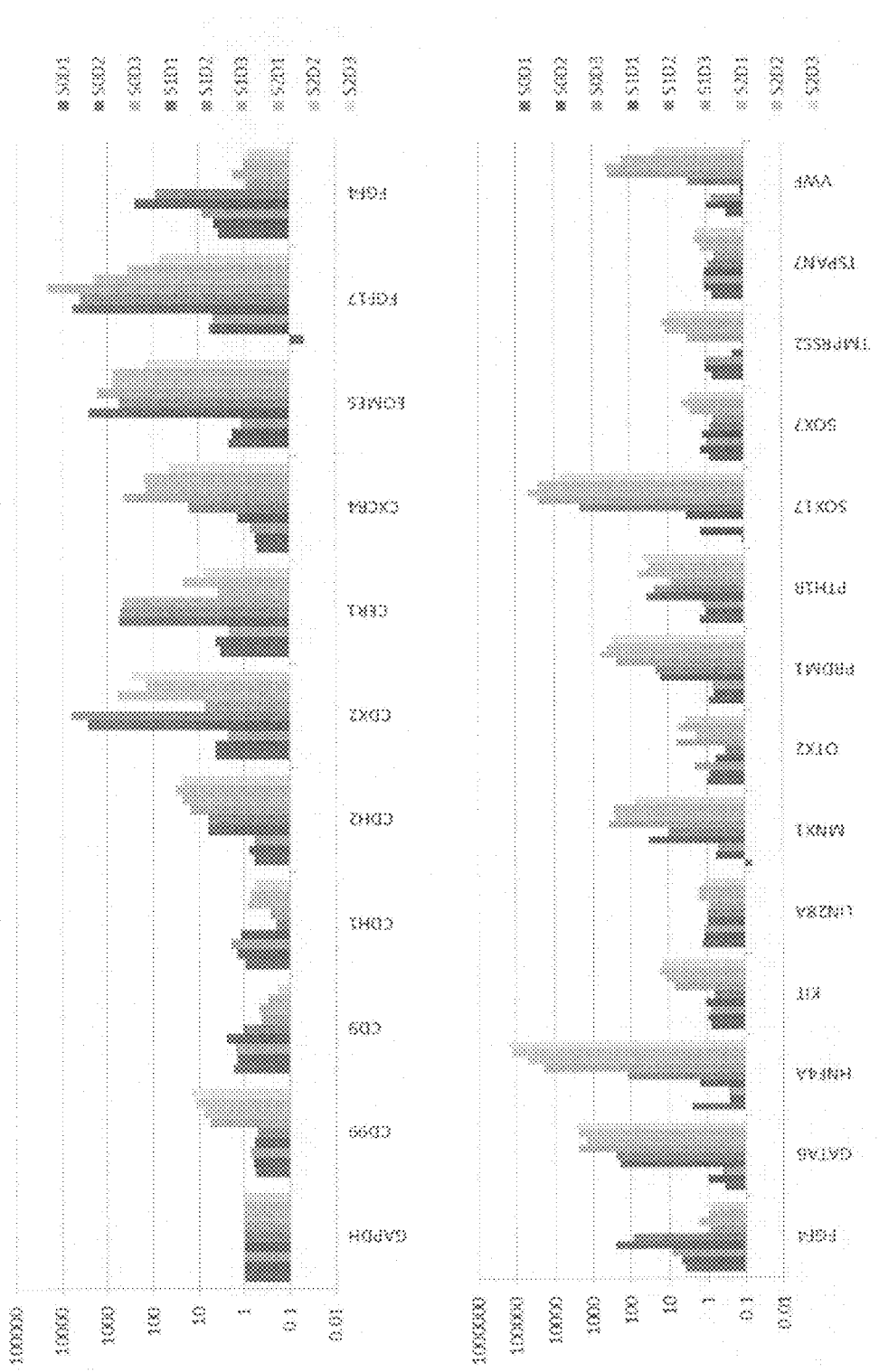
FIG. 50 shows the gene expression, as determined by qRT-PCR as a fold expression versus undifferentiated cells, for the DE array, which contains select genes associated with DE, for stage 0, day 1 to 3, stage 1, day 1 to day 3 and stage 2, day 1 to day 3 cells differentiated according to the protocol of Example 14.
Figure 51:
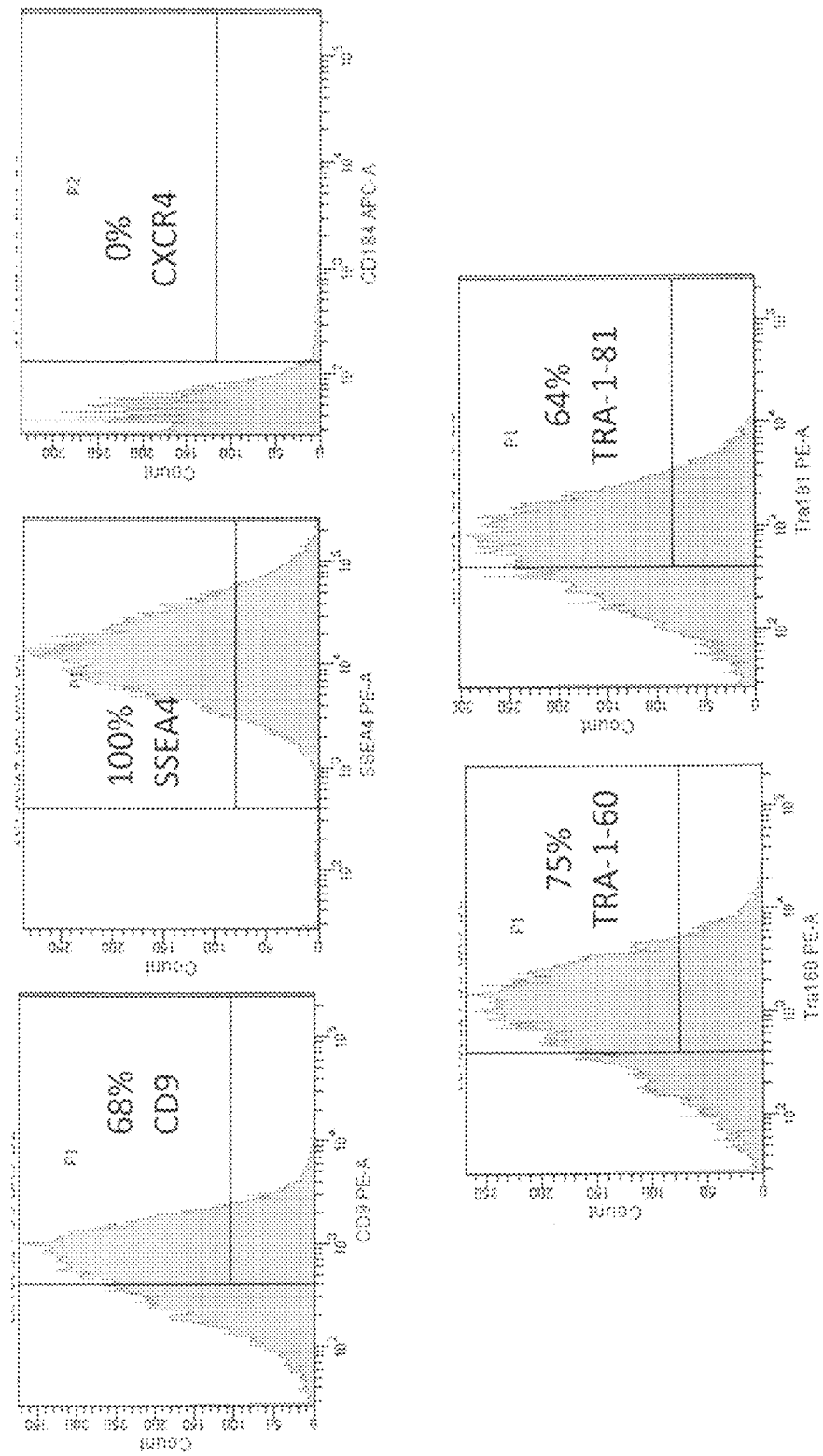
FIG. 51 shows the results of FACS for markers associated with pluripotency (CD184/CXCR4, SSEA4, TRA-1-60 and TRA-1-81) for stage 0, cells prior to being differentiated according to the protocol of Example 14. Specifically.

Using these arrays, gene expression was determined at each stage of differentiation. It was then observed that seed material cells thawed into the bioreactor showed an undifferentiated gene expression pattern at stage 0 day 1, 2, and 3 (24, 48, and 72 hours after bioreactor inoculation: FIGS. 49 and 50). These results correlated well with flow cytometry results which showed high expression levels of CD9, SSEA4, TRA-1-60, and TRA-1-81, and the absence of CXCR4/CD184 (FIG. 51). These flow cytometry and qRT-PCR data showed robust and stable expression patterns for genes of pluripotency (CD9, NANOG, POU5F1, SOX2, TDGF, and ZFP42) and no expression of genes that are characteristically expressed during differentiation (CD99, CDH2, CDX2, CER1, CXCR4, EOMES, FGF17, FGF4, FOXA2, GATA2, GATA4, GATA6, GSC, HAND2, HNF4a, KIT, MNX1, MIXL1, PRDM1, PTHR1R, SOX17, SOX7, T, TMPRSS2, and VWF) consistent with a stable pluripotent state.

At the completion of stage 0 (72 hours after reactor inoculation), the cells were moved into differentiation medium (Table 18) containing MCX and GDF8. Twenty-four hours after this media change significant alterations in gene expression patterns (FIGS. 49 and 50 fold expression versus undifferentiated control) were noted, such as a >10× increase in FOXA2, HAND2, PRDM1, PTH1R and SOX17 expression, >100× increase in CER1, FGF4, GATA4, GATA6, GSC, and MNX1 and a >1000× increase in EOMES, FGF17, MIXL1, and T expression. These increased expression levels indicated the cells were transitioning through a mesendodermal fate. It was also noted that CDX2 levels were elevated at stage 1 day 1 versus undifferentiated cells (2700× increase in expression vs. control), however this was a transient increase in expression and CDX2 levels dropped 97% by stage 1 day 3 to levels comparable to those observed prior to induction of differentiation (FIGS. 49 and 50 fold expression versus undifferentiated control).

At 72 hours after exposure to the stage 1 differentiation medium, the cells expressed a profile consistent with specification to definitive endoderm, as CXCR4 levels peaked at ~400× over historical control, FOXA2 was expressed at 136× over control and SOX17 was expressed at 470,000× over historical control. Consistent with definitive endoderm, it was also noted that gene expression of CER1, EOMES, FGF4, GSC, MIXL1, and T at the end of stage 1 (day 3) had dropped from the elevated levels observed at stage 1 day 1 (FIGS. 49 and 50 fold expression versus undifferentiated control).

Figure 52:
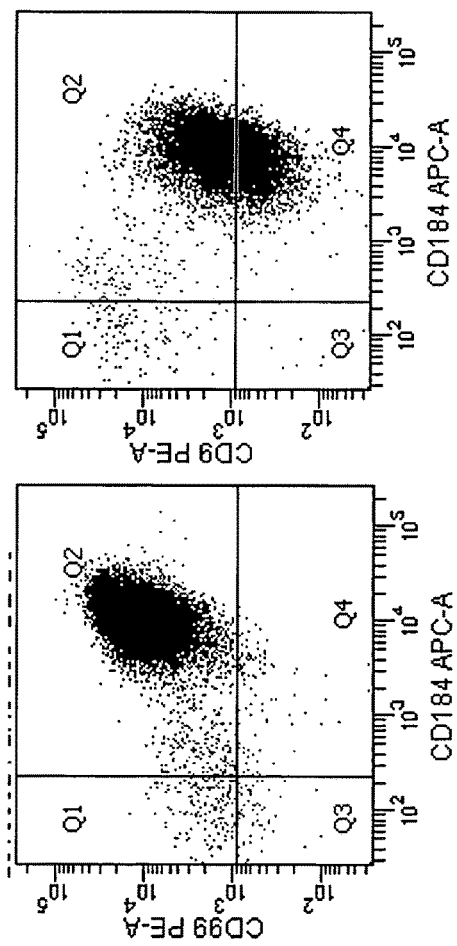
FIG. 52 shows FACS plots for the definitive endoderm markers CXCR4, CD99, and CD9 of cells differentiated to the end of stage 1 according to the protocol of Example 14.

These changes in gene expression observed with qRT-PCR correlated with results observed by flow cytometry. A near complete transition was seen from a CD9 expressing/CXCR4 negative pluripotent cell population at the initiation of differentiation (FIG. 51) to a homogeneous population of CXCR4 expressing cells (98.6% of cells CXCR4 positive) at the end of stage 1 (FIG. 52).

Figure 53:
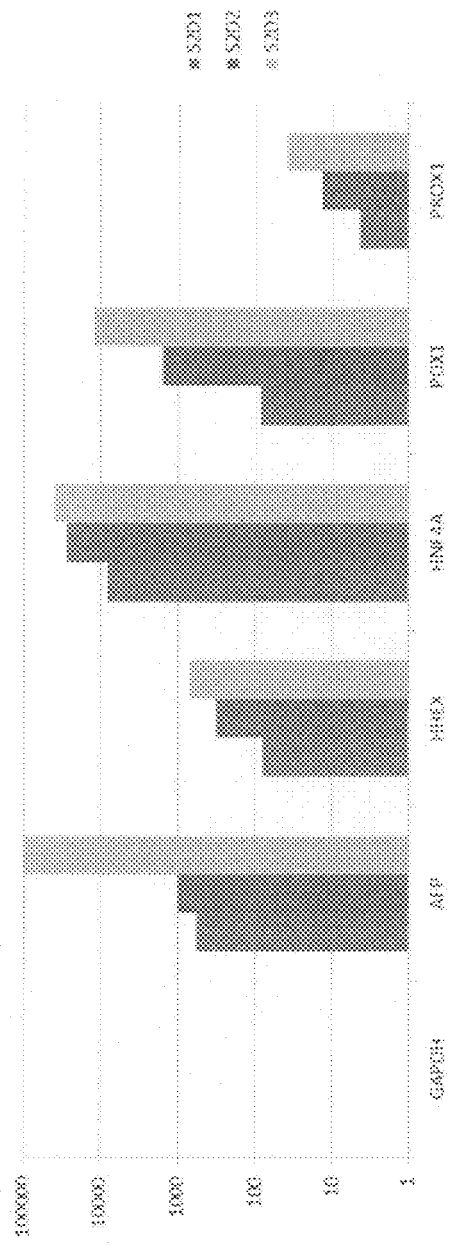
FIG. 53 shows the gene expression, as determined by qRT-PCR as a fold expression versus undifferentiated cells, for GAPDH, AFP, HHEX, HNF4a, PDX1, and PROX1 for stage 2, day 1; stage 2, day 2 and stage 2, day 3 cells differentiated according to the protocol of Example 14.

Following the completion of definitive endoderm formation (stage 1) the medium was changed to one containing FGF7, a morphogen used to induce primitive foregut formation. Consistent with formation of primitive foregut, HNF4a and GATA6 expression levels at stage 2 days 1 and 3 increased, while genes expressed at high levels on stage 1 day 3 (CXCR4, EOMES, FGF17, FGF4, MNX1, PRDM1, SOX17, and VWF) showed reduced expression by the end of stage 2 (FIGS. 50 and 53 fold expression versus undifferentiated control). The expression of foregut genes (AFP, HHEX, PDX1, and PROX1) was increased (FIG. 53 fold expression versus undifferentiated control).

Figure 54:
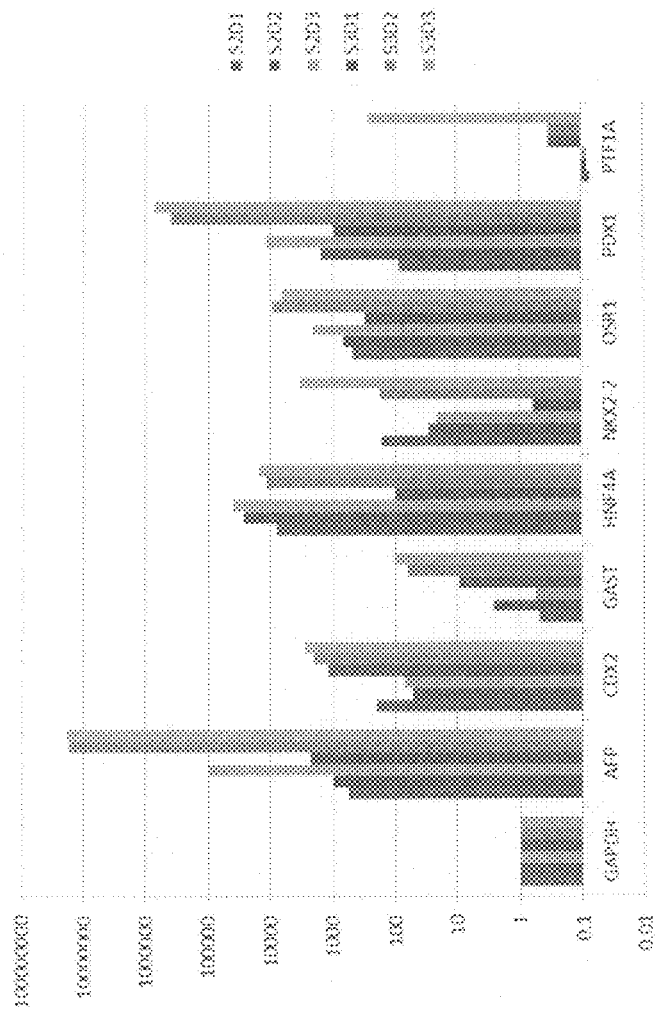
FIG. 54 shows the gene expression, as determined by qRT-PCR as a fold expression versus undifferentiated cells, for GAPDH, AFP, CDX2, GAST, HNF4A, NKX2-2, OSR1, PDX1 and PFT1A for stage 2, day 1 to day 3 and stage 3, day 1 to day 3 cells differentiated according to the protocol of Example 14.
Figure 55:
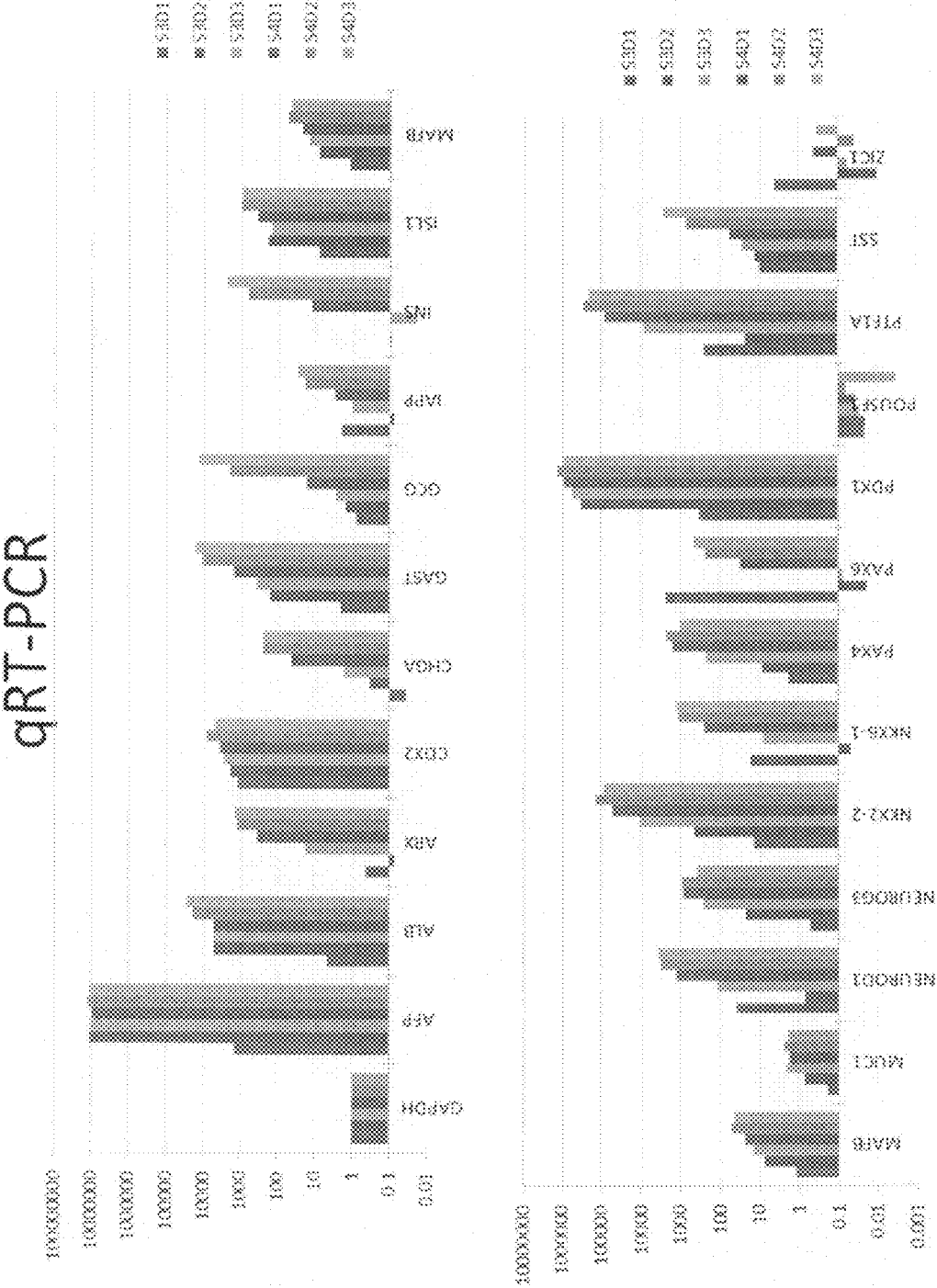
FIG. 55 shows the gene expression, as determined by qRT-PCR as a fold expression versus undifferentiated cells, for certain genes for stage 3, day 1 to 3 and stage 4, day 1 to day 3 cells differentiated according to the protocol of Example 14. Specifically, the top panel of FIG. 55 shows the gene expression for GAPDH, AFP, ALB, ARX, CDX2, CHGA, GAST, GCG, IAAP, INS, ISL1, and MAFB. The bottom panel of FIG. 55 shows the gene expression of MAFB, MUCS, NEUROD1, NEUROG3, NKX2-2, NKX6-1, PAX4, PDX1, POUSF1, PTF1A, SST and ZlC1.

After the cells had been cultured in stage 2 medium for 72 hours, the culture was switched to a stage 3 medium (Table 18). Once in this medium the cells expressed markers consistent with an endodermal pancreatic lineage as measured by qRT-PCR assay for gene expression. Gene expression for PDX1 increased 60 fold from 12,000× over control at the end of stage 2 day 3 to 739,000× over control at the end of stage 3 day 3. These data indicated the cells were specifying to a pancreatic fate (FIG. 54). Supporting this observation were increased expression levels versus undifferentiated control for a host of genes commonly expressed in pancreas (ARX, GAST, GCG, INS, ISL1, NEUROD1, NGN3, NKX2.2, NKX6.1, PAX4, PAX6, PTF1A, and SST) as shown in FIGS. 54 and 55. Interestingly no OCT4/POU5F1 expression (37 sample Cts by qRT-PCR) and high expression levels for other markers of endodermal lineages AFP, ALB, and CDX2 were also observed. This indicates that the cell population in the bioreactor differentiated from a pluripotent cell population first to a relatively plastic gut tube fate and then further differentiated to a pancreatic fate (FIGS. 54 and 55).

Figure 56:
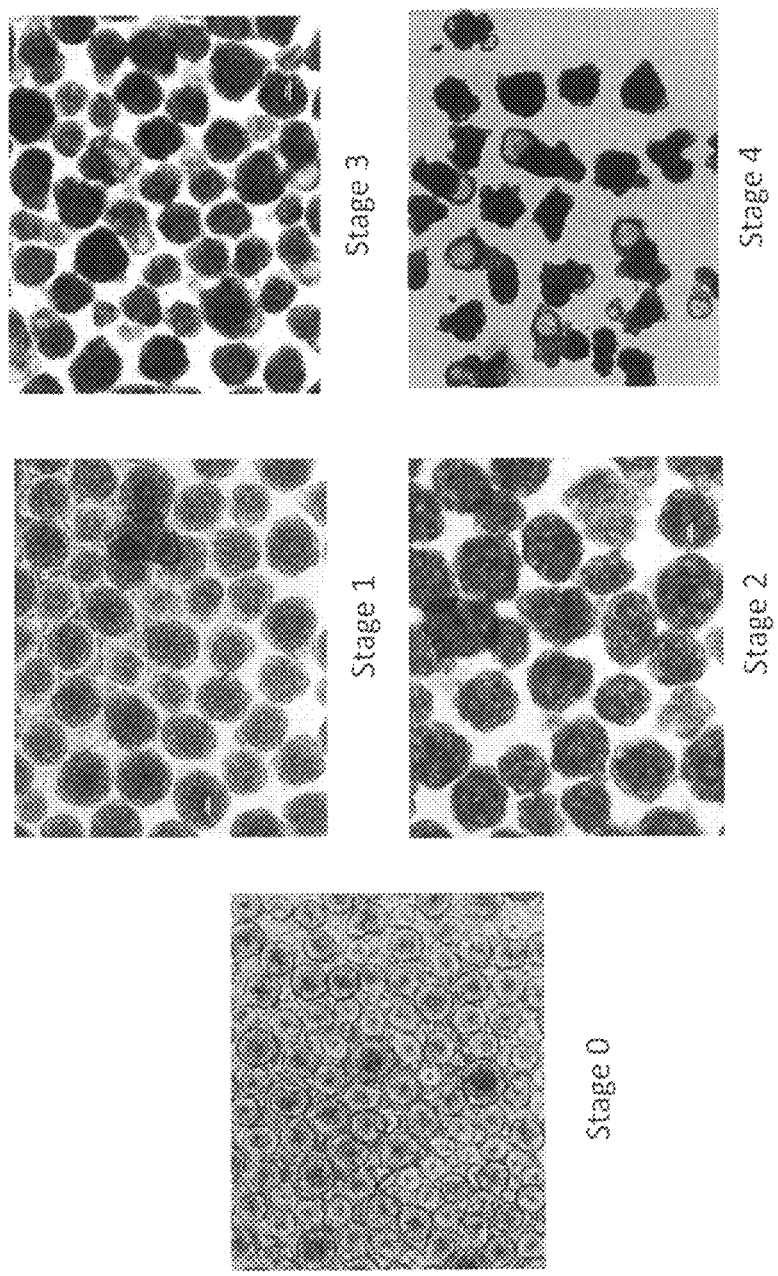
FIG. 56 shows end stage micrographs for cells differentiated according to the protocol of Example 14. Visible in FIG. 56 are representative micrographs (4×) of cell clusters at stage 0 and at the end of differentiation of stages 1 to 4.
Figure 57:
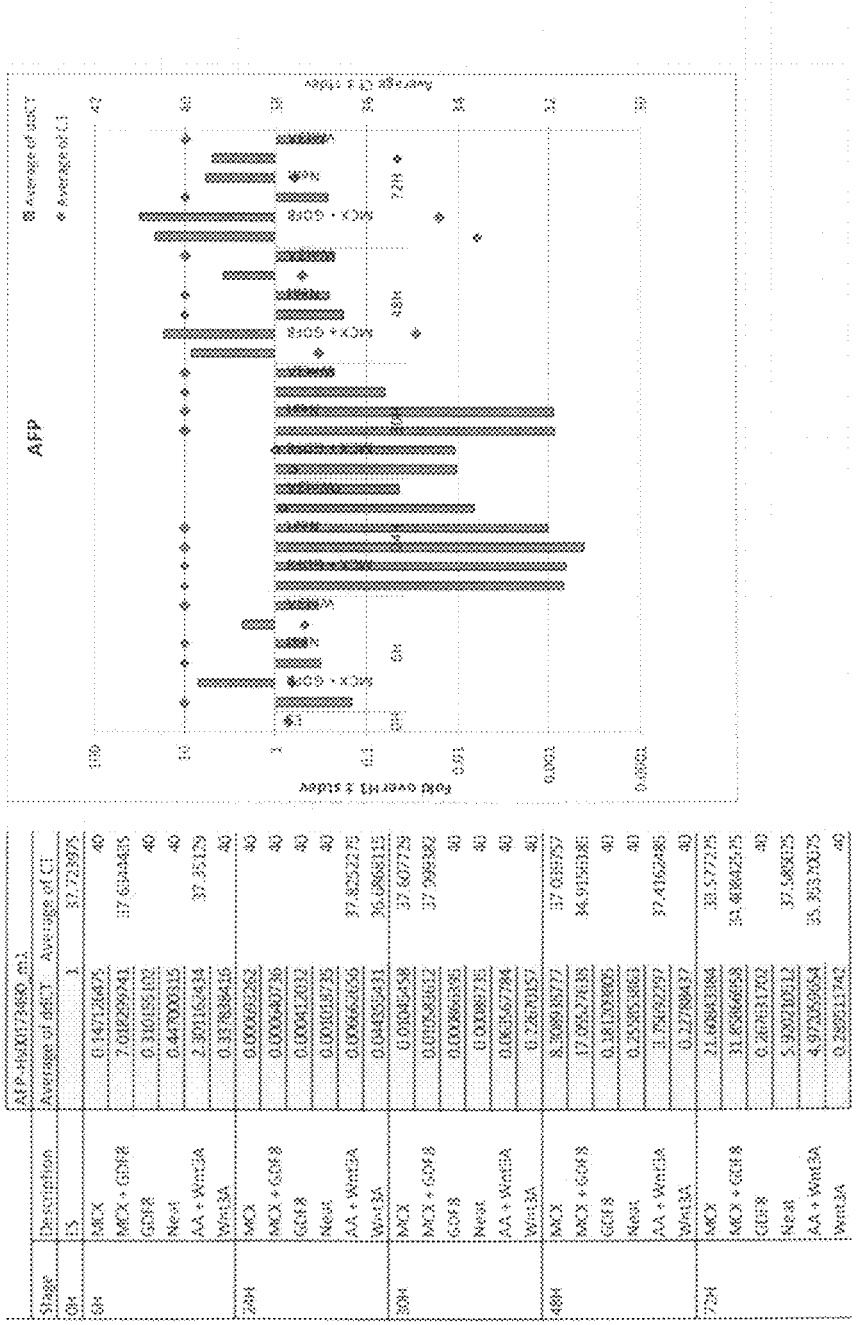
Figure 58:
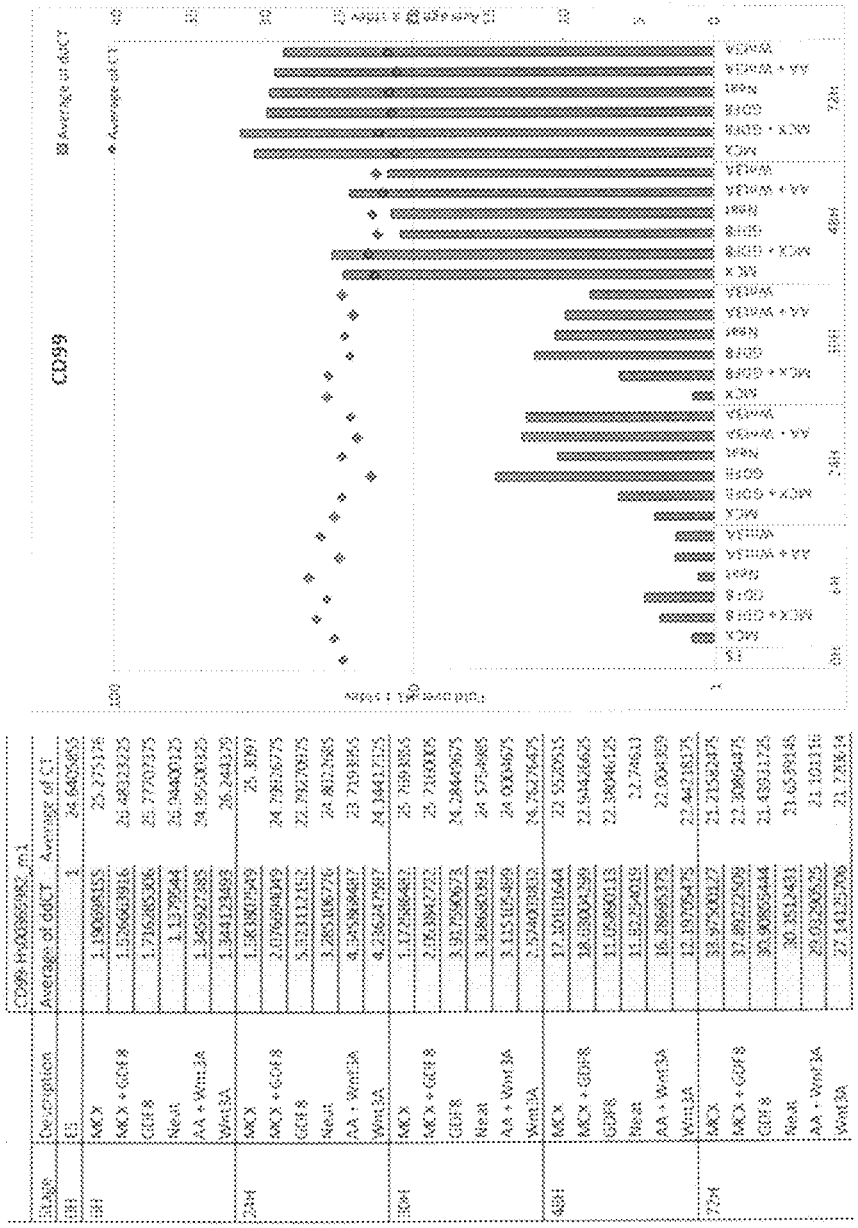
Figure 59:
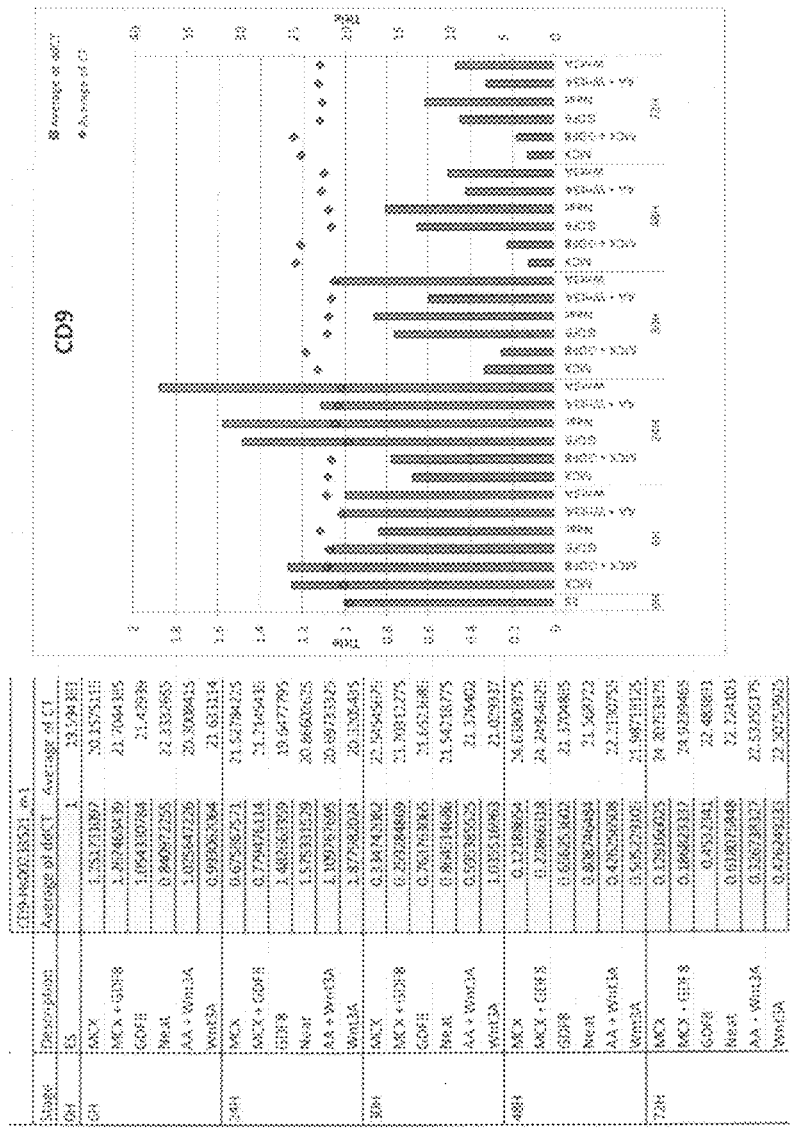
Figure 60:
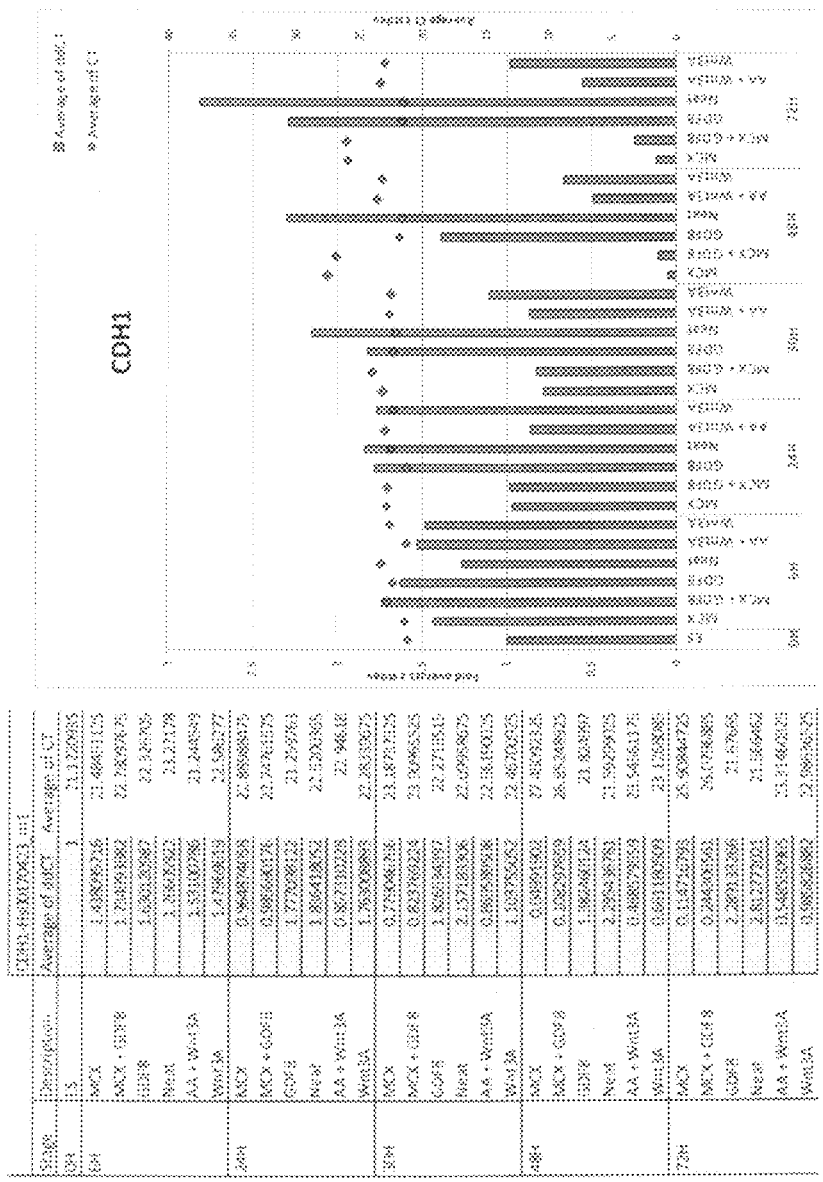
Figure 61:
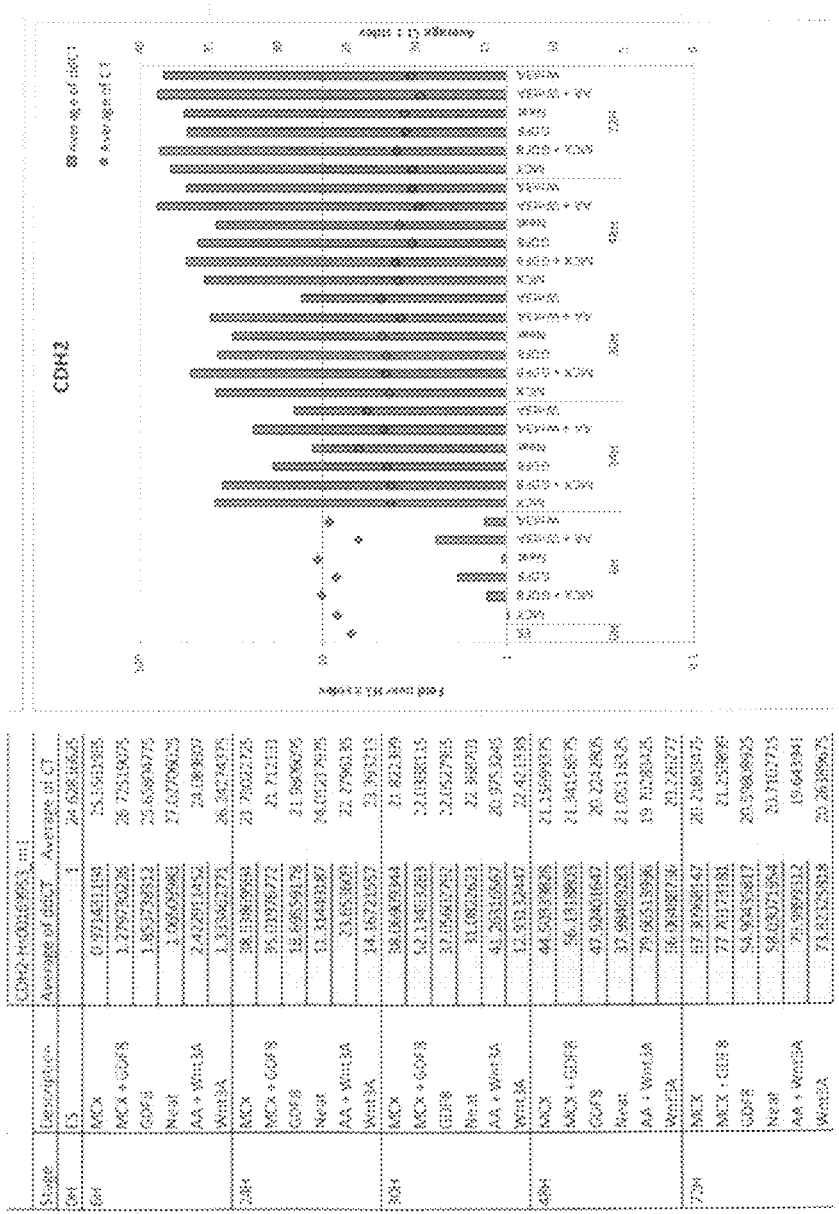
Figure 62:
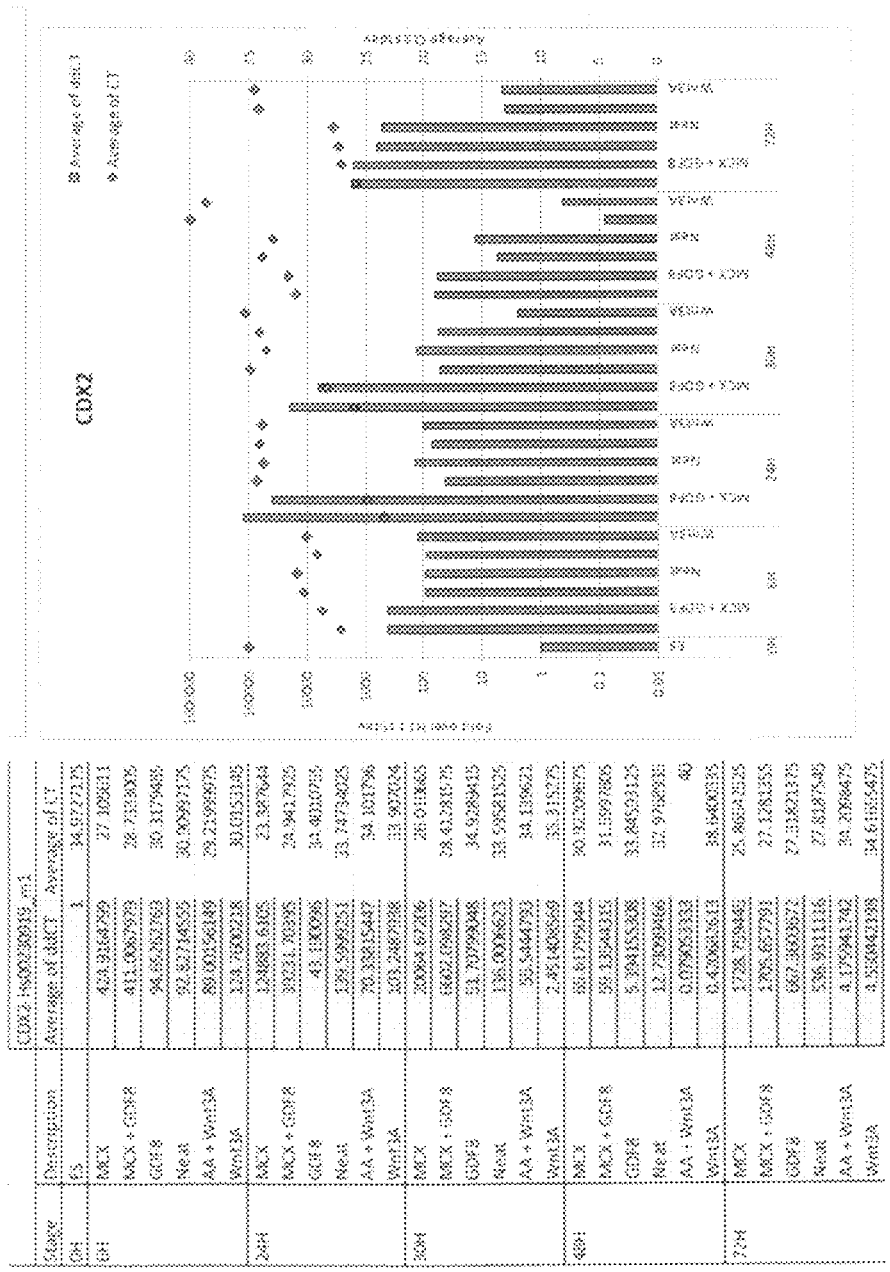
Figure 63:
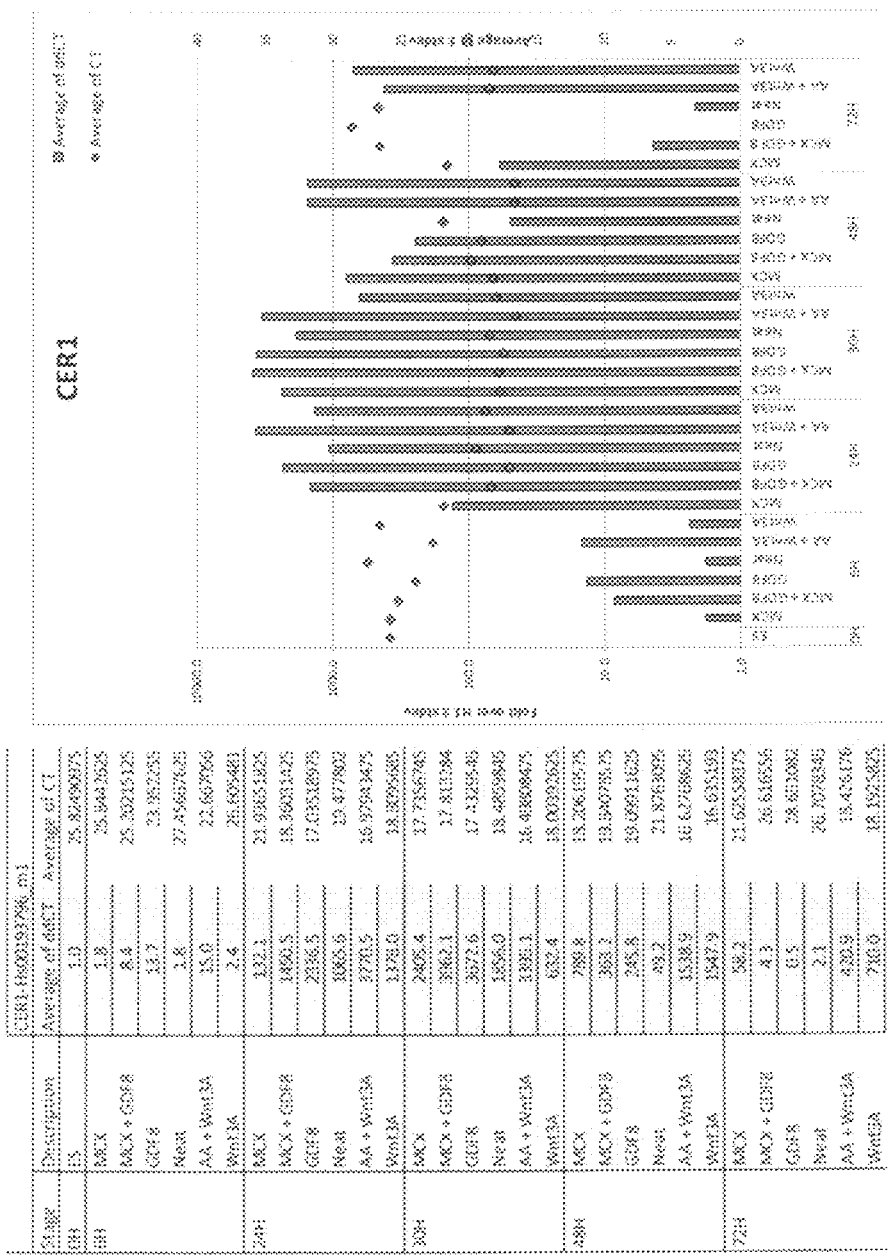
Figure 64:
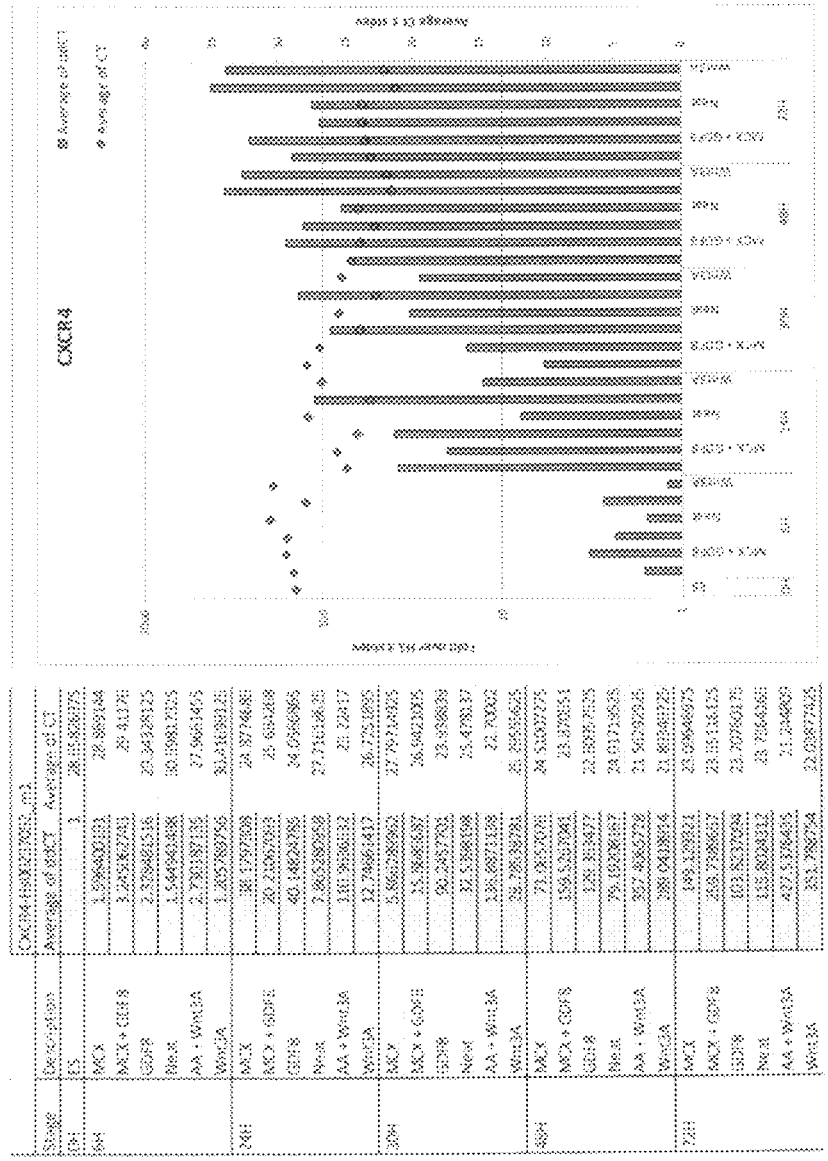
Figure 65:
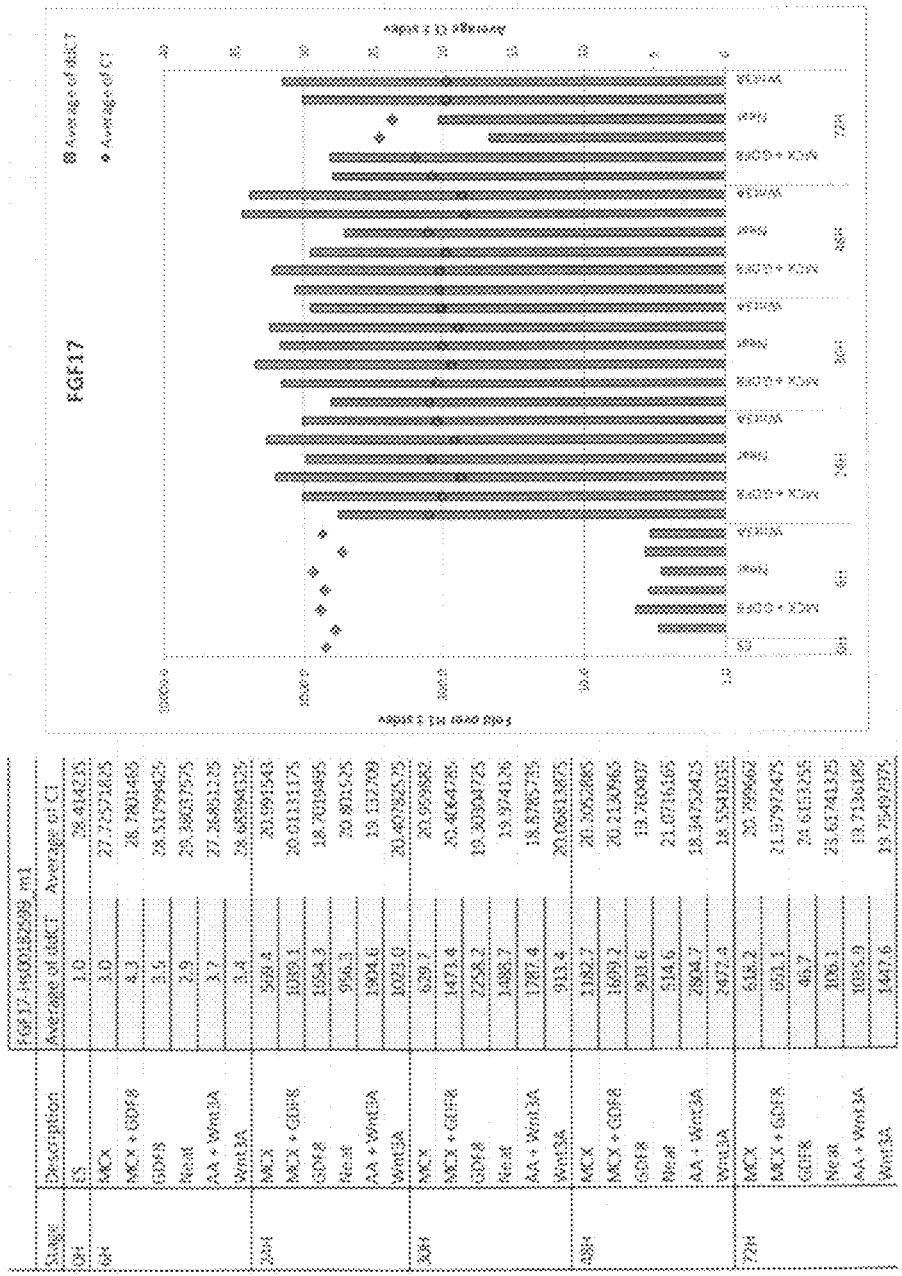
Figure 66:
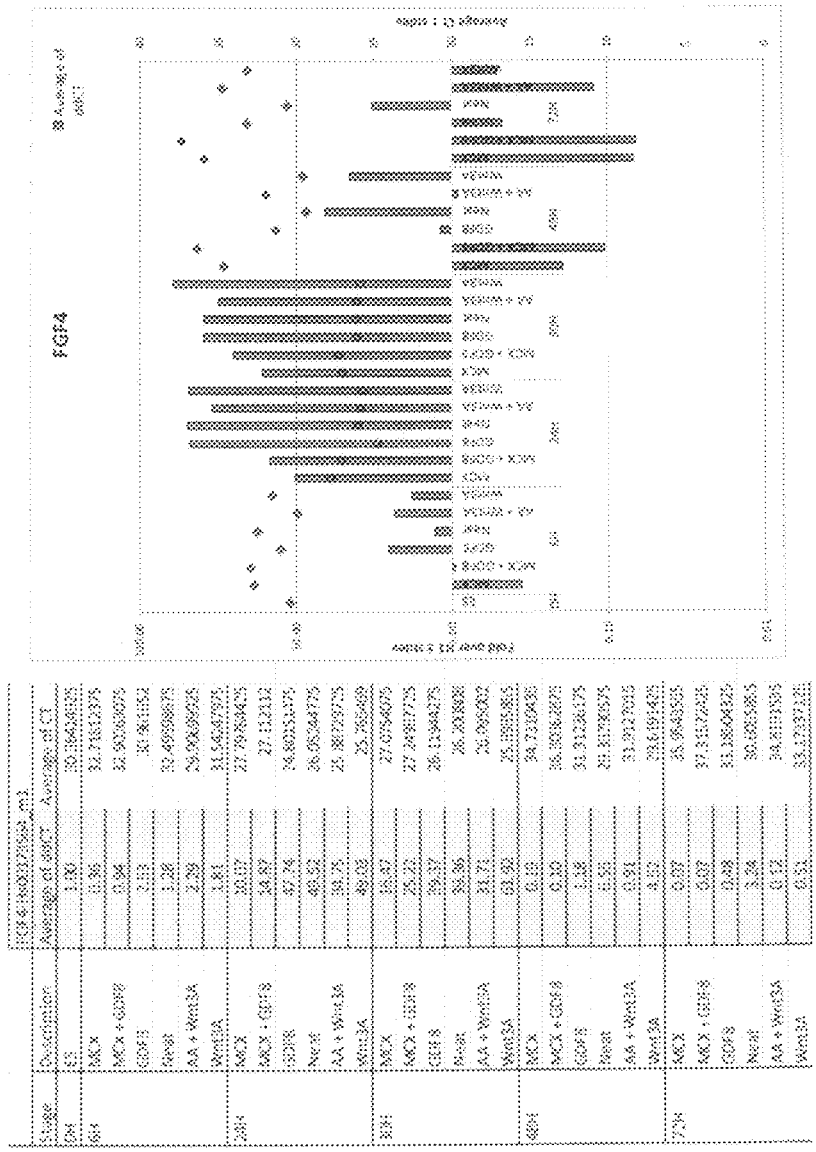
Figure 67:
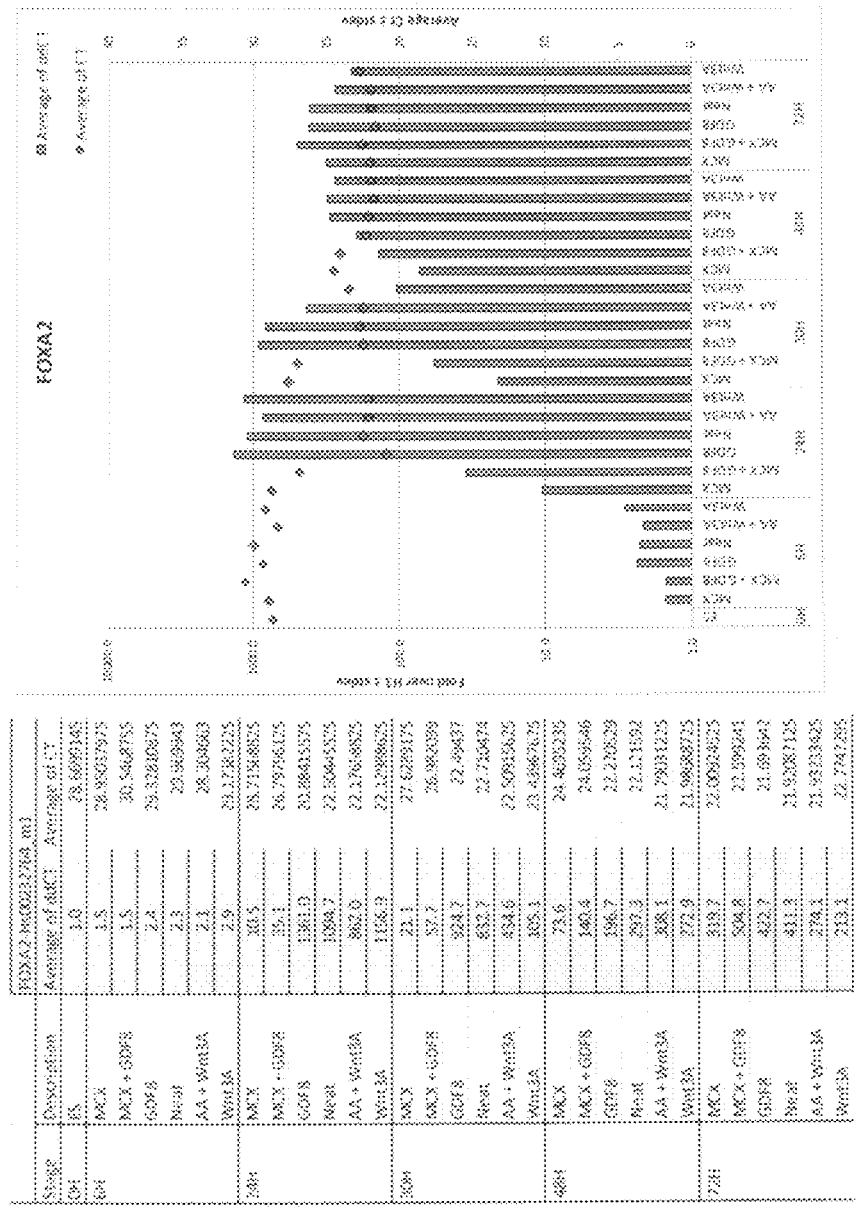
Figure 69:
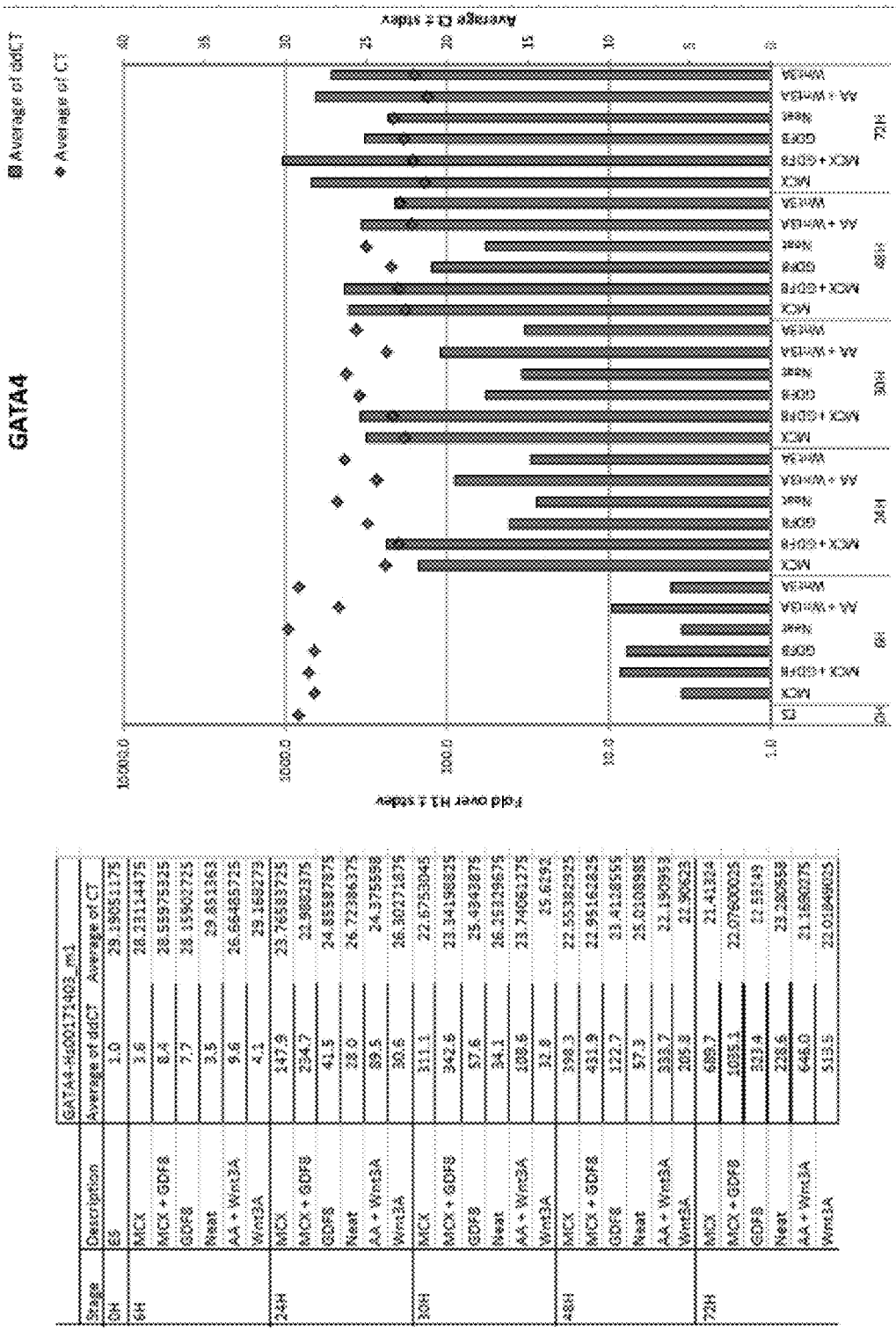
Figure 70:
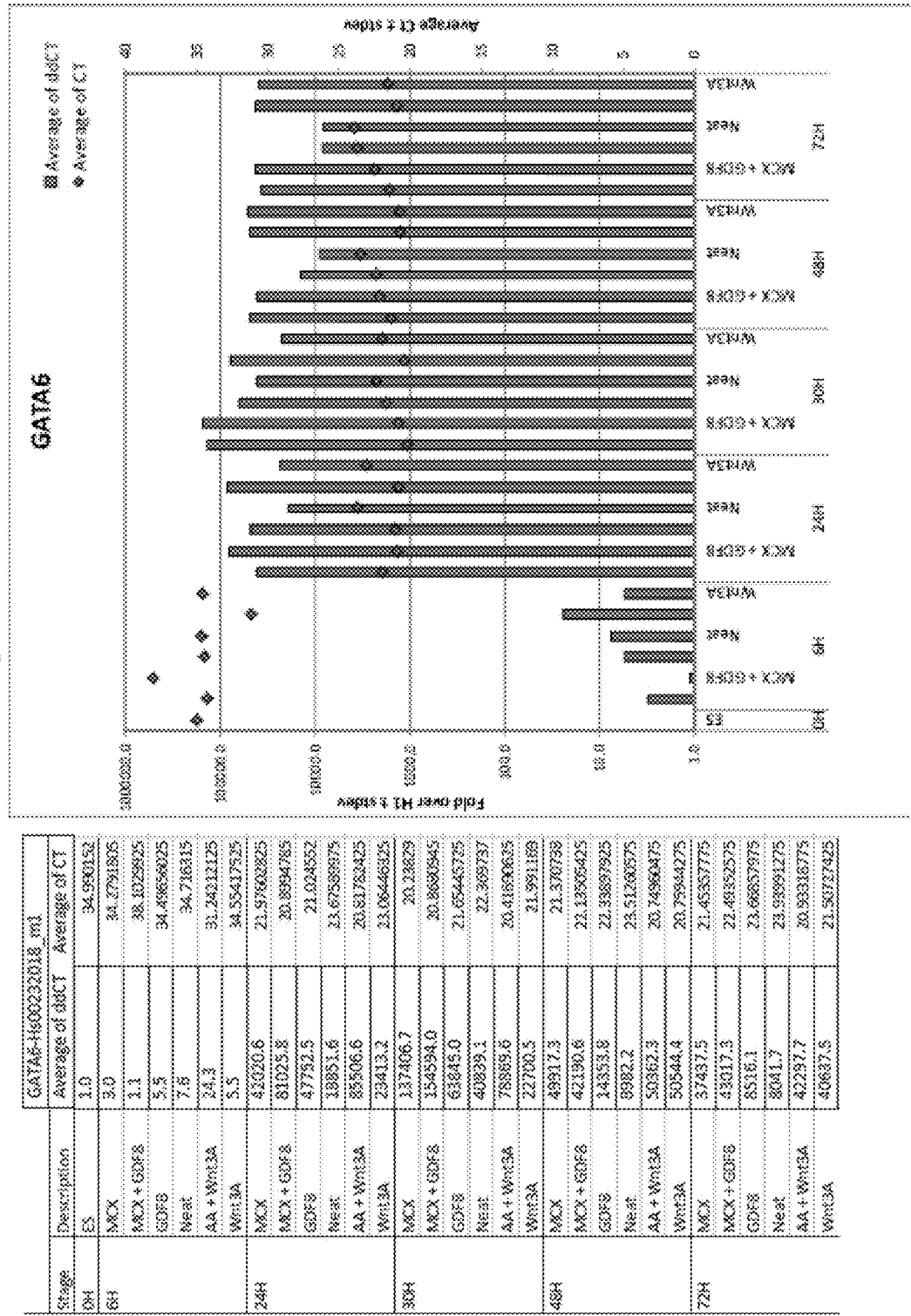
Figure 71:
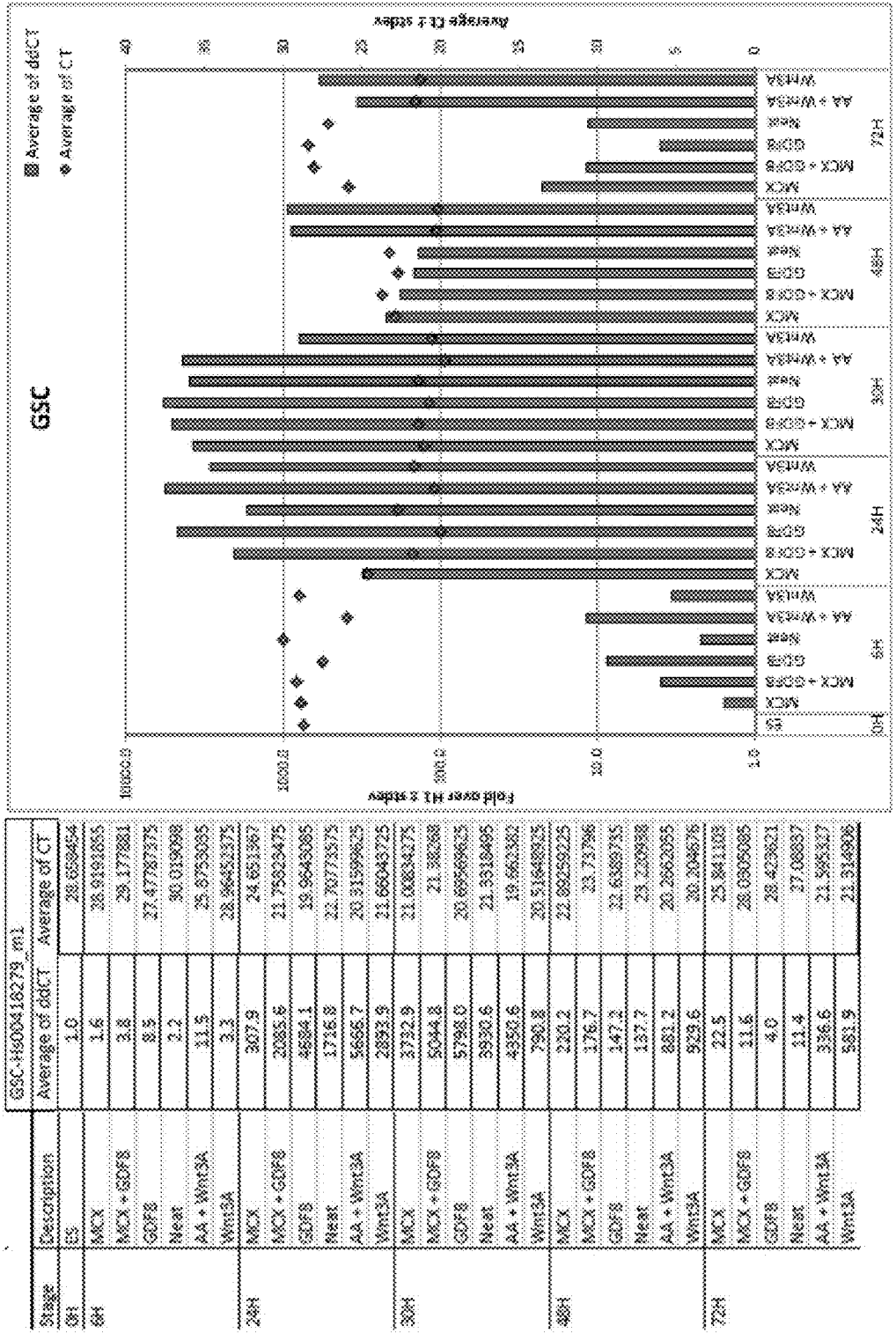
Figure 72:
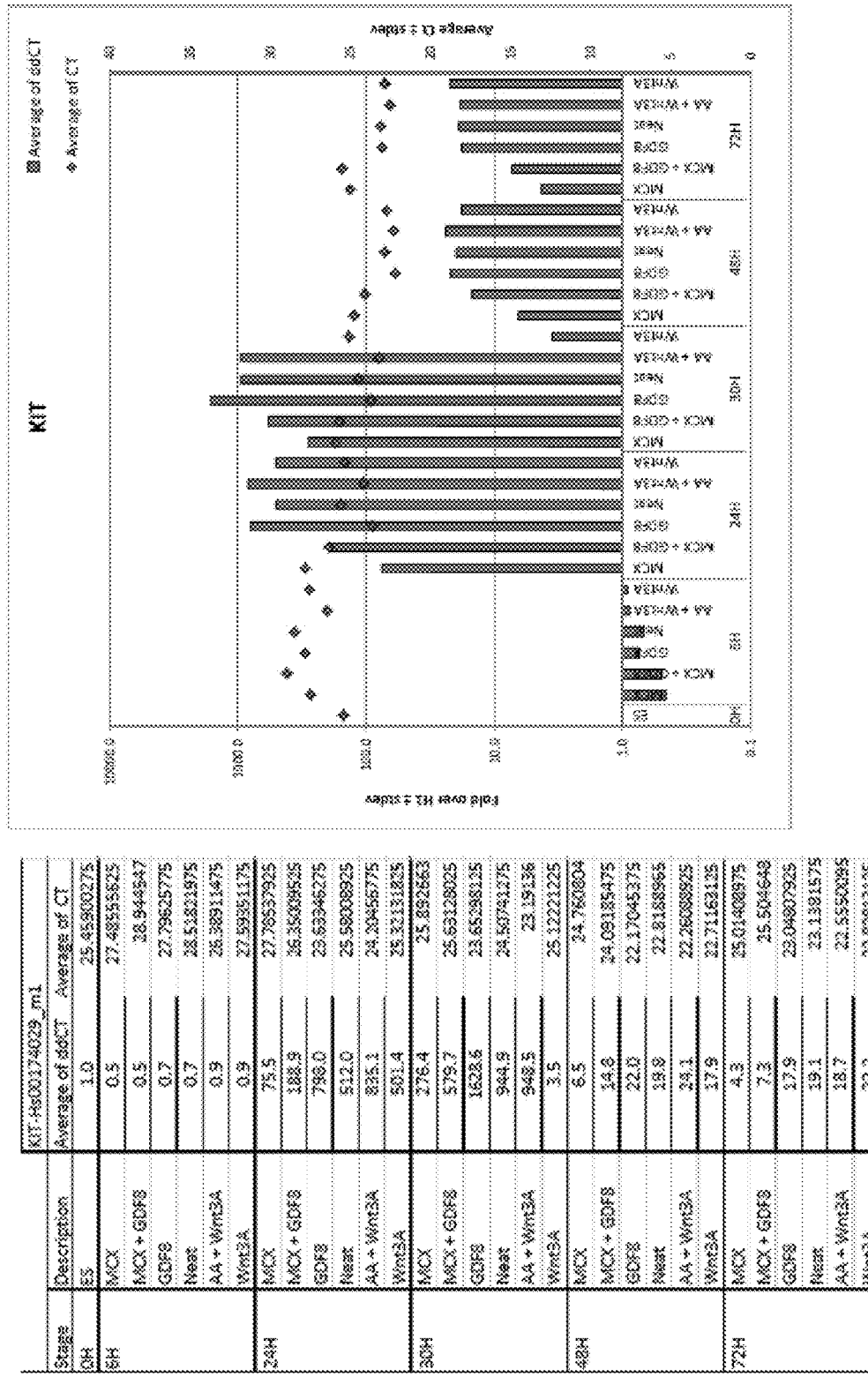
Figure 73:
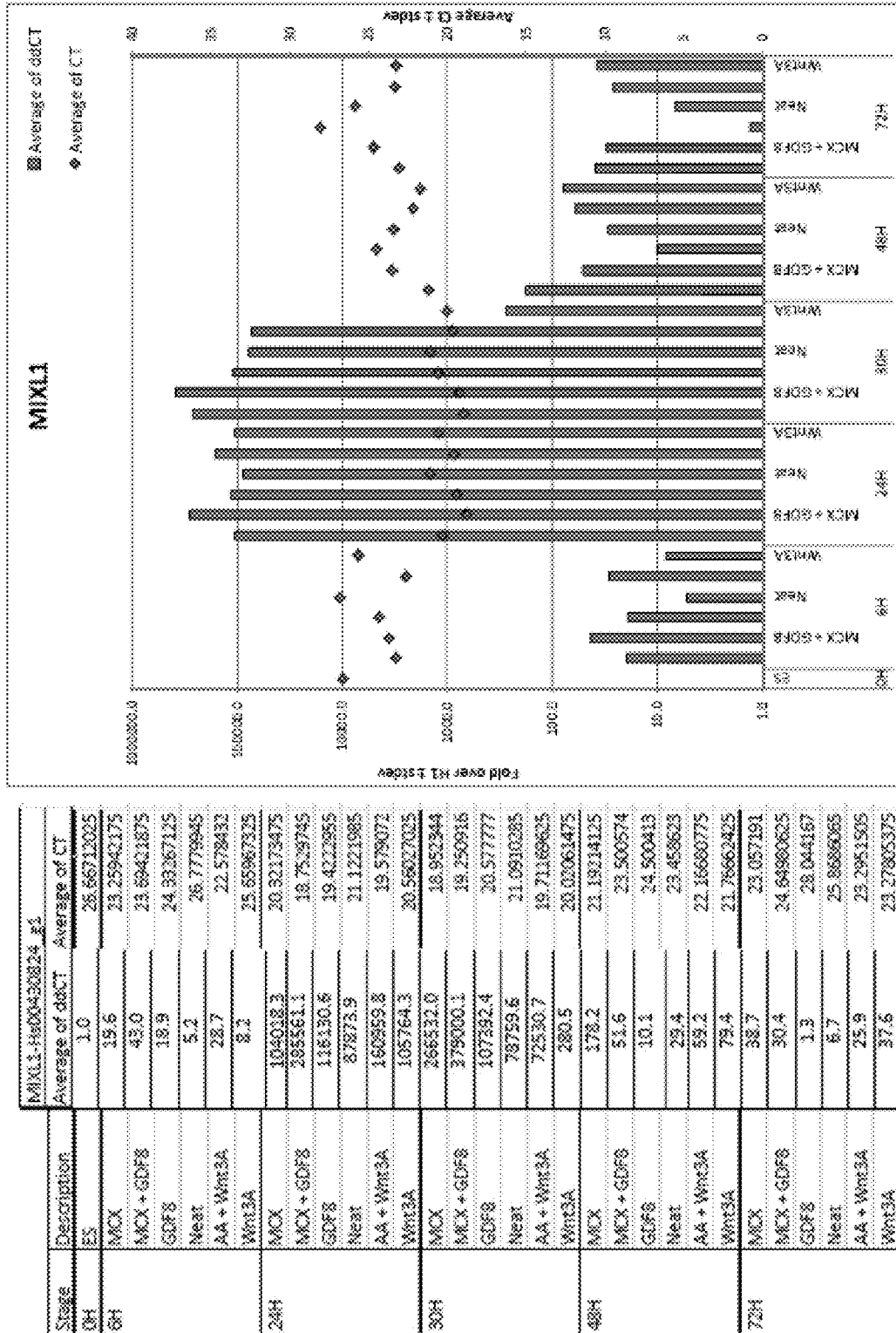
Figure 74:
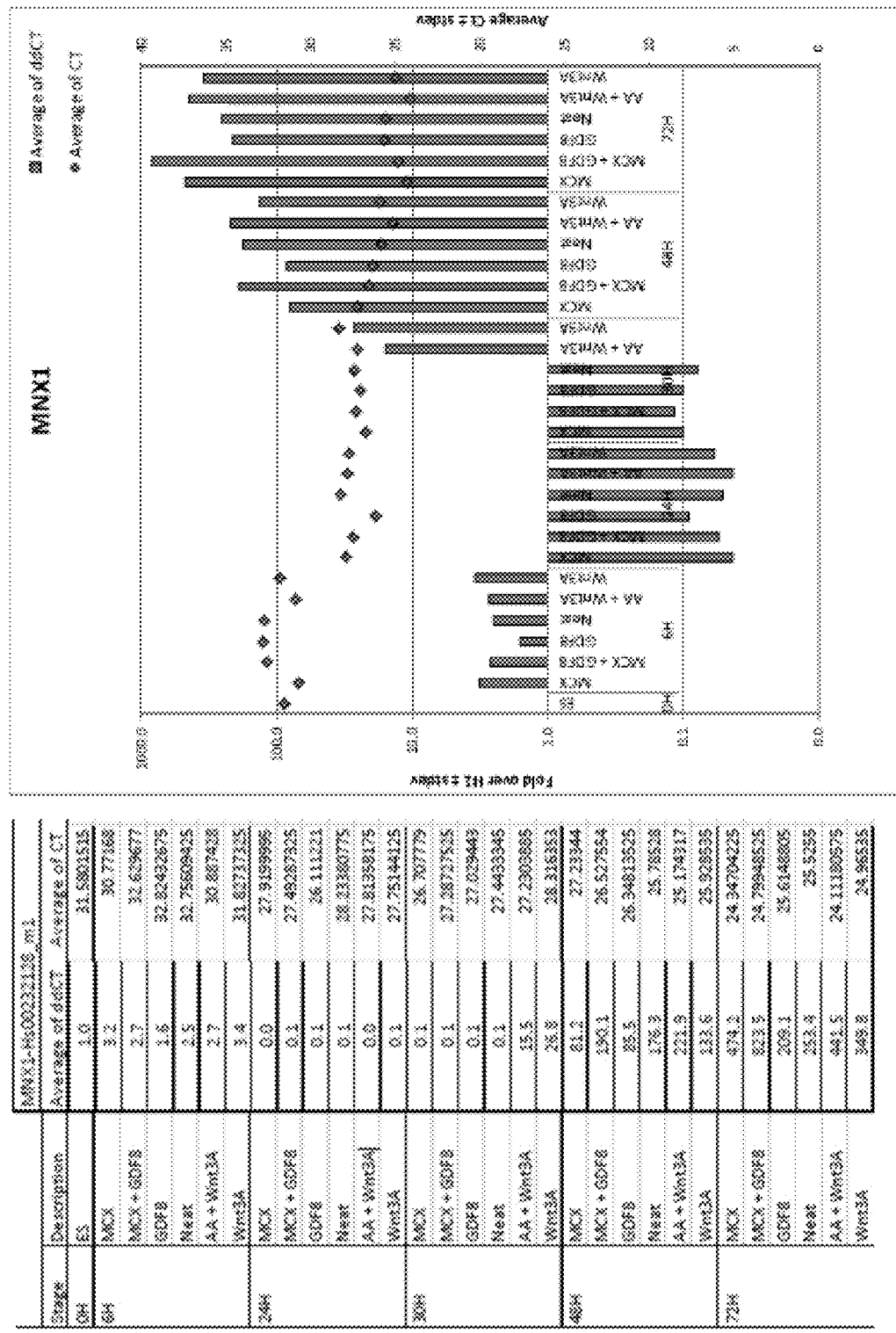
Figure 75:
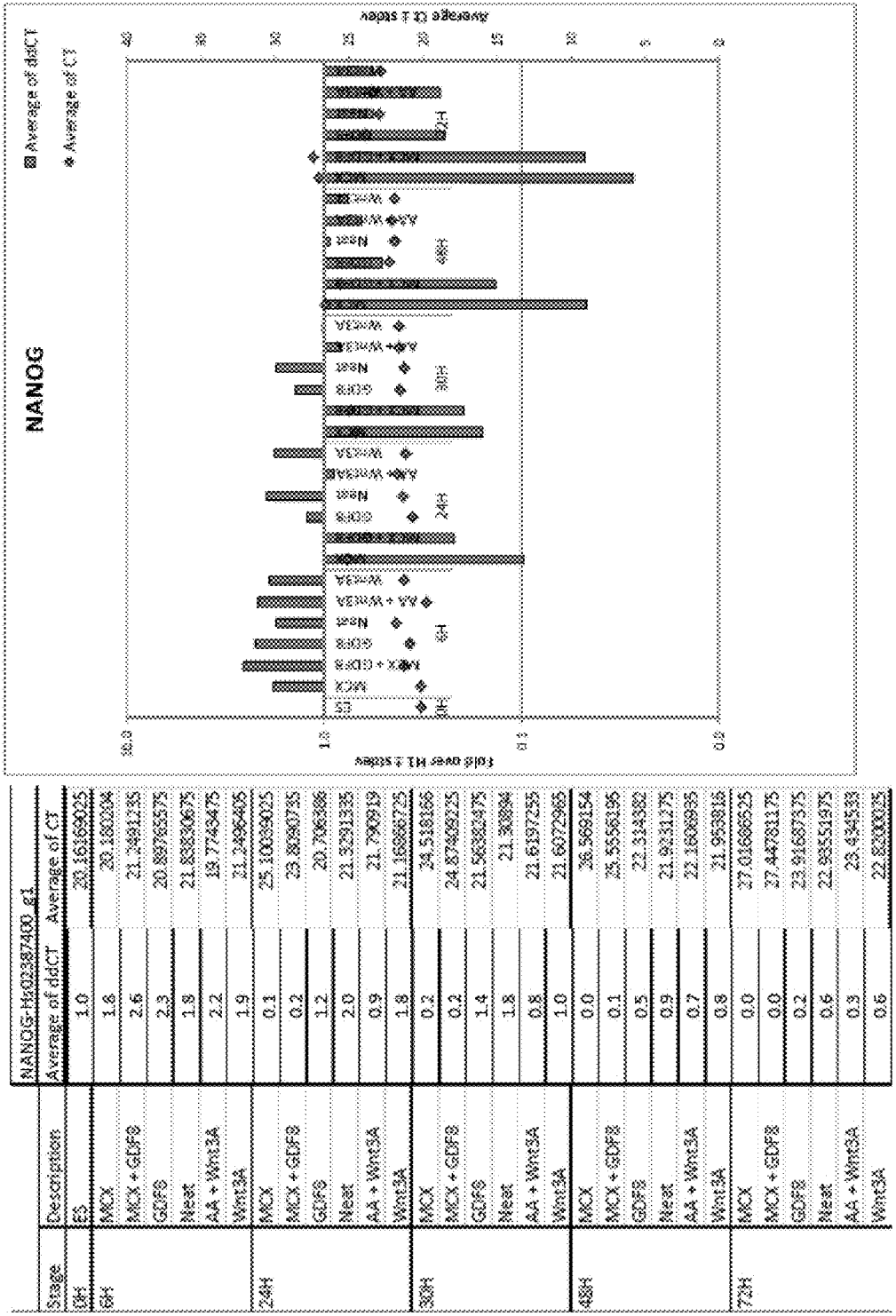
Figure 76:
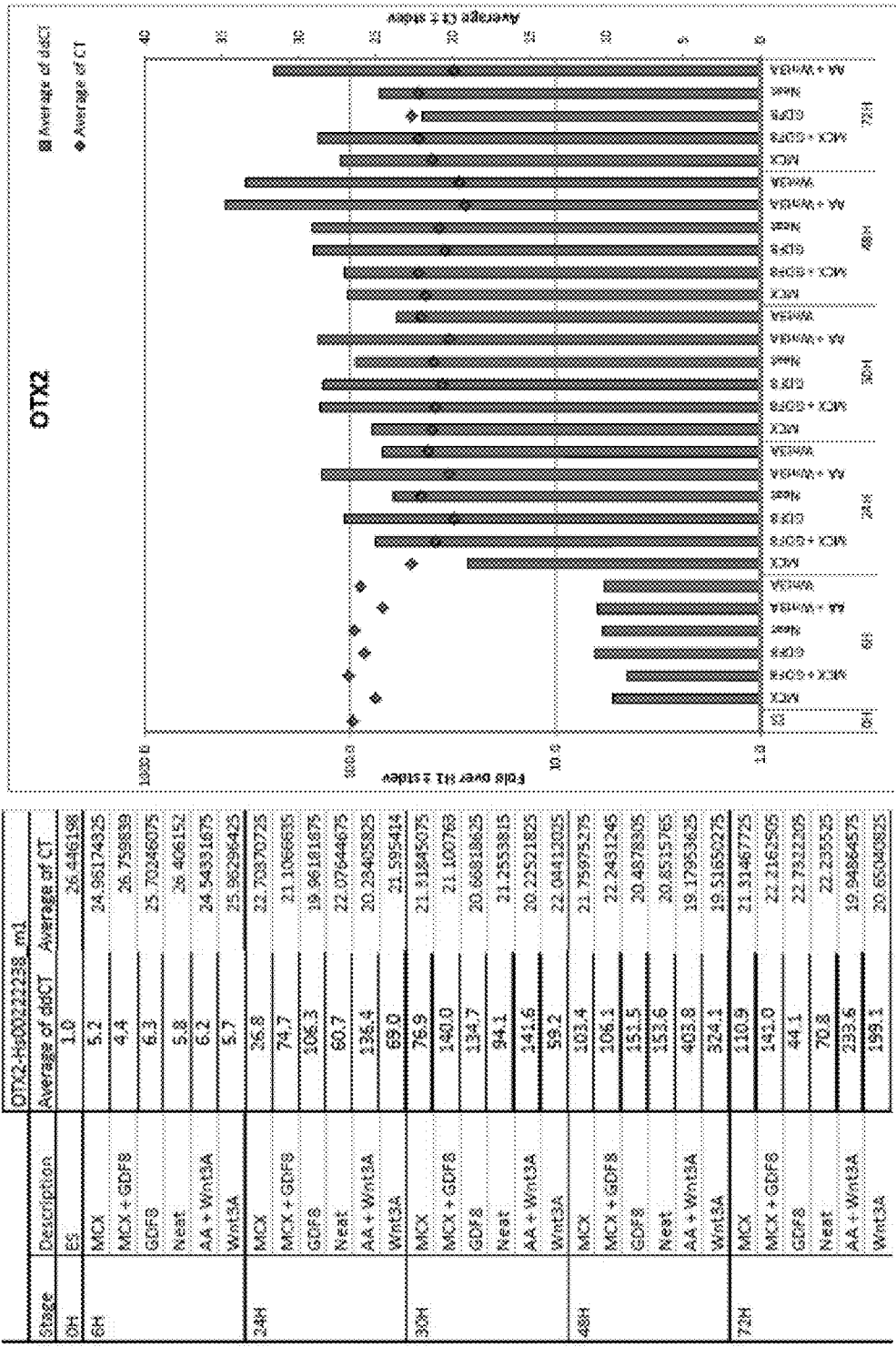
Figure 77:
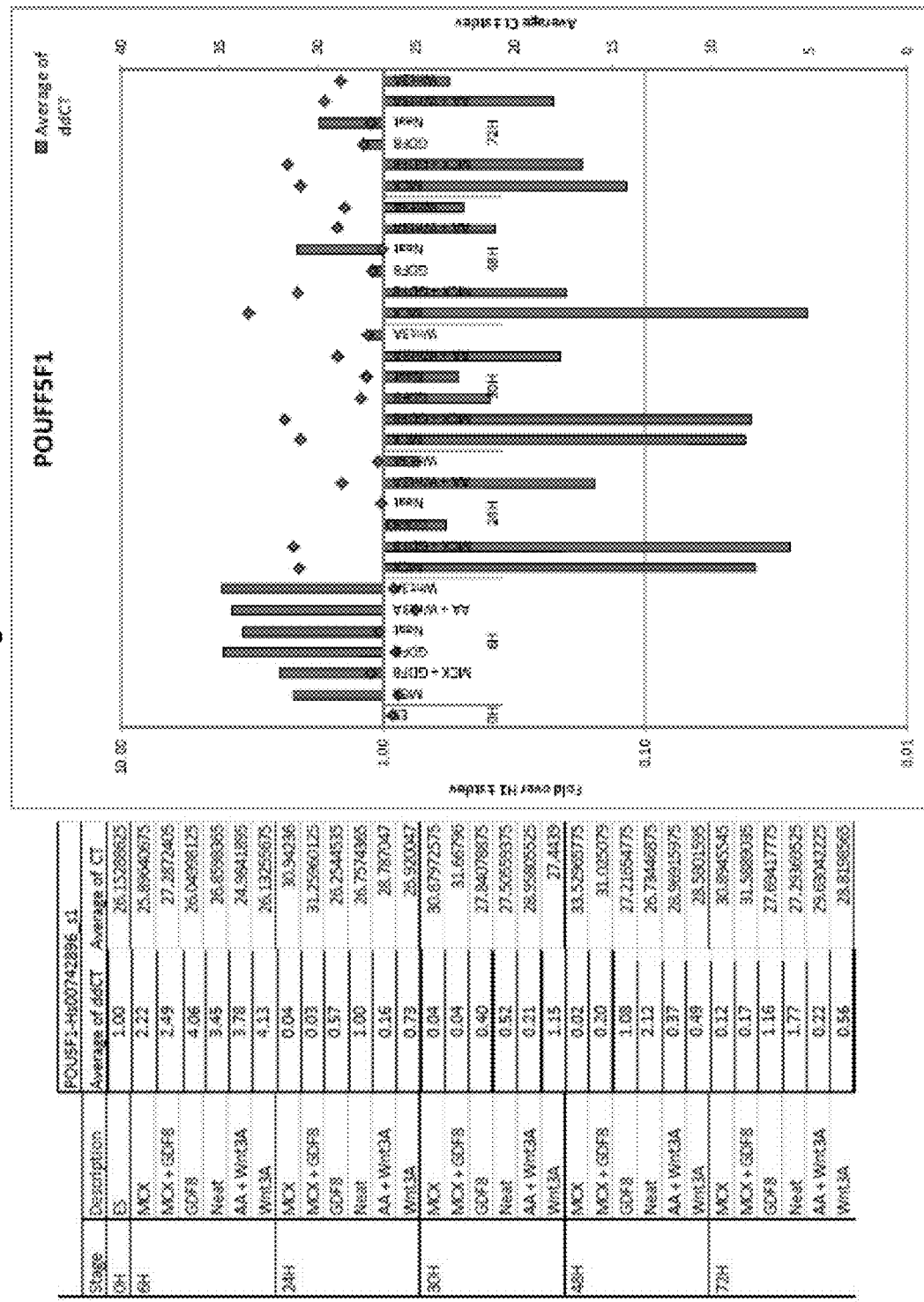
Figure 78:
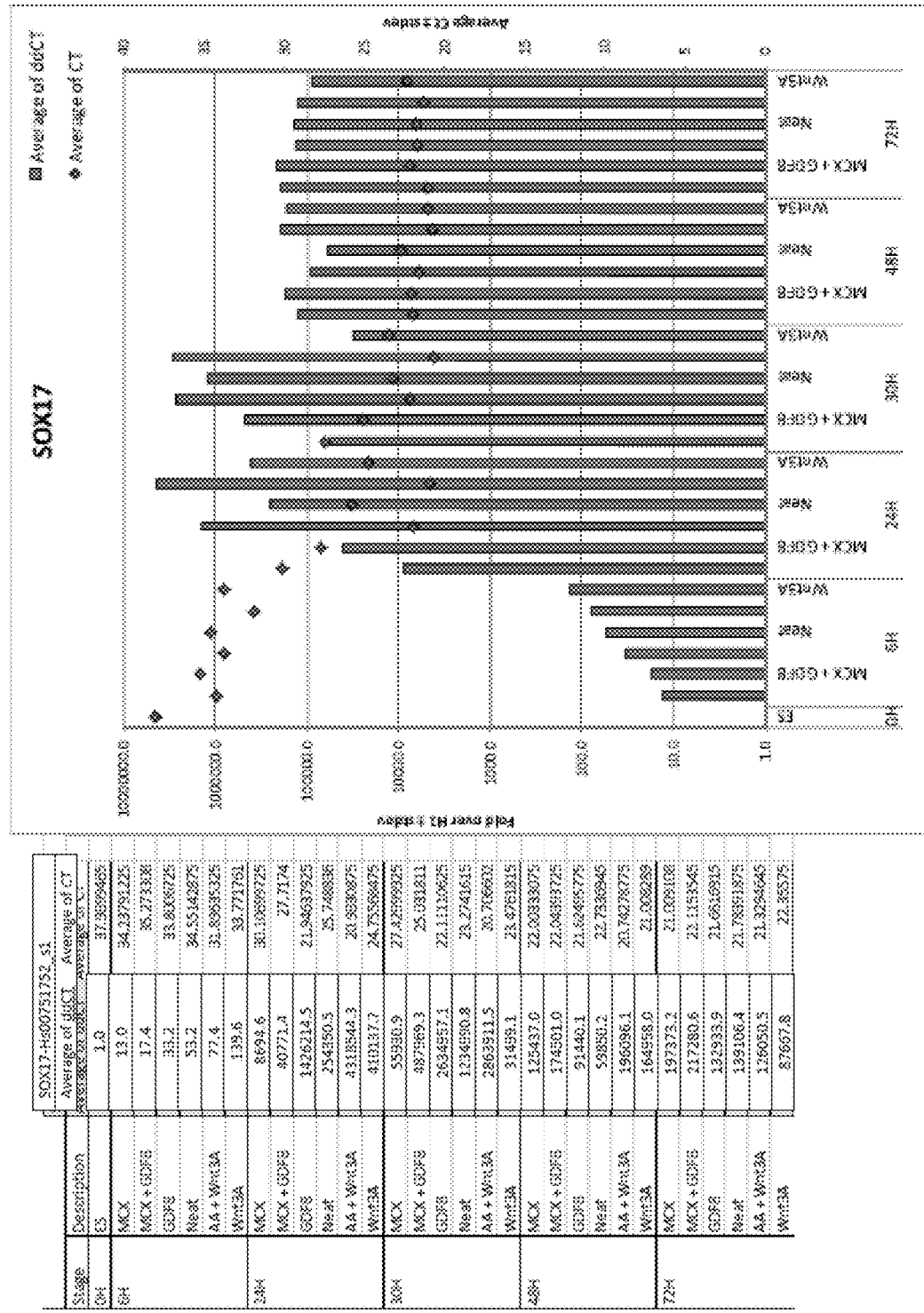
Figure 79:
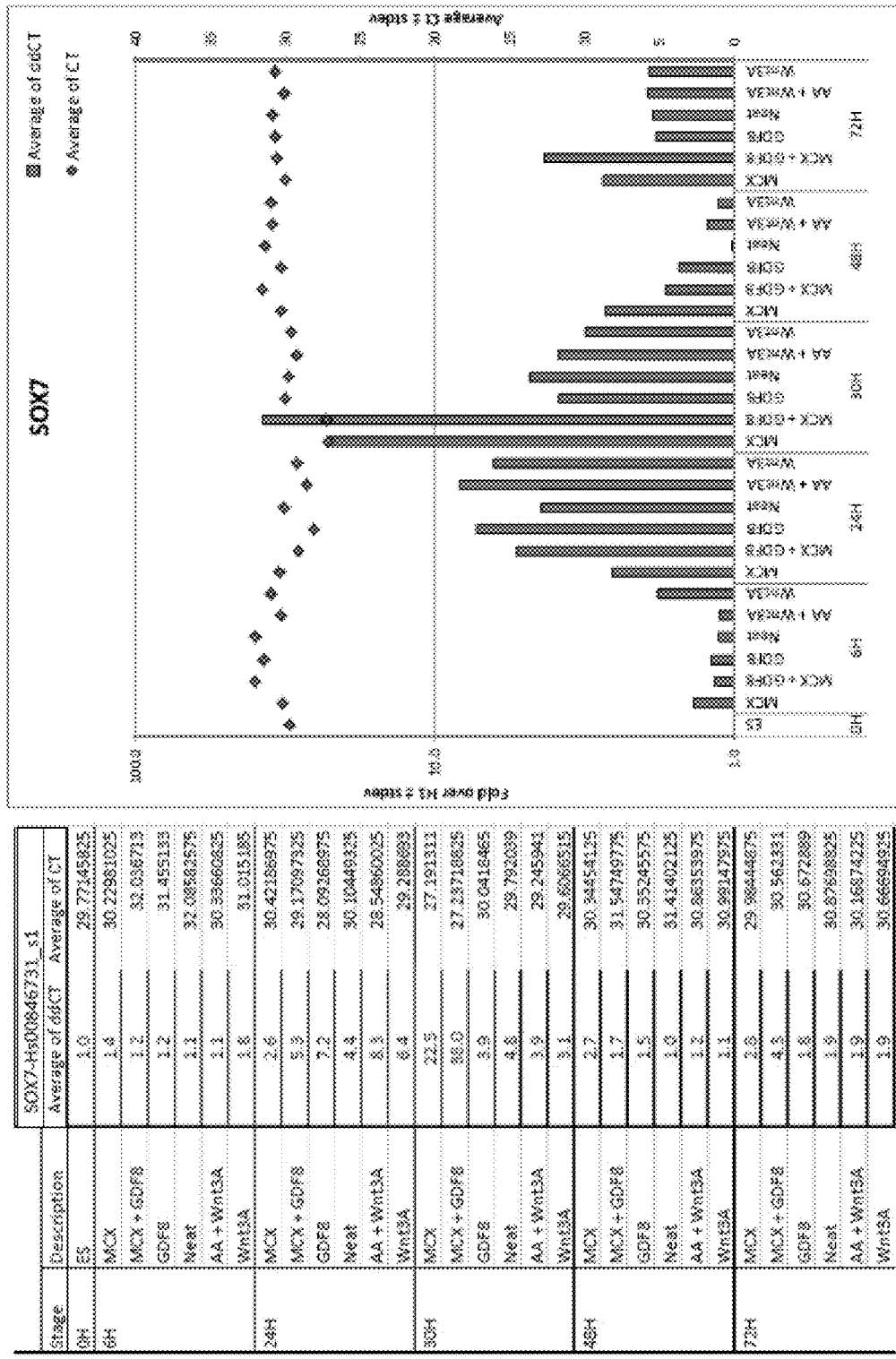
Figure 80:
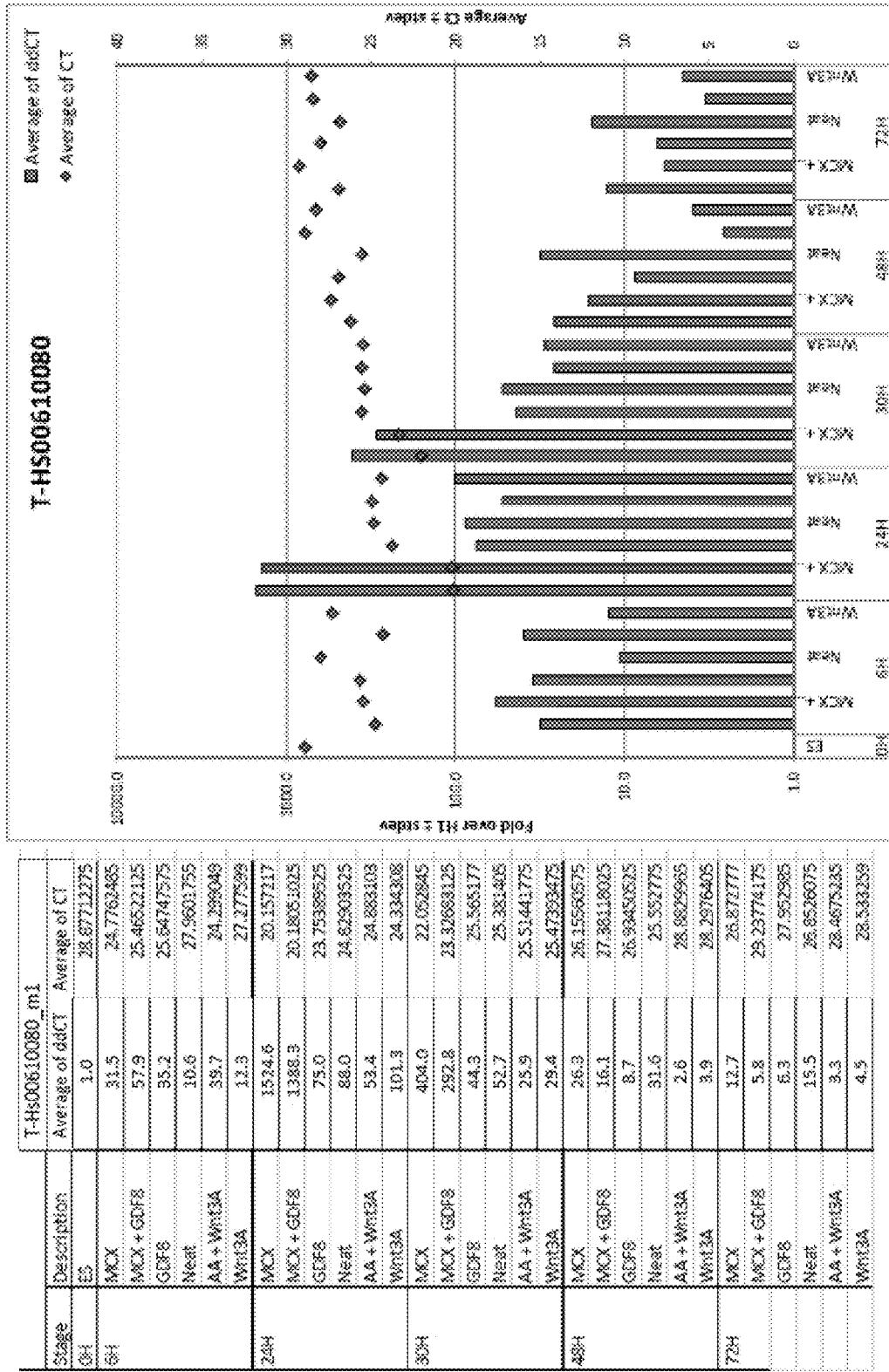

At the end of the four stage differentiation process the cells retained high levels of PDX1 (95.6% positive by FACS, ~1,000,000 fold induction over control by qRT-PCR) and FOXA2 (99.5% positive by FACS) expression. The cells showed an expression pattern consistent with pancreatic progenitor cells (39.2% positive for NKX6.1 by FACS) and a population of pancreatic endocrine cells (9.4% positive for PAX6, 12.4% positive for Chromogranin, 15.2% positive for NKX2.2; all by FACS). This stage specific marker expression pattern indicated an efficient stage-wise differentiation from a pluripotent population to pancreatic precursor cells. These results observed with flow cytometry, were confirmed by qRT-PCR. It was also noted that a host of genes commonly expressed in pancreas (ARX, GAST, GCG, IAPP, INS, ISL1, MAFB, NEUROD1, NGN3, NKX2.2, NKX6.1, PAX4, PAX6, PTF1A, and SST) all had increased expression levels on stage 4 day 3. (FIG. 55). For reference, a representative micrograph (4×) of cell clusters at the end of each stage is shown in FIG. 56.

TABLE 18

| Starting Day/Date: | Stage 1 | Stage 2 | Stage 3 | Stage 4 |
|---|---|---|---|---|
| Basal Media | MCDB131 Cust (3.64 g/L NaCO$_3$) | MCDB131 Cust (3.64 g/L NaCO$_3$) | MCDB131 Cust (3.64 g/L NaCO$_3$) | MCDB131 Cust (3.64 g/L NaCO$_3$) |
| Supplement | 2% FAF-BSA 2.5 mM glucose 1:50,000 ITS-X Glutamax 1:100 | 2% FAF-BSA 2.5 mM glucose 1:50,000 ITS-X Glutamax 1:100 | 2% FAF-BSA 2.5 mM glucose 1:200 ITS-X Glutamax 1:100 | 2% FAF-BSA 2.5 mM glucose 1:200 ITS-X Glutamax 1:100 |
| Growth factors | Day 1 and 2 only: GDF8 100 ng/mL | FGF7 50 ng/mL | FGF7 50 ng/mL | None |
| Small molecules | Day 1 only: MCX [2 µM] | | RA [2 µM] SANT [0.25 µM] TPPB [100 nM] Day 1 only LDN [100 nM] | SANT [0.25 µM] TPPB [100 nM] |
| Days | 3 | 3 | 3 | 3 |
| NOTES: All Days refer to 0 H | Media change Days 1 and 2, No change Day 3 | Media change Days 1 and 3, No change Day 2 | Media change Days 1 and 2, No change Day 3 | Media change Day 1 and end of Day 3 if S4 is extended |

TABLE 18a

| BX replicate | Seed Material | CD9 | CD184 | SSEA4 | TRA-1-60 | TRA-1-81 |
|---|---|---|---|---|---|---|
| 1 | KC | 83.3 | 0.1 | 99.9 | 94.5 | 85.8 |
| 2 | HW | 95.5 | 0.2 | 100 | 91 | 84 |
| 3 | ISM (Pink) | 95.8 | 0.1 | 100 | 76.1 | 36.5 |
| 4 | ISM (Pink) | 93.2 | 0 | 99.9 | 78.6 | 64.5 |
| 5 | ISM 1 | 97.8 | 0.2 | 99 | 74.8 | 66.4 |
| 6 | ISM 2 | 98.6 | 0.2 | 100 | 92.2 | 86 |
| 7 | ISM 1 | 98.1 | 0.1 | 99.9 | 88.8 | 80.3 |
| 8 | ISM 1 | 99.1 | 0.1 | 99.9 | 93.8 | 83.3 |
| 9 | ISM 2 | 97.2 | 0.1 | 99.9 | 88.3 | 81 |
| 10 | ISM5 | 98 | 0.1 | 99.3 | 93.1 | 85.7 |
| 11 | ISM6 | 72.6 | 0.2 | 99.9 | 94.7 | 88.9 |
| 12 | ISM6 | 85.9 | 0.7 | 99.4 | 71.9 | 54.1 |
| | Average | 93.6 | 0.1 | 99.8 | 87.8 | 76.6 |
| | St. Deviation | 8.3 | 0.1 | 0.3 | 7.6 | 15.5 |

TABLE 18b

| Stage-Day-Time | Viable Cell density (M cells/mL) | CD9 | CD184 | SSEA4 | TRA-1-60 | TRA-1-81 |
|---|---|---|---|---|---|---|
| S0D3-24H | 0.626 | 95.8 | 0.1 | 99.8 | 87.9 | 74 |

| Stage-Day-Time | Viable Cell density (M cells/mL) | CD9 | CD184 | CD99 | | |
|---|---|---|---|---|---|---|
| S1D3-24H | 0.9 | 50.7 | 98.9 | 99 | | |

| Stage-Day-Time | Viable Cell density (M cells/mL) | NKX6.1 | CHROMG. | NKX2.2 | PDX1 | FOXA2 |
|---|---|---|---|---|---|---|
| S4D1-24H | 0.943 | 69.3 | 14.2 | 23.6 | 98.8 | 99.7 |

TABLE 18b-continued

| | Viable Cell density (M cells/mL) | NKX6.1 | CHROMG. | CDX2 | SOX2 | NKX2.2 | PD PDX1 | FOX FOXA2 | NEU NEUROD |
|---|---|---|---|---|---|---|---|---|---|
| S4D3-24H | 1.002 | 66.2 | 35.6 | 0.3 | 15.8 | 38.1 | 9 99 | 9 99 | 45. 45.6 |

Materials:
- human embryonic stem (hES) cell line H1, (WA01 cells, WiCell, Madison Wis.)
- PBS (Catalog#14190, Invitrogen)
- Y-27632 (Axxora Catalog#ALX-270-333, San Diego, Calif.)
- EDTA, (Lonza, Catalog#17-7-11E)
- NucleoCounter®-(ChemoMetec A/S, Cat#YC-T100, Allerod, Denmark)
- Non-Tissue Culture Treated 6 well dishes (Becton Dickinson, Catalog# Falcon 351146, Franklin Lakes, N.J.)
- Accutase®, (Sigma-Aldrich, Catalog# A-6964, St. Louis, Mo.)
- pH, and dissolved oxygen (DO) bioreactor probes (FermProbe® pH electrode 225 mm, Model # F-635, and DO OxyProbe® 12 mm Sensor, Model # D-145 from Broadley-James Corporation, Irvine Calif.)
- Immune-protective macro encapsulation device (TheraCyte™, Irvine Calif.)
- HUMAN C-PEPTIDE ELISA (MERCODIA CAT#10-1141-01)
- GlutaMAX™, MCDB131, and ITS-X Invitrogen
- FAF-BSA (Proliant)
- Retinoic Acid, Glucose 45% (2.5M), SANT (Shh inhibitor) (Sigma)
- GDF8 (Peprotech)
- MCX
- FGF7 (R & D Systems)
- LDN-193189 (BMP receptor antagonist) (Stemgent)
- TPPB (PKC activator) (ChemPartner)

Example 15

Differentiation of Human Embryonic Stem Cells from Cell Line WA01 into Definitive Endoderm: Role of MCX/GDF8 as a Cell Cycle Regulator in Suspension Culture Clusters from pluripotent human embryonic stem cell line H1 (NIH code: WA01) were seeded at $0.5 \times 10^6$ cells/ml in Erlenmeyer shaker flasks in MCDB-131 medium containing 3.64 g/ml sodium bicarbonate and 5.5 mM glucose (Catalog # A13051 DJ, Invitrogen, CA), which was supplemented with 2% fatty acid free BSA (Catalog #68700, Proliant, IA), 1× GlutaMAX™ (Catalog #35050-079, Invitrogen, CA), an additional 2.5 mM glucose (Catalog #G8769, Sigma) and ITS-X at 1:50,000 stock concentration (Catalog #51500056, Invitrogen, CA). MCDB-131 medium supplemented in this manner will be referred to as stage 1 basal medium or "Neat" medium for the purposes of this example. The GSK3B inhibitor, 14-Prop-2-en-1-yl-3,5,7,14,17,23,27-heptaazatetracyclo [19.3.1.1~2,6~.1~8,12~]heptacosa-1(25),2(27),3,5,8(26),9,11,21,23-nonaen-16-one, U.S. patent application Ser. No. 12/494,789; incorporated herein by reference in its entirety will be referred to as "MCX".

Clusters were treated on the first day of differentiation with one of six conditions: (1) Neat, (2) 3 µM MCX plus 100 ng/ml GDF-8 (Catalog #120-00, Peprotech), (3) 3 µM MCX only, (4) 100 ng/ml GDF-8 only, (5) 20 ng/ml WNT-3A (Catalog #1324-WN-002, R&D Systems, MN) plus 100 ng/ml Activin A (Catalog #338-AC, R&D Systems, MN), or (6) 20 ng/ml WNT-3A only.

Media in each of the conditions was changed at 24 and 48 hours after the initiation of differentiation. At these times, cells in conditions 1, 2, 3, and 4 were changed to fresh stage 1 basal media supplemented with 100 ng/ml GDF8 while cells in conditions 5 and 6 were changed to fresh stage 1 basal media supplemented with 00 ng/ml Activin A.

One hour prior to initiation of differentiation, and 5, 23, 29, 47, or 71 hours after the initiation of differentiation (referred to as "Time 0"), suspension samples were transferred to a non-tissue culture treated six well dish and incubated with EdU (Click-iT® EdU Kit, Life Technologies Corporation, Carlsbad, Calif.) for one hour. The EdU incubated cells were then assessed by flow cytometry at times 0, 6, 24, 30, 48, or 72 hours after initiation of differentiation to measure the percentage of cells in G0/G1, S, or G2/M stages of the cell cycle (FIGS. 81-87).

Figure 81:
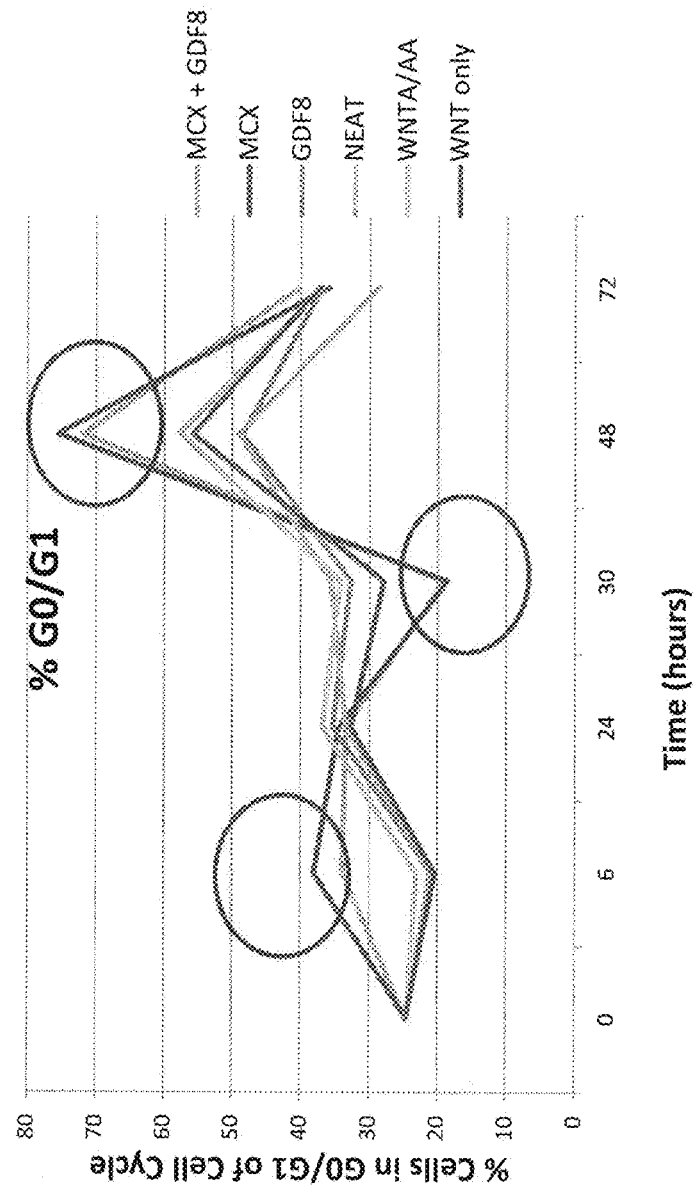
FIG. 81 shows the percentage of cells in G0/G1 of Cell Cycle for cells after 6 hours, 24 hours, 30 hours, 48 hours, and 72 hours of differentiation according to various embodiments of the protocol of Example 15. Specifically.
Figure 82:
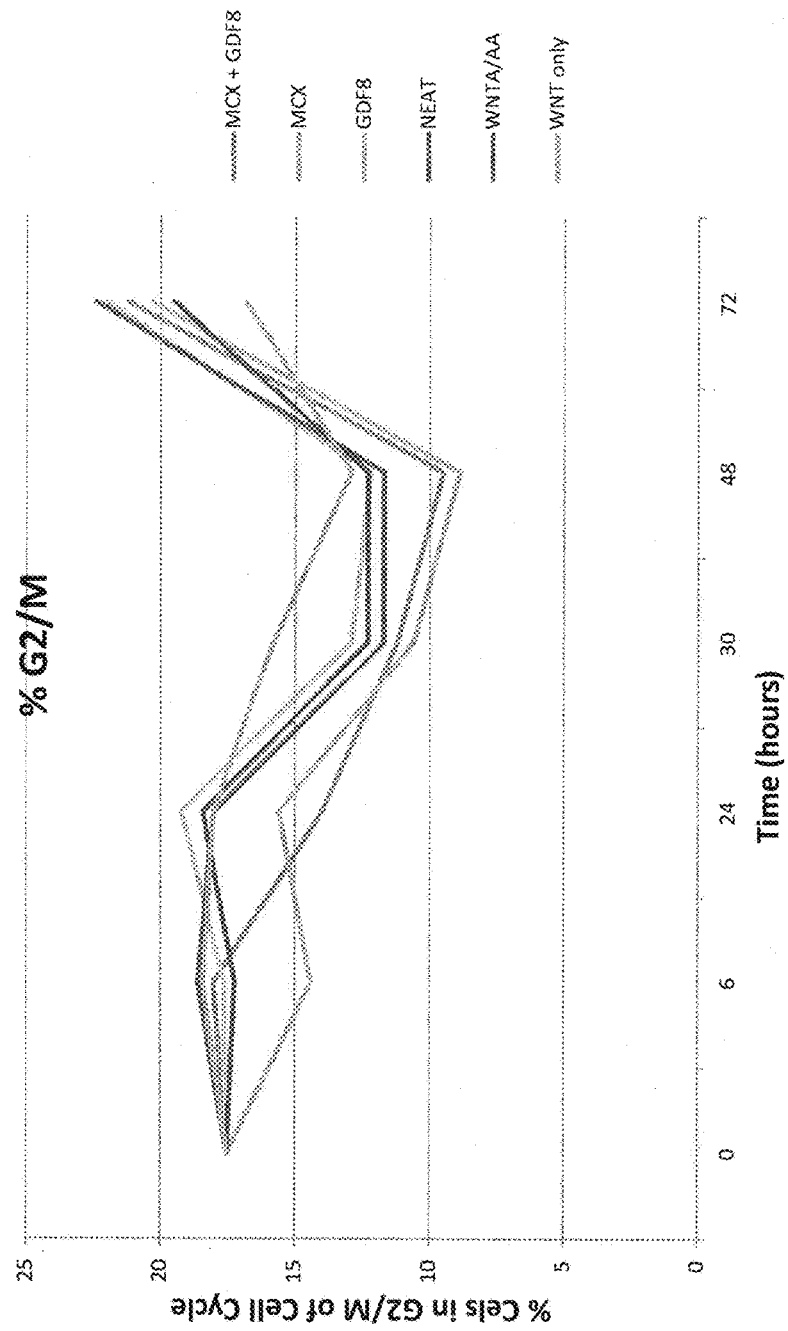
FIG. 82 shows the effects of EDU treatment on the cell clusters differentiated according to the protocol of Example 15. The left hand panel of shows percentage of cells in G2/M of Cell Cycle for cells after 0 hours, 6 hours, 24 hours, 30 hours, 48 hours, and 72 hours of differentiation according to various embodiments of the protocol of Example 15. Specifically, the left hand panel shows the results for clusters that were treated on the first day of differentiation with one of six conditions: (1) Neat, (2) 3 µM MCX plus 100 ng/ml GDF-8 (Catalog #120-00, Peprotech), (3) 3 µM MCX only, (4) 100 ng/ml GDF-8 only, (5) 20 ng/ml WNT-3A (Catalog #1324-WN-002, R&D Systems, MN) plus 100 ng/ml Activin A (Catalog #338-AC, R&D Systems, MN), or (6) 20 ng/ml WNT-3A only. In one set of data, these clusters were also treated with EDU. The right hand panel of FIG. 82 shows the % Cells that are EDU positive 0 hours, 6 hours, 24 hours, 30 hours, 48 hours, and 72 hours of differentiation according to various embodiments of the protocol of Example 15.
Figure 82:
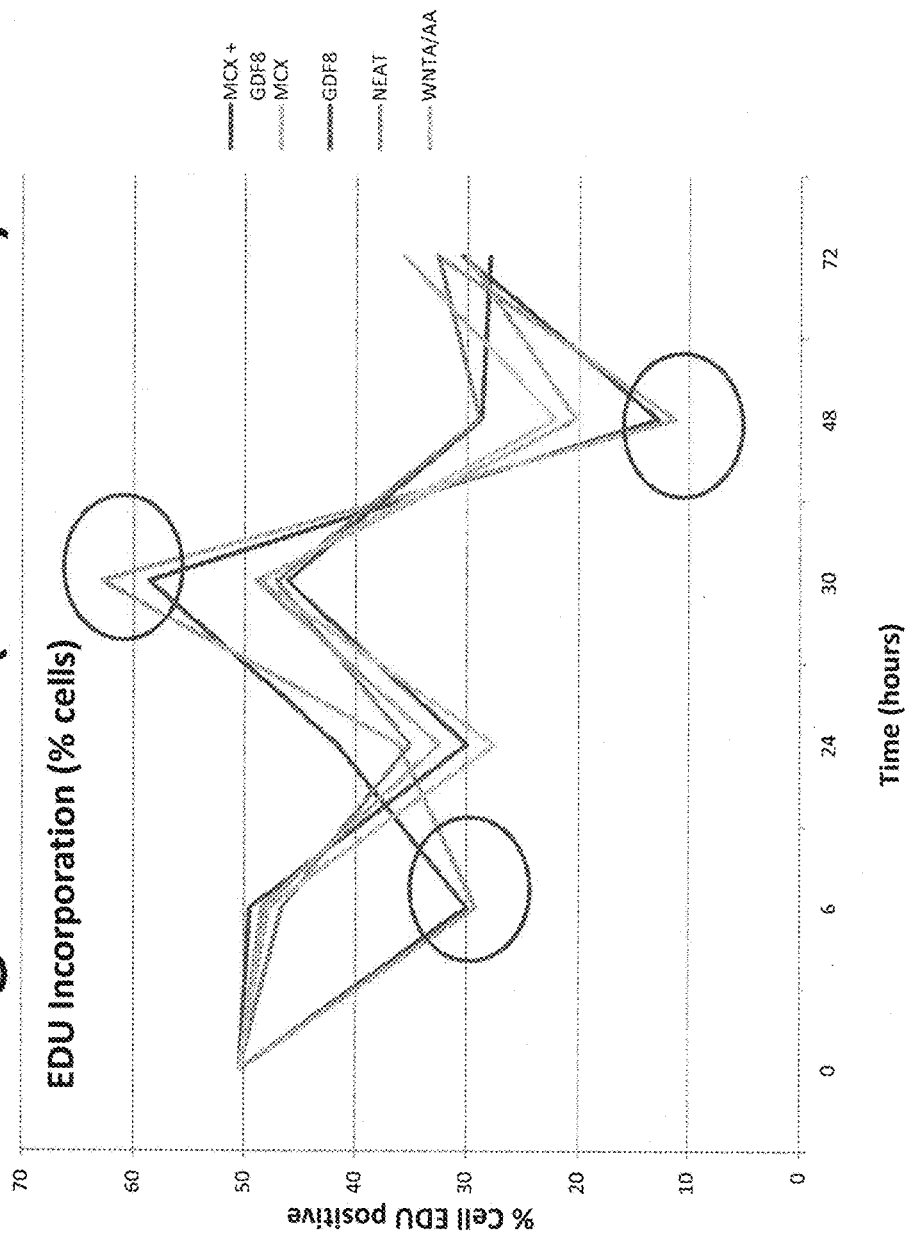

Following this protocol, significant differences in the percentage of cells in G0/G1, S, or G2/M stages of the cell cycle were observed (FIGS. 82-87) and it was noted that MCX and MCX+GDF8 treated cells had a nearly 40% reduction in the incorporation of EdU compared to the other four treatment conditions (FIG. 81). This reduction in EdU incorporation was matched by a 38% increase in G0/G1 cells from the MCX+GDF8 treated sample and a 54% increase in G0/G1 cells for the MCX only treated cells. These changes to EdU incorporation and the increased transition to G0/G1 at 6 hours following initiation of differentiation were not observed in cells treated with GDF8, WNT3A, WNT-3A+Activin A, or neat medium. Rather, cells treated with GDF8, WNT-3A, WNT-3A+Activin A, or neat medium demonstrated a minimal reduction in the percentage of cells with EdU incorporation (mean, 48.1%, SD±1.2) and an average 13% decrease in the number of cells in G0/G1 six hours after the initiation of differentiation (Standard Deviation, ±5%) as shown in FIGS. 81 and 82.

Similar differences were observed later in the process in the spread between G0/G1 values for cells treated with MCX or MCX+GDF8 compared to the other treatment conditions. At 30 hours after time 0, MCX or MCX+GDF8 treated cells had 43-45% fewer cells in G0/G1 as compared to cells treated with WNT-3A+Activin A, GDF8, WNT-3A, or neat medium. This gap between percentage of G0/G1 cells was retained at 48 hours after initiation of differentiation, as 71.9-75.5% of cells treated with MCX or MCX+GDF8 were in G0/G1 of the cell cycle, while 48.5% of GDF8, 55.8% of WNT3A, 57.7% of WNT-3A+Activin A, or 49% of neat medium treated cells were in G0/G1. In addition to the observed differences in EDU incorporation and G0/G1 profiles, MCX or MCX+GDF8 treated cells had 15-33% more cells in the S phase of cell cycle at 30 and 48 hours after time 0 when compared with WNT3A+Activin A, GDF8, WNT-3A, or neat medium treated cells (FIGS. 84 and 85).

The data (gene expression for CD99, CD9, CDH1, CDH2, CDX2, CER1, CXCR4, FGF17, FGF4, FOXA2, GATA4, GATA6, GSC, KIT, MIXL1, MNX1, NANOG, OTX2, POU5F1, SOX17, SOX7, and T, shown in FIGS. 57-80 and 88*a*-88*n*) indicated that in suspension culture, addition of MCX with or without the TGF-β family member, GDF8, for the first day of differentiation generated definitive endoderm comparable to that obtained when cells are treated with 20 ng/ml WNT-3A plus 100 ng/ml Activin A on day one, as measured by gene expression at the end of definitive endoderm formation. However, consistent with the differences in cell cycle observed through the process of forming definitive endoderm, intermediate differences in gene expression were seen. In samples treated with MCX or MCX+GDF8 the genes T (brachyury), GATA4, and CDX2 were induced at levels substantially higher than cells treated with WNT-3A+ Activin A or the other three tested conditions in the first 24 hours of differentiation (FIGS. 88 *c, e,* and *n*). Conversely, the expression of genes for pluripotency (NANOG and POU5F1/OCT4) was dramatically reduced by 24 hours in samples treated with MCX or MCX+GDF8 when compared to the starting cell population or the other four conditions tested (FIGS. 88*i* and 88*k*). The magnitude of induction of expression for genes such as FGF4, FOXA2, and SOX17 was much lower in MCX or MCX+GDF8 samples when compared to the other four conditions tested at 24 hours after the initiation of differentiation, however by 48 hours all samples expressed FGF4, FOXA2, and SOX17 at comparable levels. (FIGS. 88*e*, 88*f,* and 88*l*).

Example 16

Generating Ectodermal and Mesodermal Tissues Using a Scalable Suspension Differentiation Process This example demonstrates a process capable of both expanding and differentiating pluripotent stem cells (PSC) to achieve a scalable manufacturing process for generation of ectodermal or mesodermal tissues.

Two cell lines were suspension expanded to provide seed material for these studies: a sub-clone of the H1 (WA01) hES cell line—WB0106 and an induced pluripotent stem cell (iPSC) line generated from umbilical tissue cells (UTC). As described in prior examples, suspension expanded cells were frozen at high density in a controlled rate freezer, then thawed to inoculate a closed 3 liter glass bioreactor (DAS-GIP; Julich, Germany) or disposable 3 liter single use bioreactor (Mobius, EMD Millipore Corporation, Billerica, Mass.) at a final cell concentration of $0.225 \times 10^6$ cells/mL. The cells inoculated into the stirred tank bioreactor formed cell clusters in the continuously stirred tank, and were maintained in pluripotency medium (E8™, supplemented with 2% BSA) in the reactor for three days total. At 72 hours after inoculation, pluripotent cell differentiation was initiated by transferring cell clusters to plastic disposable Erlenmeyer flasks (PETG 125 mL flask, Cat#4112, Thermo Scientific Rochester N.Y.) in their respective differentiation medium (Table 19) to form mesoderm/cardiac tissue (1) or ectoderm/neural tissue (2).

Once the staged differentiation process was initiated, the cells were maintained for ten (10) days at 100 rpm in a humidified, 5% $CO_2$ incubator on a shaker platform (MAXQ 416 hp, Thermo Scientific, Rochester N.Y.). At 1 day, 3 days, 5 days, and 7 days after the initiation of differentiation medium in the flask was exchanged for fresh medium made as described in Table 19. qRT-PCR samples were taken prior to starting differentiation for reference and then 3, 5, 7, and 10 days after initiating differentiation.

In order to determine if ectodermal or mesodermal specific changes in mRNA expression patterns could be detected by qRT-PCR, three Applied Biosystems Low Density Arrays (Life™, Carlsbad, Calif.) designated Pluripotency, Definitive Endoderm (DE), and stage 6 (S6) were used and the results were compared to the appropriate undifferentiated pluripotent stem cell sample as control to standardize expression.

Using these arrays, the gene expression pattern of pluripotent cells cultured in ectodermal (FIG. 89) or mesodermal (FIG. 90) differentiation medium was determined. It was observed that cells differentiated in shaker flasks under either condition demonstrated reduced pluripotent gene expression for genes of pluripotency like NANOG, POU5F1/OCT4, TDGF1, and ZFP42 over extended culture from day 3 to day 10 as measured by Pluripotency Array. The expression of CXCR4 increased in samples from hES or iPS cells differentiated to either ectoderm or mesoderm. These results correlated with qRT-PCR data showing high expression of genes characteristic of differentiation. Cells treated with ectodermal differentiation medium expressed increased levels of ARX, NEUROD, NKX6.1, PAX6 (>100 fold), and ZIC1 (>1000 fold) by qRT-PCR from 3 to 10 days after initiation of differentiation (FIG. 91). These data were confirmed by FACS array, which showed that three (3) days after beginning the initiation of differentiation to an ectodermal fate both iPSC and hES cells maintained high expression of SOX2 (a gene required for both pluripotency and neural stem cells), but lost expression of POU5F1/OCT4 (a gene required for pluripotency) while gaining PAX6 expression (a gene of neural and endocrine differentiation) (FIG. 92).

Similar kinetics of differentiation in cells treated with mesodermal differentiation medium were also observed. As pluripotent gene expression dropped over the course of the 10 day differentiation (FIG. 90), an early induction was observed for genes characteristic of the early, transient mesendoderm fate (CER1, EOMES, CKIT, and VWF) at day 3 and these genes expression levels declined to near baseline by day 10 (FIG. 93). It was also observed that expression of characteristic mesoderm genes at 3, 5, 7, and 10 days after initiation of differentiation showed early and increasing gene expression (CDH2, CDX2, GATA6, HNF4a, MNX1, PRDM1, and SOX17 in FIG. 93). The same pattern of gene induction was observed in both iPS and hES cell samples indicating the differentiation process was directed and not spontaneous in nature.

These changes in gene expression observed by qRT-PCR correlated with results observed by phase contrast microscopy and immunstained cryo-sections of clusters. By day 10 in the mesodermal differentiated suspension culture, about 1 in 10 clusters began to spontaneously "beat" suggesting the cells had differentiated to myo-cardial tissue (FIG. 94, left panel, day 10, white bars). Stained cross sections of some clusters showed a striated, end to end, 3-tubulin staining pattern indicative of muscle formation (FIG. 94, right panel).

A strikingly different morphological pattern was observed for clusters differentiated to an ectodermal fate (FIG. 95, left panel) when compared to clusters differentiated to mesoderm (FIG. 94). The clusters throughout ectodermal differentiation were larger and denser than cells differentiated to a mesodermal fate, and the ectodermal differentiated cells expressed less total 3 tubulin. Those cells which did express 3 tubulin showed a more dendritic pattern of staining (FIG. 95, right panel, white arrows) characteristic of neurons.

These results, in combination with qRT-PCR and FACS data, indicate that cells banked and expanded in suspension can be differentiated in suspension culture to mesodermal or ectodermal fates in a directed and reproducible manner.

While the invention has been described and illustrated herein by reference to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entirety.

TABLE 19

| Starting Day/Date: | Neural Differentiation Days 0-4 | Neural Differentiation Day 5-10 | Cardiac Differentiation Days 0-6 | Cardiac Differentiation Days 7-10 |
|---|---|---|---|---|
| Basal Media | MCDB131 (2.5 g/L NaCO$_3$ final) | MCDB131 Cust (2.5 g/L NaCO$_3$ final) | MCDB131 Cust (2.5 g/L NaCO$_3$ final) | MCDB131 Cust (2.5 g/L NaCO$_3$) |
| Supplement | 2% FAF-BSA 2.5 mM glucose Glutamax 1:100 1:100 ITS-X | 2% FAF-BSA 2.5 mM glucose Glutamax 1:100 1:100 ITS-X or 1X B-27 | 2% FAF-BSA 2.5 mM glucose Glutamax 1:100 | 2% FAF-BSA 2.5 mM glucose Glutamax 1:100 1X B-27 |
| Small molecules | LDN [100 nM] ALKVi [7.5 µM] | none | First 24 hrs only: MCX [2 µM] Days 3 and 4 only: IWP-4 [8 µM] | |
| Days | 3 | 3 | 3 | 3 |
| NOTES: All Days refer to time after initiation | Media change: Days 0, 1 and 3 | Media change: Days 5 and 7 | Media change: Days 0, 1, 3, and 5 | Media change Day 7 |

TABLE 20

Materials:

human umbilical cord tissue-derived cells (as disclosed in U.S. Pat. No. 7,510,873)
Inducible pluripotent stem cells
parthenotes
human embryonic stem (hES) cell line H1, (WA01 cells, WiCell, Madison WI)
PBS (Catalog# 14190, Invitrogen)
Y-27632 (Axxora Catalog#ALX-270-333, San Diego, CA)
EDTA, (Lonza, Catalog# 17-7-11E)
NucleoCounter ®-(ChemoMetec A/S, Cat#YC-T100, Allerod Denmark)
Non-Tissue Culture Treated 6 well dishes (Becton Dickinson, Catalog# Falcon 351146, Franklin Lakes, NJ)
Accutase ®, (Sigma, Catalog# A-6964, St. Louis, MO)
pH, and dissolved oxygen (DO)bioreactor probes (FermProbe ® pH electrode 225 mm, Model # F-635, and DO OxyProbe ® 12 mm Sensor, Model # D-145 from Broadley-James Corporation, Irvine CA)
Immune-protective macro encapsulation device (TheraCyte ™, Irvine CA)
HUMAN C-PEPTIDE ELISA (MERCODIA CAT# 10-1141-01)
GlutaMAX ™, MCDB131, and ITS-X Life Technologies Corporation, Grand Island NY
FAF-BSA (Proliant)
Retinoic Acid, Glucose 45% (2.5M), SANT (Shh inhibitor) (Sigma)
GDF8 (Peprotech)
MCX TABLE 20-continued Materials:

IWP-4 (WNT3 inhibitor) Stemgent
MCDB131 media
MCDB131 media (customized)-modified to raise the NaCO$_3$ level to 3.64 g/L.

What is claimed is:

1. An in vitro method of producing three-dimensional cell clusters of pluripotent stem cells comprising the steps of:
   a. treating pluripotent stem cells cultured in a planar adherent culture with a chelating agent or enzyme to release cell aggregates from the planar adherent culture;
   b. suspending the cell aggregates from the planar adherent culture in a culture medium in the presence of a Rho-kinase inhibitor without centrifuging the cell aggregates and without dissociating the cell aggregates to single cells;
   c. diluting the culture using culture media and a Rho-kinase inhibitor to a concentration of cells from about 1 to about 1.5 million cells/ml;
   d. transferring the suspension of cell aggregates to a dynamic suspension culture; and
   e. expanding the suspension of cell aggregates in the dynamic suspension culture to generate cell clusters, wherein the cell clusters maintain pluripotency.

2. The method of claim 1, wherein the pluripotent stem cells are treated with an enzyme selected from neutral protease or Accutase.

3. The method of claim 2, wherein the enzyme is neutral protease.

4. The method of claim 1, wherein the pluripotent stem cells are selected from the group consisting of induced pluripotent stem cells, human umbilical cord tissue-derived cells, parthenotes, human embryonic stem cells (hES) and amniotic fluid derived-cells.

5. The method of claim 4, wherein the cells are H1 hES.

6. The method of claim 1, wherein the cells in the cell cluster express CD9, SSEA4, TRA-1-60, and TRA-1-81, and lack expression of CXCR4.

7. The method of claim 1, wherein the pluripotent stem cells are treated with a chelating agent.

8. The method of claim 7, wherein the chelating agent is ethylenediaminetetraacetic acid (EDTA).

9. A method of differentiating cell clusters of pluripotent stem cells in a dynamically agitated suspension culture system comprising:
 a. treating pluripotent stem cells cultured in a planar adherent culture with a chelating agent or enzyme to release cell aggregates from the planar adherent culture;
 b. suspending the cell aggregates from the planar adherent culture in culture medium in the presence of a Rho-kinase inhibitor without centrifuging the cell aggregates and without dissociating the cell aggregates to single cells;
 c. diluting the culture using culture media and a Rho-kinase inhibitor to a concentration of cells from about 1 to about 1.5 million cells/ml;
 d. transferring the suspension of cell aggregates to a dynamic agitated suspension culture;
 e. expanding the suspension of cell aggregates in the dynamic agitated suspension culture to generate pluripotent cell clusters, wherein the cell clusters express CD9, SSEA4, TRA-1-60, and TRA-1-81, and lack expression of CXCR4; and
 f. differentiating the pluripotent cell clusters in the dynamic agitated suspension culture system to generate a gut tube cell population, a neural precursor cell population or a cardiomyocyte precursor population.

10. The method of claim 9, wherein the pluripotent stem cells are selected from the group consisting of induced pluripotent stem cells, human umbilical cord tissue-derived cells, parthenotes, human embryonic stem cells (hES) and amniotic fluid derived-cells.

11. The method of claim 9, wherein the method generates a gut tube cell population which expresses β cell transcription factors.

12. The method of claim 11, wherein the transcription factors are PDX1 and/or NKX6.1.

13. The method of claim 9, wherein the method comprises differentiating the pluripotent cell clusters in a dynamic agitated suspension culture system to generate a gut tube cell population.

14. The method of claim 9, wherein the method comprises differentiating the pluripotent cell clusters in a dynamic agitated suspension culture system to generate a neural precursor cell population.

15. The method of claim 9, wherein the method comprises differentiating the pluripotent cell clusters in a dynamic agitated suspension culture system to generate a cardiomyocyte precursor population.

16. The method of claim 9, wherein the pluripotent stem cells are treated with a chelating agent.

17. The method of claim 16, wherein the chelating agent is EDTA.

18. The method of claim 9, wherein the pluripotent stem cells are treated with an enzyme.

19. The method of claim 18, wherein the enzyme is a neutral protease or Accutase.

20. The method of claim 9, wherein the step of differentiating comprises culturing at an oxygen range from about hypoxia to about 30% of ambient, a lipid in the range of 0.1% to about 2%, or the combination thereof.

21. The method of claim 13, wherein the method comprises differentiating the three-dimensional pluripotent stem cell clusters to definitive endoderm cells in a culture medium supplemented with either (i) a cyclic aniline-pyridinotriazine and GDF8 or (ii) WNT3A and activin A.

22. The method of claim 21, wherein the cyclic aniline-pyridinotriazine is 14-Prop-2-en-1-yl-3,5,7,14,17,23,27-heptaazatetracyclo[19.3.1.1~2,6-~.1~8,12.~[heptacosa-1 (25),2(27),3,5,8(26),9,11,21,23-non-aen-16-one.

23. The method of claim 1, wherein the dynamic agitated suspension culture system comprises microcarriers.

24. The method of claim 9, wherein the dynamic agitated suspension culture system comprises microcarriers.

25. An in vitro method of producing pluripotent stem cell clusters comprising the steps of:
 a. treating pluripotent stem cells cultured in a planar adherent culture with an enzymatic or chelating agent at room temperature for a time sufficient to release the pluripotent stem cells as cell aggregates;
 b. removing said enzymatic or chelating agent;
 c. adding culture media supplemented with a Rho-kinase inhibitor to the cell aggregates and suspending the cell aggregates in culture without centrifuging the cell aggregates and without dissociating the cell aggregates to single cells;
 d. transferring the suspension of cell aggregates to a dynamic suspension culture system; and
 e. expanding the suspension of cell aggregates in the dynamic suspension culture to generate cell clusters, wherein the cells in the cell clusters are pluripotent.

26. The method of claim 25, wherein the method comprises use of chelating agent.

27. The method of claim 26, wherein the chelating agent is EDTA.

28. The method of claim 27, wherein the method comprises use of an enzymatic agent.

29. The method of claim 25, wherein the enzymatic agent is a neutral protease or Accutase.

30. The method of claim 25, wherein the pluripotent stem cells are selected from the group consisting of induced pluripotent stem cells, human umbilical cord tissue-derived cells, parthenotes, human embryonic stem cells (hES) and amniotic fluid derived-cells.

31. The method of claim 25 further comprising differentiating the three-dimensional pluripotent stem cell clusters in the dynamic agitated suspension culture system to generate a gut tube cell population, a neural precursor cell population or a cardiomyocyte precursor population.

* * * * *